(12) United States Patent
Ramnauth et al.

(10) Patent No.: US 8,106,043 B2
(45) Date of Patent: Jan. 31, 2012

(54) BENZOXAZINES, BENZOTHIAZINES, AND RELATED COMPOUNDS HAVING NOS INHIBITORY ACTIVITY

(75) Inventors: Jailall Ramnauth, Brampton (CA); Subhash C. Annedi, Mississauga (CA); Sarah Silverman, Toronto (CA); Peter Dove, Toronto (CA); Shawn Maddaford, Mississauga (CA); Suman Rakhit, Mississauga (CA)

(73) Assignee: NeurAxon, Inc., Mississauga (CA)

( * ) Notice: Subject to any disclaimer, the term of this patent is extended or adjusted under 35 U.S.C. 154(b) by 81 days.

(21) Appl. No.: 12/498,185

(22) Filed: Jul. 6, 2009

(65) Prior Publication Data

US 2010/0009975 A1    Jan. 14, 2010

Related U.S. Application Data

(60) Provisional application No. 61/133,887, filed on Jul. 3, 2008.

(51) Int. Cl.
*A61K 31/5415* (2006.01)

(52) U.S. Cl. ........................ 514/224.2; 544/51
(58) Field of Classification Search ............... 544/51
See application file for complete search history.

(56) References Cited

U.S. PATENT DOCUMENTS

| 5,521,145 | A | 5/1996 | Takano et al. |
| 7,141,595 | B2 | 11/2006 | Ramnauth et al. |
| 2006/0258721 | A1 | 11/2006 | Maddaford et al. |

FOREIGN PATENT DOCUMENTS

| CA | 2207628 | 6/1996 |
| CA | 2494323 | 2/2004 |
| CA | 2607219 | 2/2007 |
| CA | 2643822 | 10/2007 |
| WO | WO 00/63197 | 10/2000 |
| WO | WO 2008/100463 | 8/2008 |

OTHER PUBLICATIONS

Chapter II Demand (PCT/CA2009/000923), filed Jan. 5, 2010.
International Preliminary Report on Patentability (PCT/CA2009/000923), mailed Oct. 21, 2010.
Abdel-Majid et al., "Reductive Amination of Aldehydes and Ketones with Sodium Triacetoxyborohydride. Studies on Direct and Indirect Reductive Amination Procedures," *J. Org. Chem.* 61(11):3849-3862, 1996.
Hanson et al., "The Bromination and Nitration of Some (2H)-1,4-Benzoxazin-3(4H)-ones," *J. Chem. Res.* 2003(11):681, 2003.
Hartwig, "Evolution of a Fourth Generation Catalyst for the Amination and Thioetherification of Aryl Halides," *Acc. Chem. Res.* 41(11):1534-1544, 2008.
Huang and Buchwald, "New Ammonia Equivalents for the Pd-Catalyzed Amination of Aryl Halides," *Org. Lett.* 3(21):3417-3419, 2001.
Ram et al., "Synthesis and Biological Activity of Some New 1-Aryl-3-Benzoxazinyldihydro-Pyrimidinediones," *Indian J. Chem.* 29B:697-699, 1990.
Shridhar et al., "Synthesis & Hypoglycemic Activity of (3-Oxo-3,4-Dihydro-2H-1,4-Benzoxazin-6/7-yl)Biguanidine Hydrochlorides," *Indian J. Chem.* 24B:1293-1294, 1985.
Wolfe et al., "Simple, Efficient Catalyst System for the Palladium-Catalyzed Amination of Aryl Chlorides, Bromides, and Triflates," *J. Org. Chem.* 65(4):1158-1174, 2000.
International Search Report and Written Opinion for PCT/CA2009/000923 (mailed Sep. 8, 2009).

*Primary Examiner* — James O Wilson
*Assistant Examiner* — Brian McDowell
(74) *Attorney, Agent, or Firm* — Clark & Elbing LLP

(57) ABSTRACT

The present invention features benzothiazines that inhibit nitric oxide synthase (NOS), particularly those that selectively inhibit neuronal nitric oxide synthase (nNOS) in preference to other NOS isoforms, and that have the formula:

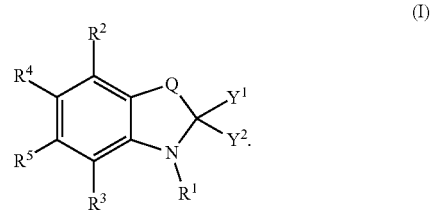

(I)

The NOS inhibitors of the invention, alone or in combination with other pharmaceutically active agents, can be used for treating or preventing various medical conditions.

25 Claims, 6 Drawing Sheets

BENZOXAZINES, BENZOTHIAZINES, AND RELATED COMPOUNDS HAVING NOS INHIBITORY ACTIVITY

CROSS-REFERENCE TO RELATED APPLICATIONS

This application claims benefit of U.S. Provisional Application No. 61/133,887, filed Jul. 3, 2008, which is hereby incorporated by reference.

BACKGROUND OF THE INVENTION

The present invention relates to the fields of benzoxazines, benzothiazines, and related compounds and to their medical use.

Nitric oxide (NO) has diverse roles both in normal and pathological processes, including the regulation of blood pressure, in neurotransmission, and in the macrophage defense systems (Snyder, S. H. and Bredt, D. S., *Scientific American*, May; 266(5) 1992: 68). NO is synthesized by three isoforms of nitric oxide synthase, a constitutive form in endothelial cells (eNOS), a constitutive form in neuronal cells (nNOS), and an inducible form found in macrophage cells (iNOS). These enzymes are homodimeric proteins that catalyze a five-electron oxidation of L-arginine, yielding NO and citrulline. The role of NO produced by each of the NOS isoforms is quite unique. Overstimulation or overproduction of individual NOS isoforms, especially nNOS and iNOS, plays a role in several disorders, including septic shock, arthritis (Boughton-Smith et al., *IDrugs* 1:321-334, 1998 and Cochrane et al., *Med. Res. Rev.* 16: 547-563, 1996), diabetes, ischemia-reperfusion injury, pain (Larson et al., *Pain* 86:103-111, 2000), and various neurodegenerative diseases (Kerwin et al., *J. Med. Chem.* 38:4343, 1995), while eNOS inhibition leads to unwanted effects such as enhanced white cell and platelet activation, hypertension, and increased atherogenesis (Valance et al., *Nature Rev. Drug Disc.* 1:939, 2002).

NOS inhibitors have the potential to be used as therapeutic agents in many disorders. However, the preservation of physiologically important nitric oxide synthase function suggests the desirability of the development of isoform-selective inhibitors that preferentially inhibit nNOS, or nNOS and iNOS, over eNOS. Specifically, selective NOS inhibitors, particularly for nNOS or iNOS, are candidates for use in the treatment of chronic pain states such as neuropathic pain, chronic tension type headache or transformed migraine wherein the pain state results from the persistence of peripheral and/or central sensitization.

SUMMARY OF THE INVENTION

The invention features a compound having the formula:

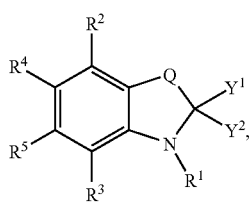

(I)

wherein,
Q is —O—(CHR$^6$)$_{1-3}$ or —S—(CHR$^6$)$_{1-3}$—;

R$^1$ and each R$^6$ is, independently, H, optionally substituted C$_{1-6}$ alkyl, optionally substituted C$_{1-4}$ alkaryl, optionally substituted C$_{1-4}$ alkheterocyclyl, optionally substituted C$_{2-9}$ heterocyclyl, optionally substituted C$_{3-8}$ cycloalkyl, optionally substituted C$_{1-4}$ alkcycloalkyl or —(CR$^{1A}$R$^{1B}$)$_n$NR$^{1C}$R$^{1D}$;

R$^{1A}$ and R$^{1B}$ are, independently, H, hydroxy, halo (e.g., fluoro), optionally substituted C$_{1-6}$ alkyl, optionally substituted C$_{1-6}$ alkoxy, optionally substituted C$_{1-4}$ alkcycloalkyl, optionally substituted C$_{1-4}$ alkaryl, optionally substituted C$_{1-4}$ alkheterocyclyl, optionally substituted C$_{1-4}$ alkheteroaryl, optionally substituted C$_{3-8}$ cycloalkyl, or optionally substituted C$_{2-9}$ heterocyclyl, or R$^{1A}$ and R$^{1B}$ combine to form =O;

R$^{1C}$ and R$^{1D}$ are, independently, H, hydroxy, optionally substituted C$_{1-6}$ alkyl, optionally substituted C$_{1-6}$ alkoxy, optionally substituted C$_{1-4}$ alkcycloalkyl, optionally substituted C$_{1-4}$ alkaryl, optionally substituted C$_{1-4}$ alkheterocyclyl, optionally substituted C$_{1-4}$ alkheteroaryl, optionally substituted C$_{3-8}$ cycloalkyl, optionally substituted C$_{2-9}$ heterocyclyl, or an N-protecting group, or R$^{1C}$ and R$^{1D}$ combine to form an optionally substituted C$_{2-9}$ heterocyclyl or an N-protecting group;

n is an integer between 1-6;

each of R$^2$ and R$^3$ is, independently, H, hal, optionally substituted C$_{1-6}$ alkyl, optionally substituted C$_{6-10}$ aryl, optionally substituted C$_{1-6}$ alkaryl, optionally substituted C$_{2-9}$ heterocyclyl, hydroxy, optionally substituted C$_{1-6}$ alkoxy, optionally substituted C$_{1-6}$ thioalkoxy, (CH$_2$)$_{r2}$NHC(NH)R$^{2A}$, or (CH$_2$)$_{r2}$NHC(S)NHR$^{2A}$, or optionally substituted C$_{1-4}$ alkheterocyclyl, wherein r2 is an integer from 0 to 2, R$^{2A}$ is optionally substituted C$_{1-6}$ alkyl, optionally substituted C$_{6-10}$ aryl, optionally substituted C$_{1-4}$ alkaryl, optionally substituted C$_{2-9}$ heterocyclyl, optionally substituted C$_{1-4}$ alkheterocyclyl, optionally substituted C$_{1-6}$ thioalkoxy, optionally substituted C$_{1-4}$ thioalkaryl, optionally substituted aryloyl, optionally substituted C$_{1-4}$ thioalkheterocyclyl, or optionally substituted amino;

each of R$^4$ and R$^5$ is independently H, hal, (CH$_2$)$_{r2}$NHC(NH)R$^{2A}$, or (CH$_2$)$_{r2}$NHC(S)NHR$^{2A}$;

wherein Y$^1$ and Y$^2$ are each H, or Y$^1$ and Y$^2$ together are =O, or Y$^1$ and Y$^2$ are independently H, optionally substituted C$_{1-6}$ alkyl, optionally substituted C$_{6-10}$ aryl, optionally substituted C$_{1-6}$ alkaryl, optionally substituted C$_{2-9}$ heterocyclyl, hydroxy, optionally substituted C$_{1-6}$ alkoxy, optionally substituted C$_{1-6}$ thioalkoxy, or optionally substituted C$_{1-4}$ alkheterocyclyl;

wherein one and only one of R$^2$, R$^3$, R$^4$, and R$^5$ is (CH$_2$)$_{r2}$NHC(NH)R$^{2A}$ or (CH$_2$)$_{r2}$NHC(S)NHR$^{2A}$;

or a pharmaceutically acceptable salt or prodrug thereof.

In some embodiments, one of R$^1$ and R$^6$ is not H.

In some embodiments, R$^6$ is H.

In some embodiments, R$^{1C}$ and R$^{1D}$ are, independently, H, optionally substituted C$_{1-6}$ alkyl, optionally substituted C$_{1-6}$ alkoxy, optionally substituted C$_{1-4}$ alkcycloalkyl, optionally substituted C$_{1-4}$ alkaryl, optionally substituted C$_{1-4}$ alkheterocyclyl, optionally substituted C$_{1-4}$ alkheteroaryl, optionally substituted C$_{3-8}$ cycloalkyl, optionally substituted C$_{2-9}$ heterocyclyl, or an N-protecting group, or R$^{1C}$ and R$^{1D}$ combine to form an optionally substituted C$_{2-9}$ heterocyclyl or an N-protecting group In some embodiments, Y$^1$ and Y$^2$ are each H, or Y$^1$ and Y$^2$ together are =O, or Y$^1$ and Y$^2$ are independently H, optionally substituted C$_{1-6}$ alkyl, optionally substituted C$_{6-10}$ aryl, optionally substituted C$_{1-6}$ alkaryl, optionally substituted $C_{2-9}$ heterocyclyl, optionally substituted $C_{1-6}$ alkoxy, optionally substituted $C_{1-6}$ thioalkoxy, or optionally substituted $C_{1-4}$ alkheterocyclyl.

In some embodiments, $R^2$, $R^3$, $R^4$, or $R^5$ may have the formula:

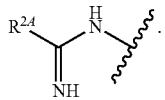

(II)

In further embodiments, $R^{2A}$ has the formula:

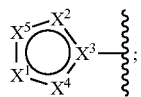

(III)

wherein each of $X^1$, $X^2$, $X^4$, and $X^5$ is independently selected from O, S, $NR^7$, N, or $CR^8$; $X^3$ is selected from N or C;

$R^7$ is H, optionally substituted $C_{1-6}$ alkyl, or an N-protecting group;

$R^8$ is H, hal, optionally substituted $C_{1-6}$ alkyl, hydroxy, optionally substituted $C_{1-6}$ alkoxy, or optionally substituted $C_{1-6}$ thioalkoxy, wherein at least one of $X^1$, $X^2$, $X^4$, and $X^5$ is not $CR^8$. In particular, $R^{2A}$ may have the formula:

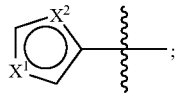

(III-A)

wherein each of $X^1$ and $X^2$ is independently selected from O, S, NH, N, or CH; and wherein at least one of $X^1$ and $X^2$ is not CH. In certain other embodiments, $X^1$ is CH, and $X^2$ is S. In still other embodiments, $X^1$ is CH, and $X^2$ is O.

In some embodiments, the compound has a structure selected from:

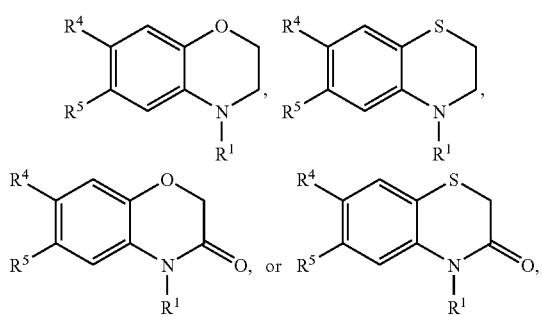

wherein one of $R^4$ and $R^5$ has the following structure:

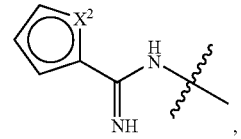

and wherein $X^2$ is O or S.

In some embodiments, Q is O—$(CHR^6)_{1-2}$ or S—$(CHR^6)_{1-2}$; and $R^1$ and each $R^6$ are, independently, H, optionally substituted $C_{1-6}$ alkyl, optionally substituted $C_{1-4}$ alkaryl, optionally substituted $C_{1-4}$ alkheterocyclyl, or optionally substituted $C_{2-9}$ heterocyclyl.

In other embodiments, $Y^1$ and $Y^2$ are each H, and Q is O—$CHR^6$, O—$(CHR^6)_2$, or O—$(CHR^6)_3$; or $Y^1$ and $Y^2$ together are =O, and Q is O—$CHR^6$, O—$(CHR^6)_2$, or O—$(CHR^6)_3$.

In other embodiments, $Y^1$ and $Y^2$ are each H, and Q is S—$CHR^6$, S—$(CHR^6)_2$, or S—$(CHR^6)_3$; or $Y^1$ and $Y^2$ together are =O, and Q is S—$CHR^6$, S—$(CHR^6)_2$, or S—$(CHR^6)_3$.

In some embodiments, $R^1$ is optionally substituted $C_{1-6}$ alkyl, optionally substituted $C_{2-9}$ heterocyclyl, optionally substituted $C_{1-4}$ alkheterocyclyl, optionally substituted $C_3$-$C_8$ cycloalkyl, or —$(CR^{1A}R^{1B})_n NR^{1C}R^{1D}$. In other embodiments, $R^1$ is amino$C_{1-6}$alkyl. In still other embodiments, $R^1$ is optionally substituted $C_{1-4}$ alkheterocyclyl, where the heterocyclyl is a 5- or 6-membered cyclic amine. In specific embodiments, a 5-membered cyclic amine is substituted with a carboxylic acid, ester (e.g., a $C_{1-6}$ ester), or amide. In some embodiments, $R^1$ is optionally substituted $C_{2-9}$ heterocyclyl. In other embodiments, the heterocyclyl is optionally substituted pyrrolidinyl or optionally substituted piperidinyl, e.g.,

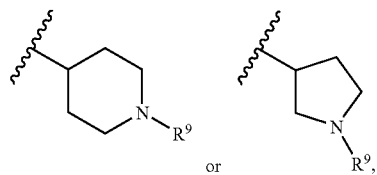

where $R^9$ is H, optionally substituted $C_{1-6}$ alkyl or an N-protecting group. In specific embodiments $R^9$ is H. In other embodiments, $R^1$ is —$(CR^{1A}R^{1B})_n NR^{1C}R^{1D}$. In certain embodiments, $R^{1A}$ and $R^{1B}$ are each H. In further embodiments, n is 2 or 3. In other embodiments, $NR^{1C}$ is H, and $NR^{1D}$ is —$CH_3$, —$CH_2CH_3$, —$(CH_2)_2OH$, or —$CH_2CO_2H$. In still other embodiments, $R^1$ is —$CH_2CH_2N(CH_3)_2$. In other embodiments, $R^1$ is —$CH_2CH_2NHCH_3$.

In certain embodiments, $R^1$ is an optionally substituted $C_3$-$C_8$ cycloalkyl. In certain embodiments, the $C_3$-$C_8$ cycloalkyl is substituted by an optionally substituted amino In other embodiments, one of $R^4$ or $R^5$ is H or F.

Specific preferred compounds of formula (I) include:
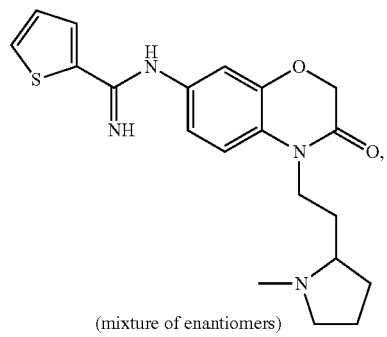
(mixture of enantiomers)
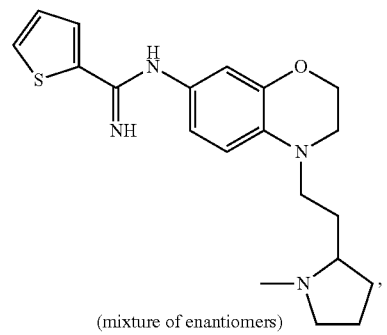
(mixture of enantiomers)
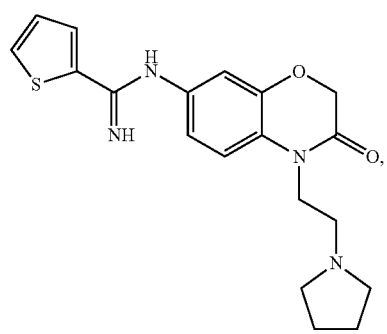
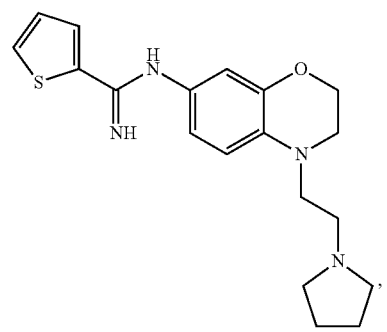
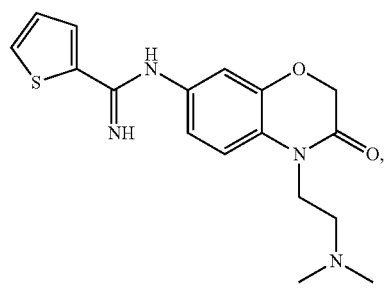
-continued
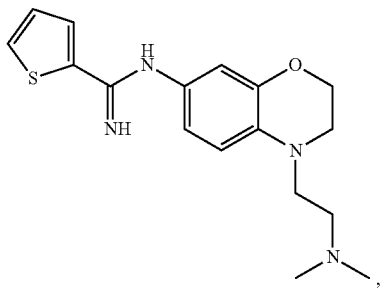
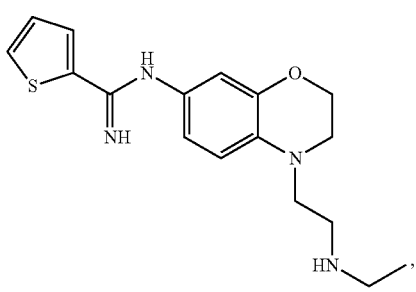
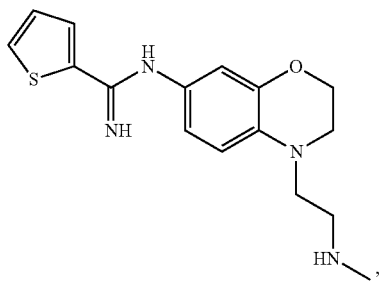
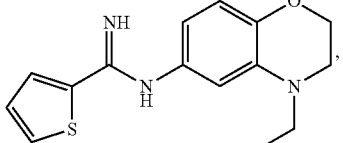
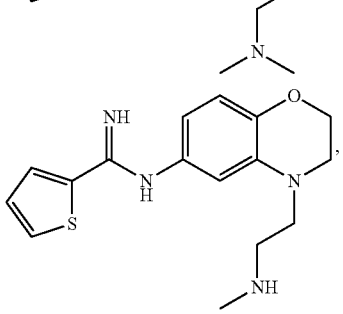
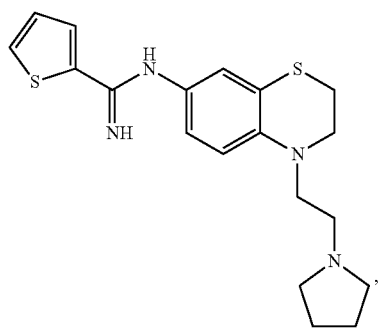

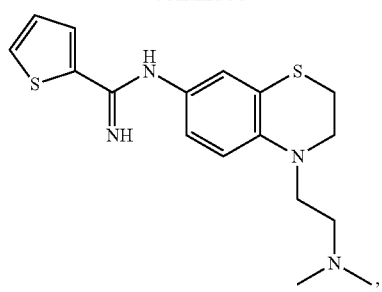
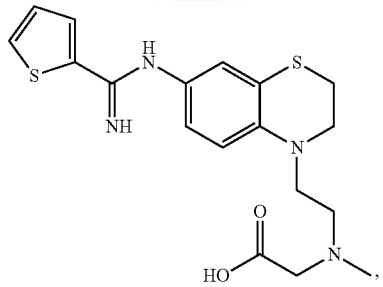
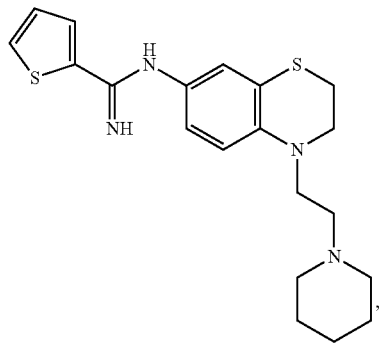
(mixture of enantiomers)
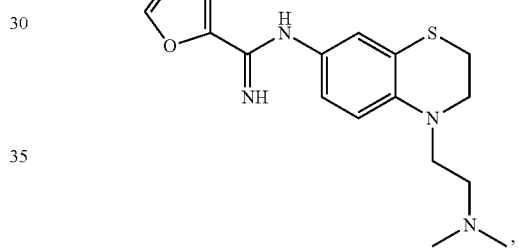
(-)-S-isomer
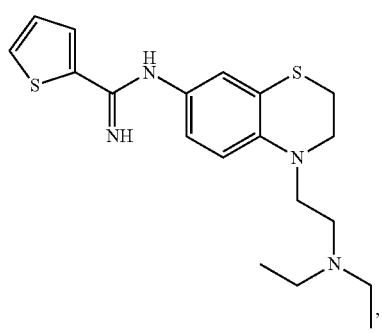
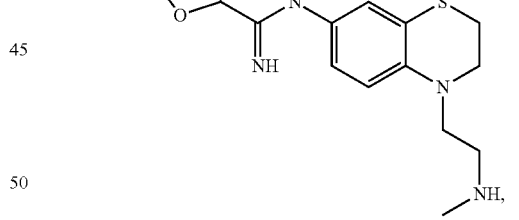
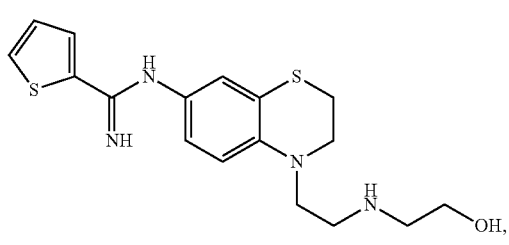

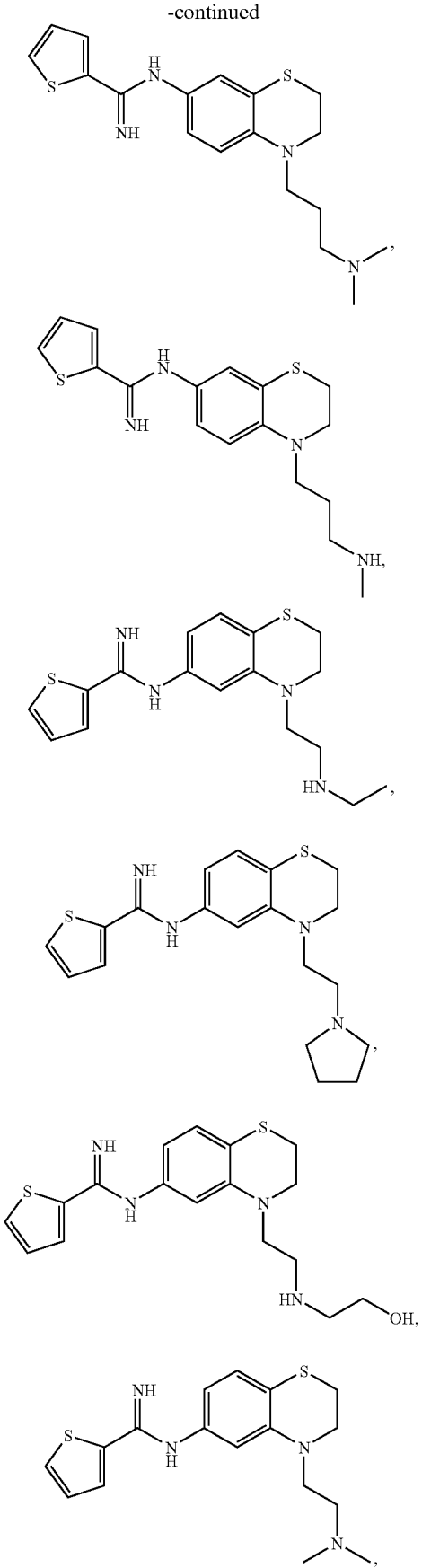
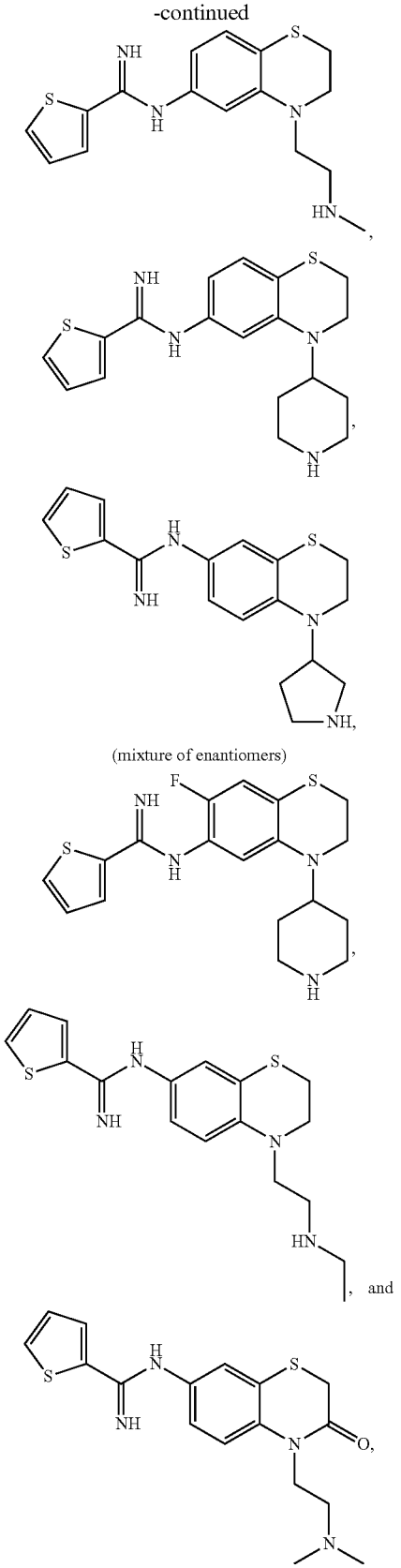
or a pharmaceutically acceptable salt thereof, e.g., the dihydrochloride salt.

The invention also features a pharmaceutical composition comprising a compound of formula (I), or a pharmaceutically acceptable salt or prodrug thereof, and a pharmaceutically acceptable excipient.

Preferably, a compound of the invention selectively inhibits neuronal nitric oxide synthase (nNOS), particularly over endothelial nitric oxide synthase (eNOS) or inducible nitric oxide synthase (iNOS) or both.

Preferably, the $IC_{50}$ or $K_i$ value observed for the compound is at least 2 times lower for nNOS than for eNOS and/or iNOS. More preferably, the $IC_{50}$ or $K_i$ value is at least 5, 20, 50, or 100 times lower (i.e., more potent in nNOS). In one embodiment, the $IC_{50}$ or $K_i$ value is between 2 times and 100 times lower. In another embodiment, the $IC_{50}$ or $K_i$ in eNOS is greater than 10 µM. More preferably eNOS $IC_{50}$ is greater than 20 µM, most preferably eNOS $IC_{50}$ or Ki is greater than 30 µM, as a threshold level of eNOS may be needed to avoid any direct eNOS mediated constriction of human vascular tissue.

In another embodiment of the invention, the $IC_{50}$ or $K_i$ of iNOS and nNOS is between 2 and greater than 100 times lower than eNOS. Most preferably, the $IC_{50}$ or $K_i$ of nNOS or iNOS is at least 20, 50, or 100 fold lower. In another embodiment, compounds of the invention are selective nNOS inhibitors.

The invention further features a method of treating or preventing a condition in a mammal, such as a human, caused by the action of nitric oxide synthase (NOS), e.g., nNOS, that includes administering an effective amount of a compound of the invention to the mammal. Examples of such conditions include: headache (e.g., migraine headache (with or without aura), chronic tension type headache (CTTH), migraine with allodynia, medication overuse headache, cluster headache, chronic headache, or transformed migraine); neuropathic pain (AIDS associated painful neuropathy, central post-stroke pain (CPSP), diabetic neuropathy, chemotherapy induced neuropathic pain (e.g., paclitaxel, cis-Platin, Doxorubicin etc.), postherpetic neuralgia, or trigeminal neuralgia), chronic inflammatory pain (e.g., pain that results from osteoarthritis, rheumatoid arthritis, ankylosing spondylitis, psoriatic arthritis, undifferentiated spondyloarthropathy, or reactive arthritis); visceral pain; neuroinflammation; medication-induced hyperalgesia and/or allodynia (e.g., opioid-induced hyperalgesia/allodynia or triptan ($5-HT_{1D/1B}$ agonists)-induced hyperalgesia or allodynia); acute pain (optionally in combination with an opioid treatment); chronic pain; bone cancer pain; chemical dependencies or addictions (e.g., drug addiction; cocaine addiction; nicotine addiction; metamphetamine-induced neurotoxicity; ethanol tolerance, dependence, or withdrawal; or morphine/opioid induced tolerance, dependence, hyperalgesia, or withdrawal); CNS disorders (e.g., epilepsy, anxiety, depression (alone or in combination), attention deficit hyperactivity disorder (ADHD), psychosis, or dementia); neurodegenerative diseases or nerve injury (e.g., acute spinal cord injury, AIDS associated dementia, Parkinson's disease, Alzheimer's disease, amyotrophic lateral sclerosis (ALS), Huntington's disease, multiple sclerosis, neurotoxicity, or head trauma); cardiovascular related conditions (e.g., stroke, coronary artery bypass graft (CABG) associated neurological damage, hypothermic cardiac arrest (HCA), post-stroke pain, cardiogenic shock, reperfusion injury, or vascular dementia); or gastrointestinal disorders (e.g., ileostomy-associated diarrhea or dumping syndrome).

In other embodiments, a compound of the invention can be used for the treatment of chronic pain with central sensitization. In other embodiments, the pain with components of central sensitization is neuropathic pain. In other embodiments, the neuropathic pain is selected from postherpetic neuralgia, diabetic neuropathy, central (thalamic) pain, post-stroke pain, HIV-associated pain, phantom limb pain, neuropathic pain resulting from post-surgical trauma or nerve injury, and chemotherapy-induced neuropathies.

In other embodiments, a compound of the invention can be used for the treatment of chronic inflammatory pain. In other embodiments, the chronic inflammatory pain relates to ankylosing spondylitis, reactive arthritis (Reiter's syndrome), psoriatic arthritis, undifferentiated spondyloarthropathy, rheumatoid arthritis, and osteoarthritis.

In other embodiments, a compound of the invention can be used for the treatment of headaches with underlying mechanisms of central sensitization. In other embodiments, headache is selected from migraine, chronic tension type headache (CTTH), cluster headache, transformed migraine, and medication overuse headache.

Still other embodiments include use of a compound of the invention for treatment of interstitial cystitis or opiate withdrawal or migraine prophylaxis.

A compound of the invention can also be used in combination with one or more other therapeutic agents for the prevention or treatment of one of the aforementioned conditions.

Exemplary agents useful in combination with a compound of the invention, include opioids, antidepressants, antiepileptics, non-steroidal anti-inflammatory drugs (NSAIDs), anti-arrhythmics, GABA-B antagonists, alpha-2-adrenergic receptor agonists, serotonin $5HT_{1B/1D}$ agonists, N-methyl-D-aspartate antagonists, cholecystokinin B antagonists, substance P antagonists (NK1), anti-inflammatory compounds, DHP-sensitive L-type calcium channel antagonists, omega-conotoxin-sensitive N-type calcium channel antagonists, P/Q-type calcium channel antagonists, adenosine kinase antagonists, adenosine receptor $A_1$ agonists, adenosine receptor $A_{2a}$ antagonists, adenosine receptor $A_3$ agonists, adenosine deaminase inhibitors, adenosine nucleoside transport inhibitors, vanilloid VR1 receptor agonists, cannabinoid CB1/CB2 agonists, AMPA receptor antagonists, kainate receptor antagonists, sodium channel blockers (e.g., Nav1.8 blocker for neuropathic pain), nicotinic acetylcholine receptor agonists, a $K_{ATP}$ potassium channel, $K_{v1.4}$ potassium channel, $Ca^{2+}$-activated potassium channel, SK potassium channel, BK potassium channel, IK potassium channel, or KCNQ2/3 potassium channel opening agents, muscarinic M3 antagonists, muscarinic M1 agonists, muscarinic M2/M3 partial agonists/antagonists, and antioxidants. Specific examples of therapeutic agents that are useful in combination with a compound of the invention are listed in Table 1. Other classes include CB1/CB2 agonists, e.g., dexanabinol (HU-211), fatty acid amide hydrolase inhibitors, P2X purinergic blockers, and NGF antagonists.

TABLE 1

Therapeutic agents useful in combination with compounds of the invention

| Class | Examples |
|---|---|
| Opioid | alfentanil, butorphanol, buprenorphine, codeine, dextromoramide, dextropropoxyphene, dezocine, dihydrocodeine, diphenoxylate, etorphine, fentanyl, hydrocodone, hydromorphone, ketobemidone, levorphanol, levomethadone, methadone, meptazinol, morphine, morphine-6-glucuronide, nalbuphine, naloxone, oxycodone, oxymorphone, pentazocine, pethidine, piritramide, remifentanil, sulfentanyl, tilidine, or tramadol |
| Antidepressant (selective serotonin reuptake inhibitor) | alaproclate, citalopram, chlomipramine, escitalopram, femoxetine, fluoxetine, fluvoxamine, paroxetine, sertraline, or zimelidine |
| Antidepressant (norepinephrine-reuptake inhibitor) | adinazolam, amitriptylinoxide, amineptine, amoxapine, atomoxetine, bupropion, butriptyline, desipramine, doxepin, desipramine, maprotiline, nortriptyline (desmethylamitriptyline), demexiptiline, dothiepin, fluacizine, imipramine, imipramine oxide, iprindole, lofepramine, maprotiline, melitracen, metapramine, norclolipramine, noxiptilin, opipramol, perlapine, pizotyline, propizepine, quinupramine, reboxetine, or tianeptine, tomoxetine, trimipramine or viloxazine |
| Antidepressant (dual serotonin/norepinephrine reuptake inhibitor) | duloxetine, milnacipran, mirtazapine, nefazodone, venlafaxine, or desvenlafaxine |
| Antidepressant (monoamine oxidase inhibitor) | amiflamine, iproniazid, isocarboxazid, M-3-PPC (Draxis), moclobemide, pargyline, phenelzine, tranylcypromine, or vanoxerine |
| Antidepressant (reversible monoamine oxidase type A inhibitor) | bazinaprine, befloxatone, brofaromine, cimoxatone, or clorgyline |
| Antidepressant (tricyclic) | amitriptyline, amoxapine, buriptyline, clomipramine, desipramine, dibenzepin, dothiepin, doxepin, imipramine, iprindole,, lofepramine, melitracen, opipramol, nortryptyline, protriptyline, or trimipramine |
| Antidepressant (other) | adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, lithium, litoxetine; lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, trazodone, tofenacin, tofisopam, toloxatone, tomoxetine, veralipride, viloxazine, viqualine, zimelidine, or zometapine |
| Antiepileptic | carbamazepine, flupirtine, gabapentin, lamotrigine, oxcarbazepine, phenytoin, pregabalin, retigabine, topiramate, or valproate |
| Non-steroidal anti-inflammatory drug (NSAID) | acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one). |
| 5HT$_{1B/1D}$ agonist | eletriptan, frovatriptan, naratriptan, rizatriptan, sumatriptan, almotriptan, donitriptan, or zolmitriptan |
| Anti-inflammatory compounds | aspirin, celecoxib, cortisone, deracoxib, diflunisal, etoricoxib, fenoprofen, ibuprofen, ketoprofen, naproxen, prednisolone, sulindac, tolmetin, piroxicam, mefenamic acid, meloxicam, phenylbutazone, rofecoxib, suprofen, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3- |

TABLE 1-continued

Therapeutic agents useful in combination with compounds of the invention

| Class | Examples |
|---|---|
| | hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one |
| N-methyl-D-aspartate antagonist and other glutamate receptor antagonists (e.g., AMPA/kainite (GluR5), MGluR, and iGluR) (Medicinal Research Reviews, 2007; 27(2): 239-278 and Basic & Clinical. Pharmacol. Toxicol. 2005, 97: 202-213) | amantadine; aptiganel; besonprodil; budipine; conantokin G; delucemine; dexanabinol; dextromethorphan; dextropropoxyphen; felbamate; fluorofelbamate; gacyclidine; glycine; ipenoxazone; kaitocephalin; ketamine; ketobemidone; lanicemine; licostinel; midafotel; memantine; D-methadone; D-morphine; milnacipran; neramexane; orphenadrine; remacemide; sulfazocine; FPL-12,495 (racemide metabolite); topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino [4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; efenprodil, CP101606, Ro256981, or 3,6,7-tetrahydro-2,3-dioxo-N-phenyl-1H,5H-pyrido[1,2,3-de]quinoxaline-5-acetamide |

Other compounds useful for treating pain are described in WO/2003/034900 and in U.S. Patent Publication No. 20030082225, each of which is hereby incorporated by reference.

NMDA antagonists in combination with nNOS inhibitors may be particularly useful in treating conditions such as inflammatory and neuropathic pain, traumatic brain injury, and Parkinson's Disease (see *Drug Discovery Today* 7(7): 403-406, 2002).

Compounds of the invention may also be employed in combination with FAAH inhibitors, such as those described in: *J. Med. Chem.* 49:4650-4656, 2006; *Neuropharmacology* 50:814-823, 2006; *Current Opinion in Chemical Biology* 7:469-475, 2003; and *Pain* 109:319-327, 2004, each of which is incorporated by reference.

Asymmetric or chiral centers may exist in any of the compounds of the present invention. The present invention contemplates the various stereoisomers and mixtures thereof. Individual stereoisomers of compounds of the present invention are prepared synthetically from commercially available starting materials that contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Alternatively, chiral compounds can be prepared by an asymmetric synthesis that favors the preparation of one enantiomer over the other. Alternatively a chiral pool synthesis (starting with an enantiomerically pure building block) can be used wherein the chiral group or center is retained in the intermediate or final product. Enantiomers are designated herein by the symbols "R," or "S," depending on the configuration of substituents around the chiral atom. Alternatively, enantiomers are designated as (+) or (−) depending on whether a solution of the enantiomer rotates the plane of polarized light clockwise or counterclockwise, respectively. In other cases, diastereomeric isomers such as cis and trans isomers may be separated by column chromatography, chiral chromatography, or recrystallization. In some cases, derivatization can improve the separation of these mixtures.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration. It is also recognized that for structures in which tautomeric forms are possible, the description of one tautomeric form is equivalent to the description of both, unless otherwise specified. For example, amidine structures of the formula —C(=NR$^Q$)NHR$^T$ and —C(NHR$^Q$)=NR$^T$, where R$^T$ and R$^Q$ are different, are equivalent tautomeric structures and the description of one inherently includes the other.

It is understood that substituents and substitution patterns on the compounds of the invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Other features and advantages will be apparent from the following description and the claims.

Definitions

The term "acyl," or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups include from 2 to 7 carbons.

The term "C$_{x-y}$ alkaryl," as used herein, represents a chemical substituent of formula —RR', where R is an alkylene group of x to y carbons and R' is an aryl group as defined herein. Similarly, by the term "C$_{x-y}$ alkheteroaryl" is meant a chemical substituent of formula —RR", where R is an alkylene group of x to y carbons and R" is a heteroaryl group as defined herein. Other groups preceded by the prefix "alk-" are defined in the same manner. Exemplary unsubstituted alkaryl groups are of from 7 to 16 carbons.

The term "alkcycloalkyl" represents a cycloalkyl group attached to the parent molecular group through an alkylene group.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkheterocyclyl" represents a heterocyclic group attached to the parent molecular group through an alkylene group. Exemplary unsubstituted alkheterocyclyl groups are of from 2 to 14 carbons.

The term "alkoxy" represents a chemical substituent of formula —OR, where R is an alkyl group of 1 to 6 carbons, unless otherwise specified.

The term "alkoxyalkyl" represents an alkyl group which is substituted with an alkoxy group. Exemplary unsubstituted alkoxyalkyl groups include between 2 to 12 carbons.

The terms "alkyl" and the prefix "alk-," as used herein, are inclusive of both straight chain and branched chain saturated groups of from 1 to 6 carbons, unless otherwise specified. Alkyl groups are exemplified by methyl, ethyl, n- and isopropyl, n-, sec-, iso- and tert-butyl, neopentyl, and the like, and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight carbon atoms; (11) hal; (12) heterocyclyl; (13) (heterocycle)oxy; (14) (heterocycle)oyl; (15) hydroxy; (16) N-protected amino; (17) nitro; (18) oxo; (19) spirocyclyl of three to eight carbon atoms; (20) thioalkoxy of one to six carbon atoms; (21) thiol; (22) —CO$_2$R$^A$, where R$^A$ is selected from the group consisting of (a) alkyl, (b) aryl, (c) alkaryl, and (d) hydrogen, where the alkylene group is of one to six carbon atoms; (23) —C(O)NR$^B$R$^C$, where each of R$^B$ and R$^C$ is, independently, selected from the group consisting of (a) hydrogen, (b) alkyl, (c) aryl and (d) alkaryl, where the alkylene group is of one to six carbon atoms; (24) —SO$_2$R$^D$, where R$^D$ is selected from the group consisting of (a) alkyl, (b) aryl and (c) alkaryl, where the alkylene group is of one to six carbon atoms; (25) —SO$_2$NR$^E$R$^F$, where each of R$^E$ and R$^F$ is, independently, selected from the group consisting of (a) hydrogen, (b) alkyl, (c) aryl and (d) alkaryl, where the alkylene group is of one to six carbon atoms; and (26) —NR$^G$R$^H$, where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfonyl," as used herein, represents an alkyl group attached to the parent molecular group through an —SO$_2$— group. Exemplary unsubstituted alkylsulfonyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonylalkyl," as used herein, represents an alkyl group, as defined herein, substituted by an alkylsulfonyl group. Exemplary unsubstituted alkylsulfonylalkyl groups are of from 2 to 12 carbons.

The term "alkynyl," as used herein, represents monovalent straight or branched chain groups of from two to six carbon atoms containing a carbon-carbon triple bond and is exemplified by ethynyl, 1-propynyl, and the like.

The term "amidine," as used herein, represents a —C(=NH)NH$_2$ group.

The term "amino," as used herein, represents —NH$_2$, —NHR$^{N1}$, or —N(R$^{N1}$)$_2$, wherein each R$^{N1}$ is, independently, H, OH, NO$_2$, NH$_2$, NR$^{N2}$$_2$, SO$_2$OR$^{N2}$, SO$_2$R$^{N2}$, SOR$^{N2}$, optionally substituted C$_{1-6}$ alkyl, optionally substituted C$_{1-6}$ alkoxy, optionally substituted C$_{1-4}$ alkcycloalkyl, optionally substituted C$_{1-4}$ alkaryl, optionally substituted C$_{1-4}$ alkheterocyclyl, optionally substituted C$_{1-4}$ alkheteroaryl, optionally substituted C$_{3-8}$ cycloalkyl, optionally substituted C$_{2-9}$ heterocyclyl, or an N-protecting group, or two R$^{N1}$ combine to form an optionally substituted C$_{2-9}$ heterocyclyl, or an N-protecting group, and wherein each R$^{N2}$ is, independently, H, an optionally substituted alkyl group, or an optionally substituted aryl group. In a preferred embodiment, amino is —NH2, or —NHR$^{N1}$, wherein each R$^{N1}$ is, independently, OH, NO$_2$, NH$_2$, NR$^{N2}_2$, SO$_2$OR$^{N2}$, SO$_2$R$^{N2}$, SOR$^{N2}$, an optionally substituted alkyl group, or an optionally substituted aryl group, and each R$^{N2}$ can be H, an optionally substituted alkyl group, or an optionally substituted aryl group.

The term "aminoalkyl," as used herein, represents an alkyl group, as defined herein, substituted by an amino group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) hal; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, (c) alkaryl, and (d) hydrogen, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The term "arylalkoxy," as used herein, represents an alkaryl group attached to the parent molecular group through an oxygen atom. Exemplary unsubstituted arylalkoxy groups are of from 7 to 16 carbons.

The term "aryloxy" represents a chemical substituent of formula —OR', where R' is an aryl group of 6 to 18 carbons, unless otherwise specified.

The term "aryloyl," as used herein, represent an aryl group that is attached to the parent molecular group through a carbonyl group. Exemplary unsubstituted aryloyl groups are of 7 or 11 carbons.

The term "azido" represents an N$_3$ group.

The term "azidoalkyl" represents an azido group attached to the parent molecular group through an alkyl group.

The term "carbonyl," as used herein, represents a C(O) group, which can also be represented as C=O.

The term "carboxaldehyde" represents a CHO group.

The term "carboxaldehydealkyl" represents a carboxaldehyde group attached to the parent molecular group through an alkylene group.

The term "chronic tension type headache" (CTTH), as used herein, means a tension type headache that meets the diagnostic criteria defined by the International Headache Society Classification, 2$^{nd}$ Edition (ICHD-2), e.g., a headache that occurs at least 15 days per month on average for a period of >3 months (at least 180 days per year).

The term "chronic migraine," which is also called "transformed migraine," as used herein, refers to the definition provided in the ICHD-2, and is "migraine headache occurring on 15 or more days per month for more than 3 months in the absence of medication overuse." Clinical guidelines for the diagnosis of chronic migraine can be found, for example, in the ICHD-2 and in Oleson et al., *Cephalalgia,* 26(6):742-746, 2006.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) hal; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms;

(34) thioalkoxyalkyl, where the alkyl and alkylene groups are independently of one to six carbon atoms; (35) —$(CH_2)_q CO_2R^A$ where q is an integer of from zero to four, and $R^A$ is selected from the group consisting of (a) alkyl, (b) aryl, (c) alkaryl, and (d) hydrogen, where the alkylene group is of one to six carbon atoms; (36) —$(CH_2)_q CONR^BR^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) —$(CH_2)_q SO_2R^D$, where q is an integer of from zero to four and where $R^D$ is selected from the group consisting of (a) alkyl, (b) aryl, and (c) alkaryl, where the alkylene group is of one to six carbon atoms; (38) —$(CH_2)_q SO_2NR^ER^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_q NR^GR^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "cycloalkyloxy" or "cycloalkoxy", as used interchangeably herein, represent a cycloalkyl group, as defined herein, attached to the parent molecular group through an oxygen atom. Exemplary unsubstituted cycloalkyloxy groups are of from 3 to 8 carbons.

The term an "effective amount" of a compound, as used herein, is that amount sufficient to effect beneficial or desired results, such as clinical results, and, as such, an "effective amount" depends upon the context in which it is being applied. For example, in the context of administering an agent that is an inhibitor of NOS, an effective amount of an agent is, for example, an amount sufficient to achieve a reduction in NOS activity as compared to the response obtained without administration of the agent.

The terms "halogen" or "hal," as used herein, represent bromine, chlorine, iodine, or fluorine.

The term "heteroaryl," as used herein, represents that subset of heterocycles, as defined herein, which are aromatic: i.e., they contain 4n+2 pi electrons within the mono- or multicyclic ring system.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocycle" includes bicyclic, tricyclic and tetracyclic groups in which any of the above heterocyclic rings is fused to one, two, or three rings, e.g., an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Examples of fused heterocycles include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include groups of the formula

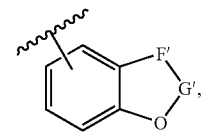

where

F' is selected from the group consisting of —$CH_2$—, —$CH_2O$— and —O—, and G' is selected from the group consisting of —C(O)— and —$(C(R')(R''))_v$—, where each of R' and R" is, independently, selected from the group consisting of hydrogen or alkyl of one to four carbon atoms, and v is one to three and includes groups, such as 1,3-benzodioxolyl, 1,4-benzodioxanyl, and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —$(CH_2)_q CO_2R^A$, where q is an integer of from zero to four, and $R^A$ is selected from the group consisting of (a) alkyl, (b) aryl, (c) alkaryl, and (d) hydrogen where the alkylene group is of one to six carbon atoms; (36) —$(CH_2)_q CONR^BR^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) —$(CH_2)_qSO_2R^D$, where q is an integer of from zero to four and where $R^D$ is selected from the group consisting of (a) alkyl, (b) aryl, and (c) alkaryl, where the alkylene group is of one to six carbon atoms; (38) —$(CH_2)_qSO_2NR^ER^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_qNR^GR^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The term "(heterocycle)oxy," as used herein, represent a heterocycle group, as defined herein, attached to the parent molecular group through an oxygen atom.

The term "(heterocycle)oyl," as used herein, represent a heterocycle group, as defined herein, attached to the parent molecular group through a carbonyl group.

The term "hydroxy," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl, and the like.

The term "N-protected amino," as used herein, refers to an amino group, as defined herein, to which is attached an N-protecting group, as defined herein.

The term "N-protecting group," as used herein, represents those groups intended to protect an amino group against undesirable reactions during synthetic procedures. Commonly used N-protecting groups are disclosed in Greene, *Protective Groups in Organic Synthesis*, 3$^{rd}$ Edition (John Wiley & Sons, New York, 1999), which is incorporated herein by reference. N-protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical.

The term "pharmaceutical composition," as used herein, represents a composition containing a compound described herein (e.g., any of Compounds (1)-(33) and compounds of Formula (I)), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66: 1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The terms "pharmaceutically acceptable solvate" or "solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "Ph" as used herein means phenyl.

The term "prevent," as used herein, refers to prophylactic treatment or treatment that prevents one or more symptoms or conditions of a disease, disorder, or conditions described herein (e.g., acute pain, chronic pain, inflammatory pain, neuropathic pain, severe pain, cancer pain, migraine (with or without aura or allodynia), or chronic tension type headache). Preventative treatment can be initiated, for example, prior to ("pre-exposure prophylaxis") or following ("post-exposure prophylaxis") an event that precedes the onset of the disease, disorder, or conditions (e.g., exposure to a migraine trigger, to another cause of pain, or to a pathogen). Preventive treatment that includes administration of a compound of the invention, or a pharmaceutical composition thereof, can be acute, short-term, or chronic. The doses administered may be varied during the course of preventative treatment. See also: Kaniecki et al., "Treatment of Primary Headache: Preventive Treatment of Migraine." In: *Standards of Care for Headache Diagnosis and Treatment*. Chicago (IL): National Headache Foundation; 2004. p. 40-52.

The term "prodrug," as used herein, represents compounds which are rapidly transformed in vivo to the parent compound of the above formula (e.g., compounds of Formula (I) and compounds (1)-(33)), for example, by hydrolysis in blood. Prodrugs of the compounds of the invention may be conventional esters. Some common esters which have been utilized as prodrugs are phenyl esters, aliphatic ($C_7$-$C_8$ or $C_8$-$C_{24}$) esters, cholesterol esters, acyloxymethyl esters, carbamates, and amino acid esters. For example, a compound of the invention that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351-4367, 1996, each of which is incorporated herein by reference. Preferably, prodrugs of the compounds of the present invention are pharmaceutically acceptable.

Each of the terms "selectively inhibits nNOS" or "a selective nNOS inhibitor" refers to a substance that inhibits or binds the nNOS isoform more effectively than the eNOS and/or iNOS isoform as measured by an in vitro assay, such as, for example, those assays described herein. Selective inhibition can be expressed in terms of an $IC_{50}$ value, a $K_i$ value, or the inverse of a percent inhibition value which is lower, or conversely a higher % inhibition when the substance is tested in an nNOS assay than when tested in an eNOS and/or iNOS assay. Preferably, the $IC_{50}$ or $K_i$ value is 2 times lower. More preferably, the $IC_{50}$ or $K_i$ value is 5, 10, 50, or even more than 100 times lower.

The term "spirocycle," as used herein, represents an alkylene diradical, both ends of which are bonded to the same carbon atom of the parent group to form a spirocyclic group and also heteroalkylene diradical, both ends of which are bonded to the same atom.

The term "sulfonyl," as used herein, represents an —S(O)$_2$— group.

The term "thioalkaryl," as used herein, represents a thioalkoxy group substituted with an aryl group The term "thioalkheterocyclyl," as used herein, represents a thioalkoxy group substituted with a heterocyclyl group.

The term "thioalkoxy," as used herein, represents an alkyl group attached to the parent molecular group through a sulfur atom. Exemplary unsubstituted thioalkoxy groups are of from 1 to 6 carbons.

The term "thiol" represents an —SH group.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Other features and advantages of the invention will be apparent from the following detailed description, the drawings, and the claims.

DETAILED DESCRIPTION

Figure 1:
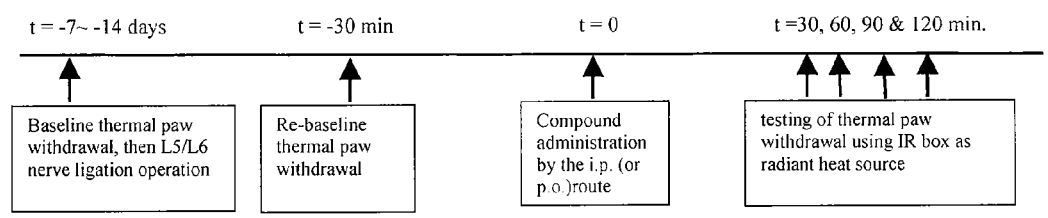
FIG. 1 shows the protocol for testing thermal hyperalgesia in the Chung neuropathic pain model. The L5/L6 spinal nerve was surgically ligated and animals allowed to recover for a period of 7-10 days. During this period animals develop neuropathic pain. The reduction of paw withdrawal latency after an infrared thermal stimulus (post-SNL) was measured following the induction period for comparison with pre-surgery baseline levels (BL). Following drug administration, thermal hyperalgesia was measured at various time points.

The invention features novel benzoxazines, benzothiazines, and related compounds having nitric oxide synthase (NOS) inhibitory activity, pharmaceutical and diagnostic compositions containing them, and their medical use. Exemplary compounds of the invention are shown in Table 2.

TABLE 2

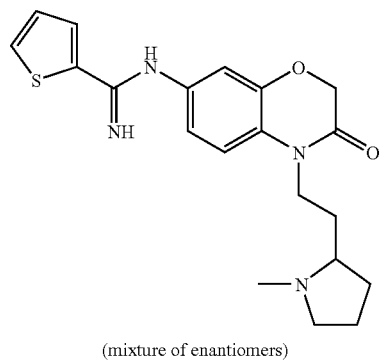
(1)

(mixture of enantiomers)

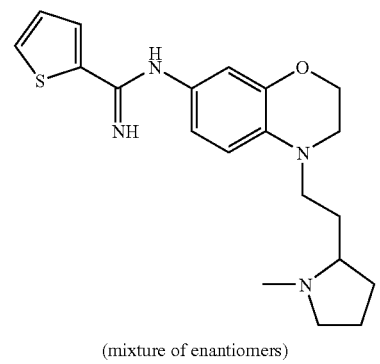
(2)

(mixture of enantiomers)

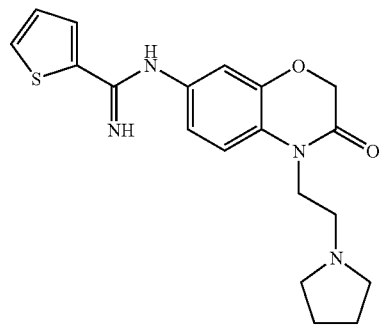
(3)

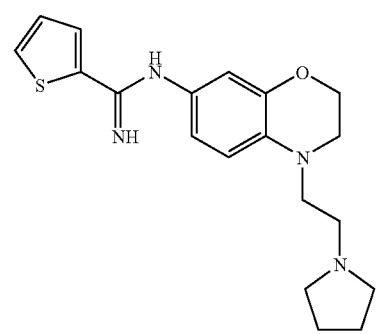
(4)

TABLE 2-continued
(5)
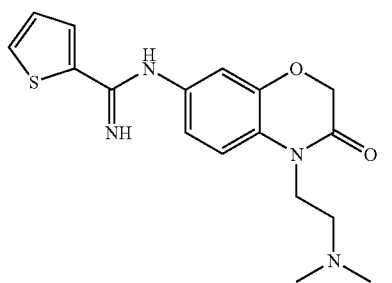
(6)
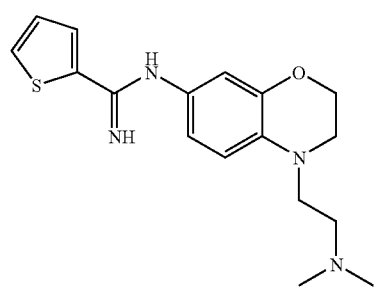
(7)
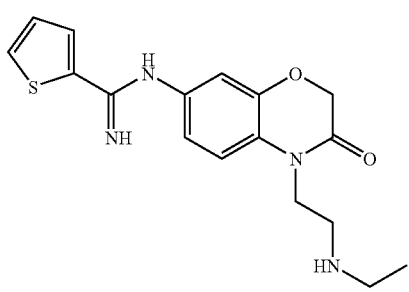
(8)
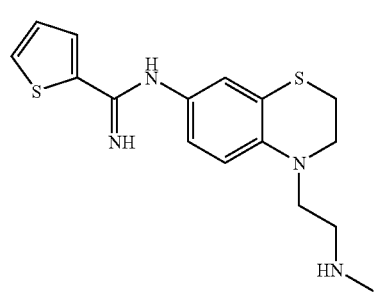
(9)
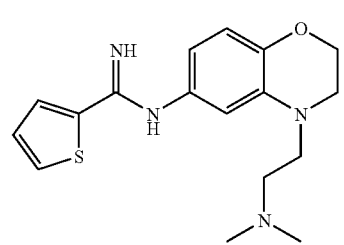
TABLE 2-continued
(10)
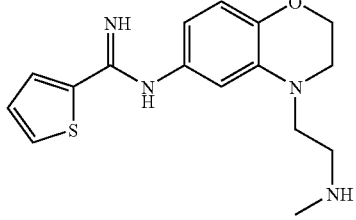
(11)
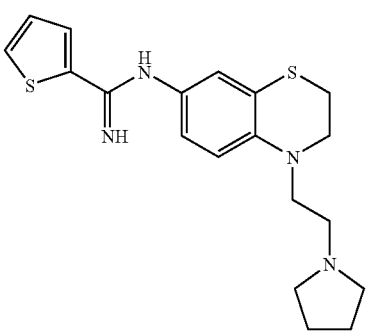
(12)
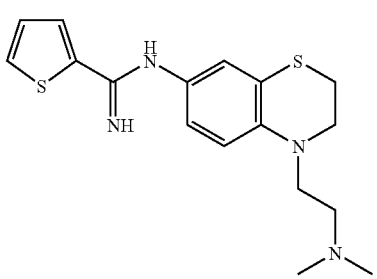
(13)
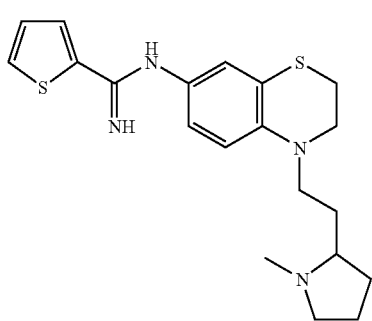
(mixture of enantiomers)
(14)
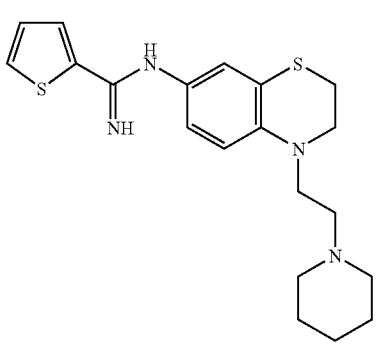

TABLE 2-continued
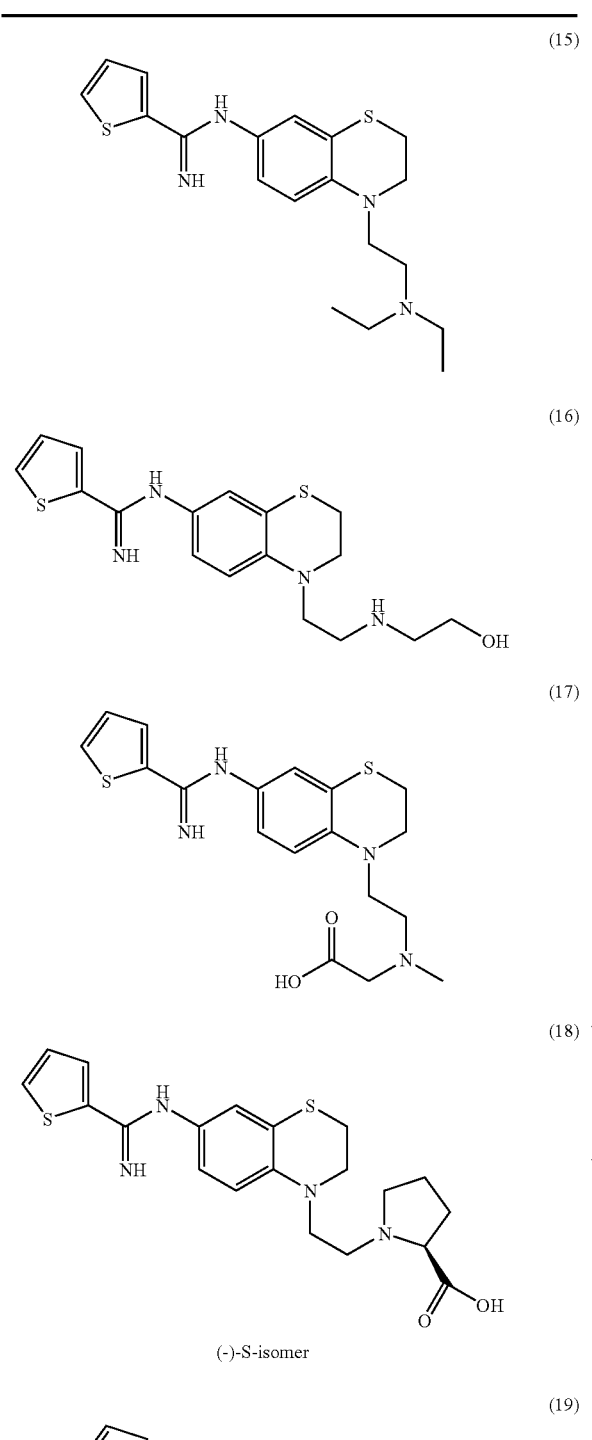
(15)
(16)
(17)
(18)
(-)-S-isomer
(19)
TABLE 2-continued
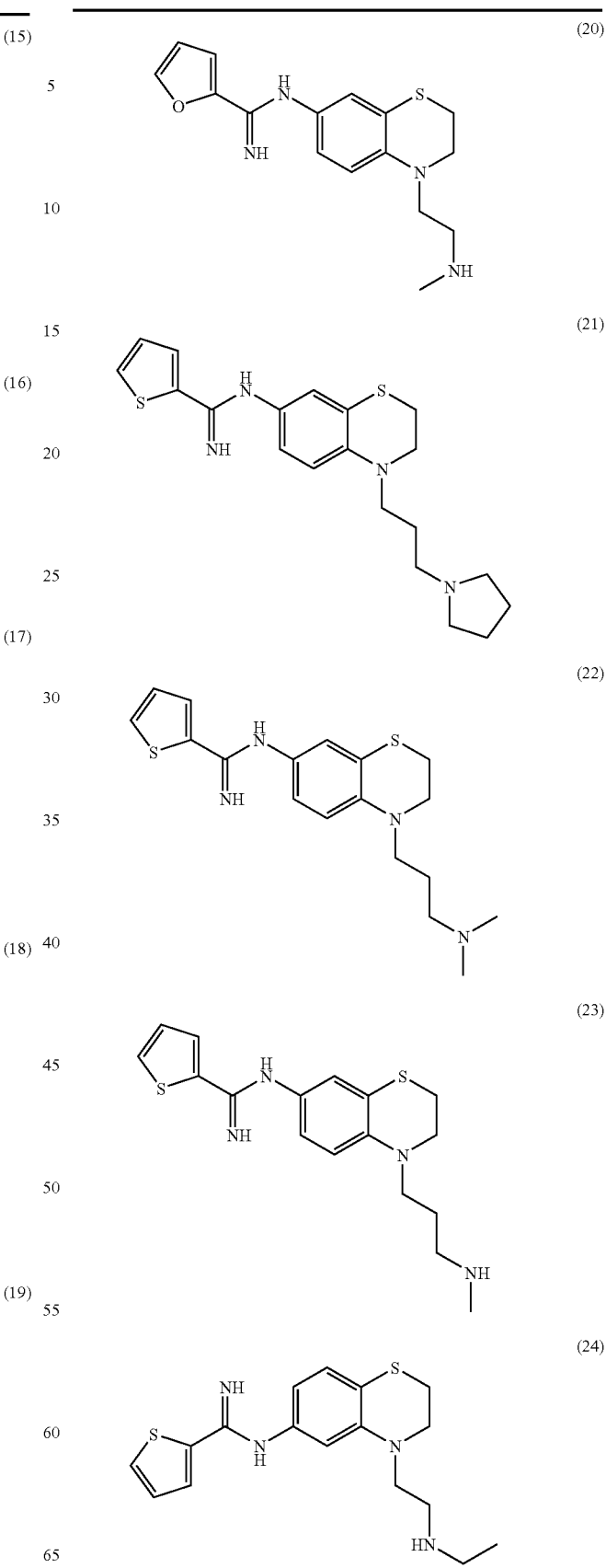
(20)
(21)
(22)
(23)
(24)

TABLE 2-continued

(25)
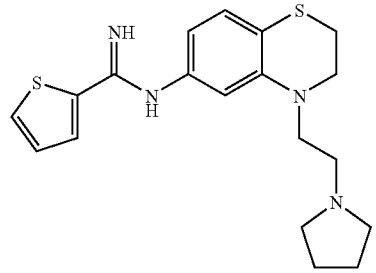

(26)
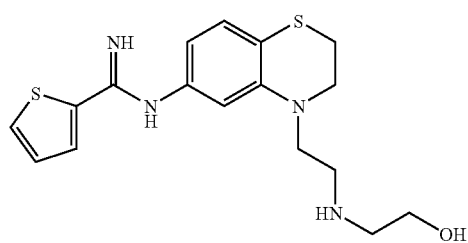

(27)
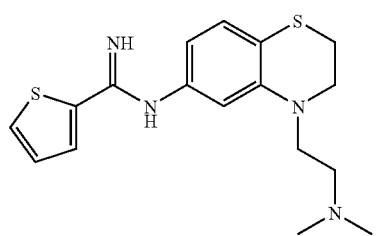

(28)
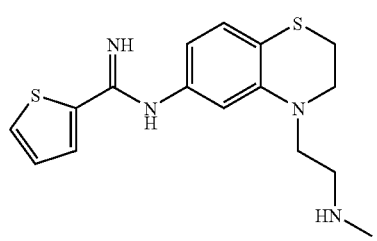

TABLE 2-continued

(30)
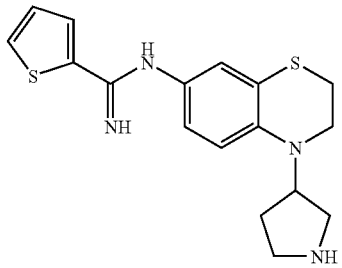

(mixture of enantiomers)

(31)
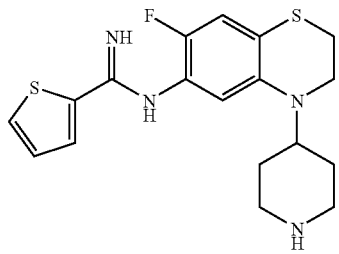

(32)
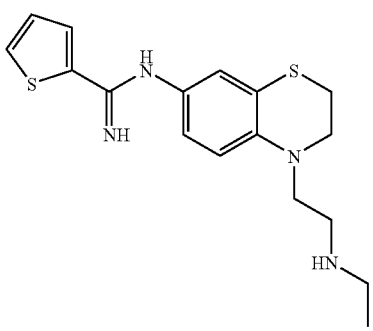

(33)
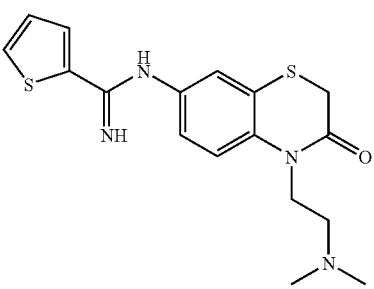

Exemplary methods for synthesizing compounds of the invention are described herein.

Methods of Preparing Compounds of the Invention

The compounds of the invention can be prepared by processes analogous to those established in the art, for example, by the reaction sequences shown in Schemes 1-5. The numbering system used for the general schemes does not necessarily correspond to that employed elsewhere in the description or in the claims.

A compound of formula C can be prepared under standard alkylating conditions by treating a compound of formula A with a compound of formula B, or a suitably protected derivative thereof, and "LG" is a leaving group such as chloro, bromo, iodo, or sulfonate (e.g., mesylate, tosylate, or triflate). Conditions to effect the alkylation of a compound of formula A with a compound of formula B may include heating a compound of formula A and a compound of formula B with or without a solvent, preferably with a suitable solvent such as DMF, optionally in the presence of a suitable base, such as potassium or sodium carbonate or sodium hydride (see Scheme 1).

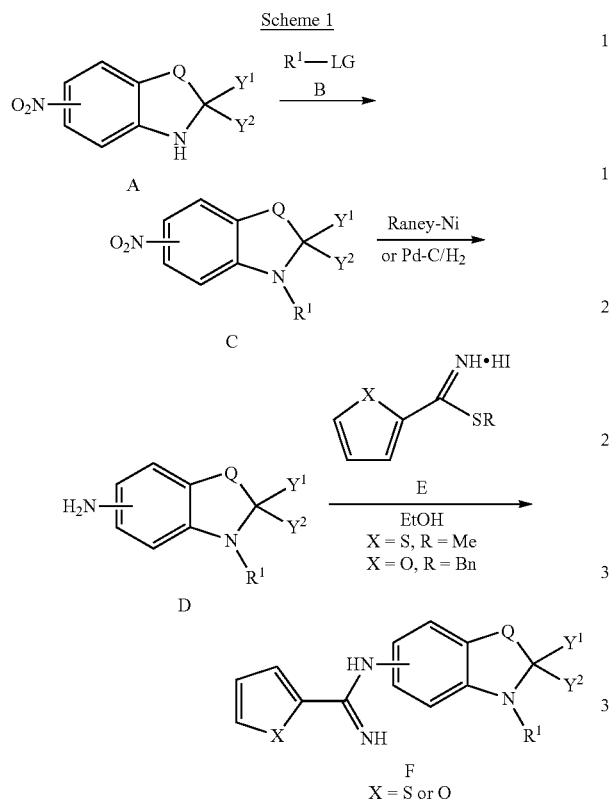

A compound of formula D can be prepared by reduction of the nitro group of a compound of formula C or a suitably protected derivative, under standard conditions as shown in Scheme 1. In one example, standard reduction conditions include the use of Raney Nickel in a polar solvent, such as methanol at refluxing temperatures. Alternatively, a compound of formula D can be prepared by the hydrogenation of a compound of formula C using a suitable catalyst (e.g., palladium on charcoal) in ethanol, or another solvent or combinations of solvents. As shown in Scheme 1, a compound of formula F can be prepared by reacting a compound of formula E with a compound of formula D according to a previous procedure (U.S. Patent Publication No. 20060258721 A1, herein incorporated by reference).

Alternatively, compound of formula K in which $R^1$ is $(CH_2)_n X^1$, where $X^1$ is

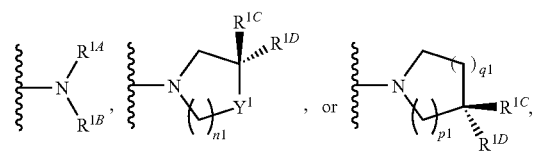

with $R^{1A}$, $R^{1B}$, $R^{1C}$, $R^{1D}$, $Y^1$ is $CH_2$, O, S, $NR^1$, n1, p1, and q1 as defined by example herein, involves the reaction of a compound of formula H, wherein LG is a suitable leaving group, such as chloro, bromo, iodo, or sulfonate (e.g., mesylate, tosylate, or triflate), with compounds of formula I under standard alkylation conditions as shown in Scheme 2. When LG is an aldehyde or ketone group, standard reductive amination conditions (e.g., Abdel-Majid et al. *J. Org. Chem.* 61:3849-3862, 1996) may be employed using a suitable reducing agent such as $NaBH_4$, $NaBH(OAc)_3$, $NaCNBH_4$, and the like, in an alcoholic solvent, such as ethanol, to produce a compound of formula J. The reductive amination may be performed in one reaction, or the imine resulting from mixing a compound of formula H with a compound of formula I can be pre-formed in situ, followed by sequential reduction with a suitable reducing agent. Compound J is converted to compound K by nitro reduction followed by amidation in a similar fashion as described in Scheme 1.

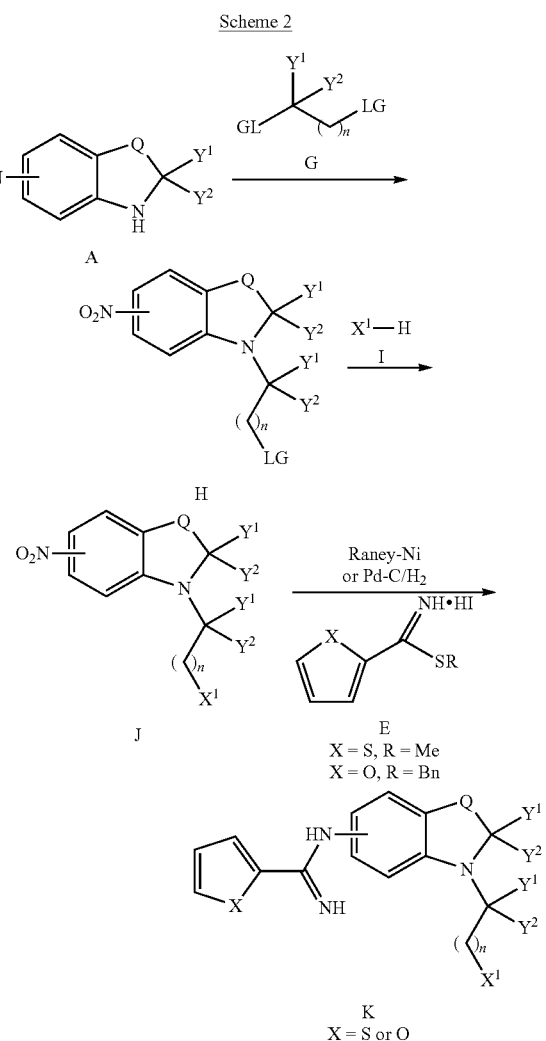

Compounds of general formula L can be prepared from a compound of formula D by amide reduction with lithium aluminum hydride in aprotic solvents (Scheme 3). Alternatively, a compound of formula L can be reduced using a suitable reducing agent, such as $BH_3$. These compounds are then converted to compound of formula M by coupling with reagent E as described in Scheme 1.

Scheme 3

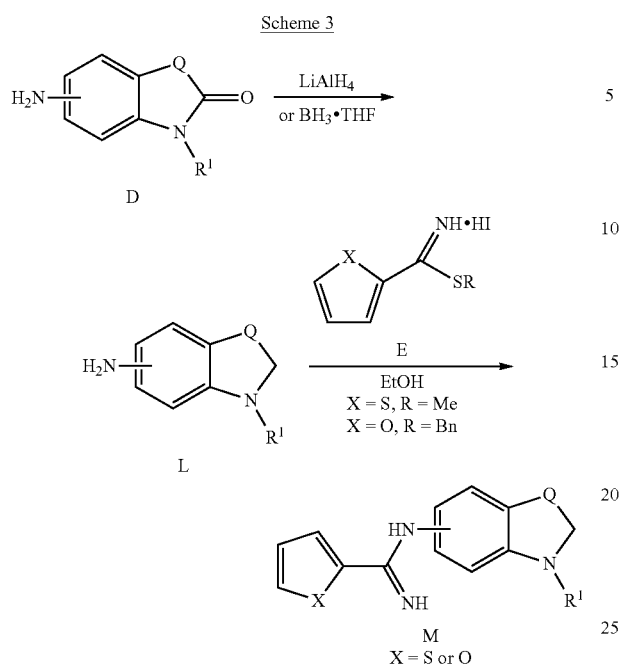

Scheme 4

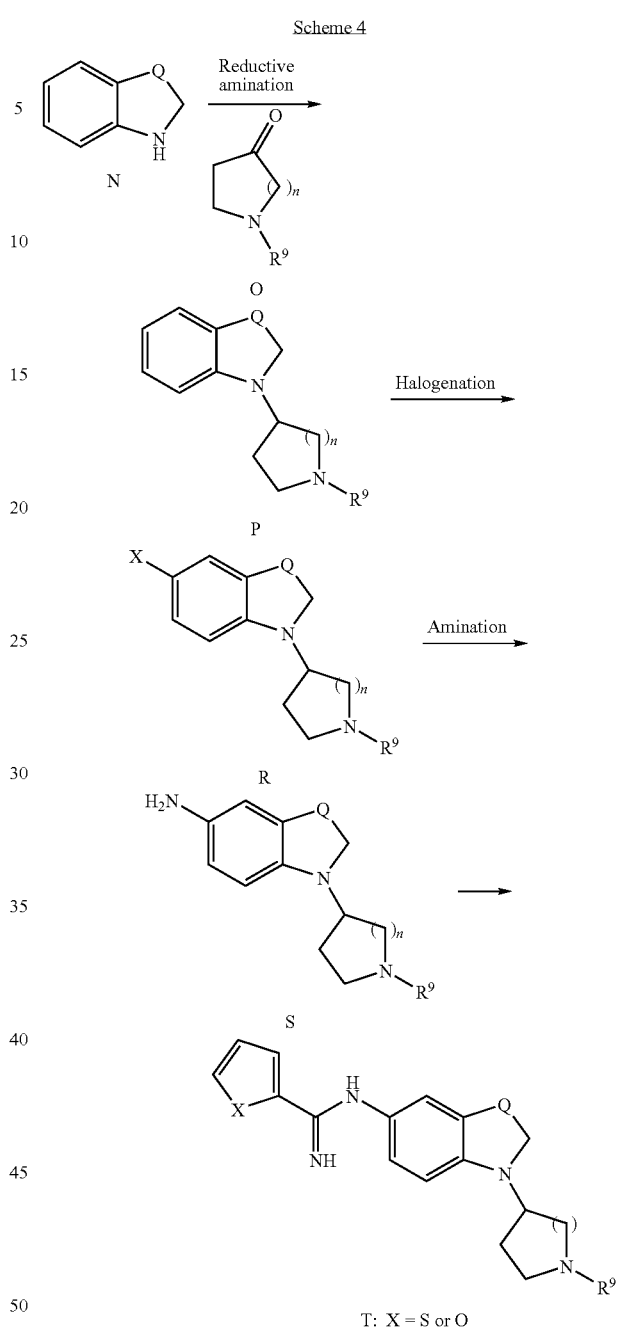

Compounds of general formula P can be prepared from compound N and compound of general formula O under standard reductive amination conditions (Scheme 4; Abdel-Majid et al. *J. Org. Chem.* 61:3849-3862, 1996). Compounds of general formula R can be prepared by aromatic halogenation of compounds of general formula P according to established procedures (see, for example, de la Mare, "Electrophilic Halogenation," Cambridge University Press, Cambridge (1976)). The preferred conditions include reacting compounds of general formula P with N-bromosuccinimide under neutral conditions A compound of formula S can be prepared by metal catalyzed amination of a compound of formula R where X is chloro, bromo, or iodo (Wolfe et al. *J. Org. Chem.* 65:1158-1174, 2000) in the presence of a suitable ammonia equivalent, such as benzophenone imine, LiN(SiMe$_3$)$_2$, Ph$_3$SiNH$_2$, NaN(SiMe$_3$)$_2$, or lithium amide (Huang and Buchwald, *Org. Lett.* 3(21):3417-3419, 2001). A preferred halogen is bromo in the presence of palladium (0) or palladium (II) catalyst. Examples of suitable metal catalysts include, for example, a palladium catalyst coordinated to suitable ligands. Suitable ligands for palladium can vary greatly and may include 4,5-bis(diphenylphosphino)-9,9-dimethylxanthene (XantPhos), 2,2'-bis(diphenylphosphino)-1,1'-binaphthyl (BINAP), bis(2-diphenylphosphinophenyl) ether (DPEphos), 1,1'-bis(diphenylphosphino)ferrocene (dppf), 1,2-bis-diphenylphosphinobutane (dppb), 1,3-bis(diphenylphosphino)propane (dppp), (o-biphenyl)-P(t-Bu)$_2$, (o-biphenyl)-P(Cy)$_2$, P(t-Bu)$_3$, P(Cy)$_3$, and others (e.g., Huang and Buchwald, *Org. Lett.* 3(21):3417-3419, 2001). Preferably the ligand is P(t-Bu)$_3$. The Pd-catalyzed amination is performed in a suitable solvent, such as THF, dioxane, toluene, xylene, DME, and the like, at temperatures between room temperature and reflux. Conversion of Compound S to T was done under conditions in Scheme 1.

A compound of formula V, where hal=F, Cl, Br, or I, can be prepared from compound U and compound O (Scheme 5) under standard reductive amination conditions as previously described in Scheme 4. When hal=F or Cl, a compound of formula Z can be prepared from a compound of formula V by reacting with W under basic conditions. A suitable base such as K$_2$CO$_3$ in a suitable solvent like DMF. In some cases, heat may be required for this transformation. Alternatively, when hal=Cl, Br or I, compound Z can be prepared from compound V and W by a transition metal catalyzed reaction. Preferred conditions involves the use of a palladium catalyst such as Pd(OAc)$_2$ or Pd$_2$(dba)$_3$ with a phosphine ligand such as Josiphos or CyPF$^t$Bu (Hartwig, *Acc. Chem. Res.*, 2008, 41, 1534). The hydroxyl group of compound Z can be converted to a LG such as chloro, bromo, iodo, or sulfonate (e.g. mesylate, tosylate, or triflate) to give compound of general formula Y by employing standard conditions. The preferred leaving group is iodo, and it can be prepared using triphenylphosphine and iodine in a suitable solvent such as THF. Compound Y can be cyclized to compound Z by heating with a base such as $K_2CO_3$ in a suitable solvent such as DMF. Compounds of formula Z can be converted to compounds of the invention A1 by nitro reduction followed by amidine coupling as described previously in Scheme 1.

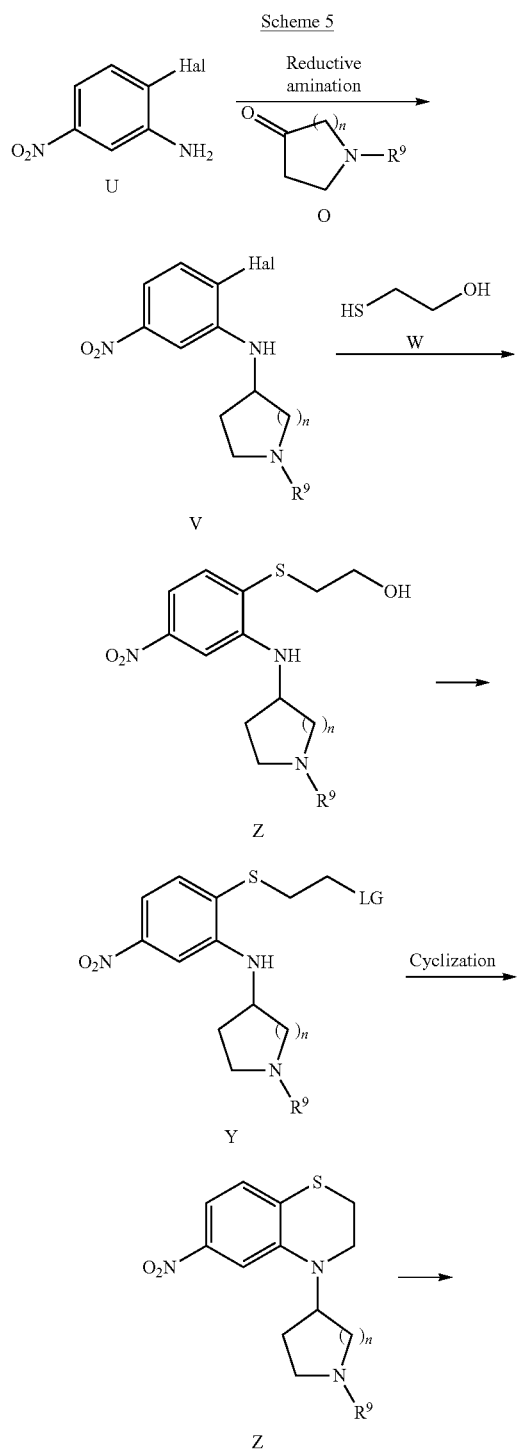

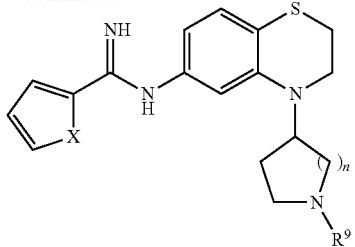

A1
X = S or O

In some cases the chemistries outlined above may have to be modified, for instance, by the use of protective groups to prevent side reactions due to reactive groups, e.g., attached as substituents. This may be achieved by means of conventional protecting groups as described in *Protective Groups in Organic Chemistry*, McOmie, Ed., Plenum Press, 1973 and in Greene and Wuts, *Protective Groups in Organic Synthesis*, John Wiley & Sons, $3^{rd}$ Edition, 1999.

The compounds of the invention, and intermediates in the preparation of the compounds of the invention, may be isolated from their reaction mixtures and purified (if necessary) using conventional techniques, including extraction, chromatography, distillation, and recrystallization.

The formation of a desired compound salt is achieved using standard techniques. For example, the neutral compound is treated with an acid in a suitable solvent, and the formed salt is isolated by filtration, extraction, or any other suitable method.

The formation of solvates of the compounds of the invention will vary depending on the compound and the solvate. In general, solvates are formed by dissolving the compound in the appropriate solvent and isolating the solvate by cooling or adding an antisolvent. The solvate is typically dried or azeotroped under ambient conditions.

Preparation of an optical isomer of a compound of the invention may be performed by reaction of the appropriate optically active starting materials under reaction conditions which will not cause racemization. Alternatively, the individual enantiomers may be isolated by separation of a racemic mixture using standard techniques, such as fractional crystallization or chiral HPLC.

A radiolabeled compound of the invention may be prepared using standard methods known in the art. For example, tritium may be incorporated into a compound of the invention using standard techniques, such as hydrogenation of a suitable precursor to a compound of the invention using tritium gas and a catalyst. Alternatively, a compound of the invention containing radioactive iodine may be prepared from the corresponding trialkyltin (preferably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halogen, preferably iodo, compound using standard palladium-catalyzed stannylation conditions, such as, for example, hexamethylditin in the presence of tetrakis(triphenylphosphine) palladium (0) in an inert solvent, such as dioxane, and at elevated temperatures, preferably 50-100° C.

Pharmaceutical Uses

The present invention features all uses for compounds of the invention, including use in therapeutic methods, whether alone or in combination with another therapeutic substance, their use in compositions for inhibiting NOS activity, e.g., nNOS, their use in diagnostic assays, and their use as research tools.

The compounds of the invention have useful NOS inhibiting activity, and therefore are useful for treating, or reducing the risk of, diseases or conditions that are ameliorated by a reduction in NOS activity. Such diseases or conditions include those in which the synthesis or oversynthesis of nitric oxide plays a contributory part.

Data substantiate the role of nitric oxide (NO) as a mediator of neurotransmission, synaptic plasticity, and pathologic pain in the central and peripheral nervous systems (Snyder, *Science* 1992, 257:494-496; Meller et al., *Pain* 52: 127-136, 1993; Praset et al., *A. Prog. Neurobiol.* 64: 51-68, 2001; and Choi et al., *J. Neurol. Sci.* 138(1-2):14-20, 1996). Multiple studies in animal models and genetic knockouts suggest a pivotal role for NO and nNOS in the pathobiology of sensitized pains such as neuropathic pain (Choi et al., *J. Neurol. Sci.* 138(1-2):14-20, 1996) and the associated behavioral responses such as thermal hyperalgesia (Meller et al., *Neurosci.* 50:7-10, 1992; Yamamoto et al., *Anesthesiology* 82:1266-1273, 1995) and mechanical allodynia (Hao et al. *Pain,* 66:313-319, 1996; Pan et al., *Anesthesiology* 89(6): 1518-23, 1998). For example, spinal nerve injury in mice leads to the development of mechanical hypersensitivity in wildtype but not nNOS knockout mice (Guan et al., *Mol. Pain,* 3:29, 2007). Similarly, systemic or intrathecally administered NOS inhibitors such as L-NAME or 7-NI can reduce nerve injury-induced mechanical hypersensitivity. This mechanical hypersensitivity is accompanied by an increase in nNOS protein expression, but not eNOS or iNOS, in the ipsilateral L5 dorsal root ganglion 7-days post-nerve injury (Guan et al., *Mol. Pain,* 3:29, 2007). Gene expression studies have shown that NIDD, a protein regulating nNOS enzyme activity, is upregulated in the spinal cord and dorsal root ganglia (DRG) in a rat model of neuropathic or inflammatory pain (Chen et al. *J. Mol. Histol.* 39(2): 125-33, 2008). In the Chung model of neuropathic pain (Spared Nerve Ligation or SNL), NOS inhibitors such as L-NAME can reduce neuropathic pain-like behavioral responses such as mechanical and cold allodynia, ongoing pain (Yoon et al., *NeuroReport* 9: 367-372, 1998) and thermal hyperalgesia (see, for example, U.S. Pat. No. 7,375,219 and PCT Publication No. WO 2009/062318, each of which is hereby incorporated by reference). NOS inhibitors have shown efficacy in other sensitized pain states with central sensitization components such as vincristine (chemotherapy) induced painful neuropathy (Kamei et al. *Pain.* 117 (1-2):112-20, 2005), Complete Freund's adjuvant (CFA)-induced chronic inflammatory pain (Chun et al., *Pain* 119: 113-123, 2005), carrageenan-induced mechanical and thermal hyperalgesia (Handy et al., *Neuropharmacology* 37:37-43, 1998; Osborne et al., *Br. J. Pharmacol.* 126(8):1840-1846, 1999), visceral hyperalgesia after intracolonic zymosan instillation (Coutinho et al. *Eur. J. Pharmacol* 429: 319-325, 2001), and postherpetic allodynia (Sasaki et al. *Neuroscience,* 150(2): 459-466, 2007).

Accordingly, the present invention features a method of treating, preventing, or reducing the risk of, a disease or condition caused by NOS activity that includes administering an effective amount of a compound of the invention to a cell or animal in need thereof. Such diseases or conditions include, for example, migraine headache (with or without aura), chronic tension type headache (CTTH), migraine with allodynia, medication overuse headache, cluster headache; neuropathic pain such as AIDS associated painful neuropathy, central post-stroke pain (CPSP), chronic headache, diabetic neuropathy, chemotherapy induced neuropathic pain (e.g., paclitaxel, cis-Platin, Doxorubicin etc.), postherpetic neuralgia, trigeminal neuralgia; chronic inflammatory pain resulting from osteoarthritis, rheumatoid arthritis, ankylosing spondylitis, psoriatic arthritis, undifferentiated spondyloarthropathy, reactive arthritis, visceral pain, neuroinflammation, medication-induced hyperalgesia and/or allodynia, e.g., opioid-induced hyperalgesia or triptan ($5\text{-HT}_{1D/1B}$ agonists)-induced hyperalgesia/allodynia, acute pain, chronic pain, diabetic neuropathy, bone cancer pain, chemical dependencies or addictions, e.g., drug addiction, cocaine addition, nicotine addition, metamphetamine-induced neurotoxicity, ethanol tolerance, dependence, or withdrawal, or morphine/opioid induced tolerance, dependence, hyperalgesia, or withdrawal, CNS disorders including but not limited to, e.g., epilepsy, anxiety, depression (alone or in combination), attention deficit hyperactivity disorder (ADHD), psychosis, or dementia, neurodegenerative diseases or nerve injury, e.g., acute spinal cord injury, AIDS associated dementia, Parkinson's disease, Alzheimer's disease, ALS, Huntington's disease, multiple sclerosis, neurotoxicity, or head trauma, cardiovascular related conditions, e.g., stroke, CABG associated neurological damage, HCAcardiogenic shock, reperfusion injury, or vascular dementia, or gastrointestinal disorders, e.g., ileostomy-associated diarrhea, or dumping syndrome.

The following description is a summary and a basis for the link between NOS inhibition (particularly nNOS or nNOS and iNOS) and some of these conditions.

Migraine with or without Aura

The first observation by Asciano Sobrero in 1847 that small quantities of nitroglycerine, an NO releasing agent, causes severe headache lead to the nitric oxide hypothesis of migraine (Olesen et al., *Cephalagia* 15:94-100, 1995). Serotonergic $5\text{HT}_{1D/1B}$ agonists, such as sumatriptan, which are used clinically in the treatment of migraine, are known to prevent the cortical spreading depression in the lissencephalic and gyrencephalic brain during migraine attack, a process resulting in widespread release of NO. Indeed, it has been shown that sumatriptan modifies the artificially enhanced cortical NO levels following infusion of glyceryl trinitrate in rats (Read et al., *Brain Res.* 847:1-8, 1999; ibid, 870(1-2):44-53, 2000). In a human randomized double-blinded clinical trial for migraine, a 67% response rate after single i.v. administration of L-N$^G$ methylarginine hydrochloride (L-NMMA, an NOS inhibitor) was observed. The effect was not attributed to a simple eNOS mediated vasoconstriction since no effect was observed on transcranial doppler determined velocity in the middle cerebral artery (Lassen et al., *Lancet* 349:401-402, 1997). In a recent adaptive clinical trial design for the treatment of acute migraine, administration of the selective iNOS inhibitor GW274150 at doses ranging from 5 to 180 mg was no different than placebo in terms of the proportion of subjects who became pain free at two hours after treatment. The same compound evaluated in a clinical trial of migraine prophylaxis (120 mg daily for 12 weeks) was also ineffective in reducing the frequency of migraine attack (Hoye et al. *Cephalalgia,* 2009, 29, 132). However, in an open pilot study using the NO scavenger hydroxycobalamin, a reduction in the frequency of migraine attack of 50% was observed in 53% of the patients and a reduction in the total duration of migraine attacks was also observed (van der Kuy et al., *Cephalgia* 22(7):513-519, 2002). The results from these clinical trials suggest that iNOS or eNOS do not play a significant role in the generation of migraine headache but rather points to the nNOS as the key isoform in migraine headache. The compounds of the invention (e.g., a compound of Formula (I) such as Compounds (1)-(33)) may also be employed for migraine prophylaxis.

Migraine with Allodynia

Clinical studies have shown that as many as 75% of patients develop cutaneous allodynia (exaggerated skin sensitivity) during migraine attacks and that its development during migraine is detrimental to the anti-migraine action of triptan $5HT_{1B/1D}$ agonists (Burstein et al., Ann. Neurol. 47:614-624, 2000; Burstein et al., Brain, 123:1703-1709, 2000). While the early administration of triptans such as sumatriptan can terminate migraine pain, late sumatriptan intervention is unable to terminate migraine pain or reverse the exaggerated skin sensitivity in migraine patients already associated with allodynia (Burstein et al., Ann. Neurol. DOI: 10.1002/ana.10785, 2003; Burstein and Jakubowski, Ann. Neurol., 55:27-36, 2004). The development of peripheral and central sensitization correlates with the clinical manifestations of migraine. In migraine patients, throbbing occurs 5-20 minutes after the onset of headache, whereas cutaneous allodynia starts between 20-120 minutes (Burstein et al., Brain, 123:1703-1709, 2000). In the rat, experimentally induced peripheral sensitization of meningeal nociceptors occurs within 5-20 minutes after applying an inflammatory soup (I.S.) to the dura (Levy and Strassman, J. Physiol., 538:483-493, 2002), whereas central sensitization of trigeminovascular neurons develops between 20-120 minutes (Burstein et al., J. Neurophysiol. 79:964-982, 1998) after I.S. administration. Parallel effects on the early or late administration of antimigraine triptans like sumatriptan on the development of central sensitization have been demonstrated in the rat (Burstein and Jakubowski, vide supra). Thus, early but not late sumatriptan prevents the long-term increase in I.S.-induced spontaneous activity seen in central trigeminovascular neurons (a clinical correlate of migraine pain intensity). In addition, late sumatriptan intervention in rats did not prevent I.S.-induced neuronal sensitivity to mechanical stimulation at the periorbital skin, nor decreased the threshold to heat (a clinical correlate of patients with mechanical and thermal allodynia in the periorbital area). In contrast, early sumatriptan prevented I.S. from inducing both thermal and mechanical hypersensitivity. After the development of central sensitization, late sumatriptan intervention reverses the enlargement of dural receptive fields and increases in sensitivity to dural indentation (a clinical correlate of pain throbbing exacerbated by bending over) while early intervention prevents its development.

Previous studies on migraine compounds such as sumatriptan (Kaube et al., Br. J. Pharmacol. 109:788-792, 1993), zolmitriptan (Goadsby et al., Pain 67:355-359, 1996), naratriptan (Goadsby et al., Br. J. Pharmacol., 328:37-40, 1997), rizatriptan (Cumberbatch et al., Eur. J. Pharmacol., 362:43-46, 1998), or L-471-604 (Cumberbatch et al., Br. J. Pharmacol. 126:1478-1486, 1999) examined their effects on nonsensitized central trigeminovascular neurons (under normal conditions) and thus do not reflect on their effects under the pathophysiological conditions of migraine. While triptans are effective in terminating the throbbing of migraine whether administered early or late, the peripheral action of sumatriptan is unable to terminate migraine pain with allodynia following late intervention via the effects of central sensitization of trigeminovascular neurons. The limitations of triptans suggest that improvement in the treatment of migraine pain can be achieved by utilizing drugs that can abort ongoing central sensitization, such as the compounds of the present invention.

It has been shown that systemic nitroglycerin increases nNOS levels and c-Fos-immunoreactive neurons (a marker neuronal activation) in rat trigeminal nucleus caudalis after 4 hours, suggesting NO likely mediates central sensitization of trigeminal neurons (Pardutz et al., Neuroreport 11(14):3071-3075, 2000). In addition, L-NAME can attenuate Fos expression in the trigeminal nucleus caudalis after prolonged (2 hours) electrical stimulation of the superior sagittal sinus (Hoskin et al. Neurosci. Lett. 266(3):173-6, 1999). Taken together with ability of NOS inhibitors to abort acute migraine attack (Lassen et al., Cephalalgia 18(1):27-32, 1998), the compounds of the invention, alone or in combination with other antinociceptive agents, represent excellent candidate therapeutics for aborting migraine in patients after the development of allodynia.

Chronic Headache (CTTH)

NO contributes to the sensory transmission in the peripheral (Aley et al., J. Neurosci. 1:7008-7014, 1998) and central nervous system (Meller and Gebhart, Pain 52:127-136, 1993). Substantial experimental evidence indicates that central sensitization, generated by prolonged nociceptive input from the periphery, increases excitability of neurons in the CNS and is caused by, or associated with, an increase in NOS activation and NO synthesis (Bendtsen, Cephalagia 20:486-508, 2000; Woolf and Salter, Science 288:1765-1769, 2000). It has been shown that experimental infusion of the NO donor, glyceryl trinitrate, induces headache in patients. In a double-blinded study, patients with chronic tension-type headache receiving L-NMMA (an NOS inhibitor) had a significant reduction in headache intensity (Ashina and Bendtsen, J. Headache Pain 2:21-24, 2001; Ashina et al., Lancet 243 (9149):287-9, 1999). Thus the NOS inhibitors of the present invention may be useful for the treatment of chronic tension-type headache.

Acute Spinal Cord Injury and Chronic or Neuropathic Pain

In humans, NO evokes pain on intracutaneous injection (Holthusen and Arndt, Neurosci. Lett. 165:71-74, 1994), thus showing a direct involvement of NO in pain. Furthermore, NOS inhibitors have little or no effect on nociceptive transmission under normal conditions (Meller and Gebhart, Pain 52:127-136, 1993). NO is involved in the transmission and modulation of nociceptive information at the periphery, spinal cord and supraspinal level (Duarte et al., Eur. J. Pharmacol. 217:225-227, 1992; Haley et al., Neuroscience 31:251-258, 1992). Lesions or dysfunctions in the CNS may lead to the development of chronic pain symptoms, known as central pain, and includes spontaneous pain, hyperalgesia, and mechanical and cold allodynia (Pagni, Textbook of Pain, Churchill Livingstone, Edinburgh, 1989, pp. 634-655; Tasker In: The Management of Pain, pp. 264-283, J. J. Bonica (Ed.), Lea and Febiger, Philadelphia, Pa., 1990; Casey, Pain and Central Nervous System Disease: The Central Pain Syndromes, pp. 1-11 K. L. Casey (Ed.), Raven Press, New York, 1991). It has been demonstrated that systemic administration (i.p.) of the NOS inhibitors 7-NI and L-NAME relieve chronic allodynia-like symptoms in rats with spinal cord injury (Hao and Xu, Pain 66:313-319, 1996). The effects of 7-NI were not associated with a significant sedative effect and were reversed by L-arginine (NO precursor). The maintenance of thermal hyperalgesia is believed to be mediated by nitric oxide in the lumbar spinal cord and can be blocked by intrathecal administration of a nitric oxide synthase inhibitor like L-NAME or soluble guanylate cyclase inhibitor methylene blue (Neuroscience 50(1):7-10, 1992).

Neuropathic pain may be due to a primary insult to the peripheral (e.g., trigeminal neuraligia) or central nervous system (e.g., thalamic pain). It is likely, however, that the pathphysiology leading to a neuropathic pain state originating from a peripheral lesion spreads over time to other areas to affect higher order neurons in the dorsal root ganglion or to alter descending inhibition of spinal pain transmission by brain centers such as periaqueductal gray, locus corealis (Zimmermann, *Eur. J. Pharmacol.* 429:23-27, 2001) or alter descending facility pathways in the rostroventromedial medulla (RVM) (Bee and Dickenson, *Pain,* 140(1): 209-23, 2008).

Thus the NOS inhibitors of the present invention may be useful for the treatment of chronic or neuropathic pain.

Diabetic Neuropathy

The endogenous polyamine metabolite agmatine is a metabolite of arginine that is both an NOS inhibitor and N-methyl-D-aspartate (NMDA) channel antagonist. Agmatine is effective in both the spinal nerve ligation (SNL) model of neuropathic pain as well as the streptozotocin model of diabetic neuropathy (Karadag et al., *Neurosci. Lett.* 339(1): 88-90, 2003). Thus compounds possessing NOS inhibitory activity, such as, for example, a compound of formula I, a combination of an NOS inhibitor and an NMDA antagonist should be effective in treating diabetic neuropathy and other neuropathic pain conditions.

Inflammatory Diseases and Neuroinflammation

LPS, a well-known pharmacological tool, induces inflammation in many tissues and activates NFκB in all brain regions when administered intravenously. It also activates pro-inflammatory genes when injected locally into the striatum (Stem et al., *J. Neuroimmunology,* 109:245-260, 2000). Recently it has been shown that both the NMDA receptor antagonist MK801 and the brain selective nNOS inhibitor 7-NI both reduce NFκB activation in the brain and thus reveal a clear role for glutamate and NO pathway in neuroinflammation (Glezer et al., *Neuropharmacology* 45(8):1120-1129, 2003). Thus, the administration of a compound of the invention, either alone or in combination with an NMDA antagonist, should be effective in treating diseases arising from neuroinflammation.

Stroke and Reperfusion Injury

The role of NO in cerebral ischemia can be protective or destructive depending on the stage of evolution of the ischemic process and on the cellular compartment producing NO (Dalkara et al., *Brain Pathology* 4:49, 1994). While the NO produced by eNOS is likely beneficial by acting as a vasodilator to improve blood flow to the affected area (Huang et al., *J. Cereb. Blood Flow Metab.* 16:981, 1996), NO produced by nNOS contributes to the initial metabolic deterioration of the ischemic penumbra, resulting in larger infarcts (Hara et al., *J. Cereb. Blood Flow Metab.* 16:605, 1996). The metabolic derangement that occurs during ischemia and subsequent reperfusion results in the expression and release of several cytokines that activate iNOS in several cell types including some of the central nervous system. NO can be produced at cytotoxic levels by iNOS, and increased levels of iNOS contribute to progressive tissue damage in the penumbra, leading to larger infarcts (Parmentier et al., *Br. J. Pharmacol.* 127:546, 1999). Inhibition of i-NOS has been shown to ameliorate cerebral ischemic damage in rats (*Am. J. Physiol.* 268:R286, 1995).

It has been shown that a synergistic neuroprotective effect is observed upon the combined administration of an NMDA antagonist (e.g., MK-801 or LY293558) with nNOS selective inhibitors (7-NI or ARL17477) in global cerebral ischemia (Hicks et al., *Eur. J. Pharmacol.* 381:113-119, 1999). Thus the compounds of the invention, administered either alone or in combination with NMDA antagonists, or compounds possessing mixed nNOS/NMDA activity, may be effective in treating conditions of stroke and other neurodegenerative disorders.

Complications Resulting from Coronary Artery Bypass Surgery

Cerebral damage and cognitive dysfunction still remains as a major complication of patients undergoing coronary artery bypass surgery (CABG) (Roch et al., *N. Eng. J. Med.* 335: 1857-1864, 1996; Shaw et al., *Q. J. Med.* 58:59-68, 1986). This cerebral impairment following surgery is a result of ischemia from preoperative cerebral microembolism. In a randomized trial of the NMDA antagonist remacemide, patients showed a significant overall postoperative improvement in learning ability in addition to reduced deficits (Arrowsmith et al., *Stroke* 29:2357-2362, 1998). Given the involvement of excitotoxicity produced by excessive release of glutamate and calcium influx, it is expected that a neuroprotective agent, such as a compound of the invention or an NMDA antagonist, either alone or in combination (as discussed above), may have a beneficial effect improving neurological outcomes after CABG.

AIDS-Associated Dementia

HIV-1 infection can give rise to dementia. The HIV-1 coat protein gp-120 kills neurons in primary cortical cultures at low picomolar levels and requires external glutamate and calcium (Dawson et al., 90(8):3256-3259, 1993). This toxicity can be attenuated by administration of a neuroprotective agent, e.g., a compound of the invention, either alone or in combination with another therapeutic agent, such as, for example, an NMDA antagonist (as discussed above).

Examples of other compounds, e.g., NMDA antagonists, useful for any of the combinations of the invention include aptiganel; besonprodil; budipine; conantokin G; delucemine; dexanabinol; felbamate; fluorofelbamate; gacyclidine; glycine; ipenoxazone; kaitocephalin; lanicemine; licostinel; midafotel; milnacipran; neramexane; orphenadrine; remacemide; topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-

4-(phenylmethyl)-piperidine; 2-methyl-6-(phenylethynyl)-pyridine; 3-(phosphonomethyl)-L-phenylalanine; and 3,6,7-tetrahydro-2,3-dioxo-N-phenyl-1H,5H-pyrido[1,2,3-de]quinoxaline-5-acetamide or those described in U.S. Pat. Nos. 6,071,966; 6,034,134; and 5,061,703.

Cardiogenic Shock

Cardiogenic shock (CS) is the leading cause of death for patients with acute myocardial infarction that is consistent with increased levels of NO and inflammatory cytokines. High levels of NO and peroxynitrite have many effects, including a direct inhibition on myocardial contractability, suppression of mitochondrial respiration in myocardium, alteration in glucose metabolism, reduced catecholamine responsivity, and induction of systemic vasodilation (Hochman, Circulation 107:2998, 2003). In a clinical study in 11 patients with persistent shock, administration of the NOS inhibitor L-NMMA resulted in increases in urine output and blood pressure and survival rate of 72% up to 30 days (Cotter et al., Circulation 101:1258-1361, 2000). In a randomized trial of 30 patients, it was reported that L-NAME reduced patient mortality from 67% to 27% (Cotter et al., Eur. Heart. J. 24(14):1287-95, 2003). Similarly, administration of a compound of the invention, either alone or in combination with another therapeutic agent, may be useful for the treatment of cardiogenic shock.

Anxiety and Depression

Recent studies of rats and mice in the forced swimming test (FST) indicate that NOS inhibitors have antidepressant activity in mice (Harkin et al. Eur. J. Pharm. 372:207-213, 1999) and that their effect is mediated by a serotonin dependent mechanism (Harkin et al., Neuropharmacology 44(5):616-623, 1993). 7-NI demonstrates anxiolytic activity in the rat plus-maze test (Yildiz et al., Pharmacology, Biochemistry and Behavior 65:199-202, 2000), whereas the selective nNOS inhibitor TRIM is effective in both the FST model of depression and anxiety in the light-dark compartment test (Volke et al., Behavioral Brain Research 140(1-2):141-7, 2003). Administration of a compound of the invention to an afflicted individual, either alone or in combination with another therapeutic agent, such as, for example, an antidepressant, may be useful for the treatment of anxiety or depression.

Attention Deficit Hyperactivity Disorder

Non-selective attention (NSA) to environmental stimuli in Spontaneously Hypertensive (SHR) and Naples Low-Excitability (NHE) rats has been used as an animal model of Attention-Deficit Hyperactivity Disorder (ADHD) (Aspide et al., Behav. Brain Res. 95(1):23-33, 1998). These genetically altered animals show increased episodes of rearing that have a shorter duration than observed in normal animals. A single injection of L-NAME at 10 mg/kg produced an increase in rearing duration. Similarly, using the more neuronally selective 7-NINA, an increase in the rearing duration was observed after rapid administration (i.p.), while a slow release single release dose or a slow multiple release dose (s.c. in DMSO) resulted in the opposite effect. Thus, administration of a compound of the invention may be useful for the treatment of ADHD.

Psychosis

Phencyclidine (PCP) is a non-competitive NMDA channel blocker that produces behavioral side effects in human and mammals consistent with those observed in patients with psychosis. In two animal models of psychosis, the nNOS selective inhibitor AR-R17477 antagonized PCP-induced hyperlocomotion and PCP-induced deficit in prepulse inhibition of the acoustic response startle (Johansson et al., Pharmacol. Toxicol. 84(5):226-33, 1999). These results suggest the involvement of nNOS in psychosis. Therefore, administration of a compound of the invention to an afflicted individual may be useful for the treatment of this or related diseases or disorders.

Head Trauma

The mechanism of neurological damage in patients with head trauma parallels that of stroke and is related to excitotoxic calcium influx from excessive glutamate release, oxidative stress and free radical production from mitochondrial dysfunction and inflammation (Drug & Market Development 9(3):60-63, 1998). Animals treated with nitric oxide synthase (NOS) inhibitors, such as 7-NI and 3-bromo-7-nitroindazole, have shown an improvement in neurological deficits after experimental traumatic brain injury (TBI) (Mesenge et al., J. Neurotrauma 13:209-14, 1996). Administration of a compound of the invention to an afflicted individual may also be useful for the treatment of neurological damage in head trauma injuries.

Hypothermic Cardiac Arrest

Hypothermic cardiac arrest (HCA) is a technique used to protect from ischemic damage during cardiac surgery when the brain is sensitive to damage during the period of blood flow interruption. Various neuroprotective agents have been used as adjunct agents during HCA and reducing nitric oxide production during HCA is predicted to result in improvements in neurological function. This is based on previous studies that showed glutamate excitotoxicity plays a role in HCA-induced neurologic damage (Redmond et al., J. Thorac. Cardiovasc. Surg. 107:776-87, 1994; Redmond et al., Ann. Thorac. Surg. 59:579-84, 1995) and that NO mediates glutamate excitotoxicity (Dawson and Snyder, J. Neurosci. 14:5147-59, 1994). In a study of 32 dogs undergoing 2 hours of HCA at 18° C., a neuronal NOS inhibitor was shown to reduce cerebral NO production, significantly reduce neuronal necrosis, and resulted in superior neurologic function relative to controls (Tseng et al., Ann. Thorac. Surg. 67:65-71, 1999). Administration of a compound of the invention may also be useful for protecting patients from ischemic damage during cardiac surgery.

Neurotoxicity and Neurodegenerative Diseases

Mitochondrial dysfunction, glutamate excitotoxicity, and free radical induced oxidative damage appear to be the underlying pathogenesis of many neurodegenerative diseases, including amyotrophic lateral sclerosis (ALS), Parkinson's disease (PD), Alzheimer's disease (AD), and Huntington's disease (HD) (Schulz et al., Mol. Cell. Biochem. 174(1-2): 193-197, 1997; Beal, Ann. Neurol. 38:357-366, 1995), and NO is a primary mediator in these mechanisms. For example, it was shown by Dawson et al., in PNAS 88(14):6368-6371, 1991, that NOS inhibitors like 7-NI and L-NAME prevent neurotoxicity elicited by N-methyl-D-aspartate and related excitatory amino acids.

(a) Parkinson's Disease

Studies have also shown that NO plays an important role in 1-methyl-4-phenyl-1,2,3,6-tetrahydropyridine (MPTP) neurotoxicity, a commonly used animal model of Parkinson's disease (Matthews et al., Neurobiology of Disease 4:114-121, 1997). MPTP is converted to MPP+ by MAO-B and is rapidly taken up by the dopamine transporter into the mitochondria of dopamine containing neurons with subsequent activation of nNOS resulting in neuronal death. Mutant mice lacking the nNOS gene, but not the eNOS gene, have reduced lesions in the substantia nigra after MPP+ injection into the striatum. In primate studies, 7-NI exerts a profound neuroprotective and antiparkinsonium effect after MPTP challenge (Hantraye et al., Nature Med. 2:1017-1021, 1996) as did the non-specific inhibitor L-NAME (T. S. Smith et. al. Neuroreport 1994, 5, 2598-2600). These results suggest that administration of an appropriate dose of an NOS inhibitor, such as, for example, a compound of the invention, can be beneficial in the treatment of Parkinson's Disease.

(b) Alzheimer's Disease (AD)

The pathology of AD is associated with β-amyloid plaques infiltrated with activated microglia and astrocytes. When cultured rat microglia are exposed to beta-amyloid, there is a prominent microglial release of nitric oxide, especially in the presence of gamma-interferon (Goodwin et al., *Brain Research* 692(1-2):207-14, 1995). In cortical neuronal cultures, treatment with nitric oxide synthase inhibitors provides neuroprotection against toxicity elicited by human beta-amyloid (Resink et al., *Neurosci. Abstr.* 21:1010, 1995). Consistent with the glutamate hypothesis of excitocicity in neurodegerative disorders, the weak NMDA antagonist amantadine increases the life expectancy of PD patients (Uitti et al., *Neurology* 46(6): 1551-6, 1996). In a preliminary, placebo-controlled study of patients with vascular- or Alzheimer's-type dementia, the NMDA antagonist memantine was associated with improved Clinical Global Impression of Change and Behavioral Rating Scale for Geriatric Patients scores (Winblad and Poritis, *Int. J. Geriatr. Psychiatry* 14:135-46, 1999). These results suggest that administration of an appropriate dose of an NOS inhibitor, such as, for example, a compound of the invention, can be beneficial in the treatment of AD.

(c) Amyotrophic Lateral Sclerosis

Amyotrophic lateral sclerosis (ALS) is a fatal neurodegenerative disease characterized by selective motor neuronal death. Accumulating evidence suggests that the pathogenesis of ALS is the insufficient clearance of glutamate through the glutamate transporter, and the specific distribution of $Ca^{2+}$-permeable AMPA receptors in spinal motor neurons, indicates a glutamate-induced neurotoxicity. Increased nNOS immunoreactivity is found in the spinal cords (Sasaki et al., *Acta Neuropathol. (Berl)* 101(4):351-7, 2001) and glial cells (Anneser et al., *Exp. Neurol.* 171(2):418-21, 2001) of ALS patients, implicating NO as an important factor in the pathogenesis of ALS. These results suggest that administration of an appropriate dose of an NOS inhibitor, such as, for example, a compound of the invention, can be beneficial in the treatment of ALS.

(d) Huntington's Disease

The pathogenesis of Huntington's disease (HD) arising from a mutation in the Htt protein is linked to excitotoxicity, oxidative stress and apoptosis, in all of which excessive NO has a clear role (Peterson et al., *Exp. Neurol.* 157:1-18, 1999). Oxidative damage is one of the major consequences of defects in energy metabolism and is present in HD models after injection of excitotoxins and mitochondrial inhibitors (A. Petersen et. al., *Exp. Neurol.* 157:1-18, 1999). This mitochrondrial dysfunction is associated with the selective and progressive neuronal loss in HD (Brown et al., *Ann. Neurol.* 41:646-653, 1997). NO can directly impair the mitochondrial respiratory chain complex IV (Calabrese et al., *Neurochem. Res.* 25:1215-41, 2000). Striatal medium spiny neurons appear to be the primary target for the generation of motor dysfunction in HD. Hyperphosphorylation and activation of NMDA receptors on these neurons likely participates in the generation of motor dysfunction. It has been shown clinically that the NMDA antagonist amantadine improves choreiform dyskinesias in HD (Verhagen Metman et al., *Neurology* 59:694-699, 2002). Given the role of nNOS in NMDA mediated neurotoxicity, it is expected that nNOS inhibitors, especially those with mixed nNOS/NMDA, or combinations of drugs with nNOS and NMDA activity will also be useful in ameliorating the effects and or progression of HD. For example, pretreatment of rats with 7-nitroindazole attenuates the striatal lesions elicited by stereotaxic injections of malonate, an injury that leads to a condition resembling Huntington's disease (Hobbs et. al., *Ann. Rev. Pharm. Tox.* 39:191-220, 1999). In a R6/1 transgenic mouse model of HD expressing a human mutated htt exon1, a 116 CAG repeat, mice at 11, 19 and 35 weeks show a progressive increase in lipid peroxidation with normal levels of superoxide dismutase (SOD) at 11 weeks similar to wild type (WT) mice; a maximum level at 19 weeks, above that observed in WT mice and corresponding to the early phase of disease progression; and finally, decreasing levels at 35 weeks below that observed in WT mice (Pérez-Sevriano et al., *Brain Res.* 951:36-42, 2002). The increase in SOD activity is attributable to a compensatory neuroprotective mechanism, with decreased levels at 35 weeks corresponding to a failed protective mechanism. Concomitant with the levels of SOD, levels of calcium dependent NOS was the same for 11 week mice in both WT and R6/1 mice, but increased significantly at 19 weeks and decreased at 35 weeks relative to WT control mice. Levels of nNOS expression also increased dramatically relative to controls at 19 weeks but were decreased significantly relative to controls at 35 weeks. No significant differences were observed in levels of eNOS expression, nor could iNOS protein be detected during progression of the disease. The progressive phenotypic expression of the disease, as measured by increased weight loss, feet clasping behavior, and horizontal and vertical movements, are consistent with changes in NOS activity and nNOS expression. Finally, the effects of L-NAME administration to both R6/2 transgenic HD mice and WT mice showed improved levels of clasping behavior at a 10 mg/kg dose similar to controls, which worsened at the highest dose of 500 mg/kg (Deckel et al., *Brain Res.* 919 (1):70-81, 2001). An improvement in weight increase in HD mice was also significant at the 10 mg/kg dose, but decreased relative to controls at high dose levels of L-NAME. These results demonstrate that administration of an appropriate dose of an NOS inhibitor, such as, for example, a compound of the invention, can be beneficial in the treatment of HD.

(e) Multiple Sclerosis (MS)

MS is in an inflammatory demyelinating disease of the CNS involving cytokines and other inflammatory mediators. Many studies suggest that NO and its reactive derivative peroxynitrite are implicated in the pathogenesis of MS (Acar et al. *J. Neurol.* 250(5):588-92, 2003; Calabrese et al., *Neurochem. Res.* 28(9):1321-8, 2003). In experimental autoimmune encephalomyelitis (EAE), a model of MS, nNOS levels are slightly increased in the spinal cord of EAE rats and treatment with 7-nitroindazole results in a significant delay in the onset of EAE paralysis (Shin, *J. Vet. Sci.* 2(3):195-9, 2001). These results suggest that administration of an appropriate dose of an NOS inhibitor, such as, for example, a compound of the invention, can be beneficial in the treatment of MS.

(f) Methamphetamine-Induced Neurotoxicity

Methamphetamine is neurotoxic by destroying dopamine nerve terminals in vivo. It has been shown that methamphetamine-induced neurotoxicity can be attenuated by treatment with NOS inhibitors in vitro (Sheng et al., *Ann. N.Y. Acad. Sci.* 801:174-186, 1996) and in in vivo animal models (Itzhak et al., *Neuroreport* 11(13):2943-6, 2000). Similarly, the nNOS selective inhibitor AR-17477AR, at 5 mg/kg s.c in mice, was able to prevent the methamphetamine-induced loss of the neurofilament protein NF68 in mouse brain and prevent the loss of striatal dopamine and homovanillic acid (HVA) (Sanchez et al., *J. Neurochem.* 85(2):515-524, 2003). These results suggest that administration of an appropriate dose of an NOS inhibitor, such as, for example, a compound of the invention, can be beneficial in the treatment of methamphetamine-induced neurotoxicity.

Administration of a compound of the invention, either alone or in combination with another therapeutic agent, such as, for example, an NMDA antagonist, may be useful for the protection or treatment of any of the neurodegenerative diseases described herein. Further, the compounds of the invention may be tested in standard assays used to assess neuroprotection (see for example, *Am. J. Physiol.* 268:R286, 1995).

Chemical Dependencies and Drug Addictions (e.g., Dependencies on Drugs, Alcohol and Nicotine)

A key step in the process of drug-induced reward and dependence is the regulation of dopamine release from mesolimbic dopaminergic neurons. Chronic application of cocaine alters the expression of the key protein controlling the synaptic level of dopamine—the dopamine transporter (DAT).

(a) Cocaine Addiction

Studies have shown that animals reliably self-administer stimulants intravenously and that dopamine is critical in their reinforcing effects. Recently NO containing neurons have been shown to co-localize with dopamine in areas of the striatum and ventral tegmental area and that NO can modulate stimulant-evoked dopamine (DA) release. Administration of dopamine D1 receptor antagonists decrease the levels of striatal NADPH-diaphorase staining, a marker for NOS activity, while D2 antagonists produce the opposite effect. L-Arginine, the substrate of NOS, is also a potent modulator of DA release. Also, multiple NO-generating agents increase DA efflux or inhibit reuptake both in vitro and in vivo. L-NAME has been shown to significantly alter cocaine reinforcement by decreasing the amount of self-administration and by increasing the inter-response time between successive cocaine injections (Pudiak and Bozarth, *Soc. Neurosci. Abs.* 22:703, 1996). This indicates that NOS inhibition by compounds of the invention may be useful in the treatment of cocaine addiction.

(b) Morphine/Opioid Induced Tolerance and Withdrawal Symptoms

There is much evidence supporting the role of both the NMDA and NO pathways in opioid dependence in adult and infant animals. Adult or neonatal rodents injected with morphine sulfate develop behavioral withdrawal after precipitation with naltrexone. The withdrawal symptoms after naltrexone initiation can be reduced by administration of NOS inhibitors, such as 7-NI or L-NAME (Zhu and Barr, *Psychopharmacology* 150(3):325-336, 2000). In a related study, it was shown that the more nNOS selective inhibitor 7-NI attenuated more of the morphine induced withdrawal symptoms including mastication, salivation and genital effects than the less selective compounds (Vaupel et al., *Psychopharmacology (Berl.)* 118(4):361-8, 1995). This indicates that NOS inhibition by compounds of the invention may be useful in the treatment of morphine/opioid induced tolerance and withdrawal symptoms.

(c) Ethanol Tolerance and Dependence

Among the factors that influence alcohol dependence, tolerance to the effects of ethanol is an important component because it favors the exaggerated drinking of alcoholic beverages (Lê and Kiianmaa, *Psychopharmacology (Berl.)* 94:479-483, 1988). In a study with rats, ethanol tolerance to motor incoordination and hypothermia develop rapidly and can be blocked by i.c.v. administration of 7-NI without altering cerebral ethanol concentrations (Wazlawik and Morato, *Brain Res. Bull.* 57(2):165-70, 2002). In other studies, NOS inhibition with L-NAME (Rezvani et al., *Pharmacol. Biochem. Behav.* 50:265-270, 1995) or by i.c.v. injection of nNOS antisense (Naassila et. al., Pharmacol. Biochem. Behav. 67:629-36, 2000) reduced ethanol consumption in these animals. This indicates that NOS inhibition by compounds of the invention may be useful in the treatment of ethanol tolerance and dependence.

Administration of a compound of the invention, either alone or in combination with another therapeutic agent, such as, for example, an NMDA antagonist, may be useful for the treatment of chemical dependencies and drug addictions.

Epilepsy

Co-administration of 7-NI with certain anticonvulsants, such as carbamazepine, shows a synergistic protective effect against amygdala-kindled seizures in rats at concentrations that do not alter roto-rod performance (Borowicz et al., *Epilepsia* 41(9):112-8, 2000). Thus, an NOS inhibitor, such as, for example, a compound of the invention, either alone or in combination with another therapeutic agent, such as, for example, an antiepileptic agent, may be useful for the treatment of epilepsy or a similar disorder. Examples of antiepileptic agents useful in a combination of the invention include carbamazepine, gabapentin, lamotrigine, oxcarbazepine, phenyloin, topiramate, and valproate.

Diabetic Nephropathy

Urinary excretion of NO byproducts is increased in diabetic rats after streptozotocin treatment and increased NO synthesis has been suggested to be involved in diabetic glomerular hyperfiltration. The neuronal isoform nNOS is expressed in the loop of Henle and mucula densa of the kidney and inhibition of this isoform using 7-NI reduces glomerular filtration without affecting renal arteriole pressure or renal blood flow (Sigmon et al., *Gen. Pharmacol.* 34(2):95-100, 2000). Both the non-selective NOS inhibitor L-NAME and the nNOS selective 7-NI normalize renal hyperfiltration in diabetic animals (Ito et al., *J. Lab Clin. Med.* 138(3):177-185, 2001). Therefore, administration of a compound of the invention may be useful for the treatment of diabetic nephropathy.

Medication Overuse Headache

Medication overuse headache (MOH) is associated with excessive use of combination analgesics, opioids, barbiturates, aspirin, NSAIDS, caffeine and triptans and is a common problem that limits the usefulness of these types of medications (Diener and Limmroth. Medication-overuse headache: a worldwide problem. *Lancet Neurol.* 2004: 3, 475-483). It is generally defined as headaches that present >15 days per month (Headache Classification Committee. The International Classification of Headache Disorders (2$^{nd}$ Ed). *Cephalalgia* 2004: 24 (Supple. 1); 9-160). It is well documented that acute treatment of patients for migraine or tension type headache are at increased risk of headache aggravation, develop daily headache, or may become refractory to treatment if the acute medication is taken excessively (Zeeberg et. al. *Cephalalgia* 2006: 26, 1192-1198). MOH patients generally are unresponsive to prophylactic medications while overusing medications. Currently the treatment of choice for MOH is discontinuation of medication although this often associated with withdrawal symptoms such as nausea, vomiting and sleep disturbances. While migraine or tension-type headache patients suffering from MOH that discontinue medication for 2 months have a reduction in headache frequency (45%), many patients were either unchanged (48%) following withdrawal or had an aggravation of headache (Zeeberg et. al. *Cephalalgia* 2006: 26, 1192-1198). Thus there remains a large unmet need for patients suffering from MOH.

It is believed that certain features of MOH, such as increased headache frequency, expansion of headache area and the development of cutaneous allodynia are a result of medication-induced central sensitization of trigeminal nociceptive pathways and periacqueductal grey area (Waeber and Moskowitz. Therapeutic implications of central and peripheral neurologic mechanisms in migraine. *Neurology:* 2003, 61 (Suppl. 4); S9-20). Similar to behavioral sensitization to psychostimulants, the repeated administration of headache medications (e.g., triptans) results in cross-sensitization among different drugs used to treat headache. Changes in synaptic plasticity involve changes in intracellular calcium and nitric oxide levels. Patients suffering from chronic headache, migraine and MOH patients show increased levels of platelet nitrate levels. Thus the development of the sensitization in MOH is likely mediated by the changes in NO and calcium levels in the CNS (Sarchielli et. al. Nitric oxide pathway, Ca2+, and serotonin content in platelets from patients suffering from chronic daily headache. *Cephalalgia* 1999: 19; 810-816). Given that the development of central sensitization is mediated by nNOS (Cizkova et. al. *Brain. Res. Bull.* 2002; 58(2): 161-171, Choi et. al. *J. Neurol. Sci.* 1996; 138(1-2): 14-20, as such, it is expected that neuronal nitric oxide synthase inhibitors, such as the compounds of the invention, will be useful in the prevention and treatment of MOH if used in concomitantly with other headache medications. It is also expected that both CTTH and migraine treatment with nNOS inhibitors will not result in the development of MOH.

Gastrointestinal Disorders nNOS constitutes more than 90% of the total NOS in the small intestine. Although iNOS is constitutively present, it accounts for less than 10% of the total NOS activity, and eNOS is essentially undetectable in the intestine (Qu X W et. al. Type I nitric oxide synthase (NOS) is the predominant NOS in rat small intestine. Regulation by platelet-activating factor. *Biochim Biophys Acta* 1999; 1451: 211-217). The main function of nNOS in the intestine is believed to be regulation of gut motility via neuronal signal transmission in the NANC components of the nervous system. NO regulates the muscle tone of the sphincter in the lower esophagus, pylorus, sphincter of Oddi, and anus. NO also regulates the accommodation reflex of the fundus and the peristaltic reflex of the intestine. NOS inhibitors are known to delay gastric emptying and colonic transit (T. Takahashi J. *Gastroenterol.* 2003; 38(5):421-30). Thus nNOS inhibitors can be therapeutic in GI disorders that would benefit from the delay of gastric emptying or slowing of colonic transit. Dumping syndrome is a disorder that in which food is emptied too quickly from the stomach, filling the small intestine with undigested food that is not adequately prepared to permit efficient absorption of nutrients in the small intestine and is often observed after gastrectomy. Therefore, administration of a compound of the invention may be useful for the treatment of gastrointestinal disorders such as dumping syndrome. The compounds of the invention may also be employed to treat other irritable bowel syndromes.

Visceral Pain

Visceral pain is the most common form of pain and is one of the most difficult forms of pain to treat. Visceral pain is distinct from somatic pain and is generally described as pain that originates from the body's internal cavities or organs and has five important clinical and sensory characteristics: (1) it is not evoked from all visceral organs (e.g., liver, kidney, lung); (2) it is not always linked to visceral injury (e.g., cutting an intestine does not evoke pain); (3) it is diffuse; (4) it is referred to other locations; and (5) it can be referred to other autonomic and motor reflexes (e.g., nausea, lower-back muscle tension from renal colic) (Lancet 353, 2145-48, 1999). Several theories have been proposed for the mechanisms of visceral pain. In the first theory, the viscera are innervated by separate classes of neurons, one concerned with autonomic regulation and the other with sensory phenomena such as pain. The second theory suggests a single homogenous class of sensory receptors that are active at low frequencies (normal regulatory signals) or at high frequencies of activation (induced by intense pain signals). However, studies indicate that the viscera is innervated by two classes of nociceptive sensory receptors: high threshold (mostly mechanical receptors found in heart, vein, lung, airways, esophagus, bilary system, small intestine, colon, ureter, urinary bladder, and uterus, which are activated by noxious stimuli) and low threshold intensity coding receptors that respond to innocuous and noxious stimuli (heart, esophagus, colon, urinary bladder, and testes). Yet another theory suggests a component of afferent fibres that are normally unresponsive to stimuli (silent nociceptors) that can become activated or sensitized during inflammation (*Trends Neurosci.* 15, 374-78, 1992). Once sensitized, these nociceptors now respond to innocuous stimuli that normally occur in the internal organs resulting in an enhanced barrage of convergent input to the spinal cord and subsequently triggering central mechanisms that amplify the effect of the peripheral input.

Visceral pain can result from neoplasm, infection, or injury. For example, visceral pain may be caused by disease or injury to an internal organ, which refers pain to other parts of the body. The compounds of the invention can be also used to treat visceral pain that is, for example, secondary to irritable bowel syndrome, inflammatory bowel syndrome, pancreatitis, diverticulitis, Crohn's disease, peritonitis, pericarditis, hepatitis, appendicitis, colitis, cholecystitis, gastroenteritis, endometriosis, dysmenorrhea, interstitial cystitis, prostatitis, pleuritis, upper gastrointestinal dyspepsia, renal colic, or biliary colic; visceral pain that is secondary to a disease of the liver, kidney, ovary, uterus, bladder, bowel, stomach, esophagus, duodenum, intestine, colon, spleen, pancreas, appendix, heart, or peritoneum; visceral pain that results from a neoplasm or injury, or visceral pain that results from infection. Visceral pain treated by the methods of the invention may be inflammatory or non-inflammatory.

Visceral pain models and assays are known in the art (e.g., Bourdu et al., *Gastroenterology* 128:1996-2008, 2005; Vera-Portocarrero et al., *Gastroenterology* 130:2155-2164, 2006; and Sparmann et al., *Gastroenterology* 112:1664-1672, 1997).

Combination Formulations and Uses Thereof

In addition to the formulations described above, one or more compounds of the invention can be used in combination with other therapeutic agents. For example, one or more compounds of the invention can be combined with another NOS inhibitor. Exemplary inhibitors useful for this purpose include, without limitation, those described in U.S. Pat. Nos. 6,235,747, 7,141,595, and 7,375,219; U.S. patent application Ser. Nos. 09/127,158, 09/325,480, 09/403,177, 09/802,086, 09/826,132, 09/740,385, 09/381,887, 10/476,958, 10/483,140, 10/484,960, 10/678,369, 10/819,853, 10/938,891, 11/436,393, 11/787,167, 12/054,083, and 12/272,656; International Publication Nos. WO 97/36871, WO 98/24766, WO 98/34919, WO 99/10339, WO 99/11620, and WO 99/62883.

In another example, one or more compounds of the invention can be combined with an antiarrhythmic agent. Exemplary antiarrhythmic agents include, without limitation, lidocaine and mixiletine.

GABA-B agonists, alpha-2-adrenergic receptor agonists, cholecystokinin antagonists, $5HT_{1B/1D}$ agonists, or CGRP antagonists can also be used in combination with one or more compounds of the invention. Non-limiting examples of alpha-2-adrenergic receptor agonists include clonidine, lofexidine, and propanolol. Non-limiting examples of cholecystokinin antagonists include L-365, 260; CI-988; LY262691; S0509, or those described in U.S. Pat. No. 5,618,811. Non-limiting examples of $5HT_{1B/1D}$ agonists that may be used in combination with a compound of the invention include dihydroegotamine, eletriptan, frovatriptan, naratriptan, rizatriptan, sumatriptan, donitriptan, or zolmitriptan. Non-limiting examples of CGRP antagonists that may be used in combination with a compound of the invention include quinine analogues as described in International Publication No. WO9709046, non-peptide antagonists as described in International Publication Nos. WO0132648, WO0132649, WO9811128, WO9809630, WO9856779, WO0018764, or other antagonists such as SB-(+)-273779 or BIBN-4096BS.

Substance P antagonists, also known as $NK_1$ receptor antagonists, are also useful in combination with one or more compounds of the invention. Exemplary inhibitors useful for this purpose include, without limitation, those compounds disclosed in U.S. Pat. Nos. 3,862,114, 3,912,711, 4,472,305, 4,481,139, 4,680,283, 4,839,465, 5,102,667, 5,162,339, 5,164,372, 5,166,136, 5,232,929, 5,242,944, 5,300,648, 5,310,743, 5,338,845, 5,340,822, 5,378,803, 5,410,019, 5,411,971, 5,420,297, 5,422,354, 5,446,052, 5,451,586, 5,525,712, 5,527,811, 5,536,737, 5,541,195, 5,594,022, 5,561,113, 5,576,317, 5,604,247, 5,624,950, and 5,635,510; International Publication Nos. WO 90/05525, WO 91/09844, WO 91/12266, WO 92/06079, WO 92/12151, WO 92/15585, WO 92/20661, WO 92/20676, WO 92/21677, WO 92/22569, WO 93/00330, WO 93/00331, WO 93/01159, WO 93/01160, WO 93/01165, WO 93/01169, WO 93/01170, WO 93/06099, WO 93/10073, WO 93/14084, WO 93/19064, WO 93/21155, WO 94/04496, WO 94/08997, WO 94/29309, WO 95/11895, WO 95/14017, WO 97/19942, WO 97/24356, WO 97/38692, WO 98/02158, and WO 98/07694; European Patent Publication Nos. 284942, 327009, 333174, 336230, 360390, 394989, 428434, 429366, 443132, 446706, 484719, 499313, 512901, 512902, 514273, 514275, 515240, 520555, 522808, 528495, 532456, and 591040.

Suitable classes of antidepressant agents that may be used in combination with a compound of the invention include, without limitation, norepinephrine re-uptake inhibitors, selective serotonin re-uptake inhibitors (SSRIs), selective noradrenaline/norepinephrine reuptake inhibitors (NARIs), monoamine oxidase inhibitors (MAOs), reversible inhibitors of monoamine oxidase (RIMAs), dual serotonin/noradrenaline re-uptake inhibitors (SNRIs), α-adrenoreceptor antagonists, noradrenergic and specific serotonergic antidepressants (NaSSAs), and atypical antidepressants.

Non-limiting examples of norepinephrine re-uptake inhibitors include tertiary amine tricyclics and secondary amine tricyclics, such as, for example, adinazolam, amineptine, amoxapine, butriptyline, demexiptiline, desmethylamitriptyline, desmethylclomipramine, demexiptiline, desipramine, doxepin, dothiepin, fluacizine, imipramine, imipramine oxide, iprindole, lofepramine, maprotiline, melitracen, metapramine, norclolipramine, nortriptyline, noxiptilin, opipramol, perlapine, pizotifen, pizotyline, propizepine, protriptyline, quinupramine, tianeptine, trimipramine, trimipramineamiltriptylinoxide, and pharmaceutically acceptable salts thereof.

Non-limiting examples of selective serotonin re-uptake inhibitors include, for example, clomipramine, femoxetine, fluoxetine, fluvoxamine, paroxetine, and sertraline, and pharmaceutically acceptable salts thereof.

Non-limiting examples of selective noradrenaline/norepinephrine reuptake inhibitors include, for example, atomoxetine, bupropion; reboxetine, tomoxetine, and viloxazine and pharmaceutically acceptable salts thereof.

Non-limiting examples of selective monoamine oxidase inhibitors include, for example, isocarboxazid, phenelzine, tranylcypromine and selegiline, and pharmaceutically acceptable salts thereof. Other monoamine oxidase inhibitors useful in a combination of the invention include clorgyline, cimoxatone, befloxatone, brofaromine, bazinaprine, BW-616U (Burroughs Wellcome), BW-1370U87 (Burroughs Wellcome), CS-722 (RS-722) (Sankyo), E-2011 (Eisai), harmine, harmaline, moclobemide, PharmaProjects 3975 (Hoechst), RO 41-1049 (Roche), RS-8359 (Sankyo), T-794 (Tanabe Seiyaku), toloxatone, K-Y 1349 (Kalir and Youdim), LY-51641 (Lilly), LY-121768 (Lilly), M&B 9303 (May & Baker), MDL 72394 (Marion Merrell), MDL 72392 (Marion Merrell), sercloremine, and MO 1671, and pharmaceutically acceptable salts thereof. Suitable reversible inhibitors of monoamine oxidase that may be used in the present invention include, for example, moclobemide, and pharmaceutically acceptable salts thereof.

Non-limiting examples of dual serotonin/norepinephrine reuptake blockers include, for example, duloxetine, milnacipran, mirtazapine, nefazodone, and venlafaxine.

Non-limiting examples of other antidepressants that may be used in a method of the present invention include adinazolam, alaproclate, amineptine, amitriptyline amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dimetacrine, dothiepin, droxidopa, enefexine, estazolam, etoperidone, fengabine, fezolamine, fluotracen, idazoxan, indalpine, indeloxazine, levoprotiline, litoxetine; medifoxamine, metralindole, mianserin, minaprine, montirelin, nebracetam, nefopam, nialamide, nomifensine, norfluoxetine, orotirelin, oxaflozane, pinazepam, pirlindone, ritanserin, rolipram, sercloremine, setiptiline, sibutramine, sulbutiamine, sulpiride, tenilox-azine, thozalinone, thymoliberin, tiflucarbine, tofenacin, tofisopam, toloxatone, veralipride, viqualine, zimelidine, and zometrapine, and pharmaceutically acceptable salts thereof, and St. John's wort herb, or *Hypencuin perforatum*, or extracts thereof.

In another example, opioids can be used in combination with one or more compounds of the invention. Exemplary opioids useful for this purpose include, without limitation, alfentanil, butorphanol, buprenorphine, dextromoramide, dezocine, dextropropoxyphene, codeine, dihydrocodeine, diphenoxylate, etorphine, fentanyl, hydrocodone, hydromorphone, ketobemidone, loperamide, levorphanol, levomethadone, meperidine, meptazinol, methadone, morphine, morphine-6-glucuronide, nalbuphine, naloxone, oxycodone, oxymorphone, pentazocine, pethidine, piritramide, propoxylphene, remifentanil, sulfentanyl, tilidine, and tramadol.

In yet another example, anti-inflammatory compounds, such as steroidal agents or non-steroidal anti-inflammatory drugs (NSAIDs), can be used in combination with one or more compounds of the invention. Non-limiting examples of steroidal agents include prednisolone and cortisone. Non-limiting examples of NSAIDs include acemetacin, aspirin, celecoxib, deracoxib, diclofenac, diflunisal, ethenzamide, etofenamate, etoricoxib, fenoprofen, flufenamic acid, flurbiprofen, lonazolac, lomoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, and 2-(3,5-difluorophenyl)-3-[4-(methylsulfonyl)phenyl]-2-cyclopenten-1-one). Compounds of the invention may also be use in combination with acetaminophen.

Any of the above combinations can be used to treat any appropriate disease, disorder, or condition. Exemplary uses for combinations of a compound of the invention and another therapeutic agent are described below.

Opioid-NOS Inhibitor Combinations in Chronic, Neuropathic Pain

Nerve injury can lead to abnormal pain states known as neuropathic pain. Some of the clinical symptoms include tactile allodynia (nociceptive responses to normally innocuous mechanical stimuli), hyperalgesia (augmented pain intensity in response to normally painful stimuli), and spontaneous pain. Spinal nerve ligation (SNL) in rats is an animal model of neuropathic pain that produces spontaneous pain, allodynia, and hyperalgesia, analogous to the clinical symptoms observed in human patients (Kim and Chung, *Pain* 50:355-363, 1992; Seltzer, *Neurosciences* 7:211-219, 1995).

Neuropathic pain can be particularly insensitive to opioid treatment (Benedetti et al., *Pain* 74:205-211, 1998) and is still considered to be relatively refractory to opioid analgesics (MacFarlane et al., *Pharmacol. Ther.* 75:1-19, 1997; Watson, *Clin. J. Pain* 16:S49-S55, 2000). While dose escalation can overcome reduced opioid effectiveness, it is limited by increased side effects and tolerance. Morphine administration is known to activate the NOS system, which limits the analgesic action of this drug (Machelska et al., *NeuroReport* 8:2743-2747, 1997; Wong et al., *Br. J. Anaesth.* 85:587, 2000; Xiangqi and Clark, *Mol. Brain. Res.* 95:96-102, 2001). However, it has been shown that the combined systemic administration of morphine and L-NAME can attenuate mechanical and cold allodynia at subthreshold doses at which neither drug administered alone was effective (Ulugol et al., *Neurosci. Res. Com.* 30(3):143-153, 2002). The effect of L-NAME co-administration on morphine analgesia appears to be mediated by nNOS, as L-NAME loses its ability to potentiate morphine analgesia in nNOS null-mutant mice (Clark and Xiangqi, *Mol. Brain. Res.* 95:96-102, 2001). Enhanced analgesia has been demonstrated in the tail-flick or paw pressure models using coadministration of L-NAME or 7-NI with either a mu-, delta-, or kappa-selective opioid agonist (Machelska et al., *J. Pharmacol. Exp. Ther.* 282:977-984, 1997).

While opioids are an important therapy for the treatment of moderate to severe pain, in addition to the usual side effects that limit their utility, the somewhat paradoxical appearance of opioid-induced hyperalgesia may actually render patients more sensitive to pain and potentially aggravate their pain (Angst and Clark, Anesthesiology, 2006, 104(3), 570-587; Chu et. al. J. Pain 2006, 7(1) 43-48). The development of tolerance and opioid induced hyperalgesia is consistent with increased levels of NO production in the brain. The reduced analgesic response to opioids is due to an NO-induced upregulated hyperalgesic response (Heinzen and Pollack, Brain Res. 2004, 1023, 175-184).

Thus, the combination of an nNOS inhibitor with an opioid (for example, those combinations described above) can enhance opioid analgesia in neuropathic pain and prevent the development of opioid tolerance and opioid-induced hyperalgesia.

Antidepressant-NOS Inhibitor Combinations for Chronic Pain, Neuropathic Pain, Chronic Headache or Migraine Many antidepressants are used for the treatment of neuropathic pain (McQuay et al., *Pain* 68:217-227, 1996) and migraine (Tomkins et al., *Am. J. Med.* 111:54-63, 2001), and act via the serotonergic or noradrenergic system. NO serves as a neuromodulator of these systems (Garthwaite and Boulton, *Annu. Rev. Physiol.* 57:683, 1995). 7-NI has been shown to potentiate the release of noradrenaline (NA) by the nicotinic acetylcholine receptor agonist DMPP via the NA transporter (Kiss et al., *Neuroscience Lett.* 215:115-118, 1996). It has been shown that local administration of antidepressants, such as paroxetine, tianeptine, and imipramine decrease levels of hippocampal NO (Wegener et al., *Brain Res.* 959:128-134, 2003). It is likely that NO is important in the mechanism by which antidepressants are effective for treating pain and depression, and that a combination of an nNOS inhibitor with an antidepressant, such as, for example, those combinations described above, will produce better treatments.

Serotonin $5HT_{1B/1D/1F}$ Agonist or CGRP Antagonist and NOS Inhibitor Combinations in Migraine Administration of glyceryl trinitrate (GTN), an NO donor, induces immediate headaches in normal individuals and results in delayed migraine attacks in migraineurs with a 4-6 hour latency period (Iversen et al., *Pain* 38:17-24, 1989). In patients with migraine attack, levels of CGRP (Calcitonin Gene Related Peptide), a potent vasodialator, in the carotid artery correlate with the onset and ablation of migraine attack (Durham, *Curr Opin Investig Drugs* 5(7):731-5, 2004). Sumatriptan, an antimigraine drug having affinity at $5HT_{1B}$, $5HT_{1D}$, and $5HT_{1F}$ receptors, reduces GTN-induced immediate headache and in parallel contracts cerebral and extracerebral arteries (Iversen and Olesen, *Cephalagia* 13(Suppl 13):186, 1993). The antimigraine drug rizatriptan also reduces plasma levels of CGRP following migraine pain reduction (Stepien et al., *Neurol. Neurochir. Pol.* 37(5):1013-23, 2003). Both NO and CGRP have therefore been implicated as a cause for migraine. Serotonin $5HT_{1B/1D}$ agonists have been shown to block NMDA receptor-evoked NO signaling in brain cortex slices (Strosznajder et al., *Cephalalgia* 19(10):859, 1999). These results suggest that a combination of a compound of the invention and a selective or non-selective $5HT_{1B/1D/1F}$ agonist or a CGRP antagonist, such as those combinations described above, would be useful for the treatment of migraine.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 0.05 mg and 3000 mg (measured as the solid form). A preferred dose ranges between 0.05-500 mg/kg, more preferably between 0.5-50 mg/kg.

A compound of the invention can be used alone or in combination with other agents that have NOS-inhibiting activity, or in combination with other types of treatment (which may or may not inhibit NOS) to treat, prevent, and/or reduce the risk of stroke, neuropathic or migraine pain, or other disorders that benefit from NOS inhibition. In combination treatments, the dosages of one or more of the therapeutic compounds may be reduced from standard dosages when administered alone. In this case, dosages of the compounds when combined should provide a therapeutic effect.

In addition to the above-mentioned therapeutic uses, a compound of the invention can also be used in diagnostic assays, screening assays, and as a research tool.

In diagnostic assays, a compound of the invention may be useful in identifying or detecting NOS activity. For such a use, the compound may be radiolabeled (as described elsewhere herein) and contacted with a population of cells of an organism. The presence of the radiolabel on the cells may indicate NOS activity.

In screening assays, a compound of the invention may be used to identify other compounds that inhibit NOS, for example, as first generation drugs. As research tools, the compounds of the invention may be used in enzyme assays and assays to study the localization of NOS activity. Such information may be useful, for example, for diagnosing or monitoring disease states or progression. In such assays, a compound of the invention may also be radiolabeled.

NOS In Vitro Inhibition Assays

The compounds of the present invention have been found to exhibit selective inhibition of the neuronal isoform of NOS (nNOS). Compounds may be examined for their efficacy in preferentially inhibiting nNOS over iNOS and/or eNOS by a person skilled in the art, for example, by using the methods described in Example 34 and herein below.

The following non-limiting examples are illustrative of the present invention:

EXAMPLES

Example 1

Synthesis of N-(4-(2-(1-methylpyrrolidin-2-yl)ethyl)-3-oxochroman-7-yl)thiophene-2-carboximidamide (1)

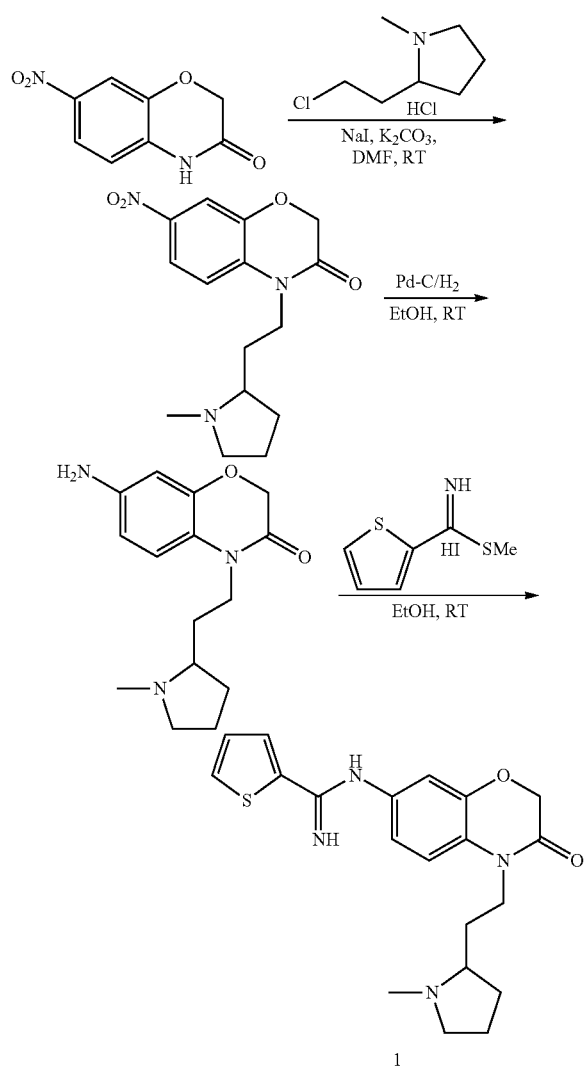

7-Nitro-2H-benzo[b][1,4]oxazin-3(4H)-one: Prepared according to reported procedure in *J. Chem. Research* (M) 2003, 1120-1128.

4-(2-(1-Methylpyrrolidin-2-yl)ethyl)-7-nitro-2H-benzo[b][1,4]oxazin-3(4H)-one: A suspension of 7-nitro-2H-benzo[b][1,4]oxazin-3(4H)-one (0.5 g, 2.575 mmol), 2-(2-chloroethyl)-1-methylpyrrolidine hydrochloride (0.94 g, 5.150 mmol), NaI (0.19 g, 1.287 mmol), and $K_2CO_3$ (2.13 g, 15.452 mmol) in dry DMF (10 mL) was stirred at room temperature overnight (18 hours). The reaction was diluted with water (150 mL), and the product was extracted into ethyl acetate (2×25 mL). The combined ethyl acetate layers were washed with brine (20 mL) and dried ($Na_2SO_4$). The solvent was evaporated, and the crude material was purified by column chromatography (3:97 (2M $NH_3$ in MeOH):$CH_2Cl_2$) to obtain the title compound (0.525 g, 67%) as a yellow solid. $^1$H NMR (DMSO-$d_6$) δ 1.47-1.65 (m, 4H), 1.79-2.13 (m, 4H), 2.18 (s, 3H), 2.89-2.95 (m, 1H), 3.98 (t, 2H, J=7.8 Hz), 4.79 (s, 2H), 7.40 (d, 1H, J=9.0 Hz), 7.80 (d, 1H, J=2.7 Hz), 7.98 (dd, 1H, J=2.4, 9.0 Hz); ESI-MS (m/z, %): 306 ($MH^+$, 100).

7-Amino-4-(2-(1-methylpyrrolidin-2-yl)ethyl)-2H-benzo[b][1,4]oxazin-3(4H)-one: A solution of 4-(2-(1-methylpyrrolidin-2-yl)ethyl)-7-nitro-2H-benzo[b][1,4]oxazin-3(4H)-one (0.49 g, 1.604 mmol) in dry ethanol (5 mL) was treated with Pd—C (~0.05 g) and purged with hydrogen gas. The flask was evacuated and purged twice with hydrogen gas. The reaction stirred at room temperature under hydrogen atmosphere (balloon pressure) for 2 hours. The reaction was filtered through a Celite bed and washed with methanol (3×10 mL). The combined organic layers were evaporated to obtain the crude title compound (0.44 g, quantitative) as a solid. $^1$H NMR (DMSO-$d_6$) δ 1.39-1.51 (m, 2H), 1.56-1.66 (m, 2H), 1.76-2.06 (m, 4H), 2.16 (s, 3H), 2.88-2.94 (m, 1H), 3.74-3.86 (m, 2H), 4.46 (s, 2H), 5.01 (s, 2H), 6.22 (d, 1H, J=2.4 Hz), 6.26 (dd, 1H, J=2.1, 8.4 Hz), 6.82 (d, 1H, J=8.4 Hz); ESI-MS (m/z, %): 276 ($MH^+$, 100).

N-(4-(2-(1-Methylpyrrolidin-2-yl)ethyl)-3-oxochroman-7-yl)thiophene-2-carboximidamide (1): A solution of 7-amino-4-(2-(1-methylpyrrolidin-2-yl)ethyl)-2H-benzo[b][1,4]oxazin-3(4H)-one (0.12 g, 0.435 mmol) in dry ethanol (5 mL) was treated with methyl thiophene-2-carbimidothioate hydroiodide (0.24 g, 0.871 mmol) at room temperature. The resulting mixture was stirred over night (18 hours). At this time, additional methyl thiophene-2-carbimidothioate hydroiodide (0.24 g, 0.871 mmol) was added, and the reaction stirred for an additional 24 hours. The reaction was diluted with saturated $NaHCO_3$ solution (25 mL), and the product was then extracted into $CH_2Cl_2$ (2×20 mL). The combined $CH_2Cl_2$ layers was washed with brine (15 mL) and dried ($Na_2SO_4$). The solvent was evaporated, and the crude material was purified by column chromatography (5:95 (2 M $NH_3$ in MeOH):$CH_2Cl_2$) to obtain title compound 1 (0.155 g, 93%) as a solid. $^1$H NMR (DMSO-$d_6$) δ 1.46-1.65 (m, 4H), 1.64-2.13 (m, 4H), 2.20 (s, 3H), 2.90-2.96 (m, 1H), 3.86-3.93 (m, 2H), 4.58 (s, 2H), 6.49-6.58 (m, 4H), 7.07-7.10 (m, 2H), 7.60 (d, 1H, J=5.4 Hz), 7.73 (d, 1H, J=3.0 Hz); ESI-MS (m/z, %): 385 ($MH^+$, 68), 274 (46), 193 (100); ESI-HRMS calculated for $C_{20}H_{25}N_4O_2S$ ($MH^+$), calculated: 385.1692, observed: 385.1687; HPLC purity 98% by area.

Example 2

Synthesis of N-(4-(2-(1-methylpyrrolidin-2-yl)ethyl)chroman-7-yl)thiophene-2-carboximidamide (2)

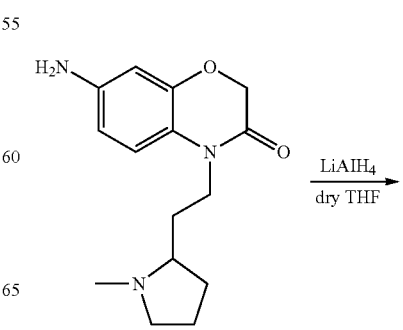

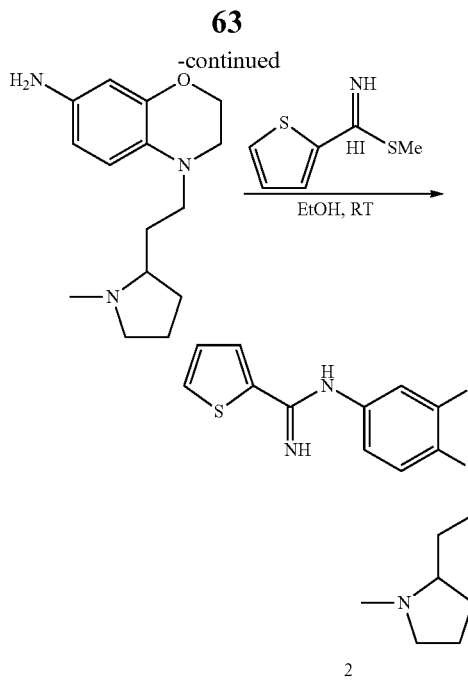

7-Amino-4-(2-(1-methylpyrrolidin-2-yl)ethyl)-2H-benzo[b][1,4]oxazin-3(4H)-one: For complete experimental details and spectral data, see Example 1.

4-(2-(1-Methylpyrrolidin-2-yl)ethyl)-3,4-dihydro-2H-benzo[b][1,4]oxazin-7-amine: A solution of LiAlH$_4$ (4.21 mL, 4.212 mmol, 1.0 M solution in THF) was treated dropwise with 7-amino-4-(2-(1-methylpyrrolidin-2-yl)ethyl)-2H-benzo[b][1,4]oxazin-3(4H)-one (0.29 g, 1.053 mmol) in dry THF (5 mL) at 0° C. The resulting mixture was brought to room temperature and stirred overnight. The reaction was carefully quenched with the sequential addition of water (0.16 mL), 2 N NaOH solution (0.16 mL), and water (0.16 mL). The reaction was filtered after stirring for 30 minutes at room temperature and washed with CH$_2$Cl$_2$ (3×10 mL). The combined CH$_2$Cl$_2$ layers were evaporated, and the crude material was purified by column chromatography (5:95 (2M NH$_3$ in MeOH):CH$_2$Cl$_2$) to obtain the title compound (0.23 g, 84%) as a syrup. $^1$H NMR (DMSO-d$_6$) δ 1.28-1.45 (m, 2H), 1.56-1.65 (m, 2H), 1.75-2.10 (m, 4H), 2.18 (s, 3H), 2.88-2.95 (m, 1H), 3.03-3.10 (m, 4H), 4.08 (t, 2H, J=4.8 Hz), 4.36 (s, 2H), 6.00 (d, 1H, J=2.4 Hz), 6.06 (dd, 1H, J=2.4, 8.5 Hz), 6.43 (d, 1H, J=8.4 Hz); ESI-MS (m/z, %): 262 (MH$^+$, 100), 163 (33), 112 (42).

N-(4-(2-(1-Methylpyrrolidin-2-yl)ethyl)chroman-7-yl) thiophene-2-carboximidamide (2): A solution of 4-(2-(1-methylpyrrolidin-2-yl)ethyl)-3,4-dihydro-2H-benzo[b][1,4]oxazin-7-amine (0.21 g, 0.803 mmol) in dry ethanol (5 mL) was treated with methyl thiophene-2-carbimidothioate hydroiodide (0.45 g, 1.606 mmol) at room temperature. The resulting mixture was stirred at room temperature for 24 hours. The reaction was diluted with saturated NaHCO$_3$ solution (20 mL), and the product was extracted into CH$_2$Cl$_2$ (2×20 mL). The combined CH$_2$Cl$_2$ layers were washed with brine (15 mL) and dried (Na$_2$SO$_4$). The solvent was evaporated, and the crude material was purified by column chromatography (5:95 (2 M NH$_3$ in MeOH):CH$_2$Cl$_2$) to obtain the title compound 2 (0.22 g, 75%) as a solid. $^1$H NMR (DMSO-d$_6$) δ 1.35-1.52 (m, 2H), 1.58-1.68 (m, 2H), 1.82-2.08 (m, 4H), 2.21 (s, 3H), 2.90-2.97 (m, 1H), 3.18-3.32 (m, 4H), 4.16 (t, 2H, J=4.5 Hz), 6.22-6.34 (m, 4H), 6.63 (d, 1H, J=8.4 Hz), 7.06 (dd, 1H, J=3.9, 5.1 Hz), 7.55 (d, 1H, J=5.1 Hz), 7.68 (d, 1H, J=3.6 Hz);

ESI-MS (m/z, %): 371 (MH$^+$, 86), 260 (56), 186 (100), 128 (81); ESI-HRMS calculated for C$_{20}$H$_{27}$N$_4$OS (MH$^+$), calculated: 371.1900, observed: 371.1903; HPLC purity 98.2% by area.

Example 3

Synthesis of N-(3-oxo-4-(2-(pyrrolidin-1-yl)ethyl)-3,4-dihydro-2H-benzo[b][1,4]oxazin-7-yl) thiophene-2-carboximidamide (3)

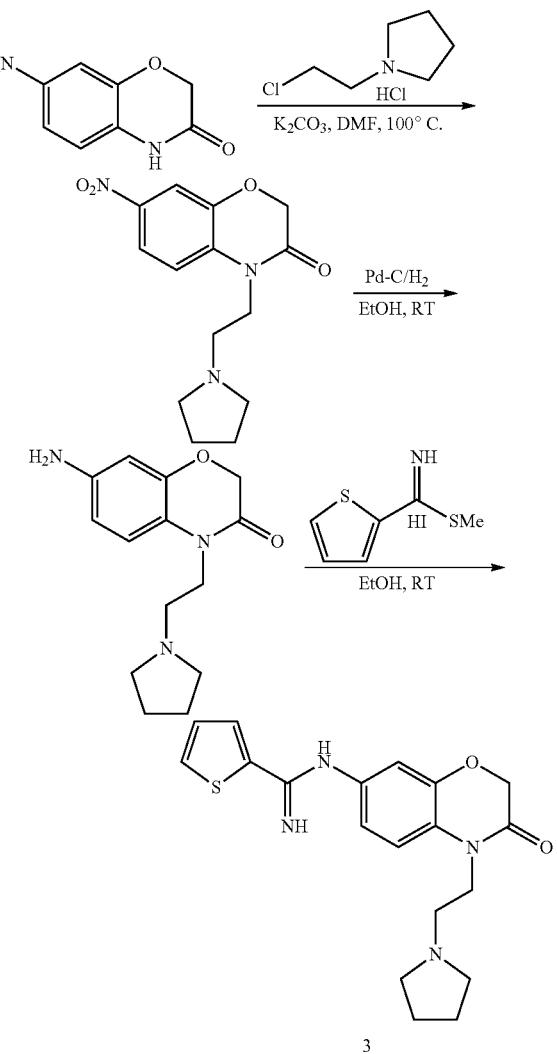

7-Nitro-2H-benzo[b][1,4]oxazin-3(4H)-one: Prepared according to reported procedure in *J. Chem. Research (M)* 2003, 1120-1128.

7-Nitro-4-(2-(pyrrolidin-1-yl)ethyl)-2H-benzo[b][1,4]oxazin-3(4H)-one: A suspension of 7-nitro-2H-benzo[b][1,4]oxazin-3(4H)-one (0.5 g, 2.575 mmol), 1-(2-chloroethyl)pyrrolidine hydrochloride (0.43 g, 2.575 mmol) and K$_2$CO$_3$ (1.06 g, 7.726 mmol) in dry DMF (5 mL) was stirred at 100° C. overnight (18 hours). The reaction was brought to room temperature, diluted with water (100 mL), and the product was extracted into ethyl acetate (2×25 mL). The combined ethyl acetate layers were washed with brine (20 mL) and dried (Na$_2$SO$_4$). The solvent was evaporated, and the crude material was purified by column chromatography (3:97 (2M NH$_3$ in MeOH):CH$_2$Cl$_2$) to obtain the title compound (0.49 g, 65%) as a solid. $^1$H NMR (DMSO-d$_6$) δ 1.62-1.70 (m, 4H), 2.46-2.54 (m, 4H, merged with DMSO-d$_6$ resonance), 2.60 (t, 2H, J=6.9 Hz), 4.08 (t, 2H, J=6.9 Hz), 4.80 (s, 2H), 7.44 (d, 1H, J=9.3 Hz), 7.80 (d, 1H, J=2.4 Hz), 7.96 (dd, 1H, J=2.7, 9.0 Hz); ESI-MS (m/z, %): 292 (MH$^+$, 100).

7-Amino-4-(2-(pyrrolidin-1-yl)ethyl)-2H-benzo[b][1,4]oxazin-3(4H)-one: A solution of 7-nitro-4-(2-(pyrrolidin-1-yl)ethyl)-2H-benzo[b][1,4]oxazin-3(4H)-one (0.46 g, 1.579 mmol) in dry ethanol (5 mL) was treated with Pd—C (~0.05 g) and purged with hydrogen gas. The reaction was stirred under hydrogen atmosphere (balloon pressure) for 4 hours. The reaction was filtered through a Celite bed and washed with methanol (3×10 mL). The combined organic layers were evaporated and dried under vacuum to obtain the crude title compound (0.4 g, 97%) as a solid. $^1$H NMR (DMSO-d$_6$) δ 1.61-1.70 (m, 4H), 2.44-2.56 (m, 6H, merged with DMSO-d$_6$), 3.90 (t, 2H, J=7.2 Hz), 4.47 (s, 2H), 5.01 (s, 2H), 6.22 (d, 1H, J=2.4 Hz), 6.25 (dd, 1H, J=2.4, 8.2 Hz), 6.84 (d, 1H, J=8.7 Hz); ESI-MS (m/z, %): 262 (MH$^+$, 100), 191 (44).

N-(3-Oxo-4-(2-(pyrrolidin-1-yl)ethyl)-3,4-dihydro-2H-benzo[b][1,4]oxazin-7-yl) thiophene-2-carboximidamide (3): A solution of 7-amino-4-(2-(pyrrolidin-1-yl)ethyl)-2H-benzo[b][1,4]oxazin-3(4H)-one (0.125 g, 0.478 mmol) in dry ethanol (5 mL) was treated with methyl thiophene-2-carbimidothioate hydroiodide (0.27 g, 0.956 mmol) at room temperature. The resulting mixture was stirred for 2 days. The reaction was then diluted with saturated NaHCO$_3$ solution (20 mL), and the product was extracted into CH$_2$Cl$_2$ (2×20 mL). The combined CH$_2$Cl$_2$ layers were washed with brine (15 mL) and dried (Na$_2$SO$_4$). The solvent was evaporated, and the crude material was purified by column chromatography (3:97 (2 M NH$_3$ in MeOH):CH$_2$Cl$_2$) to obtain the title compound 3 (0.16 g, 90%) as a solid. $^1$H NMR (DMSO-d$_6$) δ 1.64-1.72 (m, 4H), 2.46-2.54 (m, 4H, merged with DMSO-d$_6$ resonance), 2.60 (t, 2H, J=7.2 Hz), 3.99 (t, 2H, J=7.2 Hz), 4.58 (s, 2H), 6.47-6.57 (m, 4H), 7.06-7.12 (m, 2H), 7.60 (d, 1H, J=4.2 Hz), 7.73 (d, 1H, J=3.3 Hz); ESI-MS (m/z, %): 371 (MH$^+$, 66), 150 (63), 128 (100); ESI-HRMS calculated for C$_{19}$H$_{23}$N$_4$O$_2$S (MH$^+$), calculated: 371.1536, observed: 371.1548; HPLC purity 93.17% by area.

Example 4

Synthesis of N-(4-(2-(pyrrolidin-1-yl)ethyl)-3,4-dihydro-2H-benzo[b][1,4]oxazin-7-yl)thiophene-2-carboximidamide (4)

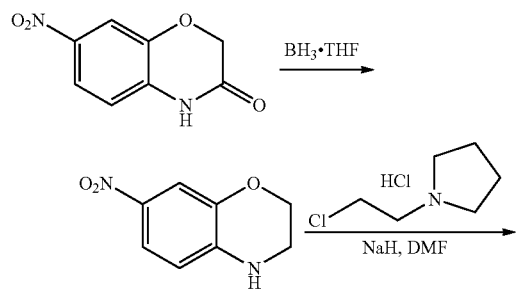

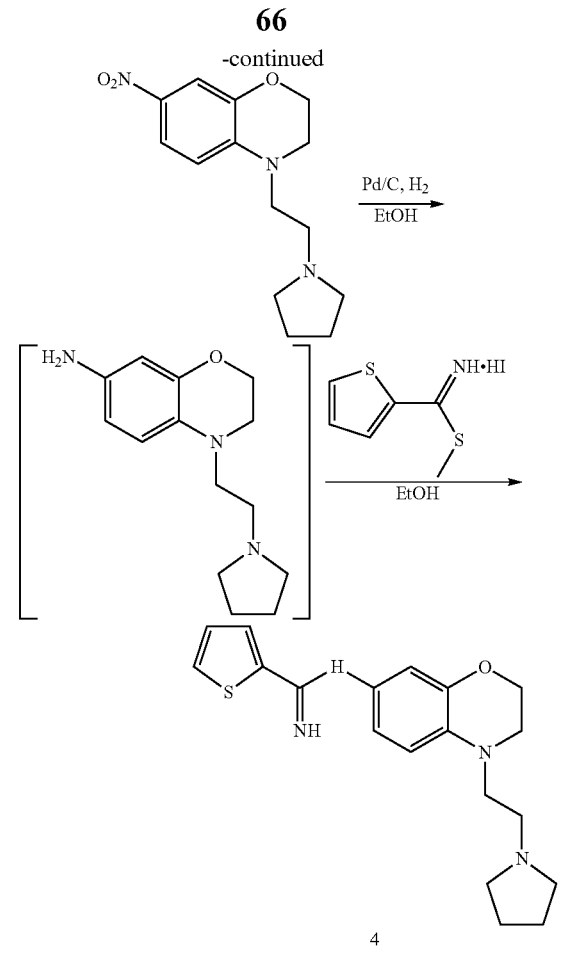

7-Nitro-2H-benzo[b][1,4]oxazin-3(4H)-one: Prepared according to a literature procedure in *J. Chem. Research (M)* 2003, 1120-1128.

7-Nitro-3,4-dihydro-2H-benzo[b][1,4]oxazine: A suspension of 7-nitro-2H-benzo[b][1,4]oxazin-3(4H)-one (300 mg, 1.545 mmol) in THF (3 mL) was treated with BH$_3$-THF complex (15.45 mL, 15.45 mmol, 1.0 M in THF), and the resulting orange solution was refluxed overnight. The reaction was cooled in an ice-bath. MeOH (15 mL) was added, and the reaction was then concentrated. A second portion of MeOH (20 mL) was added, and the solution was refluxed for 2 hours. At this time, the reaction was concentrated, and the residue was subjected to flash chromatography on silica gel (10% EtOAc:90% hexane followed by 30% EtOAc:70% hexane). An orange solid was obtained after drying under reduced pressure. (240 mg, 86%). $^1$H-NMR (DMSO-d$_6$) δ 7.68 (dd, J=2.4, 8.9 Hz, 1H), 7.54 (s, 1H), 7.47 (d, J=2.4 Hz, 1H), 6.63 (d, J=9.0 Hz, 1H), 4.15 (t, J=4.2 Hz, 2H), 3.45-3.40 (m, 2H).

7-Nitro-4-(2-(pyrrolidin-1-yl)ethyl)-3,4-dihydro-2H-benzo[b][1,4]oxazine: A solution of 7-nitro-3,4-dihydro-2H-benzo[b][1,4]oxazine (300 mg, 1.665 mmol) in DMF (10 mL) was treated with NaH (213 mg, 5.33 mmol, 60% wt in mineral oil) at 0° C., resulting in a bright orange suspension. The mixture was stirred for 10 minutes. 2-chloroethyl-pyrrolidine hydrochloride (566 mg, 3.33 mmol) was then added, and the reaction turned into a bright red suspension. The reaction was heated to 90° C. for 1 hour and then cooled to room temperature. The mixture was then diluted with water (20 mL), transferred to a separatory funnel, and extracted into EtOAc (2×15 mL). The combined organic layers were washed with brine (3×5 mL), dried (Na$_2$SO$_4$), filtered, and concentrated. The residue was subjected to flash chromatography on silica gel using CH$_2$Cl$_2$ followed by 5:95 (2M NH$_3$ in MeOH):CH$_2$Cl$_2$ to give a solid (330 mg, 72%). $^1$H-NMR (DMSO-d$_6$) δ 7.75 (dd, J=2.7, 9.3 Hz, 1H), 7.47 (d, J=2.7 Hz, 1H), 6.80 (d, J=9.0 Hz, 1H), 4.18 (t, J=4.2 Hz, 2H), 3.58-3.55 (m, 4H), 2.63 (t, J=6.9 Hz, 2H), 2.58-2.48 (m, 4H), 1.70-1.63 (m, 4H); ESI-MS (m/z, %): 278 (MH$^+$, 100), 98 (20).

N-(4-(2-(Pyrrolidin-1-yl)ethyl)-3,4-dihydro-2H-benzo[b][1,4]oxazin-7-yl)thiophene-2-carboximidamide (4): A suspension of 7-nitro-4-(2-(pyrrolidin-1-yl)ethyl)-3,4-dihydro-2H-benzo[b][1,4]oxazine (330 mg, 1.190 mmol) and Pd—C (252 mg, 0.238 mmol, 10% wt) in dry EtOH (10 mL) was purged with hydrogen gas. The reaction was stirred at room temperature for 1.5 hours under a hydrogen atmosphere (balloon pressure). The reaction mixture was filtered through a Celite pad and washed with EtOH (25 mL). The filtrate was treated with methyl thiophene-2-carbimidothioate hydroiodide (0.678 g, 2.377 mmol) and stirred for three days at room temperature. The reaction was diluted with saturated NaHCO$_3$ solution (50 mL), and the product was extracted into CH$_2$Cl$_2$ (3×25 mL). The combined organic layers were dried (Na$_2$SO$_4$) and concentrated. The residue was subjected to flash chromatography on silica gel using 2:98 MeOH:CH$_2$Cl$_2$ followed by 5:95 (2M NH$_3$ in MeOH):CH$_2$Cl$_2$ to give a yellow solid (150 mg, 36%). $^1$H-NMR (DMSO-d$_6$) δ 7.70 (d, J=3.6 Hz, 1H), 7.57 (dd, J=5.1, 0.9 Hz, 1H), 7.08 (dd, J=5.1, 3.9 Hz, 1H), 6.65 (d, J=8.4 Hz, 1H), 6.34 (dd, J=2.4, 8.4 Hz, 1H), 6.252 (d, J=2.4, 1H), 6.36-6.25 (m, 2H), 4.15 (t, J=4.2 Hz, 2H), 3.38-3.30 (m, 4H), 2.64 (t, J=7.2 Hz, 2H), 2.58-2.48 (m, 4H), 1.70-1.67 (m, 4H); ESI-MS (m/z, %): 357 (MH$^+$, 100), 260 (40), 98 (27); ESI-HRMS calculated for C$_{19}$H$_{25}$N$_4$OS (MH$^+$): 357.1743, observed: 357.1734; HPLC purity: 95.8% by area.

Example 5

N-(4-(2-(Dimethylamino)ethyl)-3-oxo-3,4-dihydro-2H-benzo[b][1,4]oxazin-7-yl)thiophene-2-carboximidamide (5)

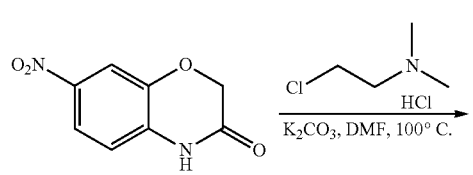

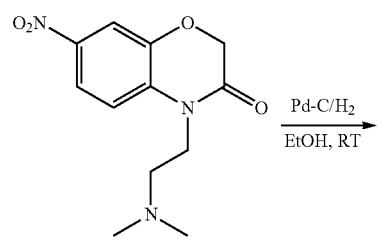

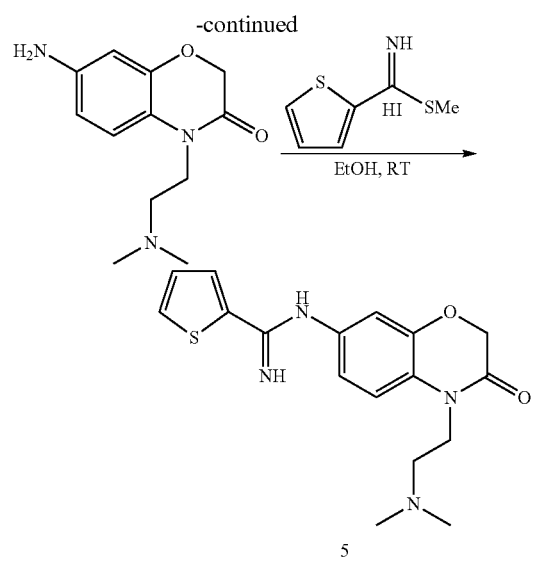

7-Nitro-2H-benzo[b][1,4]oxazin-3(4H)-one: Prepared according to reported procedure in *J. Chem. Research* (M) 2003, 1120-1128.

4-(2-(Dimethylamino)ethyl)-7-nitro-2H-benzo[b][1,4]oxazin-3(4H)-one: A suspension of 7-nitro-2H-benzo[b][1,4]oxazin-3(4H)-one (0.5 g, 2.575 mmol), 2-chloro-N,N-dimethylethanamine hydrochloride (0.37 g, 2.575 mmol), and K$_2$CO$_3$ (1.06 g, 7.726 mmol) in dry DMF (5 mL) was stirred at 100° C. overnight (18 hours). The reaction was brought to room temperature, diluted with water (100 mL), and the product was extracted into ethyl acetate (2×25 mL). The combined ethyl acetate layers were washed with brine (20 mL) and then dried (Na$_2$SO$_4$). The solvent was evaporated, and the crude material was purified by column chromatography (3:97 (2M NH$_3$ in MeOH):CH$_2$Cl$_2$) to obtain the title compound (0.52 g, 76%) as a yellow solid. $^1$H NMR (DMSO-d$_6$) δ 2.17 (s, 6H), 2.42 (t, 2H, J=6.6 Hz), 4.07 (t, 2H, J=6.6 Hz), 4.79 (s, 2H), 7.45 (d, 1H, J=9.0 Hz), 7.80 (d, 1H, J=2.7 Hz), 7.96 (dd, 1H, J=2.4, 9.0 Hz); ESI-MS (m/z, %): 266 (MH$^+$, 100), 221 (66).

7-Amino-4-(2-(dimethylamino)ethyl)-2H-benzo[b][1,4]oxazin-3(4H)-one: A solution of 4-(2-(dimethylamino)ethyl)-7-nitro-2H-benzo[b][1,4]oxazin-3(4H)-one (0.5 g, 1.884 mmol) in dry ethanol (5 mL) was treated with Pd—C (~0.05 g) and purged with hydrogen gas. The flask was evacuated and purged with hydrogen gas (twice) and stirred at room temperature under hydrogen atm. (balloon pressure) for 2 hours. The reaction was filtered through a Celite bed and washed with methanol (3×10 mL). The combined organic layers were evaporated to obtain the crude title compound (0.44 g, quantitative) as a solid. $^1$H NMR (DMSO-d$_6$) δ 2.16 (s, 6H), 2.36 (t, 2H, J=6.9 Hz), 3.88 (t, 2H, J=6.9 Hz), 4.47 (s, 2H), 5.01 (s, 2H), 6.21 (d, 1H, J=2.1 Hz), 6.25 (dd, 1H, J=2.7, 8.5 Hz), 6.84 (d, 1H, J=8.4 Hz); ESI-MS (m/z, %): 236 (MH$^+$, 31), 191 (100).

N-(4-(2-(Dimethylamino)ethyl)-3-oxo-3,4-dihydro-2H-benzo[b][1,4]oxazin-7-yl)thiophene-2-carboximidamide (5): A solution of 7-amino-4-(2-(dimethylamino)ethyl)-2H-benzo[b][1,4]oxazin-3(4H)-one (0.125 g, 0.531 mmol) in dry ethanol (10 mL) was treated with methyl thiophene-2-carbimidothioate hydroiodide (0.3 g, 1.062 mmol) at room temperature and stirred overnight (18 hours). At this time, additional methyl thiophene-2-carbimidothioate hydroiodide (0.3 g, 1.062 mmol) was added, and stirring was continued for another 24 hours. The reaction was diluted with saturated NaHCO₃ solution (20 mL), and the product was extracted into CH₂Cl₂ (2×20 mL). The combined CH₂Cl₂ layers were washed with brine (15 mL) and dried (Na₂SO₄). The solvent was evaporated, and the crude material was purified by column chromatography (5:95 (2M NH₃ in MeOH):CH₂Cl₂) to obtain the title compound 5 (0.16 g, 88%) as a solid. ¹H NMR (DMSO-d₆) δ 2.19 (s, 6H), 2.43 (t, 2H, J=6.9 Hz), 3.97 (t, 2H, J=6.9 Hz), 4.58 (s, 2H), 6.48-6.58 (m, 4H), 7.06-7.14 (m, 2H), 7.60 (d, 1H, J=5.1 Hz), 7.74 (d, 1H, J=3.3 Hz); ESI-MS (m/z, %): 345 (MH⁺, 100), 128 (85); ESI-HRMS calculated for C₁₇H₂₁N₄O₂S (MH⁺), calculated: 345.1379; observed: 345.1384; HPLC-purity: 93.15% by area.

Example 6

Synthesis of N-(4-(2-(dimethylamino)ethyl)-3,4-dihydro-2H-benzo[b][1,4]oxazin-7-yl)thiophene-2-carboximidamide (6)

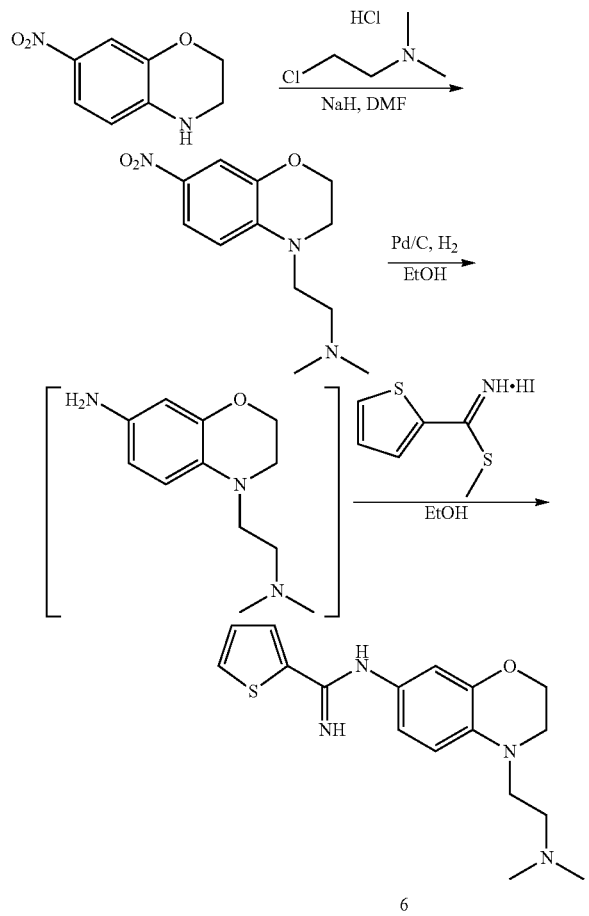

7-Nitro-3,4-dihydro-2H-benzo[b][1,4]oxazine: For complete experimental details and spectral data, see example 4.

N,N-Dimethyl-2-(7-nitro-2H-benzo[b][1,4]oxazin-4(3H)-yl)ethanamine: A solution of 7-nitro-3,4-dihydro-2H-benzo[b][1,4]oxazine (240 mg, 1.33 mmol) in DMF (10 mL) was treated with NaH (170 mg, 4.26 mmol, 60% wt in mineral oil) at 0° C., resulting in an orange mixture. The mixture was then treated with 2-chloro-N,N-dimethylethanamine hydrochloride (384 mg, 2.66 mmol), resulting in a dark red mixture. The reaction was stirred at room temperature for 1 hour. At this time, the reaction was then heated to 90° C. and stirred for another 45 minutes. The reaction was cooled to room temperature, water (15 mL) was added, and the reaction was extracted into EtOAc (2×12 mL). The combined organic layers were washed with brine (3×5 mL), dried (Na₂SO₄), filtered, and concentrated. The residue was subjected to flash chromatography on silica gel: CH₂Cl₂ followed by 5:95 (2M NH₃ in MeOH):CH₂Cl₂ to give a yellow/orange solid (210 mg, 63%). ¹H-NMR (DMSO-d₆) δ 7.75 (dd, J=2.7, 9.0 Hz, 1H), 7.48 (d, J=2.7 Hz, 1H), 6.82 (d, J=9.0 Hz, 1H), 4.18 (t, J=4.5 Hz, 2H), 3.57-3.53 (m, 4H), 2.54-2.45 (m, 2H), 2.23 (s, 6H).

N-(4-(2-(Dimethylamino)ethyl)-3,4-dihydro-2H-benzo[b][1,4]oxazin-7-yl)thiophene-2-carboximidamide (6): A suspension of N,N-dimethyl-2-(7-nitro-2H-benzo[b][1,4]oxazin-4(3H)-yl)ethanamine (210 mg, 0.836 mmol) and Pd—C (10% wt, 89 mg, 0.084 mmol) in dry EtOH (15 mL) was purged with hydrogen gas. The reaction was stirred at room temperature for 3 hours under hydrogen atmosphere (balloon pressure). The reaction mixture was then filtered through a Celite pad and washed with EtOH (15 mL). The light purple filtrate was concentrated to give crude 4-(2-(dimethylamino)ethyl)-3,4-dihydro-2H-benzo[b][1,4]oxazin-7-amine. A solution of this crude 4-(2-(dimethylamino)ethyl)-3,4-dihydro-2H-benzo[b][1,4]oxazin-7-amine (185 mg, 0.836 mmol) in dry EtOH (10 mL) was treated with methyl thiophene-2-carbimidothioate hydroiodide (477 mg, 1.672 mmol) and stirred overnight at room temperature. The reaction was diluted with saturated NaHCO₃ solution (50 mL) and the product was extracted into CH₂Cl₂ (3×25 mL). The combined organic layers were dried (Na₂SO₄) and concentrated. The residue was subjected to flash chromatography on silica gel using 2:98 MeOH:CH₂Cl₂, followed by 5:95 (2M NH₃ in MeOH):CH₂Cl₂, to give a yellow solid (150 mg, 54%). ¹H-NMR (DMSO-d₆) δ 7.69 (dd, J=3.6, 0.9 Hz, 1H), 7.56 (dd, J=5.1, 0.9 Hz, 1H), 7.07 (dd, J=5.1, 3.9 Hz, 1H), 6.64 (d, J=8.4 Hz, 1H), 6.35-6.26 (m, 4H), 4.14 (t, J=3.9 Hz, 2H), 3.33-3.29 (m, 4H), 2.42 (t, J=6.9 Hz, 2H), 2.19 (s, 6H); ESI-MS (m/z, %): 331 (MH⁺, 100), 260 (25); ESI-HRMS calculated for C₁₇H₂₃N₄OS (MH⁺): 331.1587, Observed: 331.1594; HPLC purity: 99.0% by area.

Example 7

Synthesis of N-(4-(2-(ethylamino)ethyl)-3,4-dihydro-2H-benzo[b][1,4]oxazin-7-yl)thiophene-2-carboximidamide dihydrochloride (7)

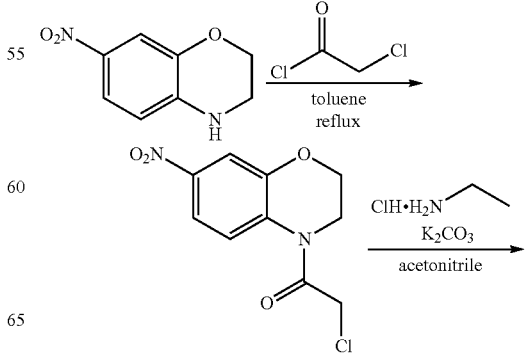

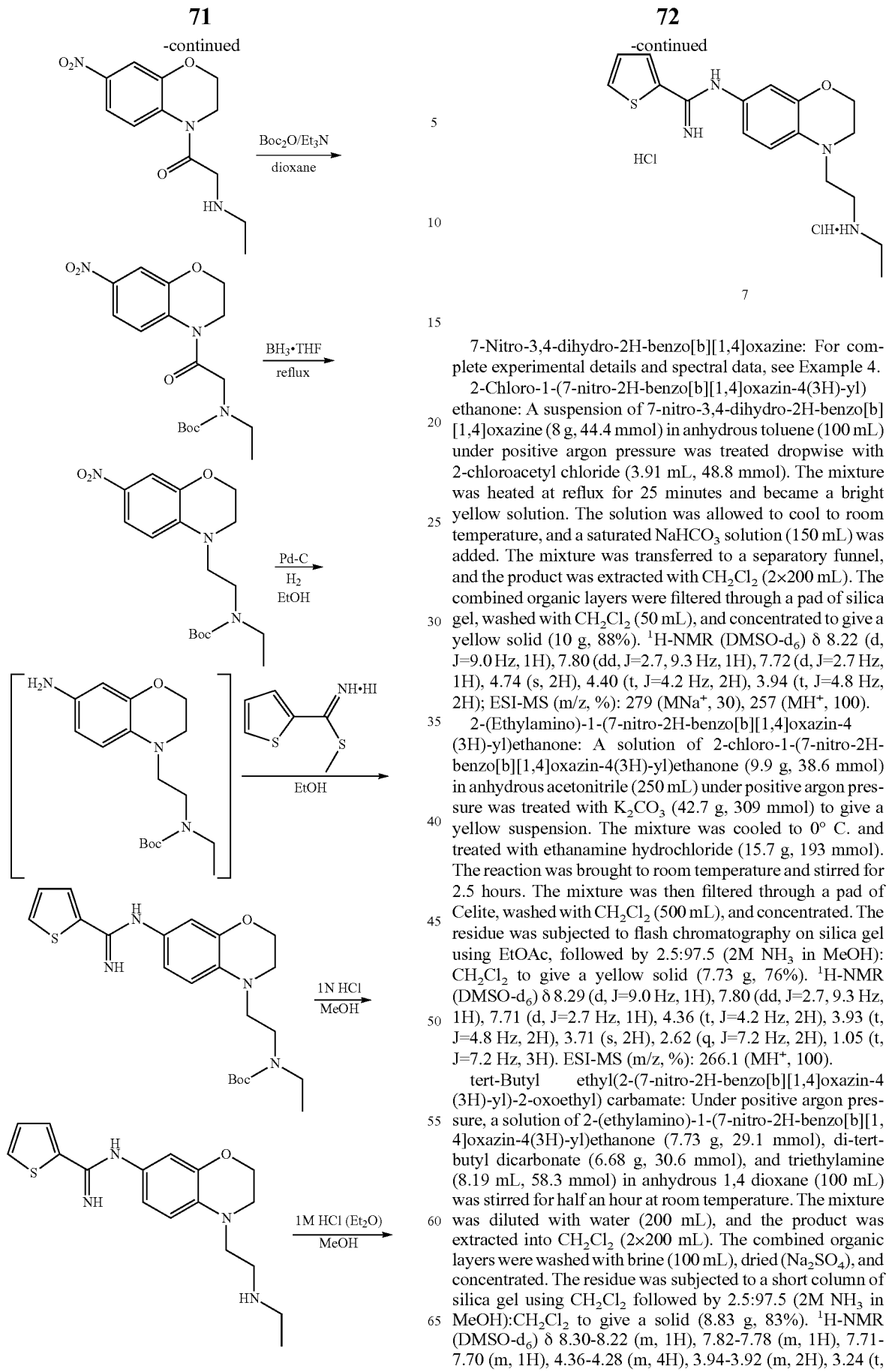

7-Nitro-3,4-dihydro-2H-benzo[b][1,4]oxazine: For complete experimental details and spectral data, see Example 4.

2-Chloro-1-(7-nitro-2H-benzo[b][1,4]oxazin-4(3H)-yl) ethanone: A suspension of 7-nitro-3,4-dihydro-2H-benzo[b][1,4]oxazine (8 g, 44.4 mmol) in anhydrous toluene (100 mL) under positive argon pressure was treated dropwise with 2-chloroacetyl chloride (3.91 mL, 48.8 mmol). The mixture was heated at reflux for 25 minutes and became a bright yellow solution. The solution was allowed to cool to room temperature, and a saturated NaHCO$_3$ solution (150 mL) was added. The mixture was transferred to a separatory funnel, and the product was extracted with CH$_2$Cl$_2$ (2×200 mL). The combined organic layers were filtered through a pad of silica gel, washed with CH$_2$Cl$_2$ (50 mL), and concentrated to give a yellow solid (10 g, 88%). $^1$H-NMR (DMSO-d$_6$) δ 8.22 (d, J=9.0 Hz, 1H), 7.80 (dd, J=2.7, 9.3 Hz, 1H), 7.72 (d, J=2.7 Hz, 1H), 4.74 (s, 2H), 4.40 (t, J=4.2 Hz, 2H), 3.94 (t, J=4.8 Hz, 2H); ESI-MS (m/z, %): 279 (MNa$^+$, 30), 257 (MH$^+$, 100).

2-(Ethylamino)-1-(7-nitro-2H-benzo[b][1,4]oxazin-4(3H)-yl)ethanone: A solution of 2-chloro-1-(7-nitro-2H-benzo[b][1,4]oxazin-4(3H)-yl)ethanone (9.9 g, 38.6 mmol) in anhydrous acetonitrile (250 mL) under positive argon pressure was treated with K$_2$CO$_3$ (42.7 g, 309 mmol) to give a yellow suspension. The mixture was cooled to 0° C. and treated with ethanamine hydrochloride (15.7 g, 193 mmol). The reaction was brought to room temperature and stirred for 2.5 hours. The mixture was then filtered through a pad of Celite, washed with CH$_2$Cl$_2$ (500 mL), and concentrated. The residue was subjected to flash chromatography on silica gel using EtOAc, followed by 2.5:97.5 (2M NH$_3$ in MeOH):CH$_2$Cl$_2$ to give a yellow solid (7.73 g, 76%). $^1$H-NMR (DMSO-d$_6$) δ 8.29 (d, J=9.0 Hz, 1H), 7.80 (dd, J=2.7, 9.3 Hz, 1H), 7.71 (d, J=2.7 Hz, 1H), 4.36 (t, J=4.2 Hz, 2H), 3.93 (t, J=4.8 Hz, 2H), 3.71 (s, 2H), 2.62 (q, J=7.2 Hz, 2H), 1.05 (t, J=7.2 Hz, 3H). ESI-MS (m/z, %): 266.1 (MH$^+$, 100).

tert-Butyl ethyl(2-(7-nitro-2H-benzo[b][1,4]oxazin-4(3H)-yl)-2-oxoethyl) carbamate: Under positive argon pressure, a solution of 2-(ethylamino)-1-(7-nitro-2H-benzo[b][1,4]oxazin-4(3H)-yl)ethanone (7.73 g, 29.1 mmol), di-tert-butyl dicarbonate (6.68 g, 30.6 mmol), and triethylamine (8.19 mL, 58.3 mmol) in anhydrous 1,4 dioxane (100 mL) was stirred for half an hour at room temperature. The mixture was diluted with water (200 mL), and the product was extracted into CH$_2$Cl$_2$ (2×200 mL). The combined organic layers were washed with brine (100 mL), dried (Na$_2$SO$_4$), and concentrated. The residue was subjected to a short column of silica gel using CH$_2$Cl$_2$ followed by 2.5:97.5 (2M NH$_3$ in MeOH):CH$_2$Cl$_2$ to give a solid (8.83 g, 83%). $^1$H-NMR (DMSO-d$_6$) δ 8.30-8.22 (m, 1H), 7.82-7.78 (m, 1H), 7.71-7.70 (m, 1H), 4.36-4.28 (m, 4H), 3.94-3.92 (m, 2H), 3.24 (t, J=2.7 Hz, 2H), 1.40, 1.30 (2×s, 9H), 1.07-1.04 (m, 3H). ESI-MS (m/z, %): 388 (MNa+, 50), 366 (MH+, 35), 266 (100).

tert-Butyl ethyl(2-(7-nitro-2H-benzo[b][1,4]oxazin-4 (3H)-yl)ethyl)carbamate: A yellow solution of tert-butyl ethyl(2-(7-nitro-2H-benzo[b][1,4]oxazin-4(3H)-yl)-2-oxo-ethyl)carbamate (8.7 g, 23.8 mmol) in anhydrous THF (50 mL) under positive argon pressure was treated with borane-THF complex (1M in THF, 47.6 mL, 47.6 mmol) to give an orange solution. The mixture was refluxed for 20 minutes. It was then cooled in an ice bath and treated dropwise with MeOH (100 mL). The solution stirred for half an hour at room temperature, and the reaction was then concentrated. The residue was subjected to flash chromatography on silica gel using 1:9 EtOAc:hexanes to give an orange solid (7.5 g, 91%). $^1$H-NMR (DMSO-$d_6$) δ 7.72 (dd, J=2.7, 9.0 Hz, 1H), 7.49-7.47 (m, 1H), 6.85-6.83 (m, 1H), 4.18 (t, J=4.2 Hz, 2H), 3.59-3.53 (m, 2H), 3.37-3.36 (m, 2H), 3.20-3.18 (m, 2H), 1.47 (s, 2H), 1.30 (br s, 9H), 1.02 (t, J=6.9 Hz, 3H); ESI-MS (m/z, %): 374 (MNa+, 86), 352 (MH+, 7.8), 296 (100), 252 (87).

tert-Butyl ethyl(2-(7-(thiophene-2-carboximidamido)-2H-benzo[b][1,4]oxazin-4(3H)-yl)ethyl)carbamate: A suspension of tert-butyl ethyl(2-(7-nitro-2H-benzo[b][1,4]oxazin-4(3H)-yl)ethyl)carbamate (7 g, 19.92 mmol) and Pd—C (2.11 g, 1.992 mmol, 10% wt) in anhydrous EtOH (100 mL) was purged with hydrogen gas. The reaction was stirred at room temperature for 16 hours under a hydrogen atmosphere (balloon pressure). The reaction mixture was filtered through a Celite pad and washed with EtOH (50 mL). The filtrate containing tert-butyl 2-(7-amino-2H-benzo[b][1,4]oxazin-4 (3H)-yl)ethyl(ethyl)carbamate was treated with methyl thiophene-2-carbimidothioate hydroiodide (11.36 g, 39.8 mmol) and stirred overnight at room temperature. The reaction was concentrated and then partitioned between saturated NaHCO$_3$ solution (150 mL) and CH$_2$Cl$_2$ (75 mL). The mixture was transferred to a separatory funnel, and the product was extracted into CH$_2$Cl$_2$ (2×100 mL). The combined organic layers were dried (Na$_2$SO$_4$) and concentrated. The residue was subjected to flash chromatography on silica gel using a sequence of eluents (CH$_2$Cl$_2$; 1:99 (2M NH$_3$ in MeOH):CH$_2$Cl$_2$; 1.75:98.25 (2M NH$_3$ in MeOH):CH$_2$Cl$_2$; and 2.5:97.5 (2M NH$_3$ in MeOH):CH$_2$Cl$_2$) to give a brown solid (4 g, 46.7%). $^1$H-NMR (CDCl$_3$) δ 7.43-7.41 (m, 2H), 7.11-7.05 (m, 1H), 6.72-6.69 (m, 1H), 6.54-6.51 (m, 2H), 4.23-4.20 (m, 2H), 3.39-3.25 (m, 8H), 1.47 (s, 9H), 1.11-1.10 (m, 3H); ESI-MS (m/z, %): 431 (MH+, 100).

N-(4-(2-(Ethylamino)ethyl)-3,4-dihydro-2H-benzo[b][1,4]oxazin-7-yl)thiophene-2-carboximidamide: Under positive argon pressure, an orange suspension of tert-butyl ethyl (2-(7-(thiophene-2-carboximidamido)-2H-benzo[b][1,4] oxazin-4(3H)-yl)ethyl)carbamate (4 g, 9.29 mmol) in MeOH (30 mL) and 1N HCl (30 mL) was refluxed for 1 hour. The mixture was then cooled to room temperature, transferred to an ice bath, and 1N NaOH (75 mL) was then added. The solution turned a milky green colour with a black suspension. The mixture was then treated with CH$_2$Cl$_2$ (50 mL) and stirred for half an hour. After this time, the mixture was transferred to a separatory funnel and the product was extracted into CH$_2$Cl$_2$ (2×50 mL). The combined organic layers were dried (Na$_2$SO$_4$) and concentrated. The residue was subjected to flash chromatography on silica gel using the following sequence of eluents: EtOAc; 1:99 (2M NH$_3$ in MeOH):CH$_2$Cl$_2$; 2.5:97.5 (2M NH$_3$ in MeOH):CH$_2$Cl$_2$; and 5:95 (2M NH$_3$ in MeOH):CH$_2$Cl$_2$. A brown solid was obtained (2 g, 65.1%). $^1$H-NMR (CDCl$_3$) δ 7.40-7.37 (m, 2H), 7.07-7.04 (m, 1H), 6.75-6.72 (m, 1H), 6.52-6.50 (m, 2H), 4.82 (brs, 2H), 4.24 (t, J=4.5 Hz, 2H), 3.39-3.31 (m, 4H), 2.86 (t, J=6.3 Hz, 2H), 2.71 (q, J=6.9 Hz, 2H), 1.13 (t, J=7.2 Hz, 3H); ESI-MS (m/z, %): 331 (MH+, 100), 260 (95); HPLC purity: 94.1% by area.

N-(4-(2-(Ethylamino)ethyl)-3,4-dihydro-2H-benzo[b][1, 4]oxazin-7-yl)thiophene-2-carboximidamide dihydrochloride (7): A suspension of N-(4-(2-(ethylamino)ethyl)-3,4-dihydro-2H-benzo[b][1,4]oxazin-7-yl)thiophene-2-carboximidamide (0.1 g, 0.303 mmol) in MeOH (3 mL), under positive argon pressure, was treated with a 1M HCl ethereal solution (1.51 mL, 1.51 mmol). The reaction stirred at room temperature for 1 hour, and the mixture was then concentrated to give a yellow-brown solid (93 mg, 76%). $^1$H-NMR (DMSO-$d_6$) δ 11.20 (brs, 1H), 9.67 (brs, 1H), 9.23 (brs, 2H), 8.67 (brs, 1H), 8.16-8.08 (m, 2H), 7.37-7.36 (m, 1H), 7.04 (d, J=8.4, 1H), 6.87-6.81 (m, 2H), 4.30-4.25 (m, 2H), 3.66 (t, J=6.3 Hz, 2H), 3.12-2.95 (m, 4H), 2.58-2.45 (m, 2H), 1.24 (t, J=7.2 Hz, 3H); ESI-MS (m/z, %): 331 (MH+, free base, 100), 260 (95); ESI-HRMS calculated for C$_{19}$H$_{25}$N$_4$OS (MH+, free base): 331.1587, observed: 331.1597; HPLC purity: 95.4% by area.

Example 8

Synthesis of N-(4-(2-(methylamino)ethyl)-3,4-dihydro-2H-benzo[b][1,4]thiazin-7-yl)thiophene-2-carboximidamide (8)

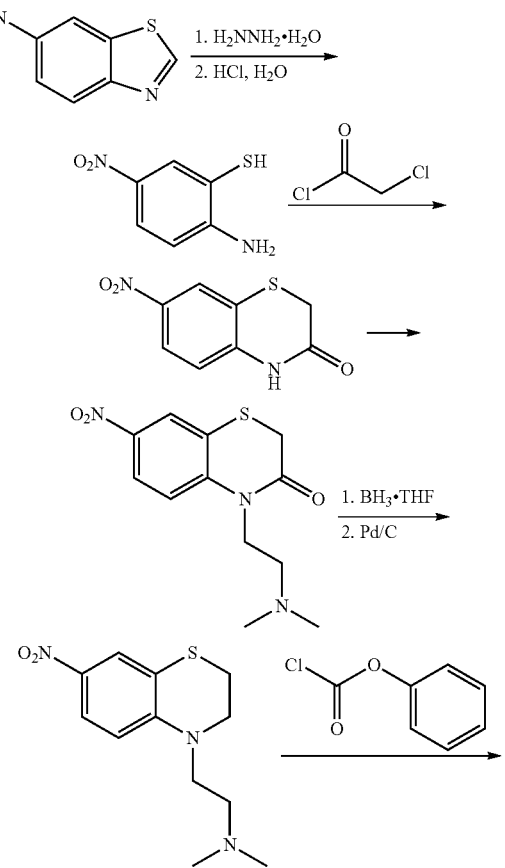

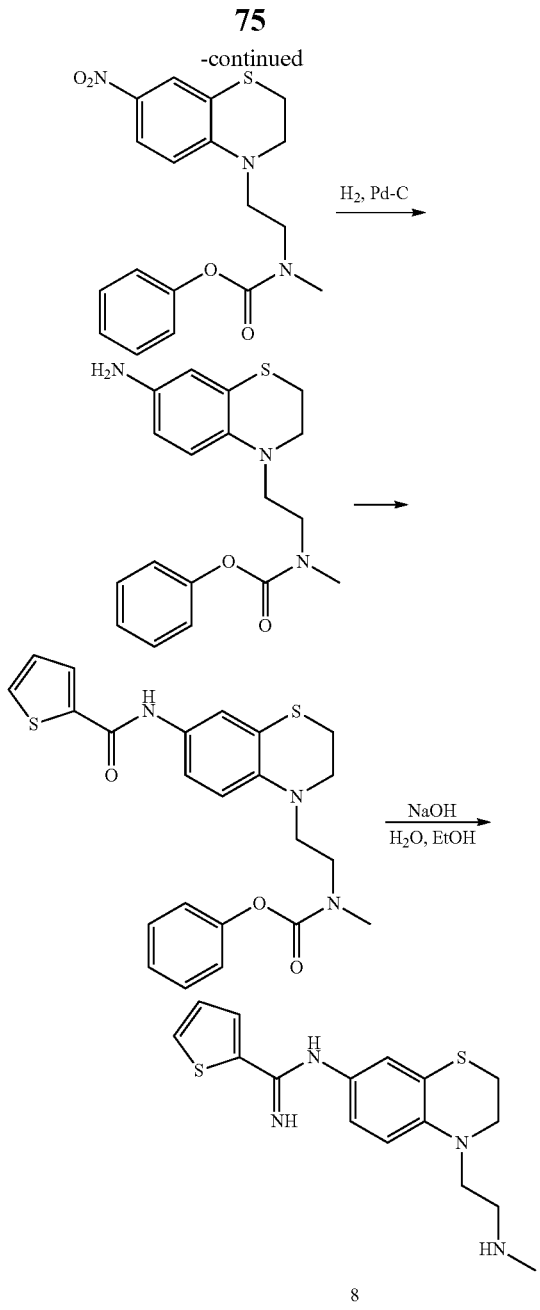

2-Amino-5-nitrobenzenethiol: To a stirred suspension of 6-nitrobenzo[d]thiazole (1.64 g, 9.10 mmol) in ethanol (16 mL) was added hydrazine hydrate (2.66 mL, 54.6 mmol). The resulting dark solution was stirred overnight at room temperature. The mixture was then diluted with water and slowly acidified with 3 M HCl, giving a yellow suspension. The mixture was then extracted with dichloromethane. The combined organics were dried, filtered, and concentrated, giving a yellow solid, used directly in the subsequent reaction. $^1$H NMR (DMSO-$d_6$) δ 8.09 (brs, 1H), 7.87 (d, J=8.7 Hz, 1H), 6.74 (d, J=9.0 Hz, 1H), 6.27 (brs, 2H); MS-EI: (m/z, %) 170 (M+, 100), 140 (28), 124 (35).

7-Nitro-2H-benzo[b][1,4]thiazin-3(4H)-one: To a stirred solution of 2-amino-5-nitrobenzenethiol (1.72 g, 10.11 mmol) in tetrahydrofuran (10 mL) was added sodium bicarbonate (2.80 g, 33.4 mmol) as a solution in water (40.0 mL). To this dark red solution was added 2-chloroacetyl chloride (0.885 mL, 11.12 mmol). The resulting mixture, which turned faint red, was then stirred at room temperature overnight. The mixture was then diluted with water and extracted three time with dichloromethane. The combined organics were dried, filtered, concentrated, and then chromatographed in 10% ethyl acetate in dichloromethane, giving the desired product (1.02 g, 48.0%). $^1$H NMR (DMSO-$d_6$) δ 11.17 (s, 1H), 8.24 (d, J=2.7 Hz, 1H), 8.07 (dd, J=9.0, 2.7 Hz, 1H), 7.13 (d, J=9.0 Hz, 1H), 3.60 (s, 2H); MS-EI: (m/z, %) 210 (M+, 100), 181 (40), 131 (46).

4-(2-(Dimethylamino)ethyl)-7-nitro-2H-benzo[b][1,4]thiazin-3(4H)-one: To a stirred suspension of 7-nitro-2H-benzo[b][1,4]thiazin-3(4H)-one (1.02 g, 4.85 mmol) and potassium carbonate (4.69 g, 34.0 mmol) in a pressure flask in DMF (30 mL) under argon was added 2-chloro-N,N-dimethylethanamine hydrochloride (3.49 g, 24.26 mmol). The flask was immediately sealed and heated with stirring to 90° C. overnight. The mixture was then cooled to room temperature, diluted with water and extracted (2× ethyl acetate). The combined organics were then washed with a 1:1 mixture of brine and water (3×) then brine (1×). The organic phase was dried, filtered, concentrated, and then chromatographed in 5% (2M $NH_3$ in MeOH) in dichloromethane, giving the desired product (755 mg, 55.3%). $^1$H NMR (DMSO-$d_6$) δ 8.30 (d, J=2.7 Hz, 1H), 8.13 (dd, J=9.3, 2.7 Hz, 1H), 7.59 (d, J=9.3 Hz, 1H), 4.11 (t, J=6.9 Hz, 2H), 3.62 (s, 2H), 2.41 (t, J=6.9 Hz, 2H), 2.17 (s, 6H); MS-EI: (m/z, %) 281 (M+, 55), 251 (65), 58 (100).

N,N-Dimethyl-2-(7-nitro-2H-benzo[b][1,4]thiazin-4(3H)-yl)ethanamine: To a stirred solution of 4-(2-(dimethylamino)ethyl)-7-nitro-2H-benzo[b][1,4]thiazin-3(4H)-one (730 mg, 2.59 mmol) in tetrahydrofuran (3 mL) under argon was added borane (1M in THF; 7.784 mL, 7.78 mmol). The resulting mixture was stirred overnight at room temperature, producing a yellow precipitate. The mixture was heated briefly to 60° C. to break up the solid. The reaction was then cooled to 0° C. and quenched with methanol (slowly, until bubbling ceased). The mixture was then concentrated, redissolved in MeOH (15 mL) and 1 M HCl (5 mL), and heated at 60° C. for 30 minutes The quenched mixture was then diluted with water and sodium carbonate, and then extracted with dichloromethane (3×). The combined organics were dried, filtered, concentrated, and then chromatographed in ethyl acetate, giving a yellow solid, and the desired complex as a borane complex, which was used directly in the subsequent reaction.

To a stirred solution of N,N-dimethyl-2-(7-nitro-2H-benzo[b][1,4]thiazin-4(3H)-yl)ethanamine-borane complex (350 mg, 1.245 mmol) in methanol (5 mL) and THF (10 mL) under argon was added 10% Pd—C (132 mg, 0.124 mmol). The mixture was then stirred overnight at room temperature. The suspension was then filtered through a pad of Celite, concentrated, and chromatographed in 5% (2M $NH_3$ in MeOH) in dichloromethane, giving the desired product (106.6 mg, 32.0%). $^1$H NMR (DMSO-$d_6$) δ 7.85-7.81 (m, 2H), 6.81 (d, J=9.0 Hz, 1H), 3.81 (t, J=5.1 Hz, 2H), 3.56 (t, J=6.9 Hz, 2H), 3.06 (t, J=5.1 Hz, 1H), 2.47 (t, J=6.9 Hz, 2H), 2.21 (s, 6H); MS-EI: (m/z, %) 267 (M+, 13), 179 (29), 58 (100).

Phenyl methyl(2-(7-nitro-2H-benzo[b][1,4]thiazin-4(3H)-yl)ethyl)carbamate: To a stirred solution of N,N-dimethyl-2-(7-nitro-2H-benzo[b][1,4]thiazin-4(3H)-yl)ethanamine (100 mg, 0.374 mmol) in dichloromethane (5 mL) under argon was added phenyl carbonochloridate (0.094 mL, 0.748 mmol). The resulting mixture was stirred at room temperature. A precipitate was observed, and triethylamine (3 drops) was added to aid dissolution (reaction turned clear). The mixture was then stirred over the weekend. The clear yellow mixture was then diluted with water and sodium carbonate and then extracted with dichloromethane (3×). The combined organics were dried, filtered, concentrated, and then chromatographed in ethyl acetate, giving the desired product (139 mg, 100%). $^1$H NMR (DMSO-$d_6$) δ 7.84-7.74 (m, 2H), 7.39-7.31 (m, 2H), 7.23-7.16 (m, 1H), 7.03-6.93 (m, 3H), 3.85-3.78 (m, 3H), 3.73-3.65 (m, 2H), 3.55-3.50 (m, 1H), 3.09, 2.97 (2s, 3H), 3.09-3.05 (m, 2H); MS-EI: (m/z, %) 373 (M+, 4), 209 (31), 179 (100), 151 (28).

Phenyl 2-(7-amino-2H-benzo[b][1,4]thiazin-4(3H)-yl) ethyl(methyl)carbamate: To a stirred solution of phenyl methyl(2-(7-nitro-2H-benzo[b][1,4]thiazin-4(3H)-yl)ethyl) carbamate (100 mg, 0.268 mmol) in tetrahydrofuran (4 mL) and ethanol (4.00 mL) under argon was added 10% Pd—C (28.5 mg, 0.027 mmol). The resulting mixture was stirred at room temperature overnight under an atmosphere of hydrogen (balloon pressure). The mixture was then filtered through a pad of Celite and concentrated, giving the desired product (81 mg, 88%) as a dark oil. MS-EI: (m/z, %) 343 (M+, 64), 179 (100), 151 (45).

Phenyl methyl(2-(7-(thiophene-2-carboximidamido)-2H-benzo[b][1,4]thiazin-4(3H)-yl)ethyl)carbamate: To a stirred solution of phenyl 2-(7-amino-2H-benzo[b][1,4]thiazin-4 (3H)-yl)ethyl(methyl)carbamate (80 mg, 0.233 mmol) in ethanol (5 mL) under argon was added methyl thiophene-2-carbimidothioate hydroiodide (133 mg, 0.466 mmol). The mixture was then stirred overnight at room temperature. The mixture was then diluted with water and sodium carbonate and then extracted with dichloromethane (2×). The combined organics were dried, filtered, concentrated, and then chromatographed in ethyl acetate, yielding the desired product (72 mg, 68%). $^1$H NMR (DMSO-$d_6$) δ 7.74-7.69 (m, 1H), 7.58-7.56 (m, 1H), 7.42-7.34 (m, 2H), 7.25-7.17 (m, 1H), 7.14-7.05 (m, 3H), 6.83-6.80 (m, 1H), 6.53-6.44 (m, 2H), 6.36 (brs, 2H), 3.63-3.55 (m, 4H), 3.49-3.45 (m, 2H), 3.11, 2.98 (2s, 3H), 3.06-3.01 (m, 2H); MS-EI: (m/z, %) 452 (M+, 97), 288 (100).

N-(4-(2-(Methylamino)ethyl)-3,4-dihydro-2H-benzo[b] [1,4]thiazin-7-yl)thiophene-2-carboximidamide (8): To a stirred solution of phenyl methyl(2-(7-(thiophene-2-carboximidamido)-2H-benzo[b][1,4]thiazin-4(3H)-yl)ethyl)carbamate (65 mg, 0.144 mmol) in ethanol (4 mL) was added sodium hydroxide (57.4 mg, 1.436 mmol) as a solution in water (2 mL). The resulting mixture was heated to 78° C. and stirred overnight. The mixture was then cooled to room temperature, diluted with water and sodium hydroxide, and extracted with dichloromethane (5×). The combined organics were dried, filtered, concentrated, and then chromatographed in 10% (2M NH$_3$ in MeOH) in dichloromethane, giving the desired product (22 mg, 46%). $^1$H NMR (DMSO-$d_6$) δ 7.69 (d, J=3.3 Hz, 1H), 7.56 (d, J=5.1 Hz, 1H), 7.07 (t, J=4.4 Hz, 1H), 6.72 (d, J=8.7 Hz, 1H), 6.53-6.44 (m, 2H), 6.29 (brs, 2H), 3.54-3.51 (m, 2H), 3.3 (m, 2H), 3.04-3.00 (m, 2H), 2.66 (t, J=6.8 Hz, 2H), 2.32 (s, 3H); MS-EI: (m/z, %) 332 (M+, 75), 288 (97), 260 (100); EI-HRMS calculated for $C_{16}H_{20}N_4S_2$ (M+), calculated: 332.1129, observed: 332.1145. HPLC: 95% by area.

Example 9

Synthesis of N-(4-(2-(dimethylamino)ethyl)-3,4-dihydro-2H-benzo[b][1,4]oxazin-6-yl)-thiophene-2-carboximidamide (9)

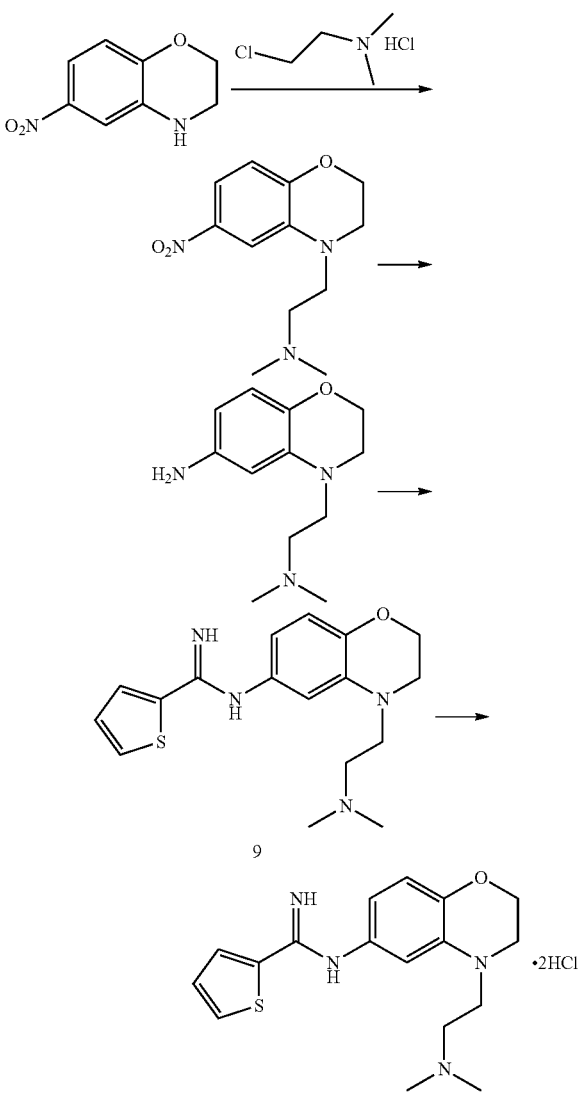

N,N-Dimethyl-2-(6-nitro-2H-benzo[b][1,4]oxazin-4 (3H)-yl)ethanamine: A solution of 6-nitro-3,4-dihydro-2H-benzo[b][1,4]oxazine (1.0 g, 5.55 mmol) in anhydrous DMF (25 mL) under argon was cooled and treated portionwise with sodium hydride (0.677 g, 16.93 mmol) at 5-10° C. 2-chloro-N,N-dimethylethanamine hydrochloride (1.599 g, 11.10 mmol) was added portionwise at 5-10° C., and the resulting heterogeneous red-brown mixture was allowed to warm to room temperature. After 3 hours at room temperature, the mixture was heated to 90° C. and stirred for 30 minutes. The mixture was cooled to room temperature, quenched by the addition of water (25 mL), and diluted with EtOAc. A small amount of 1 N NaOH was added to basify the mixture to pH ~9-10. The organic layer was separated, and the aqueous layer was further extracted with EtOAc. The combined organic layers were washed with brine (×2), dried (Na$_2$SO$_4$), filtered, and concentrated to afford a dark red oil. The material was purified on silica gel, eluting with 5% MeOH/CH$_2$Cl$_2$, to yield the title compound as a dark orange-red oil (458 mg, 32.8%). $^1$H NMR (DMSO-d$_6$) δ 7.49-7.39 (m, 2H), 6.87-6.84 (m, 1H), 4.27-4.25 (m, 2H), 3.50-3.37 (m, 4H), 2.43 (t, 2H, J=6.7 Hz), 2.19 (s, 6H); ESI-MS (m/z, %): 252 (MH$^+$, 100).

4-(2-(Dimethylamino)ethyl)-3,4-dihydro-2H-benzo[b][1,4]oxazin-6-amine: To an oven dried, argon purged 100 mL round bottom flask fitted with a magnetic stirbar was added N,N-dimethyl-2-(6-nitro-2H-benzo[b][1,4]oxazin-4(3H)-yl) ethanamine (0.10 g, 0.398 mmol) and EtOH (10 mL). At this time, stirring of the reaction began. 10% Pd—C (0.042 g, 0.040 mmol) was added, the flask was evacuated, and the mixture was subjected to hydrogenation under standard conditions (atmospheric H$_2$ pressure using a balloon). After 3 hours, the mixture was filtered through a pad of Celite and washed with ethanol. The pale peach colored solution, which darkened upon exposure to air, was concentrated to approximately 10 mL to yield the title compound. This compound was utilized immediately in the next step. ESI-MS (m/z, %): 222 (MH$^+$, 100).

N-(4-(2-(Dimethylamino)ethyl)-3,4-dihydro-2H-benzo[b][1,4]oxazin-6-yl)thiophene-2-carboximidamide: To a stirred ethanolic solution of 4-(2-(dimethylamino)ethyl)-3,4-dihydro-2H-benzo[b][1,4]oxazin-6-amine (0.088 g, 0.398 mmol) under an argon atmosphere was added methyl thiophene-2-carbimidothioate hydroiodide (0.227 g, 0.795 mmol). The resulting faintly cloudy yellow mixture stirred overnight at room temperature. After 20 hours, argon was bubbled through the mixture, which was then concentrated to afford a residue. The residue was then partitioned between EtOAc (100 mL) and saturated NaHCO$_3$ (~10 mL) solution. The aqueous layer (pH ~9) was further extracted with EtOAc, and the combined organic layers were washed with brine, dried (Na$_2$SO$_4$), filtered, and concentrated to yield a yellow residue. Purification on silica gel (dry chromatography, eluting with 5-7.5% (2M NH$_3$ MeOH)/CH$_2$Cl$_2$) yielded the title compound 9 as a yellow residue (70 mg, 53.3%). $^1$H NMR (DMSO-d$_6$) δ 7.70 (d, 1H, J=2.7 Hz), 7.57 (d, 1H, J=5.0 Hz), 7.07 (dd, 1H, J=5.0, 3.7 Hz), 6.59 (d, 1H, J=8.2 Hz), 6.30 (brs, 2H), 6.14 (s, 1H), 6.00 (d, 1H, J=8.1 Hz), 4.18-4.02 (m, 2H), 3.41-3.25 (m, 4H+H$_2$O), 2.41 (t, 2H, J=6.7 Hz), 2.17 (s, 6H); ESI-MS (m/z, %): 331 (MH$^+$, 100).

N-(4-(2-(Dimethylamino)ethyl)-3,4-dihydro-2H-benzo[b][1,4]oxazin-6-yl)thiophene-2-carboximidamide dihydrochloride: N-(4-(2-(dimethylamino)ethyl)-3,4-dihydro-2H-benzo[b][1,4]oxazin-6-yl)thiophene-2-carboximidamide (0.065 g, 0.197 mmol) was dissolved in anhydrous MeOH (5 mL) and treated with hydrogen chloride (1M in diethyl ether; 0.433 mL, 0.433 mmol) for 5 minutes at room temperature. The reaction was then concentrated to yield the title compound as a yellow solid (58.5 mg, 73.7%). $^1$H NMR (DMSO-d$_6$) δ 11.36 (brs, 1H), 11.02 (brs, 1H), 9.70 (brs, 1H), 8.69 (brs, 1H), 8.15 (app d, 2H, J=4.5 Hz), 7.37 (app t, 1H, J=4.3 Hz), 7.07 (s, 1H), 6.84 (d, 1H, J=8.3 Hz), 6.62 (d, 1H, J=8.4 Hz), 4.31-4.18 (m, 2H), 3.76-3.65 (m, 2H), 3.44-3.34 (m, 2H), 3.35-3.22 (m, 2H), 2.78, 2.77 (2×s, 6H); ESI-MS (m/z, %): 331 (MH$^+$, free base, 100); ESI-HRMS calculated for C$_{17}$H$_{23}$N$_4$OS (MH$^+$, free base): 331.1587; observed: 331.1579.

Example 10

Synthesis of N-(4-(2-(methylamino)ethyl)-3,4-dihydro-2H-benzo[b][1,4]oxazin-6-yl)-thiophene-2-carboximidamide dihydrochloride (10)

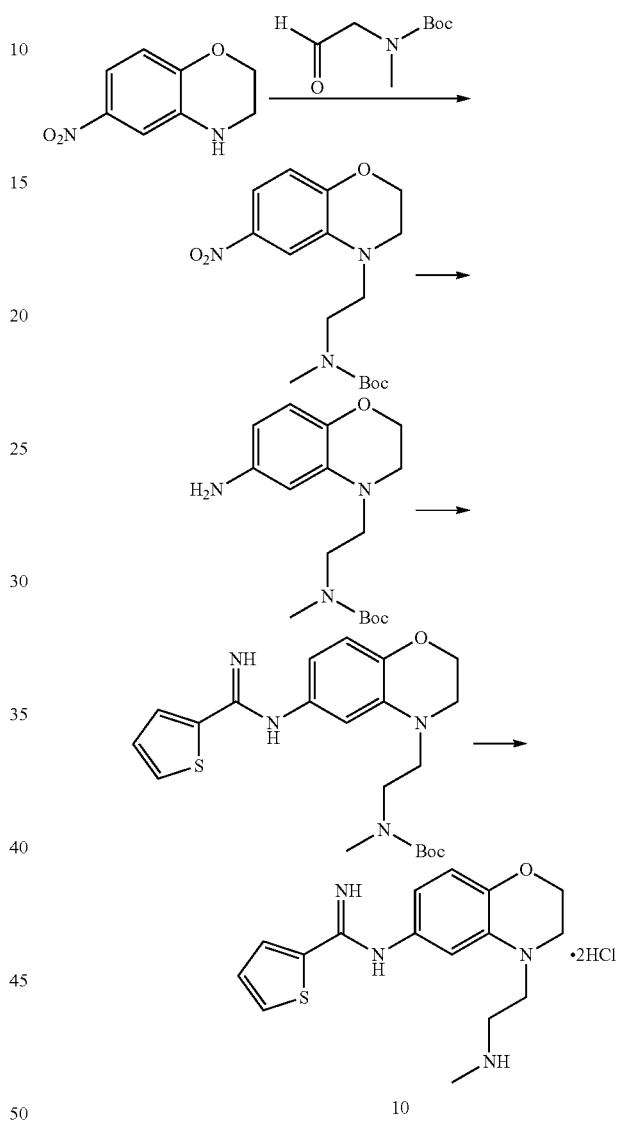

tert-Butyl methyl(2-(6-nitro-2H-benzo[b][1,4]oxazin-4(3H)-yl)ethyl)carbamate: To an oven dried, argon purged flask fitted with a magnetic stirbar was added tert-butyl methyl(2-oxoethyl)carbamate (0.135 g, 0.777 mmol), and DCE (10 mL). At this time, stirring began, and 6-nitro-3,4-dihydro-2H-benzo[b][1,4]oxazine (0.10 g, 0.555 mmol) was added, followed by acetic acid (0.064 mL, 1.110 mmol) and sodium triacetoxyborohydride (0.294 g, 1.388 mmol). The resulting mixture stirred overnight at room temperature. After 18 hours, the reaction was quenched by the addition of saturated NaHCO$_3$ (10 mL) and extracted with CH$_2$Cl$_2$. The aqueous layer was extracted further, and the combined organics were washed with brine, dried (Na$_2$SO$_4$), and concentrated. The crude product was combined with the product of a second reaction (prepared in accordance with the above procedure, with the omission of acetic acid). The combined products were purified on silica gel eluting with 50-70% EtOAc/hexanes to yield the title compound as a yellow residue (130 mg, 34.7%). $^1$H NMR (DMSO-d$_6$) δ 7.58-7.37 (m, 2H), 6.92-6.80 (m, 1H), 4.25 (t, 2H, J=4.2 Hz), 3.58-3.36 (m, 6H), 2.87-2.74 (m, 3H), 1.27, 1.18 (2×s, 9H); ESI-MS (m/z, %): 360 (MNa$^+$, 100).

tert-Butyl 2-(6-amino-2H-benzo[b][1,4]oxazin-4(3H)-yl)ethyl(methyl)carbamate

To an oven dried, argon purged round bottom flask fitted with a magnetic stirbar was added tert-butyl methyl (2-(6-nitro-2H-benzo[b][1,4]oxazin-4(3H)-yl)ethyl)carbamate (0.13 g, 0.385 mmol), EtOH (10 mL). At this time, stirring began. 10% Pd—C (0.041 g, 0.039 mmol) was added, the flask evacuated, and the material was subjected to hydrogenation under standard conditions as described herein. After 2.5 hours, the mixture was filtered through a pad of Celite and washed with ethanol. The pale peach colored solution, which darkened slowly upon exposure to air, was concentrated to a volume of ~10 mL to yield the title compound which was utilized immediately in the next step. A small portion was concentrated to dryness for analytical purposes. $^1$H NMR (DMSO-d$_6$) δ 6.34 (d, 1H, J=8.3 Hz), 6.03-5.95 (m, 1H), 5.75 (dd, 1H, J=8.3, 2.3 Hz), 4.35 (m, 2H), 3.98 (t, 2H, J=4.1 Hz), 3.30-3.15 (m, 6H), 2.81 (s, 3H), 1.38, 1.30 (2×s, 9H); ESI-MS (m/z, %): 308 (MH$^+$, 90), 252 (100).

tert-Butyl methyl(2-(6-(thiophene-2-carboximidamido)-2H-benzo[b][1,4]-oxazin-4(3H)-yl)ethyl)carbamate: To a stirred ethanolic solution of tert-butyl 2-(6-amino-2H-benzo[b][1,4]oxazin-4(3H)-yl)ethyl(methyl)carbamate (0.118 g, 0.384 mmol) under an argon atmosphere was charged methyl thiophene-2-carbimidothioate hydroiodide (0.219 g, 0.768 mmol), and the resulting yellow solution stirred at room temperature. After 44 hours, argon was bubbled through the mixture, which was then concentrated to residue and partitioned between EtOAc (100 mL) and saturated NaHCO$_3$ solution (10 mL). The aqueous layer (pH~9) was further extracted with EtOAc, and the combined organic layers were washed with brine, dried (Na$_2$SO$_4$), filtered, and concentrated to yield an orange residue. The residue was purified on silica gel twice, with the first purification using 100% EtOAc as the eluent and the second purification using 5% (2M NH$_3$ in MeOH)/CH$_2$Cl$_2$ to yield the title compound as a yellow solid (80 mg, 50.0%). $^1$H NMR (DMSO-d$_6$) δ 7.68 (d, 1H, J=2.9 Hz), 7.57 (d, 1H, J=5.0 Hz), 7.10-7.03 (m, 1H), 6.60 (d, 1H, J=8.1 Hz), 6.30 (m, 3H), 6.00 (dd, 1H, J=8.1, 1.6 Hz), 4.18-4.02 (m, 2H), 3.40-3.21 (m, 6H, merged with H$_2$O peak), 2.81 (s, 3H), 1.34, 1.29 (2×s, 9H); ESI-MS (m/z, %): 417 (MH$^+$, 100).

N-(4-(2-(methylamino)ethyl)-3,4-dihydro-2H-benzo[b][1,4]oxazin-6-yl)-thiophene-2-carboximidamide dihydrochloride: To a solution of tert-butyl methyl(2-(6-(thiophene-2-carboximidamido)-2H-benzo[b][1,4]oxazin-4(3H)-yl)ethyl)carbamate (0.07 g, 0.168 mmol) in HPLC grade MeOH (10 mL) was added 3M hydrochloric acid (0.56 mL, 1.681 mmol). The resulting yellow solution was heated to reflux under an atmosphere of argon. After 60 minutes, the reaction was cooled to room temperature and concentrated. The residue was diluted with H$_2$O (20 mL) and rinsed sequentially with CH$_2$Cl$_2$ (20 mL) and EtOAc (20 mL). The aqueous layer was concentrated and dried to yield the title compound 10 as a yellow solid (37 mg, 56.5%). $^1$H NMR (DMSO-d$_6$) δ 11.37 (brs, 1H), 9.72 (brs, 1H), 9.23 (brs, 2H), 8.66 (brs, 1H), 8.21-8.08 (m, 2H), 7.37 (app t, 1H, J=4.4 Hz), 7.03 (s, 1H), 6.84 (d, 1H, J=8.3 Hz), 6.60 (d, 1H, J=7.3 Hz), 4.31-4.20 (m, 2H), 3.70-3.45 (m, 2H, merged with H$_2$O peak), 3.40-3.34 (m, 2H), 3.18-3.02 (m, 2H), 2.60-2.50 (m, 3H); ESI-MS (m/z, %): 317 (MH$^+$, free base, 100); ESI-HRMS calculated for C$_{16}$H$_{21}$N$_4$OS (MH$^+$, free base): 317.1430; observed: 317.1422.

Example 11

Synthesis of N-(4-(2-(pyrrolidin-1-yl)ethyl)-3,4-dihydro-2H-benzo[b][1,4]thiazin-7-yl)thiophene-2-carboximidamide (11)

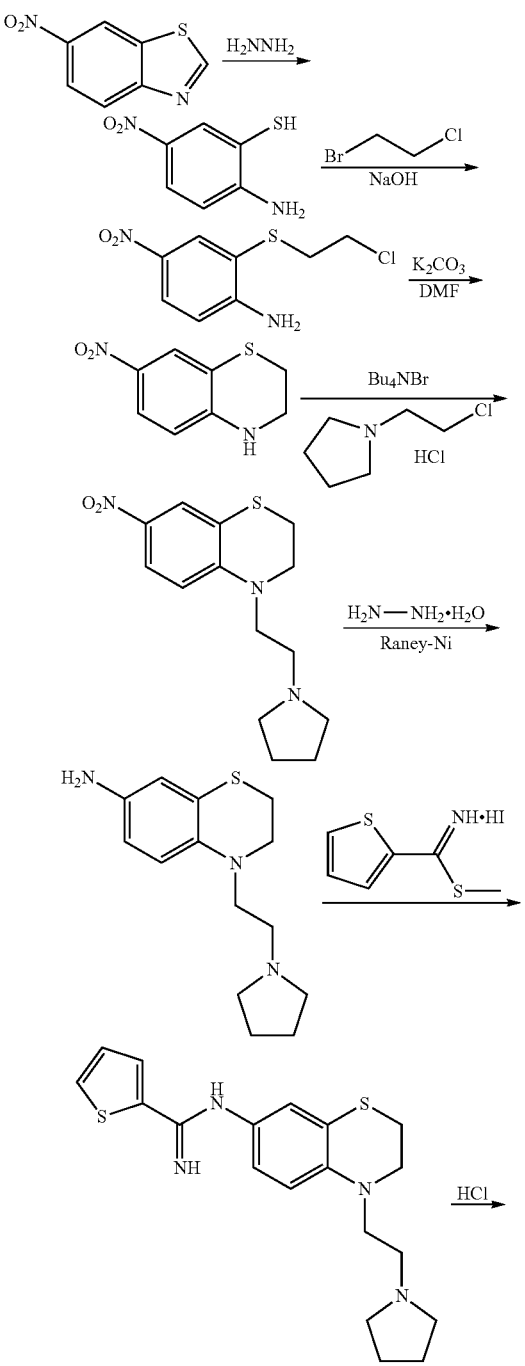

11

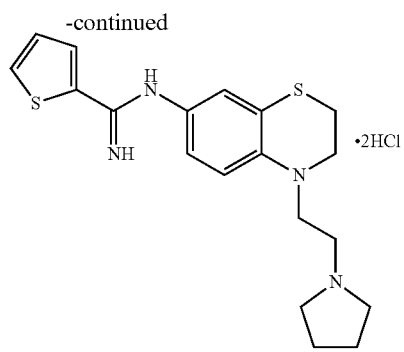

2-Amino-5-nitrobenzenethiol: To a suspension of 6-nitrobenzo[d]thiazole (5 g, 27.7 mmol) in ethanol (45 mL) was added hydrazine hydrate (8.10 mL, 166 mmol). The resulting mixture (dark red) was stirred overnight at room temperature. The mixture was then acidified by the slow, careful addition of 3M HCl in water (50 mL). This mixture was further diluted with water (50 mL), and the resulting yellow/orange precipitate was extracted with dichloromethane (3×). The combined organics were dried, filtered, and concentrated, giving an orange solid (4.62 g, 98%). $^1$H NMR (DMSO-$d_6$) δ 8.12-8.09 (m, 1H), 7.88-7.85 (m, 1H), 6.75-6.71 (m, 1H), 6.28 (brs, 2H); ESI-MS (m/z, %): 170 (MH$^+$, 100).

2-(2-Chloroethylthio)-4-nitroaniline: To a stirred suspension of 2-amino-5-nitrobenzenethiol (4.11 g, 24.15 mmol) in ethanol (50 mL) and water (10 mL) was added sodium hydroxide (0.966 g, 24.15 mmol). To the resulting solution was added 1-bromo-2-chloroethane (8.04 mL, 97 mmol), and the resulting mixture was stirred at room temperature for 3 hours. The mixture was then diluted with ethyl acetate and washed with saturated sodium carbonate (3×). The organic phase was dried, filtered, and concentrated, giving a dark yellow solid (5.13 g, 91%). $^1$H NMR (DMSO-$d_6$) δ 8.16 (d, J=2.7 Hz, 1H), 7.97 (dd, J=9.0, 2.7 Hz, 1H), 6.94 (brs, 2H), 6.79 (d, J=9.0 Hz, 1H), 3.68 (t, J=7.2 Hz, 2H), 3.11 (t, J=7.2 Hz, 2H); ESI-MS (m/z, %): 233 (MH$^+$, 100), 216 (79).

7-Nitro-3,4-dihydro-2H-benzo[b][1,4]thiazine: To a stirred solution of 2-(2-chloroethylthio)-4-nitroaniline (5.13 g, 22.05 mmol) in DMF (70 mL) was added potassium carbonate (9.14 g, 66.1 mmol), followed by sodium iodide (0.330 g, 2.205 mmol). The resulting suspension was stirred at room temperature overnight. The mixture was then diluted with water, and the resulting crystals were collected by vacuum filtration, giving the desired product (4.06 g, 94%). $^1$H NMR (DMSO-$d_6$) δ 7.81-7.73 (m, 3H), 6.58 (t, J=9.0 Hz, 1H), 3.65-3.60 (m, 2H), 3.01-2.97 (m, 2H); ESI-MS (m/z, %): 197 (MH$^+$, 100), 180 (99).

7-Nitro-4-(2-(pyrrolidin-1-yl)ethyl)-3,4-dihydro-2H-benzo[b][1,4]thiazine: A mixture of 7-nitro-3,4-dihydro-2H-benzo[b][1,4]thiazine (1 g, 5.10 mmol), 1-(2-chloroethyl)pyrrolidine hydrochloride (1.734 g, 10.19 mmol), and nBu$_4$NBr (0.082 g, 0.255 mmol) in CH$_2$Cl$_2$ (10 mL) and 50% NaOH solution (10 mL) was stirred at room temperature for 16 hours. The mixture was diluted with CH$_2$Cl$_2$ (25 mL) and water (50 mL). The mixture was transferred to a separatory funnel, and the layers were separated. The aqueous layer was extracted in CH$_2$Cl$_2$ (2×25 mL). The combined organic layers were dried (Na$_2$SO$_4$), filtered, and concentrated. The red crude material was subjected to flash chromatography on silica gel (CH$_2$Cl$_2$, then 1.75-5% (2M NH$_3$ in MeOH)/CH$_2$Cl$_2$) to give 7-nitro-4-(2-(pyrrolidin-1-yl)ethyl)-3,4-dihydro-2H-benzo[b][1,4]thiazine as a brown viscous oil (0.63 g, 42%). $^1$H NMR (DMSO-$d_6$) δ 7.86-7.82 (m, 2H), 6.82 (d, J=9.0 Hz, 1H), 3.81 (t, J=4.8 Hz, 2H), 3.58 (t, J=6.9 Hz, 2H), 3.33 (s, 4H), 3.05 (t, J=5.1 Hz, 2H), 2.63 (t, J=6.9 Hz, 2H), 2.50 (s, 4H), 1.67 (s, 4H); ESI-MS (m/z, %): 296, 294 (MH$^+$, 100), 98 (13).

4-(2-(Pyrrolidin-1-yl)ethyl)-3,4-dihydro-2H-benzo[b][1,4]thiazin-7-amine: To a solution of 7-nitro-4-(2-(pyrrolidin-1-yl)ethyl)-3,4-dihydro-2H-benzo[b][1,4]thiazine (0.637 g, 2.172 mmol) in MeOH (30 mL) was added Raney-Nickel (slurry in water) (~30 mg, 2.172 mmol) followed by hydrazine hydrate (1.056 mL, 21.72 mmol), and the mixture was immersed in a preheated oil bath and refluxed for 1 hour. The solution was cooled to room temperature, filtered through a pad of Celite, and washed with 100 mL of MeOH. The crude material was filtered through a silica plug (3.5-10% 2M NH$_3$ in MeOH/CH$_2$Cl$_2$). The solvent was evaporated to give the title product as a dark brown oil (0.61 g, quantitative). $^1$H NMR (DMSO-$d_6$) δ 6.49 (d, J=8.7 Hz, 1H), 6.26-6.23 (m, 2H), 4.42 (brs, 2H), 3.38-3.35 (m, 2H), 3.21 (t, J=7.2 Hz, 2H), 2.97-2.94 (m, 2H), 2.55 (t, J=7.2 Hz, 2H), 2.45 (brs, 4H), 1.66 (brs, 4H); ESI-MS (m/z, %): 266, 264 (MH$^+$, 100), 98 (34).

N-(4-(2-(Pyrrolidin-1-yl)ethyl)-3,4-dihydro-2H-benzo[b][1,4]thiazin-7-yl)thiophene-2-carboximidamide: Methyl thiophene-2-carbimidothioate hydroiodide (1.239 g, 4.34 mmol) was added to a mixture of 4-(2-(pyrrolidin-1-yl)ethyl)-3,4-dihydro-2H-benzo[b][1,4]thiazin-7-amine (0.572 g, 2.172 mmol) in EtOH (20 mL). The reaction was stirred overnight at room temperature. The reaction was quenched with saturated sodium bicarbonate solution (30 mL). The mixture was then extracted with CH$_2$Cl$_2$ (50 mL), and the aqueous phase was washed with CH$_2$Cl$_2$ (50 mL). The combined organic fractions were washed with brine (50 mL) and dried (Na$_2$SO$_4$). The crude material was subject to flash chromatography on silica gel (CH$_2$Cl$_2$ then 5% (2M NH$_3$ MeOH)/CH$_2$Cl$_2$). The collected fractions gave compound 11 as light brown viscous liquid (0.71 g, 88%). $^1$H NMR (DMSO-$d_6$) δ 7.69 (d, J=3.6 Hz, 1H), 7.56 (d, J=5.1 Hz, 1H), 7.08-7.06 (m, 1H), 6.67 (t, J=8.7 Hz, 1H), 6.50 (d, J=8.4 Hz, 1H), 6.46 (s, 1H), 6.32 (brs, 2H), 3.57-3.53 (m, 2H), 3.39-3.34 (m, 2H), 3.03-3.00 (m, 2H), 2.60 (t, J=7.2 Hz, 2H), 2.50 (brs, 4H), 1.68 (brs, 4H); ESI-MS (m/z, %): 375, 373 (MH$^+$, 47), 278, 276 (100), 98 (21).

N-(4-(2-(Pyrrolidin-1-yl)ethyl)-3,4-dihydro-2H-benzo[b][1,4]thiazin-7-yl)thiophene-2-carboximidamide dihydrochloride: To a stirred solution of N-(4-(2-(pyrrolidin-1-yl)ethyl)-3,4-dihydro-2H-benzo[b][1,4]thiazin-7-yl)thiophene-2-carboximidamide (0.3524 g, 0.946 mmol) in MeOH (2 mL) was added 1M HCl in ether (4.73 mL, 4.73 mmol) at room temperature. The mixture was stirred for 5 minutes under argon atmosphere and was then concentrated to give a yellow foam (0.646 g, quantitative). $^1$H NMR (DMSO-$d_6$) δ 11.51 (s, 1H), 11.23 (s, 1H), 9.68 (s, 1H), 8.69 (s, 1H), 8.15-8.11 (m, 2H), 7.37-7.34 (m, 1H), 7.08 (d, J=9.3 Hz, 1H), 7.00 (d, J=8.4 Hz, 1H), 3.81-3.76 (m. 2H), 3.66-3.64 (m, 2H), 3.56-3.46 (m, 2H), 3.33-3.30 (m, 2H), 3.13-3.10 (m, 2H), 3.06-3.00 (m, 2H), 2.00-1.86 (m, 4H); ESI-MS (m/z, %): 375, 373 (MH$^+$, free base, 66), 278, 276 (100), 98 (21); HRMS (C$_{19}$H$_{25}$N$_4$S$_2$, MH$^+$, Free base): calculated: 373.1515, observed: 373.1518. HPLC: 98% by area.

Example 12

Synthesis of N-(4-(2-(Dimethylamino)ethyl)-3,4-dihydro-2H-benzo[b][1,4]thiazin-7-yl)thiophene-2-carboximidamide dihydrochloride (12)

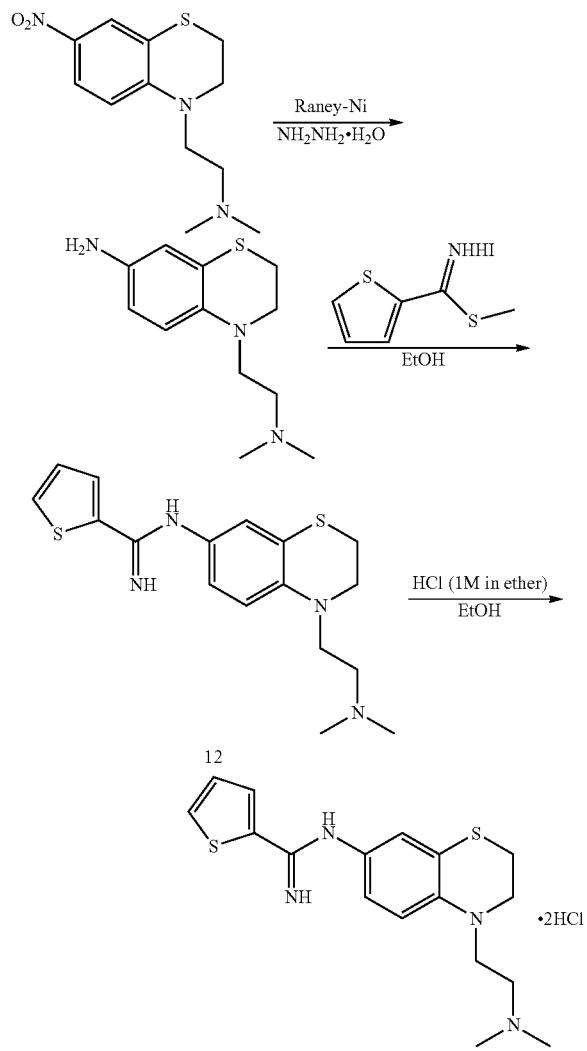

N,N-Dimethyl-2-(7-nitro-2H-benzo[b][1,4]thiazin-4(3H)-yl)ethanamine: Prepared according to the procedure reported in Example 8.

4-(2-(Dimethylamino)ethyl)-3,4-dihydro-2H-benzo[b][1,4]thiazin-7-amine: A dark mixture of N,N-dimethyl-2-(7-nitro-2H-benzo[b][1,4]thiazin-4(3H)-yl)ethanamine (1.0 g, 3.74 mmol) in methanol (10 mL) under an argon atmosphere was treated with Raney Nickel (~0.22 g, 3.74 mmol) and hydrazine hydrate (1.82 mL, 37.4 mmol). The reaction was transferred to a pre-heated oil bath at 65° C. After 50 minutes, the mixture was allowed to cool to room temperature and then poured over a pad of Celite. The Celite pad was rinsed with methanol (20 mL). The filtrate was concentrated, and the crude material was subjected to a short column on silica gel (1:9 (2M $NH_3$ in MeOH):$CH_2Cl_2$). The resulting brown residue was carried on to the next step. $^1$H-NMR (DMSO-$d_6$) δ 6.49 (d, J=9.0 Hz, 1H), 6.27-6.23 (m, 2H), 4.42 (brs, 2H), 3.40-3.30 (m, 2H), 3.18 (t, J=7.2 Hz, 2H), 2.98-2.94 (m, 2H), 2.36 (t, J=7.2 Hz, 2H), 2.16 (s, 6H); ESI-MS (m/z, %): 238 (MH$^+$, 100), 193 (56), 147 (58).

N-(4-(2-(Dimethylamino)ethyl)-3,4-dihydro-2H-benzo[b][1,4]thiazin-7-yl)thiophene-2-carboximidamide: A suspension of 4-(2-(dimethylamino)ethyl)-3,4-dihydro-2H-benzo[b][1,4]thiazin-7-amine (0.888 g, 3.74 mmol) and methyl thiophene-2-carbimidothioate hydroiodide (2.134 g, 7.48 mmol) in dry ethanol (15 mL) was stirred at room temperature overnight (16 hours). The solvent was evaporated, and the residue was partitioned between saturated $NaHCO_3$ solution (50 mL) and $CH_2Cl_2$ (25 mL). After stirring for 20 minutes, the mixture was transferred to a separatory funnel, and the organic layer was removed. The aqueous layer was extracted into $CH_2Cl_2$ (2×25 mL). The combined organic layer was dried ($Na_2SO_4$), filtered, and concentrated. The residue was subjected to column chromatography using silica gel ($CH_2Cl_2$, then 5:95 (2M $NH_3$ in MeOH):$CH_2Cl_2$) to give the title product 12 as a solid (0.44 g, 33.9%). $^1$H-NMR (DMSO-$d_6$) δ 7.69 (d, J=3.3 Hz, 1H), 7.56 (d, J=5.1 Hz, 1H), 7.07 (dd, J=4.8, 3.9 Hz, 1H), 6.66 (d, J=8.7 Hz, 1H), 6.52-6.46 (m, 2H), 6.32 (brs, 2H), 3.56-3.52 (m, 2H), 3.36-3.32 (m, 2H), 3.03-3.00 (m, 2H), 2.41 (t, J=7.2 Hz, 2H), 2.19 (s, 6H); ESI-MS (m/z, %): 347 (MH$^+$, 100), 276 (84%).

N-(4-(2-(Dimethylamino)ethyl)-3,4-dihydro-2H-benzo[b][1,4]thiazin-7-yl)thiophene-2-carboximidamide dihydrochloride: A solution of N-(4-(2-(dimethylamino)ethyl)-3,4-dihydro-2H-benzo[b][1,4]thiazin-7-yl)thiophene-2-carboximidamide (0.44 g, 1.270 mmol) in dry ethanol (10 mL) was treated with hydrochloric acid (1M in ether; 6.35 mL, 6.35 mmol) and stirred at room temperature for 1 hour. The precipitate was isolated and washed with ether to give a yellow-green powder. The powder was dried under reduced pressure. (0.46 g, 86%). $^1$H-NMR (DMSO-$d_6$) δ 11.25 (brs, 2H), 9.69 (brs, 1H), 8.69 (brs, 1H), 8.15-8.13 (m, 2H), 7.37-7.37 (m, 1H), 7.07-7.01 (m, 3H), 3.82-3.77 (m, 2H), 3.70-3.60 (m, 2H), 3.25-3.21 (m, 2H), 3.15-3.10 (m, 2H), 2.80 (d, J=3.6 Hz, 6H); ESI-MS (m/z, %): 347 (MH$^+$, free base, 100); ESI-HRMS calculated for $C_{17}H_{23}N_4S_2$ (MH$^+$, free base): 347.1358, observed: 347.1343; HPLC purity: 97% by area.

Example 13

Synthesis of N-(4-(2-(1-methylpyrrolidin-2-yl)ethyl)-3,4-dihydro-2H-benzo[b][1,4]thiazin-7-yl)thiophene-2-carboximidamide (13)

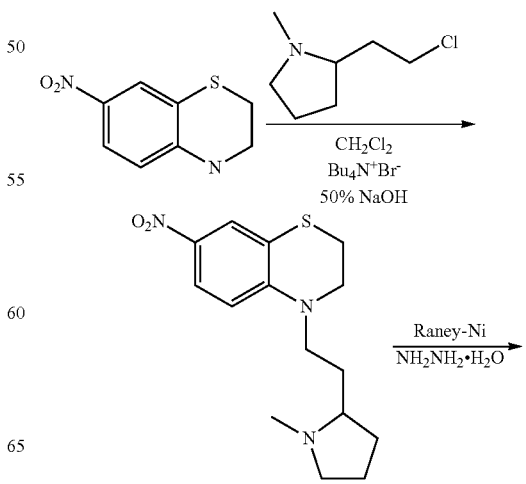

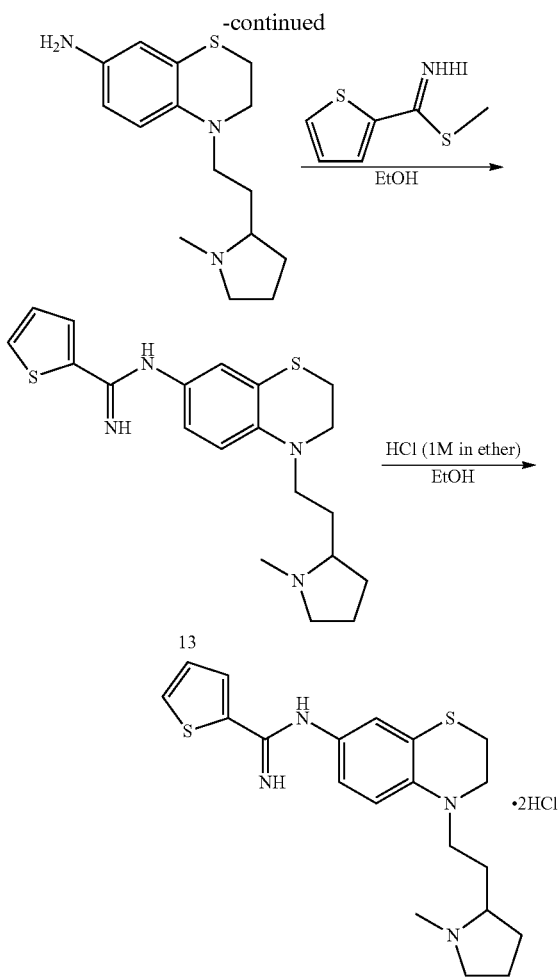

7-Nitro-3,4-dihydro-2H-benzo[b][1,4]thiazine: Prepared according to the procedure reported in Example 11.

4-(2-(1-Methylpyrrolidin-2-yl)ethyl)-7-nitro-3,4-dihydro-2H-benzo[b][1,4]thiazine: A mixture of 7-nitro-3,4-dihydro-2H-benzo[b][1,4]thiazine (1 g, 5.10 mmol), 2-(2-chloroethyl)-1-methylpyrrolidine hydrochloride (1.876 g, 10.19 mmol), and tetrabutylammonium bromide (0.082 g, 0.255 mmol) in dichloromethane (10 mL) and 50% NaOH solution (10 mL) was stirred at room temperature for 16 hours (overnight). The reaction was then diluted with dichloromethane (5 mL) and water (20 mL), and the mixture was transferred to a separatory funnel. The organic layer was removed, and the aqueous layer was extracted into dichloromethane (2×10 mL). The combined organic layers were dried ($Na_2SO_4$), filtered, and concentrated. The red crude material was subjected to column chromatography on silica gel using the Biotage purification system (80 g silicycle column; gradient: dichloromethane 3CV then ramp to 6:94 (2M $NH_3$ in methanol):dichloromethane over 15CV; 254 nm; flow: 45 mL/min) to give the title compound as yellow-orange solid (0.827 g, 52.8%). $^1$H-NMR (DMSO-$d_6$) δ 7.87 (dd, J=3.0, 9.0 Hz, 1H), 7.83 (d, J=3.0 Hz, 1H), 6.79 (d, J=9.3 Hz, 1H), 3.79-3.76 (m, 2H), 3.46 (t, J=8.1 Hz, 2H), 3.08-3.05 (m, 2H), 2.99-2.92 (m, 1H), 2.23 (s, 3H), 2.10-2.06 (m, 2H), 1.92-1.78 (m, 2H), 1.66-1.61 (m, 2H), 1.54-1.47 (m, 2H); ESI-MS (m/z, %): 308 (MH$^+$, 100).

4-(2-(1-Methylpyrrolidin-2-yl)ethyl)-3,4-dihydro-2H-benzo[b][1,4]thiazin-7-amine: A solution of 4-(2-(1-methylpyrrolidin-2-yl)ethyl)-7-nitro-3,4-dihydro-2H-benzo[b][1,4]thiazine (0.82 g, 2.67 mmol) in methanol (10 mL) under an argon atmosphere was treated with hydrazine hydrate (1.29 mL, 26.7 mmol) and a small amount of Raney Nickel (~0.15 g, 2.67 mmol). The reaction was transferred to a pre-heated oil bath at 65° C. After 3 hours, the reaction was poured over a pad of Celite, rinsing with methanol. The filtrate was concentrated, and the residue was poured over a pad of silica gel. The silica gel pad was rinsed with 1:9 (2M $NH_3$ in methanol):dichloromethane (200 mL). The filtrate was concentrated, dried under reduced pressure, and carried on to the next step. $^1$H-NMR (DMSO-$d_6$) δ 6.48 (brd, J=9.3 Hz, 1H), 6.27-6.24 (m, 2H), 4.42 (brs, 2H), 3.33-3.29 (m, 2H), 3.13-3.06 (m, 2H), 2.99-2.96 (m, 2H), 2.96-2.90 (m, 1H), 2.19 (s, 3H), 2.06-1.97 (m, 2H), 1.96-1.78 (m, 2H), 1.63-1.60 (m, 2H), 1.56-1.40 (m, 2H); ESI-MS (m/z, %): 278 (MH$^+$, 100).

N-(4-(2-(1-Methylpyrrolidin-2-yl)ethyl)-3,4-dihydro-2H-benzo[b][1,4]thiazin-7-yl)thiophene-2-carboximidamide: A suspension of 4-(2-(1-methylpyrrolidin-2-yl)ethyl)-3,4-dihydro-2H-benzo[b][1,4]thiazin-7-amine (0.7 g, 2.52 mmol) and methyl thiophene-2-carbimidothioate hydroiodide (1.439 g, 5.05 mmol) in dry ethanol (15 mL) was stirred at room temperature overnight (16 hours) under an argon atmosphere. At this time, the solvent was evaporated, and the residue was partitioned between saturated $NaHCO_3$ solution (50 mL) and dichloromethane (25 mL). The mixture was transferred to a separatory funnel, and the organic layer was removed. The aqueous layer was extracted into dichloromethane (2×25 mL). The combined organic layers were dried ($Na_2SO_4$), filtered, and concentrated. The residue was subjected to column chromatography on silica gel (sequence of eluents: 2:98 methanol:dichloromethane, 5:95 methanol:dichloromethane, and 5:95 (2M ammonia in methanol):dichloromethane) to give compound 13 as yellow syrup (0.48 g, 49%). $^1$H-NMR (DMSO-$d_6$) δ 7.69 (brd, J=2.7 Hz, 1H), 7.57 (brd, J=4.5 Hz, 1H), 7.07 (dd, J=3.9, 4.8 Hz, 1H), 6.52 (dd, J=1.8, 8.1 Hz, 2H), 6.47 (brd, J=1.8 Hz, 1H), 6.38 (brs, 2H), 3.51-3.47 (m, 2H), 3.28-3.22 (m, 2H), 3.05-3.02 (m, 2H), 2.99-2.93 (m, 1H), 2.24 (s, 3H), 2.12-2.06 (m, 2H), 1.94-1.87 (m, 2H), 1.68-1.63 (m, 2H), 1.51-1.42 (m, 2H); ESI-MS (m/z, %): 387 (MH$^+$, 90), 276 (100), 194 (50).

N-(4-(2-(1-Methylpyrrolidin-2-yl)ethyl)-3,4-dihydro-2H-benzo[b][1,4]thiazin-7-yl)thiophene-2-carboximidamide dihydrochloride: A solution of N-(4-(2-(1-methylpyrrolidin-2-yl)ethyl)-3,4-dihydro-2H-benzo[b][1,4]thiazin-7-yl)thiophene-2-carboximidamide (0.48 g, 1.242 mmol) in dry ethanol (10 mL) was treated with hydrochloric acid (1M in ether; 6.21 mL, 6.21 mmol) and stirred for half an hour. The precipitate was collected and rinsed with ether. The precipitate was dissolved in methanol and concentrated to give a yellow-orange crystalline solid (0.57 g, 100%). $^1$H-NMR (DMSO-$d_6$) δ 11.22 (brs, 1H), 11.17 (brs, 1H), 9.68 (brs, 1H), 8.72 (brs, 1H), 8.15-8.13 (m, 2H), 7.37-7.34 (m, 1H), 7.05-6.99 (m, 2H), 6.91 (brd, J=8.7 Hz, 1H), 3.66-3.64 (m, 2H), 3.55-3.41 (m, 3H), 3.38-3.22 (m, 1H), 3.12-3.09 (m, 2H), 3.00-2.97 (m, 1H), 2.76 (d, J=4.8 Hz, 3H), 2.32-2.18 (m, 2H), 1.99-1.86 (m, 3H), 1.77-1.71 (m, 1H); ESI-MS (m/z, %): 387 (MH$^+$, free base, 100), 194 (19); ESI-HRMS calculated for $C_{20}H_{27}N_4S_2$ (MH$^+$, free base): 387.1671, observed: 387.1654; HPLC purity: 97% by area.

Example 14

Synthesis of N-(4-(2-(Piperidin-1-yl)ethyl)-3,4-dihydro-2H-benzo[b][1,4]thiazin-7-yl)thiophene-2-carboximidamide (14)

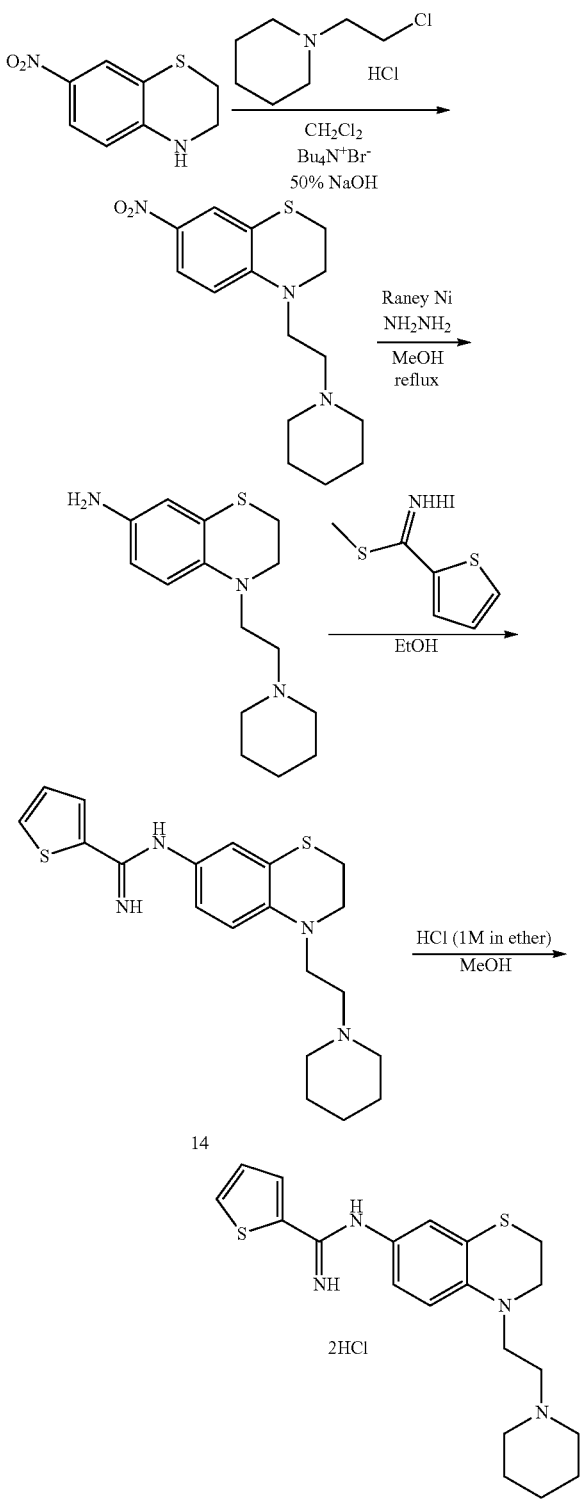

7-Nitro-3,4-dihydro-2H-benzo[b][1,4]thiazine: Prepared according to the procedure reported in Example 11.

7-Nitro-4-(2-(piperidin-1-yl)ethyl)-3,4-dihydro-2H-benzo[b][1,4]thiazine: A mixture of 7-nitro-3,4-dihydro-2H-benzo[b][1,4]thiazine (1 g, 5.10 mmol), 1-(2-chloroethyl)piperidine hydrochloride (1.876 g, 10.19 mmol), and tetrabutylammonium bromide (0.082 g, 0.255 mmol) in dichloromethane (10 mL) and 50% NaOH solution (10 mL) was stirred at room temperature overnight (16 hours). The mixture was diluted with dichloromethane (5 mL) and water (20 mL), and the mixture was then transferred to a separatory funnel. The organic layer was removed, and the aqueous layer was extracted in dichloromethane (2×10 mL). The combined organic layers were dried ($Na_2SO_4$), filtered, and concentrated. The red crude material was subjected to column chromatography on silica gel using the Biotage purification system (80 g silicycle column; solvent gradient: dichloromethane 3CV, ramp to 6:94 (2M $NH_3$ in methanol):$CH_2Cl_2$ over 15CV; 254 nm monitoring wavelength; flow=45 mL/minute), to give an orange solid (0.937 g, 59.8%). $^1$H-NMR (DMSO-$d_6$) δ 7.85-7.81 (m, 2H), 6.82 (d, J=9.0 Hz, 1H), 3.82-3.79 (m, 2H), 3.58 (t, J=6.9 Hz, 2H), 3.08-3.04 (m, 2H), 2.50-2.45 (m, 2H), 2.44-2.34 (m, 4H), 1.49-1.46 (m, 4H), 1.40-1.37 (m, 2H); ESI-MS (m/z, %): 308 (MH$^+$, 100).

4-(2-(Piperidin-1-yl)ethyl)-3,4-dihydro-2H-benzo[b][1,4]thiazin-7-amine: A mixture of 7-nitro-4-(2-(piperidin-1-yl)ethyl)-3,4-dihydro-2H-benzo[b][1,4]thiazine (0.9 g, 2.93 mmol) in methanol (10 mL) under an argon atmosphere was treated first with hydrazine hydrate (1.424 mL, 29.3 mmol) and then with Raney-Nickel (~0.172 g, 2.93 mmol). The reaction was transferred to oil bath pre-heated to 65° C. After one hour, the reaction mixture was poured over a pad of Celite. The pad of Celite was then rinsed with methanol (25 mL). The purple filtrate was concentrated and subjected to a short column on silica gel (1:9 (2M $NH_3$ in MeOH):$CH_2Cl_2$). The fractions were concentrated, and the residue was carried on to the next step. $^1$H-NMR (DMSO-$d_6$) δ 6.49 (d, J=8.7 Hz, 1H), 6.26-6.23 (m, 2H), 4.41 (s, 2H), 3.38-3.35 (m, 2H), 3.20 (t, J=7.2 Hz, 2H), 2.98-2.94 (m, 2H), 2.40-2.34 (m, 6H), 1.50-1.46 (m, 4H), 1.38-1.36 (m, 2H); ESI-MS (m/z, %): 278 (MH$^+$, 100).

N-(4-(2-(Piperidin-1-yl)ethyl)-3,4-dihydro-2H-benzo[b][1,4]thiazin-7-yl)thiophene-2-carboximidamide: A suspension of 4-(2-(piperidin-1-yl)ethyl)-3,4-dihydro-2H-benzo[b][1,4]thiazin-7-amine (0.90 g, 3.24 mmol) and methyl thiophene-2-carbimidothioate hydroiodide (1.85 g, 6.49 mmol) was stirred at room temperature overnight (16 hours) under an argon atmosphere. The reaction was concentrated, and the residue was partitioned between saturated sodium bicarbonate solution (50 mL) and dichloromethane (25 mL). After stirring for an hour, the mixture was poured into a separatory funnel. The organic layer was removed, and the aqueous layer was extracted into dichloromethane (2×20 mL). The combined organic layers were dried ($Na_2SO_4$), filtered, and concentrated. The residue was subjected to column chromatography on silica gel (2:98 to 5:95 MeOH:$CH_2Cl_2$ followed by 5:95 (2M $NH_3$ in MeOH):$CH_2Cl_2$) to give compound 14 as yellow solid (0.288 g, 23%). $^1$H-NMR (DMSO-$d_6$) δ 7.69 (d, J=3.3 Hz, 1H), 7.57 (d, J=4.5 Hz, 1H), 7.09-7.06 (m, 1H), 6.67 (d, J=8.7 Hz, 1H), 6.52-6.47 (m, 2H), 6.39 (brs, 2H), 3.56-3.53 (m, 2H), 3.39-3.33 (m, 2H), 3.03-3.01 (m, 2H), 2.45-2.39 (m, 6H), 1.49-1.48 (m, 4H), 1.39-1.38 (m, 2H); ESI-MS (m/z, %): 387 (MH$^+$, 77), 276 (46), 194 (100).

N-(4-(2-(Piperidin-1-yl)ethyl)-3,4-dihydro-2H-benzo[b][1,4]thiazin-7-yl)thiophene-2-carboximidamide dihydrochloride: A solution of N-(4-(2-(piperidin-1-yl)ethyl)-3,4-dihydro-2H-benzo[b][1,4]thiazin-7-yl)thiophene-2-carboximidamide (0.288 g, 0.745 mmol) in anhydrous methanol (8 mL) was treated with hydrochloric acid (1M in ether; 3.72 mL, 3.72 mmol). The reaction was stirred at room temperature for 0.5 hours and then concentrated to give an orange solid (0.34 g, 99%). $^1$H-NMR (DMSO-$d_6$) δ 11.21 (brs, 1H), 11.16 (brs, 1H), 9.67 (brs, 1H), 8.69 (brs, 1H), 8.15 (brd, J=4.8 Hz, 1H), 8.11 (brd, J=3.0 Hz, 1H), 7.38-7.35 (m, 1H), 7.11-6.98 (m, 3H), 3.89-3.84 (m, 2H), 3.68-3.64 (m, 2H), 3.45-3.42 (m, 2H), 3.22-3.15 (m, 2H), 3.12-3.09 (m, 2H), 2.89-2.88 (m, 2H), 1.87-1.71 (m, 5H), 1.42-1.38 (m, 1H); ESI-MS (m/z, %): 387 (MH$^+$, free base, 100), 194 (23); ESI-HRMS calculated for $C_{20}H_{27}N_4S_2$ (MH$^+$, free base): 387.1671, observed: 337.1657; HPLC purity: 99% by area.

Example 15

Synthesis of N-(4-(2-(Diethylamino)ethyl)-3,4-dihydro-2H-benzo[b][1,4]thiazin-7-yl)thiophene-2-carboximidamide (15)

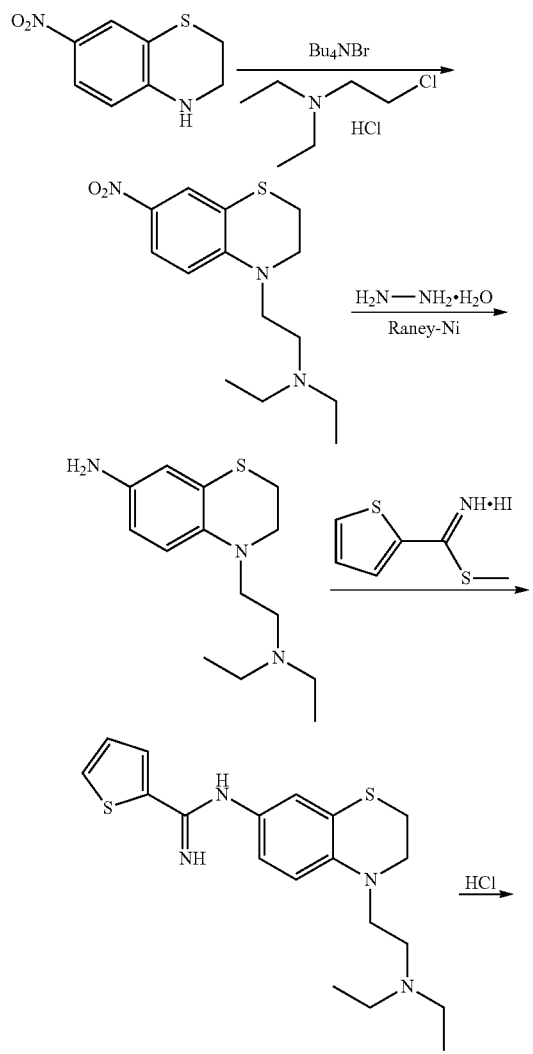

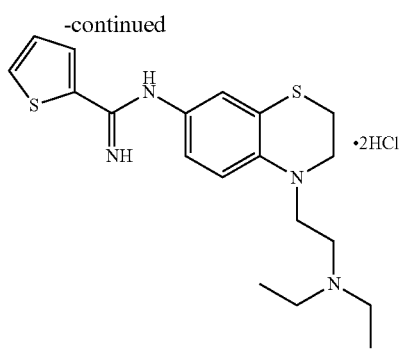

7-Nitro-3,4-dihydro-2H-benzo[b][1,4]thiazine: Prepared according to the procedure reported in Example 11.

N,N-Diethyl-2-(7-nitro-2H-benzo[b][1,4]thiazin-4(3H)-yl)ethanamine: A mixture of 7-nitro-3,4-dihydro-2H-benzo[b][1,4]thiazine (1 g, 5.10 mmol), 2-chloro-N,N-diethylethanamine hydrochloride (1.754 g, 10.19 mmol), and nBu$_4$NBr (0.082 g, 0.255 mmol) in CH$_2$Cl$_2$ (10 mL) and water (10 mL) was stirred at room temperature for 16 hours. The mixture was diluted with CH$_2$Cl$_2$ (5 mL) and water (20 mL). The mixture was transferred to a separatory funnel, and the layers were separated. The aqueous layer was extracted with CH$_2$Cl$_2$ (2×10 mL). The combined organic layers were dried (Na$_2$SO$_4$), filtered, and concentrated. The red crude material was subjected to flash chromatography on silica gel (CH$_2$Cl$_2$ then 1.75-3.5% (2M NH$_3$ in MeOH):CH$_2$Cl$_2$) to give a brown oil (1.15 g, 77%). $^1$H NMR (DMSO-$d_6$) δ 7.86-7.81 (m, 2H), 6.81 (d, J=9 Hz, 1H), 3.85-3.82 (m, 2H), 3.53 (t, J=6.6 Hz, 2H), 3.07-3.04 (m, 2H), 2.58 (t, J=6.3 Hz, 2H), 2.52-2.45 (m, 4H), 0.92 (t, J=7.2 Hz, 6H); ESI-MS (m/z, %): 298, 296 (MH$^+$, 100).

4-(2-(Diethylamino)ethyl)-3,4-dihydro-2H-benzo[b][1,4]thiazin-7-amine: To a stirred solution of N,N-diethyl-2-(7-nitro-2H-benzo[b][1,4]thiazin-4(3H)-yl)ethanamine (1.109 g, 3.76 mmol) in MeOH (30 mL) was added Raney-Nickel (slurry in water; ~0.1 g, 3.76 mmol) followed by hydrazine hydrate (1.828 mL, 37.6 mmol). The mixture was immersed in a preheated oil bath and refluxed for 30 minutes. The solution was cooled to room temperature, filtered through Celite, and washed with MeOH. The crude material was filtered through a silica plug (3.5% (2M NH$_3$ in MeOH):CH$_2$Cl$_2$). The solvent was evaporated to give the product as dark brown oil (1.07 g, quantitative). $^1$H NMR (CDCl$_3$) δ 6.58 (d, J=8.7 Hz, 1H), 6.45 (d, J=2.7 Hz, 1H), 6.40 (dd, J=2.7, 8.7 Hz, 1H), 3.53-3.50 (m, 2H), 3.30 (m, 4H), 3.03-2.99 (m, 2H), 1.03 (t, J=7.2 Hz, 6H); ESI-MS (m/z, %): 268, 266 (MH$^+$, 100), 100 (52).

N-(4-(2-(Diethylamino)ethyl)-3,4-dihydro-2H-benzo[b][1,4]thiazin-7-yl)thiophene-2-carboximidamide: Methyl thiophene-2-carbimidothioate hydroiodide (2.266 g, 7.94 mmol) was added to a mixture of 4-(2-(diethylamino)ethyl)-3,4-dihydro-2H-benzo[b][1,4]thiazin-7-amine (1.054 g, 3.97 mmol) in EtOH (20 mL). The mixture was stirred for 2 days at room temperature. The reaction was quenched with saturated sodium bicarbonate solution (30 mL) and extracted with CH$_2$Cl$_2$ (50 mL). The aqueous phase was washed with CH$_2$Cl$_2$ (50 mL). The combined organic fractions were washed with brine (50 mL) and dried (Na$_2$SO$_4$). The crude material was subject to flash chromatography on silica gel (CH$_2$Cl$_2$ followed by 3.5% (2M NH$_3$ in MeOH):CH$_2$Cl$_2$). The collected fractions were concentrated, and the sample was subjected again to flash chromatography on silica gel (2.5% MeOH:CH$_2$Cl$_2$). The collected fractions were concentrated to give compound 15 as a brown solid. (1.23 g, 83%). $^1$H NMR (CDCl$_3$) δ 7.40-7.36 (m, 2H), 7.05 (dd, J=3.9, 4.8 Hz, 1H), 6.73 (m, 3H), 3.65-3.61 (m, 1H), 3.39 (t, J=7.2 Hz, 2H), 3.05-3.02 (m, 2H), 2.67-2.54 (m, 6H), 1.04 (t, J=7.2 Hz, 6H); ESI-MS (m/z, %): 377, 375 (MH$^+$, 35), 278, 276 (100).

N-(4-(2-(Diethylamino)ethyl)-3,4-dihydro-2H-benzo[b][1,4]thiazin-7-yl)thiophene-2-carboximidamide dihydrochloride: To a stirred solution of N-(4-(2-(diethylamino)ethyl)-3,4-dihydro-2H-benzo[b][1,4]thiazin-7-yl)thiophene-2-carboximidamide (1.149 g, 3.07 mmol) in MeOH (5 mL) was added 1M HCl in ether (15.35 mL, 15.35 mmol) at room temperature. The mixture was stirred for 5 minutes under argon atmosphere and concentrated to give a yellow solid (1.37 g, quantitative). $^1$H NMR (DMSO-d$_6$) δ 11.24 (s, 2H), 9.68 (s, 1H), 8.69 (s, 1H), 8.15-8.13 (m, 2H), 7.37-7.34 (m, 1H), 7.12-7.00 (m, 3H), 3.88-3.83 (m, 2H), 3.69-3.66 (m, 2H), 3.17-3.10 (m, 8H), 1.25 (t, J=7.2 Hz, 6H); ESI-MS (m/z, %): 377, 375 (MH$^+$, free base, 58), 278, 276 (100); ESI-HRMS calculated for C$_{19}$H$_{25}$N$_4$S$_2$ (MH$^+$, free base), calculated: 375.1671, observed: 375.1667; HPLC: 95% by area.

Example 16

Synthesis of N-(4-(2-(2-hydroxyethylamino)ethyl)-3,4-dihydro-2H-benzo[b][1,4]thiazin-7-yl)thiophene-2-carboximidamide dihydrochloride (16)

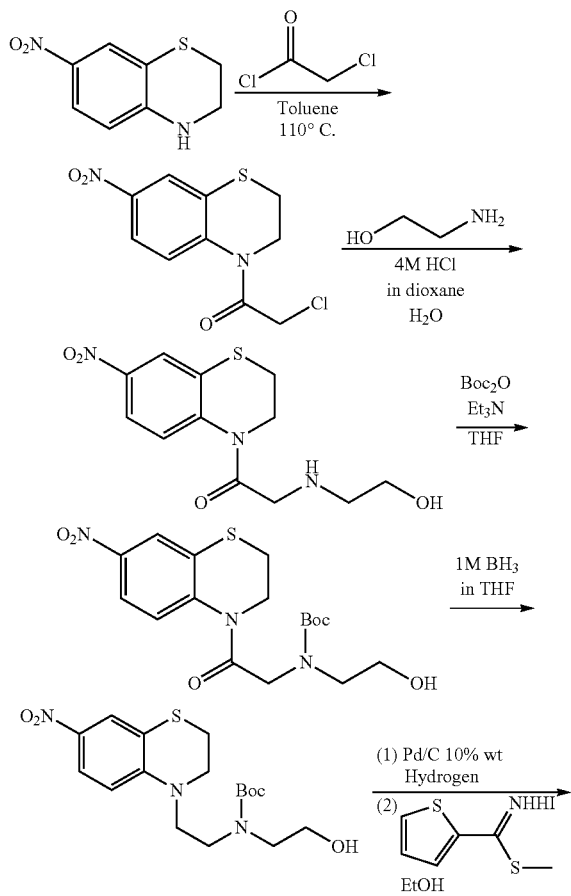

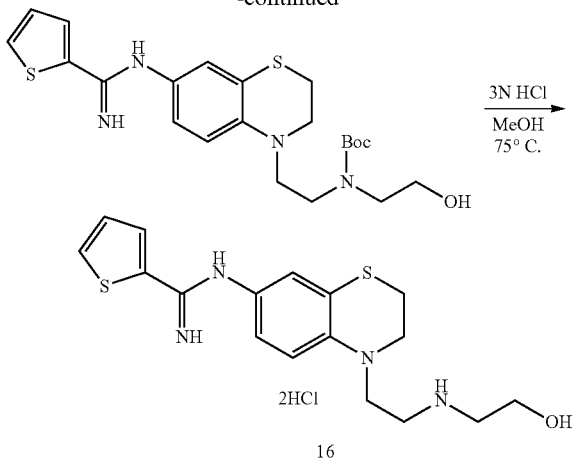

7-Nitro-3,4-dihydro-2H-benzo[b][1,4]thiazine: Prepared according to the procedure reported in Example 11.

2-Chloro-1-(7-nitro-2H-benzo[b][1,4]thiazin-4(3H)-yl)ethanone: 2-Chloroacetyl chloride (4.08 mL, 50.9 mmol) was added dropwise to a solution containing 7-nitro-3,4-dihydro-2H-benzo[b][1,4]thiazine (5 g, 25.5 mmol) in toluene (30 mL). The mixture was refluxed at 110° C. for 20 minutes. The mixture was quenched with saturated sodium bicarbonate solution (100 mL). The mixture was transferred to a separatory funnel and extracted with EtOAc (4×100 mL). The crude material was filtered through a pad of silica gel and washed with EtOAc. The filtrate was concentrated to give a yellow-brown solid. $^1$H-NMR (DMSO-d$_6$) δ 8.12 (d, J=2.7 Hz, 1H), 7.94 (dd, J=2.7, 9.0 Hz, 1H), 7.72 (d, J=9.0 Hz, 1H), 4.63 (s, 2H), 3.96 (t, J=5.1 Hz, 2H), 3.32 (t, J=5.4 Hz, 2H, overlap with solvent peak); ESI-MS (m/z, %): 273 (MH$^+$, 100), 295 (40).

2-(2-Hydroxyethylamino)-1-(7-nitro-2H-benzo[b][1,4]thiazin-4(3H)-yl)ethanone: A solution of 2-chloro-1-(7-nitro-2H-benzo[b][1,4]thiazin-4(3H)-yl)ethanone (1.0 g, 3.67 mmol) in THF (20 mL) was treated with 4M HCl in 1,4-dioxane (4.58 mL, 18.33 mmol), followed by the slow addition of a solution of 2-aminoethanol (2.207 mL, 36.7 mmol) in water (4 mL). The dark solution was stirred at room temperature for 24 hours. The mixture was diluted with EtOAc (50 mL) and saturated sodium bicarbonate (100 mL), then stirred for 20 minutes. The contents were poured into a separatory funnel, and the organic layer was separated, dried (Na$_2$SO$_4$), filtered, and concentrated to give a dark yellow residue. This residue was subjected to flash chromatography on silica gel using 5:95 MeOH:CH$_2$Cl$_2$ followed by 5:95 (2M NH$_3$ in MeOH):CH$_2$Cl$_2$ to give a yellow residue (320 mg, 29.4%). $^1$H-NMR (CDCl$_3$) δ 8.14 (d, J=2.7 Hz, 1H), 7.95 (dd, J=2.7, 9.0 Hz, 1H), 7.37 (d, J=9.0 Hz, 1H), 4.02 (t, J=5.1 Hz, 2H), 3.61 (t, J=5.1 Hz, 2H), 3.57 (s, 2H), 3.28 (t, J=5.4 Hz, 2H), 2.77 (t, J=4.8 Hz, 2H); ESI-MS (m/z, %): 298 (MH$^+$, 100%).

tert-Butyl 2-hydroxyethyl(2-(7-nitro-2H-benzo[b][1,4]thiazin-4(3H)-yl)-2-oxoethyl)carbamate: A solution of 2-(2-hydroxyethylamino)-1-(7-nitro-2H-benzo[b][1,4]thiazin-4(3H)-yl)ethanone (300 mg, 1.009 mmol) in THF (15 mL) was treated with Boc anhydride (231 mg, 1.059 mmol) followed by triethylamine (0.422 mL, 3.03 mmol). The yellow solution was stirred at room temperature for 18 hours (overnight). The solution was diluted with EtOAc (20 mL) and treated with saturated sodium bicarbonate solution (20 mL). The mixture was transferred to a separatory funnel and extracted. After extraction, the organic layer was separated, dried (Na$_2$SO$_4$), and filtered through a silica gel plug. The pad was rinsed with EtOAc (10 mL), and the filtrate was concentrated to give a yellow residue. This residue was subjected to silica gel chromatography using the Biotage purification system (column: Silicycle 40 g; 30% EtOAc/70% hexanes gradient to 90% EtOAc/10% hexanes over 10 column volumes; flow rate=35 mL/min; collection wavelength: 254 nm). A yellow residue was obtained after drying under reduced pressure (270 mg, 67.3%). $^1$H-NMR (CDCl$_3$) (mixture of rotamers) δ 8.15 (dd, J=2.7, 8.1 Hz, 1H), 7.94 (dd, J=2.4, 8.7 Hz, 1H), 7.58 and 7.31 (2×d, J=9.0 Hz, 1H), 4.41 (brs, 1H), 4.12-3.88 (m, 4H), 3.82-3.66 (m, 2H), 3.48 and 3.11 (2×t, J=4.5 Hz, 2H), 3.29 (t, J=4.5 Hz, 2H), 1.46 and 1.40 (2×s, 9H); ESI-MS (m/z, %): 420 (M+Na, 70), 398 (MH$^+$, 40), 298 (100).

tert-Butyl 2-hydroxyethyl(2-(7-nitro-2H-benzo[b][1,4]thiazin-4(3H)-yl)ethyl)carbamate: A solution of tert-butyl 2-hydroxyethyl(2-(7-nitro-2H-benzo[b][1,4]thiazin-4(3H)-yl)-2-oxoethyl)carbamate (250 mg, 0.629 mmol) in THF (10 mL) was cooled to 0° C. then treated with borane in THF (1M) (6.29 mL, 6.29 mmol) The resulting bright yellow solution was allowed to warm to room temperature and then stirred at this temperature for 2.5 days. The mixture was cooled to 0° C., and the reaction was then carefully quenched with MeOH (dropwise addition at first; 20 mL total). The cooling bath was removed, and the yellow solution was stirred for 20 minutes then concentrated. The orange residue was dissolved in MeOH (50 mL) and concentrated to dryness. This residue was dissolved in EtOAc (20 mL) and filtered through a pad of silica gel. The silica pad was eluted with EtOAc (100 mL). The filtrate was concentrated to give an orange residue which was dried under reduced pressure for 4 hours (230 mg, 95%). $^1$H-NMR (CDCl$_3$) δ 7.97 (brs, 1H), 7.87 (brd, J=8.7 Hz, 1H), 6.85-6.71 (m, 1H), 3.81 (brs, 5H), 3.61 (brs, 2H), 4.54-3.31 (m, 4H), 3.02 (overlapping t, 2H), 1.47 (brs, 9H); ESI-MS (m/z, %): 406 (M+Na, 60), 384 (MH$^+$, 10), 328 (60), 284 (100).

tert-Butyl 2-hydroxyethyl(2-(7-(thiophene-2-carboximidamido)-2H-benzo[b][1,4]thiazin-4(3H)-yl)ethyl)carbamate: A round bottom flask containing tert-butyl 2-hydroxyethyl(2-(7-nitro-2H-benzo[b][1,4]thiazin-4(3H)-yl)ethyl) carbamate (220 mg, 0.574 mmol) under argon was charged with palladium on activated carbon (10% wt; 61.0 mg, 0.057 mmol). The mixture was purged with argon prior to the addition of EtOH (20 mL). The resulting suspension was evacuated using a pump, and hydrogen was let into the system via a balloon. The mixture was stirred under a balloon filled with hydrogen for 3 hours. The hydrogen balloon was removed, and methyl thiophene-2-carbimidothioate hydroiodide (327 mg, 1.147 mmol) was added to the reaction. The suspension was stirred at room temperature for 17 hours (overnight). After this time, the mixture was filtered through a pad of Celite, which was then rinsed with MeOH (10 mL). The filtrate was concentrated, and the residue was partitioned between saturated sodium bicarbonate solution (50 mL) and CH$_2$Cl$_2$ (100 mL). The mixture was transferred to a separatory funnel and extracted. After extraction, the organic layer was separated, dried (Na$_2$SO$_4$), filtered, and concentrated to give a dark residue. This residue was subjected to flash chromatography on silica gel using 2:98 MeOH/CH$_2$Cl$_2$ followed by 3.5:96.5 (2M NH$_3$ in MeOH):CH$_2$Cl$_2$ to give a yellow solid (140 mg, 52.7%). $^1$H-NMR (DMSO-d$_6$) δ 7.69 (brd, J=3.0 Hz, 1H), 7.57 (d, J=5.1 Hz, 1H), 7.07 (dd, J=3.9, 4.8 Hz, 1H), 6.82-6.75 (m, 1H), 6.53-6.42 (m, 2H), 6.32 (brs, 2H), 4.73 (t, J=5.4 Hz, 1H), 3.54 (brs, 2H), 3.50-3.42 (m, 2H), 3.38 (brs, 4H, overlap with solvent peak), 3.27-3.19 (m, 2H), 3.08- 2.96 (m, 2H), 1.41 (brs, 9H); ESI-MS (m/z, %): 463 (MH$^+$, 100), 398 (60); HPLC purity: 96.4% a/a.

N-(4-(2-(2-Hydroxyethylamino)ethyl)-3,4-dihydro-2H-benzo[b][1,4]thiazin-7-yl)thiophene-2-carboximidamide dihydrochloride: To a solution of tert-butyl 2-hydroxyethyl (2-(7-(thiophene-2-carboximidamido)-2H-benzo[b][1,4]thiazin-4(3H)-yl)ethyl)carbamate (130 mg, 0.281 mmol) in MeOH (10 mL) was added 3N HCl (2.81 mL, 8.43 mmol). The yellow solution was heated at 75° C. for 30 minutes. At this time, the reaction was filtered and concentrated to half its volume. The yellow solution was then extracted with 2×50 mL CH$_2$Cl$_2$, and the aqueous layer was concentrated to dryness to give a yellow residue. This residue was dried under reduced (high vacuum) pressure to give compound 16 as yellow powder. $^1$H-NMR (CD$_3$OD) δ 7.98-7.94 (m, 2H), 7.29 (pseudo t, J=4.2 Hz, 1H), 7.04-6.94 (m, 3H), 3.79 (brt, J=4.8 Hz, 2H), 3.72-3.65 (m, 4H), 3.28 (brs, 2H), 3.16 (brt, J=5.1 Hz, 2H), 3.09-3.06 (m, 2H); ESI-MS (m/z, %): 363 (MH$^+$, free base, 100), 276 (90); ESI-HRMS calculated for C$_{17}$H$_{23}$N$_4$O$_1$S$_2$ (MH$^+$, free base): 363.1307, observed: 363.1316; HPLC purity: 96.2% a/a.

Example 17

Synthesis of 2-(methyl(2-(7-(thiophene-2-carboximidamido)-2H-benzo[b][1,4]thiazin-4(3H)-yl)ethyl) amino)acetic acid dihydrochloride (17)

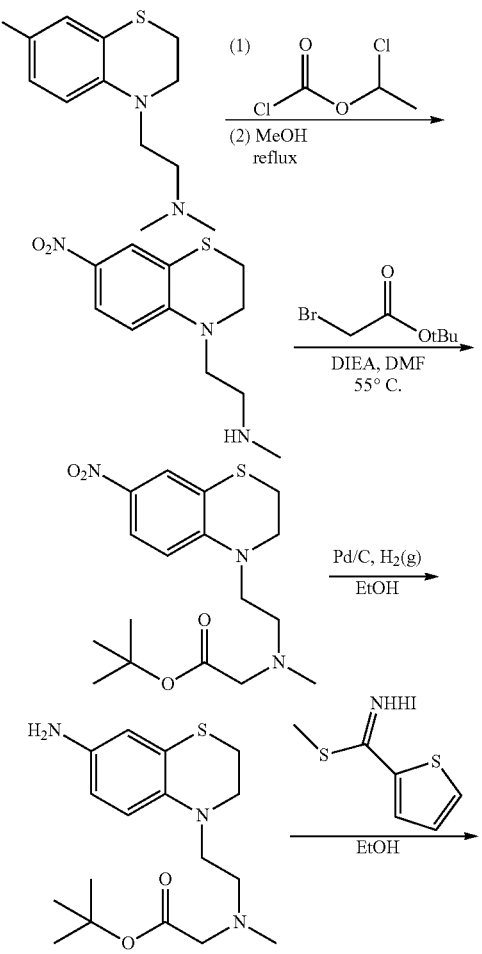

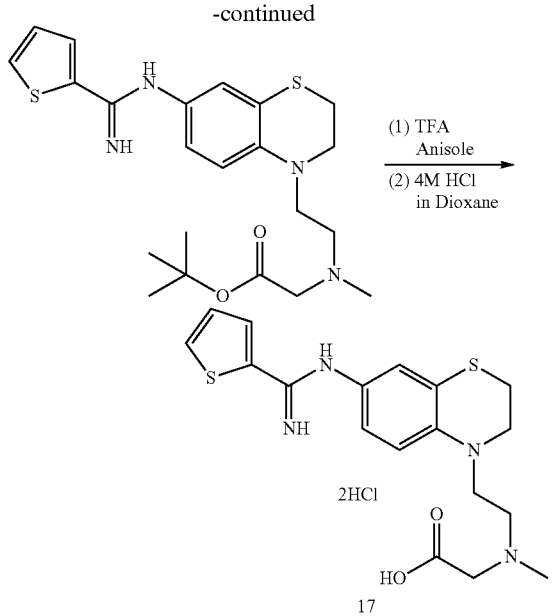

N,N-Dimethyl-2-(7-nitro-2H-benzo[b][1,4]thiazin-4 (3H)-yl)ethanamine: Prepared according to the procedure reported in Example 8.

N-Methyl-2-(7-nitro-2H-benzo[b][1,4]thiazin-4(3H)-yl) ethanamine: A solution of N,N-dimethyl-2-(7-nitro-2H-benzo[b][1,4]thiazin-4(3H)-yl)ethanamine (1.65 g, 6.17 mmol) in ClCH$_2$CH$_2$Cl (20 mL) was cooled to 0° C. (ice/water bath) then treated with alpha chloroethylchoroformate (1.009 mL, 9.26 mmol) dropwise. The resulting suspension was heated at 88° C. for 1.5 hours then concentrated to dryness. The residue was dissolved in MeOH (50 mL) and heated at reflux for 2 hours. The dark mixture was concentrated and partitioned between saturated sodium bicarbonate solution (50 mL) and CH$_2$Cl$_2$ (200 mL). The mixture was transferred to a separatory funnel and extracted. After extraction, the organic layer was separated, dried (Na$_2$SO$_4$), filtered, and concentrated to give a brown residue. This residue was subjected to flash chromatography on silica gel using 5:95 (2M NH$_3$ in MeOH):CH$_2$Cl$_2$ as the eluent to give a yellow residue (980 mg, 62.7%). $^1$H-NMR (CDCl$_3$) δ 7.97 (d, J=2.7 Hz, 1H), 7.87 (d, J=2.7, 9.3 Hz, 1H), 6.68 (d, J=9.3 Hz, 1H), 3.86-3.82 (m, 2H), 3.55 (t, J=6.6 Hz, 2H), 3.04-3.01 (m, 2H), 2.87 (t, J=6.6 Hz, 2H), 2.49 (s, 3H), 1.32 (brs, 1H).

tert-Butyl 2-(methyl(2-(7-nitro-2H-benzo[b][1,4]thiazin-4(3H)-yl)ethyl)amino)acetate: A solution of N-methyl-2-(7-nitro-2H-benzo[b][1,4]thiazin-4(3H)-yl)ethanamine (0.95 g, 3.75 mmol), diisopropylethyl amine (1.960 mL, 11.25 mmol), and tert-butyl bromoacetate (0.61 mL, 4.13 mmol) in DMF (20 mL) was heated at 55° C. for 17 hours (overnight). The yellow solution was diluted with brine (40 mL) and extracted with EtOAc (100 mL). The organic extract was separated and rinsed with brine (20 mL). The organic layer was dried (Na$_2$SO$_4$), filtered, and concentrated to give a yellow residue. This residue was subjected to flash chromatography on silica gel using 2.5:97.5 MeOH:CH$_2$Cl$_2$ to give a yellow brown residue. Two fractions were collected, with the latter containing a non-polar yellow spot (950 mg, 68.9%). $^1$H-NMR (CDCl$_3$) δ 7.96 (d, J=2.7 Hz, 1H), 7.88 (d, J=2.7, 9.3 Hz, 1H), 6.65 (d, J=9.3 Hz, 1H), 3.88-3.83 (m, 2H), 3.55 (t, J=7.2 Hz, 2H), 3.20 (s, 2H), 3.02-2.99 (m, 2H), 2.76 (t, J=7.2 Hz, 2H), 2.44 (s, 3H), 1.46 (s, 9H); ESI-MS (m/z, %): 368 (MH$^+$, 20), 312 (100).

tert-Butyl 2-((2-(7-amino-2H-benzo[b][1,4]thiazin-4 (3H)-yl)ethyl)(methyl)amino)acetate: A round bottom flask containing tert-butyl 2-(methyl(2-(7-nitro-2H-benzo[b][1,4]thiazin-4(3H)-yl)ethyl)amino)acetate (925 mg, 2.52 mmol) was purged with argon and then charged with palladium on carbon (10% wt; 268 mg, 0.252 mmol). To this mixture was added EtOH (40 mL). The resulting suspension was evacuated using a pump, and hydrogen was let into the system via a balloon. The mixture was stirred under a balloon filled with hydrogen for 3 hours. The balloon was removed, and argon was bubbled through the suspension for 10 minutes. The mixture was filtered through a pad of Celite, and the Celite pad was rinsed with methanol (20 mL). The filtrate was concentrated, and the residue was dried under reduced pressure to give the title compound (850 mg, quantitative). $^1$H-NMR (CDCl$_3$) δ 6.59 (d, J=8.7 Hz, 1H), 6.45 (d, J=2.4 Hz, 1H), 6.40 (dd, J=2.7, 8.4 Hz, 1H), 3.54-3.45 (m, 2H), 3.33 (t, J=7.2 Hz, 2H), 3.27 (brs, 2H), 3.20 (s, 2H), 3.04-2.98 (m, 2H), 2.71 (t, J=7.5 Hz, 2H), 2.42 (s, 3H), 1.46 (s, 9H); ESI-MS (m/z, %): 338 (MH$^+$, 95), 282 (100).

tert-Butyl 2-(methyl(2-(7-(thiophene-2-carboximidamido)-2H-benzo[b][1,4]thiazin-4(3H)-yl)ethyl)amino)acetate: To a solution of tert-butyl 2-((2-(7-amino-2H-benzo[b][1,4]thiazin-4(3H)-yl)ethyl)(methyl)amino)acetate (850 mg, 2.52 mmol) in EtOH (25 mL) was added methyl thiophene-2-carbimidothioate hydroiodide (1.43 g, 5.04 mmol). The resulting suspension was stirred at room temperature for 17 hours (overnight). At this time, the suspension was diluted with 20 mL CH$_2$Cl$_2$ to give a dark yellow solution. Argon was then bubbled through this solution for 30 minutes. The solution was transferred to a separatory funnel containing saturated sodium bicarbonate solution (50 mL) and CH$_2$Cl$_2$ (100 mL) then extracted. After extraction, the organic layer was separated, dried (Na$_2$SO$_4$), filtered, and concentrated to give a dark residue. This residue was subjected to flash chromatography on silica gel using 2:98 MeOH:CH$_2$Cl$_2$ followed by 2.5:97.5 (2M NH$_3$ in MeOH):CH$_2$Cl$_2$ to give a yellow-green residue (420 mg, 37.3%). Some impure fractions were collected (~340 mg). $^1$H-NMR (CDCl$_3$) δ 7.43-7.35 (m, 2H), 7.06 (pseudo t, J=4.8 Hz, 1H), 7.71 (brd, J=8.1 Hz, 2H), 6.65 (dd, J=1.8, 8.4 Hz, 1H), 4.91 (brs, 2H), 3.66-3.58 (m, 2H), 3.43 (t, J=7.2 Hz, 2H), 3.21 (s, 2H), 3.07-2.99 (m, 2H), 2.74 (t, J=7.5 Hz, 2H), 2.45 (s, 3H), 1.47 (s, 9H); ESI-MS (m/z, %): 447 (MH$^+$, 100), 391 (50); HPLC purity: 99.7% a/a.

2-(Methyl(2-(7-(thiophene-2-carboximidamido)-2H-benzo[b][1,4]thiazin-4(3H)-yl)ethyl)amino)acetic acid dihydrochloride: An oven dried round bottom flask, equipped with a magnetic stirbar under argon, was charged with tert-butyl 2-(methyl(2-(7-(thiophene-2-carboximidamido)-2H-benzo [b][1,4]thiazin-4(3H)-yl)ethyl)amino)acetate (200 mg, 0.448 mmol) in CH$_2$Cl$_2$ (3 mL), and the solution was cooled to 0° C. (ice/water bath). To this solution was added anisole (0.098 mL, 0.896 mmol) followed by the dropwise addition of trifluoroacetic acid (2.92 mL, 26.9 mmol). The reaction was stirred at 0° C. for 20 minutes. The ice bath was then removed, and the mixture was stirred for 3 additional hours. At this time, the mixture was concentrated and treated with 4.0 M HCl in 1,4-dioxane (4 mL). The resulting suspension was diluted with Et$_2$O (20 mL) and then stirred for 20 minutes. The mixture was filtered, and the solid was washed with Et$_2$O (20 mL). The solid was dried under reduced pressure to give compound 17 as light yellow powder (200 mg, 96%). An HPLC analysis indicated that the sample contained ~3.4% of the starting material. $^1$H-NMR (CD$_3$OD) δ 7.99 (d, J=5.1 Hz, 1H), 7.97 (d, J=3.6 Hz, 1H), 7.31 (pseudo t, J=4.5 Hz, 1H), 7.11-6.99 (m, 2H), 6.95 (d, J=8.7 Hz, 1H), 4.16 (s, 2H), 3.81 (brt, J=6.9 Hz, 2H), 3.68 (brt, J=4.8 Hz, 2H), 3.52-3.39 (m, 2H), 3.10 (brt, J=4.8 Hz, 2H), 3.03 (s, 3H); ESI-MS (positive ion mode): 391 (MH+, free base, 100); ESI-MS (negative ion mode): 389 (M-1, free base, 100); ESI-HRMS calculated for $C_{18}H_{23}N_4O_2S_2$ (MH+, free base): 391.1256, Observed: 391.1255; HPLC purity: 96.64% a/a.

Example 18

Synthesis of (S)-1-(2-(7-(Thiophene-2-carboximidamido)-2H-benzo[b][1,4]thiazin-4(3H)-yl)ethyl)pyrrolidine-2-carboxylic acid dihydrochloride (18)

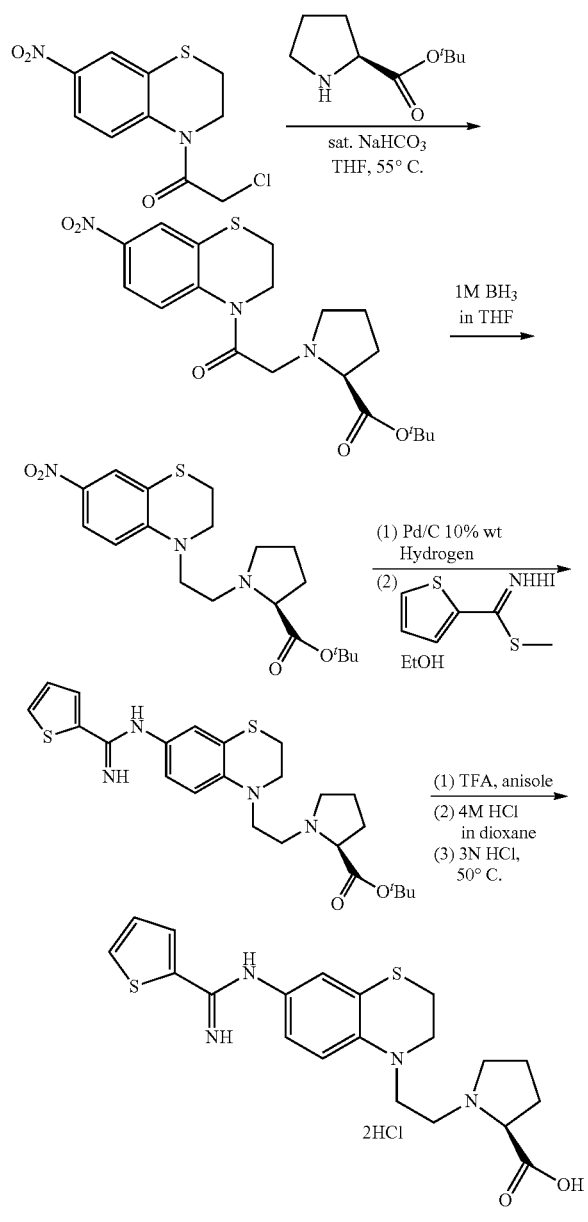

18

2-Chloro-1-(7-nitro-2H-benzo[b][1,4]thiazin-4(3H)-yl) ethanone: Prepared according to the reported procedure in Example 16.

(S)-tert-Butyl-1-(2-(7-nitro-2H-benzo[b][1,4]thiazin-4 (3H)-yl)-2-oxoethyl)pyrrolidine-2-carboxylate: A solution of 2-chloro-1-(7-nitro-2H-benzo[b][1,4]thiazin-4(3H)-yl) ethanone (1.0 g, 3.67 mmol) in THF (20 mL) was treated with (S)-tert-butyl pyrrolidine-2-carboxylate (0.942 g, 5.50 mmol), followed by saturated sodium bicarbonate (4 mL). The mixture was heated at 55° C. for 3 hours then stirred at room temperature overnight (17 hours). The mixture was diluted with EtOAc (50 mL) and saturated sodium bicarbonate (10 mL) then stirred for 20 minutes. The contents were poured into a separatory funnel, and the organic layer was separated, dried ($Na_2SO_4$), filtered, and concentrated to give a dark yellow residue. This residue was subjected to silica gel chromatography using the Biotage purification system (column: Silicycle 40 g; 20:80 EtOAc:hexanes gradient to 60:40 EtOAc:hexanes over 8 column volumes; flow rate: 35 mL/min; collection wavelength: 254 nm). A yellow residue was obtained (1.47 g, 98%). $^1$H-NMR (CDCl$_3$) δ 8.09 (d, J=2.4 Hz, 1H), 7.91 (dd, J=2.4, 8.7 Hz, 1H), 7.75 (d, J=9.0 Hz, 1H), 4.10 (brs, 2H), 3.74 (brd, J=13.2 Hz, 1H), 3.40 (brd, J=13.5 Hz, 1H), 3.37-3.21 (m, 3H), 3.12-3.04 (m, 1H), 2.61 (brdd, J=8.1, 16.2 Hz, 1H), 2.21-2.07 (m, 1H), 1.95-1.77 (m, 3H), 1.43 (s, 9H); ESI-MS (m/z, %): 408 (MH+, 50), 352 (100).

(S)-tert-Butyl-1-(2-(7-nitro-2H-benzo[b][1,4]thiazin-4 (3H)-yl)ethyl)pyrrolidine-2-carboxylate: 1M Borane in THF (17.18 mL, 17.18 mmol) was added to (S)-tert-butyl 1-(2-(7-nitro-2H-benzo[b][1,4]thiazin-4(3H)-yl)-2-oxoethyl)pyrrolidine-2-carboxylate (1.4 g, 3.44 mmol), and the resulting yellow solution was stirred at room temperature overnight (17 hours). The yellow solution was cooled to 0° C. and carefully quenched with MeOH (10 mL). The solution was concentrated, dissolved in MeOH (50 mL), and concentrated again to give a dark yellow residue. This residue was subjected to silica gel chromatography using the Biotage purification system (column: Silicycle 80 g; 20:80 EtOAc:hexanes gradient to 60:40 EtOAc:hexanes over 10 column volumes; flow rate=45 mL/min; collection wavelength: 254 nm). A yellow residue was obtained (550 mg, 40.7%). $^1$H-NMR (CDCl$_3$) δ 7.96 (d, J=2.7 Hz, 1H), 7.87 (dd, J=2.7, 9.3 Hz, 1H), 6.68 (d, J=9.3 Hz, 1H), 3.86-3.82 (m, 2H), 3.57 (t, J=7.5 Hz, 2H), 3.24-3.10 (m, 2H), 3.05-2.96 (m, 3H), 2.75-2.63 (m, 1H), 2.52-2.41 (m, 1H), 2.15-2.04 (m, 1H), 1.97-1.78 (m, 3H), 1.44 (s, 9H); ESI-MS (m/z, %): 394 (MH+, 25), 338 (100).

(S)-tert-Butyl-1-(2-(7-(thiophene-2-carboximidamido)-2H-benzo[b][1,4]thiazin-4(3H)-yl)ethyl)pyrrolidine-2-carboxylate: A round bottom flask containing (S)-tert-butyl 1-(2-(7-nitro-2H-benzo[b][1,4]thiazin-4(3H)-yl)ethyl) pyrrolidine-2-carboxylate (525 mg, 1.334 mmol) was purged with argon. This flask was charged with palladium on activated carbon (10% wt; 142 mg, 0.133 mmol) followed by EtOH (25 mL). The resulting suspension was evacuated using a pump, and hydrogen was let into the system via a balloon. The mixture was stirred under a balloon filled with hydrogen for 2 hours. At this time, the hydrogen balloon was removed, and methyl thiophene-2-carbimidothioate hydroiodide (761 mg, 2.67 mmol) was added to the mixture. The suspension was stirred at room temperature for 17 hours (overnight). At this time, the mixture was filtered through a pad of Celite, and the pad was rinsed with MeOH (20 mL). The filtrate was concentrated, and the residue partitioned between saturated sodium bicarbonate solution (50 mL) and $CH_2Cl_2$ (100 mL). The mixture was transferred to a separatory funnel and extracted. After extraction, the organic layer was separated, dried ($Na_2SO_4$), filtered, and concentrated to give a dark residue. This residue was subjected to flash chromatography on silica gel using 2:98 MeOH:$CH_2Cl_2$ followed by 3.5:96.5 (2M $NH_3$ in MeOH):$CH_2Cl_2$ to give a yellow-green residue (398 mg, 63.1%). $^1$H-NMR (CDCl$_3$) δ 7.39 (dd, J=1.2, 5.1

Hz, 1H), 7.37 (dd, J=1.2, 3.9 Hz, 1H), 7.05 (dd, J=3.6, 4.8 Hz, 1H), 6.73 (brd, J=5.1 Hz, 1H), 6.71 (brs, 1H), 6.65 (dd, J=2.1, 8.7 Hz, 1H), 4.86 (brs, 2H), 3.63-3.60 (m, 2H), 3.44 (t, J=7.5 Hz, 2H), 3.25-3.19 (m, 1H), 3.11 (brdd, J=5.4, 8.4 Hz, 1H), 3.04-2.94 (m, 3H), 2.71-2.59 (m, 1H), 2.45 (brdd, J=7.8, 16.2 Hz, 1H), 2.13-1.99 (m, 1H), 1.97-1.74 (m, 3H), 1.45 (s, 9H); ESI-MS (m/z, %): 473 (MH$^+$, 90), 417 (85), 276 (100); HPLC Purity: 99.6% a/a.

(S)-1-(2-(7-(Thiophene-2-carboximidamido)-2H-benzo[b][1,4]thiazin-4(3H)-yl)ethyl)pyrrolidine-2-carboxylic acid dihydrochloride: A solution of (S)-tert-butyl 1-(2-(7-(thiophene-2-carboximidamido)-2H-benzo[b][1,4]thiazin-4(3H)-yl)ethyl)pyrrolidine-2-carboxylate (200 mg, 0.423 mmol) in CH$_2$Cl$_2$ (5 mL) was treated with anisole (0.092 mL, 0.846 mmol). The reaction was cooled to 0° C., and trifluoroacetic acid (2.76 mL, 25.4 mmol) was then added. The mixture was stirred at 0° C. for 2 hours then concentrated to dryness. To this residue was added 4M HCl in dioxane (3.17 mL, 12.69 mmol), and the resulting suspension was stirred for 20 minutes. This mixture was diluted with Et$_2$O (10 mL) and stirred for 1 hour. The solid was filtered, washed with Et$_2$O (10 mL), and then dried under reduced pressure. The solid was dissolved in 3N HCl (4.0 mL, 12.00 mmol) and heated at 50° C. for 1 hour. The yellow solution was concentrated and dried under reduced pressure to give compound 18 as yellow solid (200 mg, 97%). $^1$H-NMR (CD$_3$OD) δ 7.98-7.94 (m, 2H), 7.28 (dd, J=4.2, 4.8 Hz, 1H), 7.05-7.01 (m, 2H), 6.92 (d, J=8.7 Hz, 1H), 4.42 (dd, J=7.8, 9.0 Hz, 1H), 3.85-3.56 (m, 6H), 3.48-3.29 (m, 2H), 3.13-3.03 (m, 2H), 2.62-2.47 (m, 1H), 2.26-2.10 (m, 2H), 2.08-1.92 (m, 1H); ESI-MS (m/z, %): 417 (MH$^+$, free base, 100); ESI-HRMS calculated for C$_{20}$H$_{25}$N$_4$O$_2$S$_2$ (MH$^+$, free base): 417.1419, observed: 417.1399; HPLC purity: 99.5% a/a; Optical Rotation: $^{25}[\alpha]_{589}$=-27.0°, c=0.52 in MeOH.

Example 19

Synthesis of N-(4-(2-(dimethylamino)ethyl)-3,4-dihydro-2H-benzo[b][1,4]thiazin-7-yl)furan-2-carboximidamide (19)

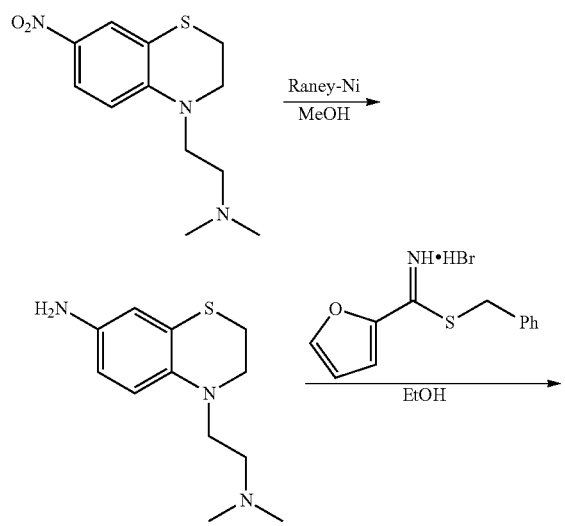

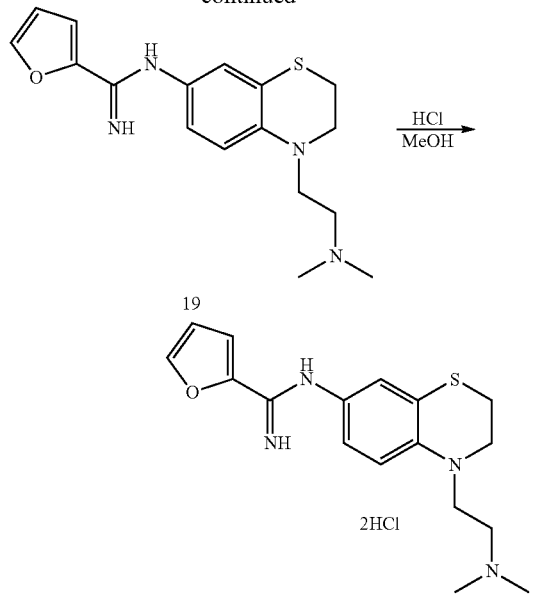

N,N-Dimethyl-2-(7-nitro-2H-benzo[b][1,4]thiazin-4(3H)-yl)ethanamine: Prepared according to the procedure reported in Example 8.

4-(2-(Dimethylamino)ethyl)-3,4-dihydro-2H-benzo[b][1,4]thiazin-7-amine: To a solution of N,N-dimethyl-2-(7-nitro-2H-benzo[b][1,4]thiazin-4(3H)-yl)ethanamine (0.9695 g, 3.63 mmol) in MeOH (20 mL) was added Raney-Nickel (slurry in water; ~0.1 g, 3.63 mmol) followed by hydrazine hydrate (1.82 mL, 37.4 mmol). The mixture was immersed in a preheated oil bath and refluxed for 20 minutes. The solution was cooled to room temperature and filtered through a pad of Celite. The filter pad was washed with MeOH, and the crude material was concentrated. The crude material was filtered through a plug of silica gel (2.5:97.5 (2M NH$_3$ in MeOH):CH$_2$Cl$_2$). The collected fractions gave brown viscous oil (0.84 g, 99%). $^1$H NMR (CDCl$_3$) δ 6.58 (d, J=8.7 Hz, 1H), 6.45 (d, J=2.7 Hz, 1H), 6.40 (dd, J=2.7, 8.7 Hz, 1H), 3.51-3.48 (m, 2H), 3.30 (t, J=7.2 Hz, 2H), 3.03-3.00 (m, 2H), 2.48 (t, J=7.5 Hz, 2H), 2.27 (s, 6H); ESI-MS (m/z, %): 240, 238 (MH$^+$, 100).

N-(4-(2-(Dimethylamino)ethyl)-3,4-dihydro-2H-benzo[b][1,4]thiazin-7-yl)furan-2-carboximidamide: Benzyl furan-2-carbimidothioate hydrobromide (1.139 g, 3.82 mmol) was added to a mixture of 4-(2-(dimethylamino)ethyl)-3,4-dihydro-2H-benzo[b][1,4]thiazin-7-amine (0.829 g, 3.49 mmol) in EtOH (20 mL). The mixture was stirred for 2 days under argon atmosphere. The solution was quenched with saturated sodium bicarbonate (50 mL). The solution was transferred to a separatory funnel, diluted with water (50 mL), and extracted with CH$_2$Cl$_2$ (50 mL). The aqueous phase was washed with CH$_2$Cl$_2$ (50 mL). The combined organic fractions were washed with brine (50 mL) and dried (Na$_2$SO$_4$). The crude material was subjected to flash chromatography on silica gel (2.5-5% (2M NH$_3$ in MeOH):CH$_2$Cl$_2$). The collected fractions gave compound 19 as a brown oil (1.03 g, 90%). $^1$H NMR (CDCl$_3$) δ 7.46 (s, 1H), 7.03 (brs, 1H), 6.73-6.68 (m, 3H), 6.50 (brs, 1H), 5.03 (brs, 2H), 3.62-3.59 (m, 2H), 3.40 (t, J=7.2 Hz, 2H), 3.05-3.02 (m, 2H), 2.52 (t, J=7.5 Hz, 2H), 2.29 (s, 6H); ESI-MS (m/z, %): 333, 331 (MH$^+$, 91), 260, 262 (100).

N-(4-(2-(Dimethylamino)ethyl)-3,4-dihydro-2H-benzo[b][1,4]thiazin-7-yl)furan-2-carboximidamide dihydrochloride: N-(4-(2-(Dimethylamino)ethyl)-3,4-dihydro-2H-benzo[b][1,4]thiazin-7-yl)furan-2-carboximidamide (0.166 g, 0.504 mmol) was dissolved in MeOH (2 mL). 1M HCl in ether (2.52 mL, 2.52 mmol) was added to the solution at room temperature, and the reaction was stirred for 5 minutes under argon atmosphere. The mixture was concentrated to give a light yellow solid (0.18 g, 93%). $^1$H NMR (DMSO-$d_6$) δ 11.36 (s, 1H), 11.25 (brs, 1H), 9.68 (s, 1H), 8.69 (s, 1H), 8.23 (s, 1H), 7.91 (d, J=2.7 Hz, 1H), 7.07-6.96 (m, 3H), 6.90 (d, J=1.8 Hz, 1H), 3.82-3.77 (m, 2H), 3.67-3.63 (m, 2H), 3.25-3.22 (m, 2H), 3.12-3.09 (m, 2H), 2.80 (s, 3H), 2.78 (s, 3H); ESI-MS (m/z, %): 333, 331 (MH$^+$, free base, 100), 260, 262 (57); HRMS calculated for $C_{17}H_{23}N_4OS$ (MH$^+$, free base): calculated: 331.1587, observed: 331.1589; HPLC purity: 98% by area.

Example 20

Synthesis of N-(4-(2-(methylamino)ethyl)-3,4-dihydro-2H-benzo[b][1,4]thiazin-7-yl)furan-2-carboximidamide (20)

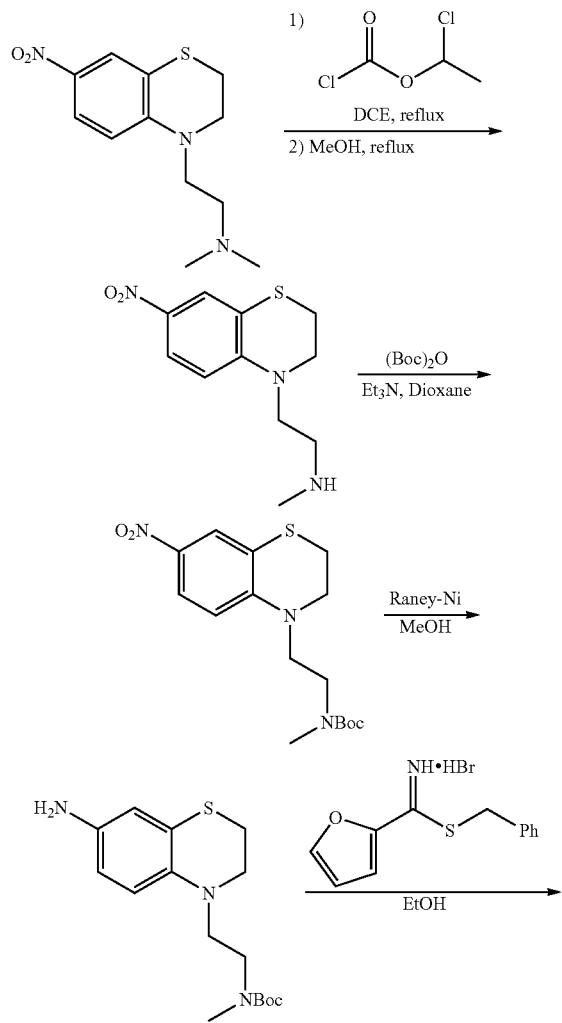

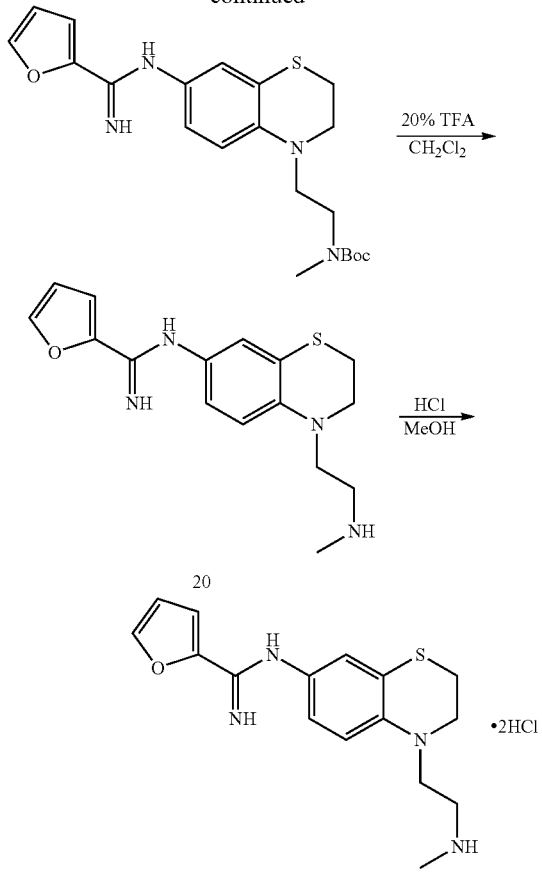

N,N-Dimethyl-2-(7-nitro-2H-benzo[b][1,4]thiazin-4(3H)-yl)ethanamine: Prepared according to the procedure reported in Example 8.

N-Methyl-2-(7-nitro-2H-benzo[b][1,4]thiazin-4(3H)-yl)ethanamine: 1-Chloroethyl chloroformate (0.612 mL, 5.61 mmol) was added to a solution of N,N-dimethyl-2-(7-nitro-2H-benzo[b][1,4]thiazin-4(3H)-yl)ethanamine (1.0 g, 3.74 mmol) in 1,2-dichloroethane (20 mL) at 0° C. in an argon atmosphere. The solution was brought to room temperature and refluxed under vigorous stirring for 3 hours. The solution was concentrated and then refluxed in MeOH (20 mL). The solution was concentrated to give dark brown viscous oil (1.05 g, quantitative). $^1$H NMR (CDCl$_3$) δ 7.96 (d, J=2.4 Hz, 1H), 7.86 (dd, J=2.7, 9.3 Hz, 1H), 6.67 (d, J=9.3 Hz, 1H), 3.85-3.82 (m, 2H), 3.55 (t, J=6.9 Hz, 2H), 3.03-3.00 (m, 2H), 2.86 (t, J=6.9 Hz, 2H), 2.48 (s, 3H); ESI-MS (m/z, %): 256, 254 (MH$^+$, 100).

tert-Butyl methyl(2-(7-nitro-2H-benzo[b][1,4]thiazin-4(3H)-yl)ethyl)carbamate: To a stirred solution of N-methyl-2-(7-nitro-2H-benzo[b][1,4]thiazin-4(3H)-yl)ethanamine (1.022 g, 4.04 mmol) and triethylamine (1.135 mL, 8.08 mmol) in dioxane (20 mL) under argon atmosphere was added di-tert-butyl dicarbonate (0.984 mL, 4.24 mmol). The resulting solution was stirred overnight at room temperature. The solution was then diluted with water (50 mL) and extracted with CH$_2$Cl$_2$ (50 mL). The organic phase was washed with brine (50 mL) and dried (Na$_2$SO$_4$). The crude material was subject to flash chromatography on silica gel (20-50% EtOAc:hexanes). The collected fractions were concentrated to give yellow-brown oil (0.95 g, 67%). $^1$H NMR (CDCl$_3$) δ 7.97 (s, 1H), 7.87 (d, J=9.0 Hz, 1H), 6.76-6.66 (m, 1H), 3.80 (brs, 2H), 3.60-3.54 (m, 2H), 3.47-3.45 (m, 2H), 3.03-2.99 (m, 2H), 2.92-2.88 (m, 3H), 1.42 (s, 9H); ESI-MS (m/z, %): 278, 276 (M+Na, 72), 356, 354 (MH+, 19), 298, 300 (100), 256, 254 (74).

tert-Butyl 2-(7-amino-2H-benzo[b][1,4]thiazin-4(3H)-yl) ethyl(methyl)carbamate: To a solution of tert-butyl methyl(2-(7-nitro-2H-benzo[b][1,4]thiazin-4(3H)-yl)ethyl)carbamate (0.8811 g, 2.493 mmol) in MeOH (20 mL) was added Raney-Nickel (slurry in water; 0.5 g, 2.493 mmol) followed by hydrazine hydrate (1.213 mL, 24.93 mmol). The mixture was then immersed in a preheated oil bath and refluxed for 5 minutes The solution was cooled to room temperature and filtered through a pad of Celite. The filter pad was washed with MeOH, and the crude material was concentrated. The crude material was then filtered through a silica plug (70% EtOAc/hexanes). The collected fractions were concentrated to give brown oil (0.78 g, 98%). $^1$H NMR (CDCl$_3$) δ 6.64-6.58 (m, 1H), 6.45 (d, J=2.4 Hz, 1H), 6.39 (d, J=8.4 Hz, 1H), 3.53-3.50 (m, 2H), 3.39-3.28 (m, 4H), 3.01-2.98 (m, 2H), 2.90 (s, 3H), 1.45 (s, 9H); ESI-MS (m/z, %): 326, 324 (MH+, 95), 268 (100).

tert-Butyl 2-(7-(furan-2-carboximidamido)-2H-benzo[b][1,4]thiazin-4(3H)-yl)ethyl(methyl)carbamate: Benzyl furan-2-carbimidothioate hydrobromide (1.199 g, 4.02 mmol) was added to a mixture of tert-butyl 2-(7-amino-2H-benzo[b][1,4]thiazin-4(3H)-yl)ethyl(methyl)carbamate (0.763 g, 2.361 mmol) in EtOH (20 mL). The mixture was stirred under room temperature overnight. The mixture was quenched with saturated sodium bicarbonate solution (50 mL), diluted with water (50 mL), and extracted with CH$_2$Cl$_2$ (2×50 mL). The organic phase was washed with brine (50 mL) and dried (Na$_2$SO$_4$). The crude material was subject to flash chromatography on silica gel (2.5-5% (2M NH$_3$ in MeOH):CH$_2$Cl$_2$). The collected fractions were concentrated to give a white foam (0.88 g, 90%). $^1$H NMR (CDCl$_3$) δ 7.85 (s, 1H), 7.44 (s, 1H), 6.74-6.69 (m, 1H), 6.62 (d, J=7.5 Hz, 1H), 4.72 (brs, 2H), 3.64-3.60 (m, 2H), 3.41 (s, 4H), 3.04-3.01 (m, 2H), 2.92 (s, 3H), 1.45 (s, 9H); ESI-MS (m/z, %): 419, 417 (MH+, 100).

N-(4-(2-(Methylamino)ethyl)-3,4-dihydro-2H-benzo[b][1,4]thiazin-7-yl)furan-2-carboximidamide: A solution of tert-butyl 2-(7-(furan-2-carboximidamido)-2H-benzo[b][1,4]thiazin-4(3H)-yl)ethyl(methyl)carbamate (0.823 g, 1.978 mmol) in CH$_2$Cl$_2$ (20 mL) was cooled to 0° C. and was treated with trifluoroacetic acid (5 mL). The mixture was stirred at 0° C. under argon atmosphere for 2 hours. The mixture was quenched with 1N NaOH solution (70 mL) and transferred to a separatory funnel. The solution was diluted with water (50 mL) and extracted with CH$_2$Cl$_2$ (2×50 mL). The organic phase was washed with brine (50 mL) and dried (Na$_2$SO$_4$). The crude material was concentrated and subjected to flash chromatography on silica gel (5-15% (2M NH$_3$ MeOH):CH$_2$Cl$_2$). The collected fractions were concentrated to give compound 20 as a yellow viscous oil (0.47 g, 76%). $^1$H NMR (CDCl$_3$) δ 7.85 (s, 1H), 7.44-7.43 (m, 1H), 6.77-6.74 (m, 2H), 6.70 (d, J=2.4 Hz, 1H), 6.62 (dd, J=2.4, 8.7 Hz, 1H), 3.59-3.56 (m, 2H), 3.47 (s, 1H), 3.40 (t, J=6.6 Hz, 2H), 3.05-3.01 (m, 2H), 2.81 (t, J=6.3 Hz, 2H), 2.48 (s, 3H); ESI-MS (m/z, %): 319, 317 (MH+, 96), 260 (100).

N-(4-(2-(Methylamino)ethyl)-3,4-dihydro-2H-benzo[b][1,4]thiazin-7-yl)furan-2-carboximidamide dihydrochloride: N-(4-(2-(methylamino)ethyl)-3,4-dihydro-2H-benzo[b][1,4]thiazin-7-yl)furan-2-carboximidamide (0.4353 g, 1.376 mmol) was dissolved in MeOH (3 mL). 1M HCl in ether (6.88 mL, 6.88 mmol) was added to the solution at room temperature, and the reaction was stirred for 5 minutes under argon atmosphere. The mixture was concentrated to give a yellow solid (0.59 g, quantitative). $^1$H NMR (DMSO-d$_6$) δ 11.31 (s, 1H), 9.58 (s, 1H), 9.30 (brs, 2H), 8.82 (s, 1H), 8.57 (s, 1H), 7.98 (s, 1H), 7.30 (d, J=1.2 Hz, 1H), 7.06-7.03 (m, 2H), 6.97 (dd, J=2.4, 8.7 Hz, 1H), 3.74-3.63 (m, 4H), 3.13-3.05 (m, 4H), 2.58-2.55 (m, 3H); ESI-MS (m/z, %): 319, 317 (MH+, free base, 100), 260 (98); HRMS calculated for C$_{16}$H$_{20}$N$_4$OS (MH+, free base), calculated: 317.1430, observed: 317.1417; HPLC purity: 99% by area.

Example 21

Synthesis of N-(4-(3-(pyrrolidin-1-yl)propyl)-3,4-dihydro-2H-benzo[b][1,4]thiazin-7-yl)thiophene-2-carboximidamide (21)

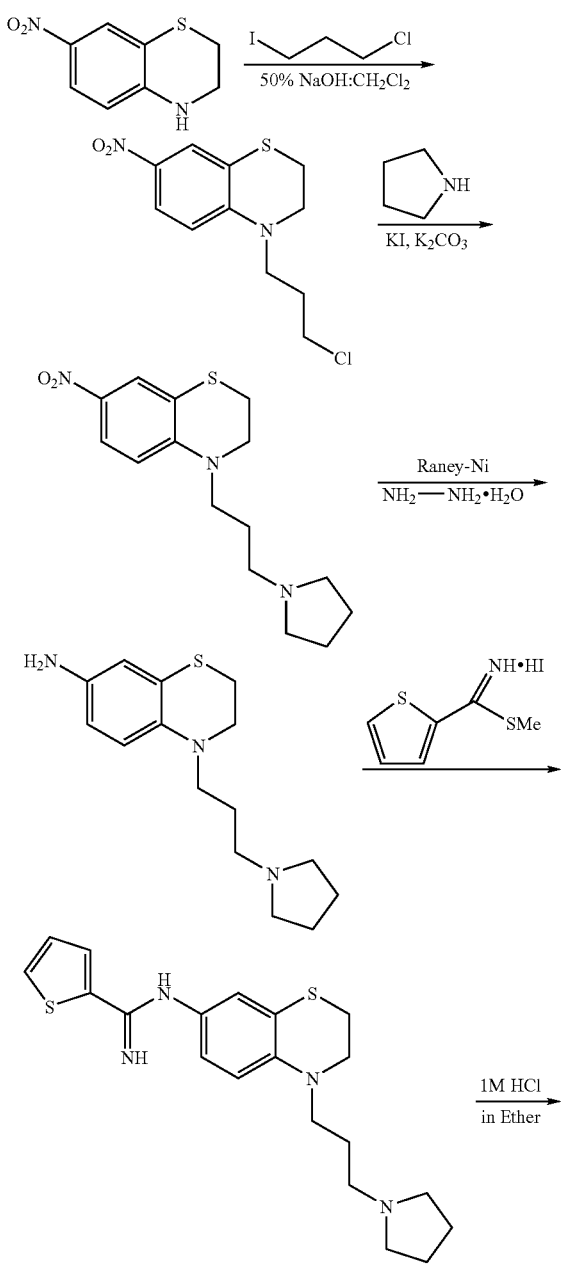

21

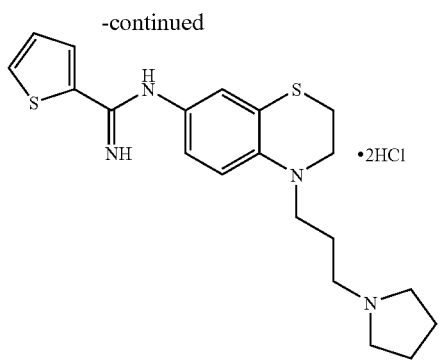

7-Nitro-3,4-dihydro-2H-benzo[b][1,4]thiazine: Prepared according to the procedure reported in Example 11.

4-(3-Chloropropyl)-7-nitro-3,4-dihydro-2H-benzo[b][1,4]thiazine: A solution of 7-nitro-3,4-dihydro-2H-benzo[b][1,4]thiazine (1.0 g, 5.10 mmol) and 1-chloro-3-iodopropane (1.075 mL, 10.19 mmol) in $CH_2Cl_2$ (10 mL) was treated with 50% NaOH solution (10 mL), followed by tetrabutylammonium bromide (0.082 g, 0.255 mmol) at room temperature. The resulting mixture was stirred overnight (16 hours) at room temperature and then refluxed for 4 hours. The reaction was brought to room temperature and diluted with water (50 mL), and the product was extracted into $CH_2Cl_2$ (3×25 mL). The combined $CH_2Cl_2$ layers were washed with brine (20 mL) and dried ($Na_2SO_4$). The solvent was evaporated, and the crude material was purified by column chromatography (1:4 to 2:3 EtOAc:hexanes) to obtain the title compound (0.65 g, 47%) as a solid. $^1$H NMR ($CDCl_3$) δ 7.96 (d, 1H, J=2.7 Hz), 7.88 (dd, 1H, J=2.7, 9.3 Hz), 6.64 (d, 1H, J=9.3 Hz), 3.84-3.80 (m, 2H), 3.65-3.60 (m, 4H), 3.05-3.02 (m, 2H), 2.16-2.08 (m, 2H); ESI-MS (m/z, %): 273 (MH$^+$, 100).

7-Nitro-4-(3-(pyrrolidin-1-yl)propyl)-3,4-dihydro-2H-benzo[b][1,4]thiazine: A solution of 4-(3-chloropropyl)-7-nitro-3,4-dihydro-2H-benzo[b][1,4]thiazine (0.54 g, 1.980 mmol) in dry acetonitrile (20 mL) was treated with pyrrolidine (1.637 mL, 19.80 mmol), potassium carbonate (2.74 g, 19.80 mmol), and potassium iodide (0.657 g, 3.96 mmol) at room temperature. The resulting mixture was stirred at 60° C. overnight (18 hours). The reaction was brought to room temperature and diluted with water (50 mL), and the product was extracted into ethyl acetate (2×25 mL). The combined ethyl acetate layers were washed with brine (20 mL) and then dried ($Na_2SO_4$). The solvent was evaporated, and the crude material was purified by flash column chromatography (5:95 (2 M $NH_3$ in MeOH):$CH_2Cl_2$) to obtain the title product (0.57 g, 94%) as a syrup. $^1$H NMR (DMSO-$d_6$) δ 7.84-7.80 (m, 2H), 6.87 (d, 1H, J=9.6 Hz), 3.79-3.75 (m, 2H), 3.49 (t, 2H, J=6.9 Hz), 3.08-3.05 (m, 2H), 2.44-2.40 (m, 6H), 1.76-1.69 (m, 6H); ESI-MS (m/z, %): 308 (MH$^+$, 100).

4-(3-(Pyrrolidin-1-yl)propyl)-3,4-dihydro-2H-benzo[b][1,4]thiazin-7-amine: A solution of 7-nitro-4-(3-(pyrrolidin-1-yl)propyl)-3,4-dihydro-2H-benzo[b][1,4]thiazine (0.55 g, 1.789 mmol) in dry methanol (10 mL) was treated with hydrazine hydrate (0.652 mL, 17.89 mmol) followed by Raney-Nickel (0.1 g, 1.789 mmol) at room temperature. The resulting mixture was stirred at reflux for 5 minutes using a preheated oil bath. The reaction was then brought to room temperature, filtered through a pad of Celite, and washed with methanol (3×10 mL). The combined methanol layers were evaporated, and the crude material was purified by flash column chromatography (5:95 (2 M $NH_3$ in MeOH):$CH_2Cl_2$) to obtain the title product (0.45 g, 91%) as a syrup. $^1$H NMR (DMSO-$d_6$) δ 6.51 (d, 1H, J=9.3 Hz), 6.26-6.23 (m, 2H), 4.41 (s, 2H), 3.37-3.30 (m, 2H, merged with water peak), 3.11 (t, 2H, J=6.9 Hz), 2.98-2.95 (m, 2H), 2.42-2.37 (m, 6H), 1.67-1.60 (m, 6H).

N-(4-(3-(Pyrrolidin-1-yl)propyl)-3,4-dihydro-2H-benzo[b][1,4]thiazin-7-yl)thiophene-2-carboximidamide: A solution of 4-(3-(pyrrolidin-1-yl)propyl)-3,4-dihydro-2H-benzo[b][1,4]thiazin-7-amine (0.43 g, 1.550 mmol) in dry ethanol (15 mL) was treated with methyl thiophene-2-carbimidothioate hydroiodide (0.884 g, 3.10 mmol) at room temperature, and the resulting mixture was stirred overnight (18 hours). The reaction was diluted with saturated $NaHCO_3$ solution (30 mL), and the product was extracted into $CH_2Cl_2$ (3×20 mL). The combined $CH_2Cl_2$ layers were washed with brine (20 mL) and then dried ($Na_2SO_4$). The solvent was evaporated, and the crude material was purified by column chromatography (5:95 (2 M $NH_3$ in MeOH):$CH_2Cl_2$,) to obtain the title product 21 (0.51 g, 85%) as a solid. $^1$H NMR (DMSO-$d_6$) δ 7.68 (d, 1H, J=4.5 Hz), 7.55 (d, 1H, J=5.1 Hz), 7.06 (dd, 1H, J=3.6, 4.9 Hz), 6.70 (d, 1H, J=8.7 Hz), 6.52-6.44 (m, 2H), 6.32 (brs, 2H), 3.51-3.48 (m, 2H), 3.27 (t, 2H, J=7.2 Hz), 3.04-3.00 (m, 2H), 2.48-2.40 (m, 6H), 1.80-1.60 (m, 6H); ESI-MS (m/z, %): 387 (MH$^+$, 68), 276 (100), 194 (75); HPLC purity: 98.32% by area.

N-(4-(3-(Pyrrolidin-1-yl)propyl)-3,4-dihydro-2H-benzo[b][1,4]thiazin-7-yl)thiophene-2-carboximidamide dihydrochloride: A solution of N-(4-(3-(pyrrolidin-1-yl)propyl)-3,4-dihydro-2H-benzo[b][1,4]thiazin-7-yl)thiophene-2-carboximidamide (0.48 g, 1.242 mmol) in dry methanol (10 mL) was treated with hydrochloric acid (1 M solution in ether; 3.72 mL, 3.72 mmol) at room temperature, and the resulting mixture was stirred for 15 minutes. The solvent was then evaporated, and the product was dried under vacuum to obtain the dihydrochloride salt (0.55 g, 96%) as a solid. $^1$H NMR (DMSO-$d_6$) δ 11.34 (brs, 1H), 11.28 (s, 1H), 9.68 (s, 1H), 8.69 (s, 1H), 8.16-8.12 (m, 2H), 7.35 (t, 1H, J=4.2 Hz), 3.66-3.60 (m, 2H), 3.50-3.40 (m, 4H), 3.16-3.05 (m, 4H), 3.02-2.92 (m, 2H), 2.06-1.84 (m, 2H); ESI-MS (m/z, %): 387 (MH$^+$, free base, 92), 276 (87), 194 (100); ESI-HRMS calculated for $C_{20}H_{27}N_4S_2$ (MH$^+$, free base), calculated: 387.1671, observed: 387.1659; HPLC purity: 98.58% by area.

Example 22

Synthesis of N-(4-(3-(Dimethylamino)propyl)-3,4-dihydro-2H-benzo[b][1,4]thiazin-7-yl)thiophene-2-carboximidamide (22)

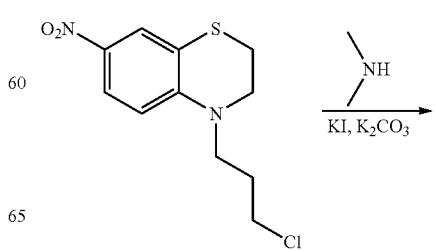

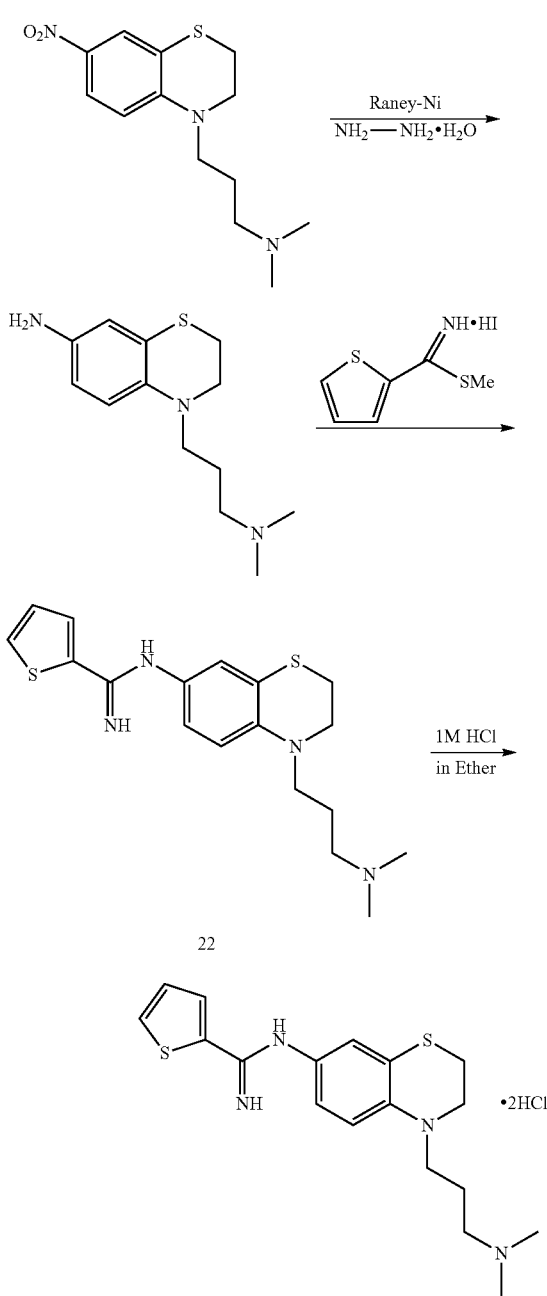

4-(3-Chloropropyl)-7-nitro-3,4-dihydro-2H-benzo[b][1,4]thiazine: Prepared according to reported procedure in Example 21.

N,N-Dimethyl-3-(7-nitro-2H-benzo[b][1,4]thiazin-4(3H)-yl)propan-1-amine: A solution of 4-(3-chloropropyl)-7-nitro-3,4-dihydro-2H-benzo[b][1,4]thiazine (0.7 g, 2.57 mmol), dimethylamine (2M solution in THF) (2.57 mL, 5.13 mmol), potassium iodide (0.426 g, 2.57 mmol), and potassium carbonate (1.773 g, 12.83 mmol) in dry acetonitrile (20 mL) was stirred at 80° C. for 6 hours in a sealed tube. The reaction was then brought to room temperature and diluted with water (60 mL), and the product was extracted into ethyl acetate (3×20 mL). The combined ethyl acetate layers were washed with brine (20 mL) and dried (Na$_2$SO$_4$). The solvent was evaporated, and the crude material was purified by column chromatography (1:9 (2 M NH$_3$ in MeOH):CH$_2$Cl$_2$) on silica gel to obtain the title product (0.3 g, 42%) as a thick syrup. $^1$H NMR (DMSO-d$_6$) δ 7.85-7.80 (m, 2H), 6.85 (d, 1H, J=8.7 Hz), 3.77 (t, 2H, J=5.1 Hz), 3.47 (t, 2H, J=7.2 Hz), 3.06 (t, 2H, J=5.1 Hz), 2.24 (t, 2H, J=6.6 Hz), 2.14 (s, 6H), 1.75-1.65 (m, 2H); ESI-MS (m/z, %): 282 (MH$^+$, 100).

4-(3-(Dimethylamino)propyl)-3,4-dihydro-2H-benzo[b][1,4]thiazin-7-amine: A solution of N,N-dimethyl-3-(7-nitro-2H-benzo[b][1,4]thiazin-4(3H)-yl)propan-1-amine (0.27 g, 0.960 mmol) in dry methanol (10 mL) was treated with hydrazine hydrate (0.349 mL, 9.60 mmol), followed by Raney-Nickel (0.1 g, 0.096 mmol) at room temperature. The resulting mixture was refluxed for 5 minutes in a pre-heated oil bath. The reaction was then brought to room temperature, filtered through a pad of Celite, and washed with methanol (3×10 mL). The combined methanol layers were evaporated, and the crude material was purified by flash column chromatography (5:95 (2 M NH$_3$ in MeOH):CH$_2$Cl$_2$) on silica gel to obtain the title product (0.24 g, 99%) as a syrup. $^1$H NMR (DMSO-d$_6$) δ 6.50 (dd, 1H, J=2.4, 7.0 Hz), 6.26-6.23 (m, 2H), 4.41 (s, 2H), 3.32-3.30 (m, 2H), 3.09 (t, 2H, J=7.2 Hz), 2.98-2.95 (m, 2H), 2.21 (t, 2H, J=6.9 Hz), 2.11 (s, 6H), 1.63-1.54 (m, 2H); ESI-MS (m/z, %): 252 (MH$^+$, 100).

N-(4-(3-(Dimethylamino)propyl)-3,4-dihydro-2H-benzo[b][1,4]thiazin-7-yl)thiophene-2-carboximidamide: A solution of 4-(3-(dimethylamino)propyl)-3,4-dihydro-2H-benzo[b][1,4]thiazin-7-amine (0.22 g, 0.875 mmol) in dry ethanol (10 mL) was treated with methyl thiophene-2-carbimidothioate hydroiodide (0.499 g, 1.750 mmol) at room temperature, and the resulting mixture was stirred over night (18 hours) at room temperature. The reaction was diluted with saturated NaHCO$_3$ solution (25 mL), and the product was extracted into CH$_2$Cl$_2$ (3×20 mL). The combined CH$_2$Cl$_2$ layers were washed with brine (15 mL) and dried (Na$_2$SO$_4$). The solvent was evaporated, and the crude material was purified by column chromatography (5:95 (2M NH$_3$ in MeOH):CH$_2$Cl$_2$) on silica gel to obtain the title product 22 (0.27 g, 86%) as a solid. $^1$H NMR (DMSO-d$_6$) δ 7.68 (d, 1H, J=3.0 Hz), 7.56 (d, 1H, J=5.1 Hz), 7.06 (dd, 1H, J=3.9, 4.8 Hz), 6.69 (d, 1H, J=8.7 Hz), 6.52-6.45 (m, 2H), 6.33 (brs, 2H), 3.51-3.48 (m, 2H), 3.25 (t, 2H, J=7.2 Hz), 3.04-3.01 (m, 2H), 2.25 (t, 2H, J=6.9 Hz), 2.14 (s, 6H), 1.70-1.61 (m, 2H); ESI-MS (m/z, %): 361 (MH$^+$, 93), 276 (100); HPLC purity: 98.23% by area.

N-(4-(3-(Dimethylamino)propyl)-3,4-dihydro-2H-benzo[b][1,4]thiazin-7-yl)thiophene-2-carboximidamide dihydrochloride: A solution of N-(4-(3-(dimethylamino)propyl)-3,4-dihydro-2H-benzo[b][1,4]thiazin-7-yl)thiophene-2-carboximidamide (0.16 g, 0.444 mmol) in dry methanol (5 mL) was treated with hydrogen chloride (1M solution in ether; 1.331 mL, 1.331 mmol) at room temperature. The mixture was stirred for 15 minutes, the solvent was evaporated, and the residue was dried under high vacuum to obtain the title product (0.19 g, 99%) as a solid. $^1$H NMR (DMSO-d$_6$) δ 11.22 (s, 1H), 10.91 (brs, 1H), 9.67 (s, 1H), 8.69 (s, 1H), 8.15-8.11 (m, 2H), 7.36 (t, 1H, J=4.5 Hz), 7.04-6.88 (m, 3H), 3.64-3.61 (m, 2H), 3.41 (t, 2H, J=6.9 Hz), 3.14-3.02 (m, 4H), 2.72 (d, 6H, J=4.8 Hz), 2.06-1.98 (m, 2H); ESI-MS (m/z, %): 361 (MH$^+$, free base, 91), 276 (100); ESI-HRMS calculated for C$_{18}$H$_{25}$N$_4$S$_2$ (MH$^+$, free base), calculated: 361.1515, observed: 361.1515; HPLC purity: 98.15% by area.

Example 23

Synthesis of N-(4-(3-(methylamino)propyl)-3,4-dihydro-2H-benzo[b][1,4]thiazin-7-yl)thiophene-2-carboximidamide (23)

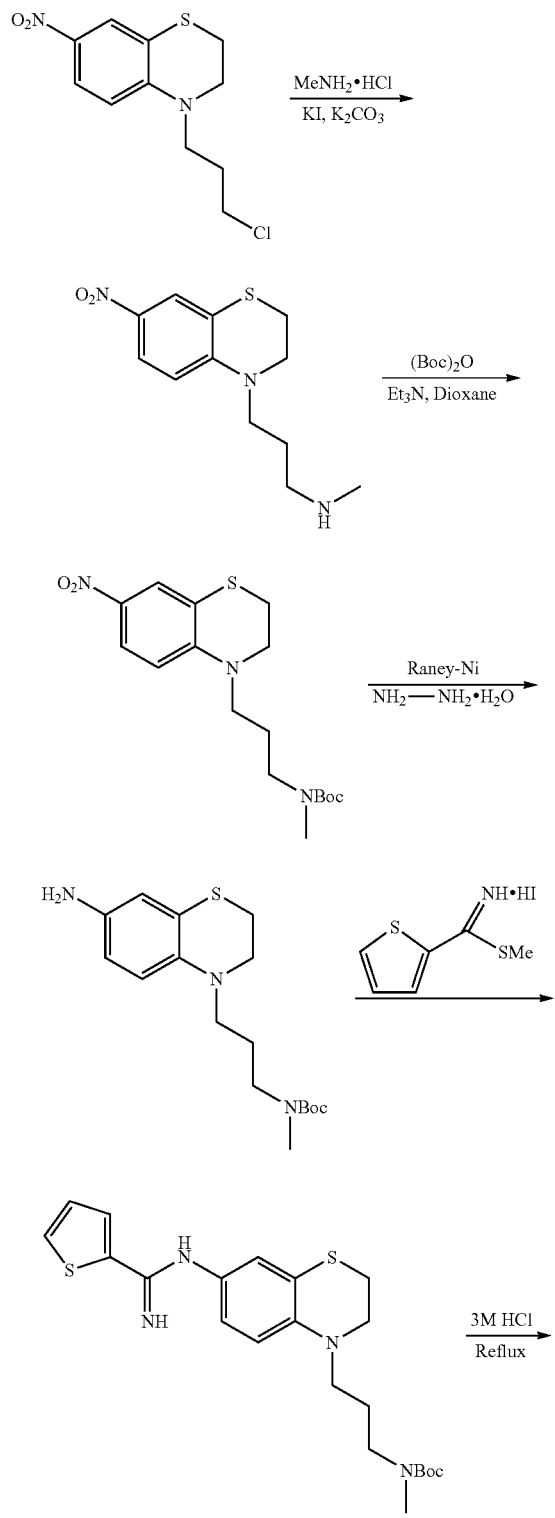

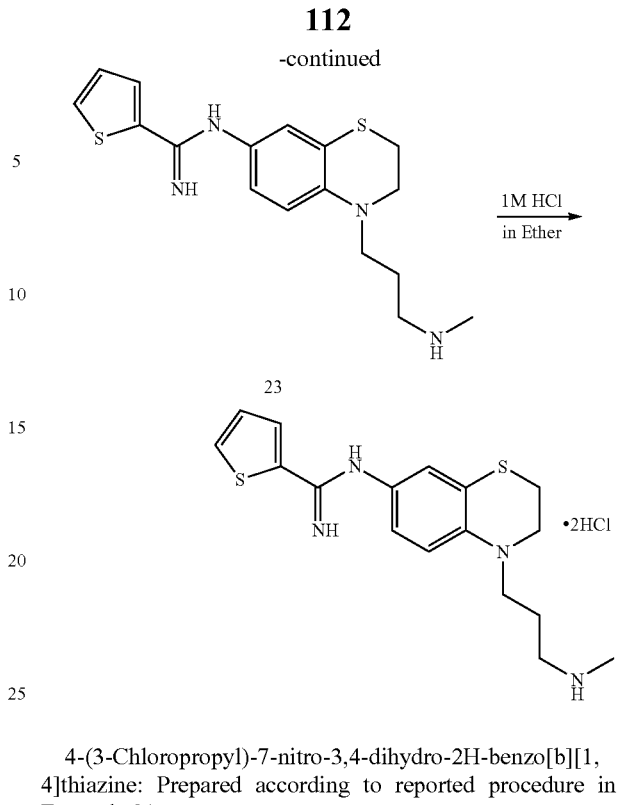

4-(3-Chloropropyl)-7-nitro-3,4-dihydro-2H-benzo[b][1,4]thiazine: Prepared according to reported procedure in Example 21.

N-Methyl-3-(7-nitro-2H-benzo[b][1,4]thiazin-4(3H)-yl)propan-1-amine: A solution of 4-(3-chloropropyl)-7-nitro-3,4-dihydro-2H-benzo[b][1,4]thiazine (1.1 g, 4.03 mmol), methylamine hydrochloride (0.545 g, 8.07 mmol), potassium iodide (0.669 g, 4.03 mmol), and potassium carbonate (2.79 g, 20.16 mmol) in dry acetonitrile (25 mL) was stirred at 80° C. in a sealed tube for 6 hours. The reaction was brought to room temperature and diluted with water (100 mL), and the product was extracted into ethyl acetate (3×25 mL). The combined ethyl acetate layers were washed with brine (20 mL) and dried ($Na_2SO_4$). The solvent was evaporated, and the crude material was purified by flash column chromatography (1:9 (2M $NH_3$ in MeOH):$CH_2Cl_2$) on silica gel to obtain the title compound (0.8 g, 74%) as a thick syrup. $^1$H NMR (DMSO-$d_6$) δ 7.84-7.81 (m, 2H), 6.86 (d, 1H, J=9.9 Hz), 3.78-3.75 (m, 2H), 3.50 (t, 2H, J=7.5 Hz), 3.08-3.04 (m, 2H), 2.48 (t, 2H, J=6.9 Hz), 2.27 (s, 3H), 1.74-1.64 (m, 2H); ESI-MS (m/z, %): 268 (MH$^+$, 100).

tert-Butyl methyl(3-(7-nitro-2H-benzo[b][1,4]thiazin-4(3H)-yl)propyl)carbamate: A solution of N-methyl-3-(7-nitro-2H-benzo[b][1,4]thiazin-4(3H)-yl)propan-1-amine (0.77 g, 2.88 mmol) in dry 1,4-dioxane (20 mL) was treated with triethylamine (1.214 mL, 8.64 mmol) followed by di-tert-butyl dicarbonate (0.736 mL, 3.17 mmol) at room temperature. The reaction stirred for 4 hours. The solvent was then evaporated, and the crude material was purified by flash column chromatography (1:1 EtOAc:hexanes) on silica gel to obtain the title product (1.02 g, 96%) as a yellow solid. $^1$H NMR (CDCl$_3$) δ 7.97 (d, 1H, J=2.4 Hz), 7.88 (dd, 1H, J=2.7, 9.3 Hz), 6.56 (d, 1H, J=9.3 Hz), 3.79-3.76 (m, 2H), 3.41 (t, 2H, J=7.8 Hz), 3.31 (t, 2H, J=6.9 Hz), 3.04-3.00 (m, 2H), 2.88 (s, 3H), 1.92-1.82 (m, 2H), 1.46 (s, 9H); ESI-MS (m/z, %): 390 (M+Na, 56), 368 (MH$^+$, 10), 312 (60), 268 (100).

tert-Butyl 3-(7-amino-2H-benzo[b][1,4]thiazin-4(3H)-yl)propyl(methyl)carbamate: A suspension of tert-butyl methyl(3-(7-nitro-2H-benzo[b][1,4]thiazin-4(3H)-yl)propyl)carbamate (0.6 g, 1.633 mmol) in dry methanol (10 mL) was treated with Raney-Nickel (0.1 g, 1.633 mmol) followed by hydrazine hydrate (0.595 mL, 16.33 mmol) at room temperature. The resulting mixture was refluxed for 10 minutes in a pre-heated oil bath. The reaction was then brought to room temperature, filtered through a pad of Celite, and washed with methanol (3×10 mL). The combined methanol layers were evaporated, and the crude material was purified by flash column chromatography (5:95 (2M $NH_3$ in MeOH):$CH_2Cl_2$) on silica gel to obtain title product (0.55 g, quantitative) as a brown syrup. $^1$H NMR (DMSO-$d_6$) δ 6.46 (d, 1H, J=9.6 Hz), 6.25-6.21 (m, 2H), 4.44 (s, 2H), 3.32-3.28 (m, 2H), 3.19 (t, 2H, J=6.9 Hz), 3.04 (t, 2H, J=7.2 Hz), 3.00-2.97 (m, 2H), 2.77 (s, 3H), 1.74-1.62 (m, 2H), 1.38 (s, 9H); ESI-MS (m/z, %): 338 (MH$^+$, 100), 337 (96), 282 (54).

tert-Butyl methyl(3-(7-(thiophene-2-carboximidamido)-2H-benzo[b][1,4]thiazin-4(3H)-yl)propyl)carbamate: A solution of tert-butyl 3-(7-amino-2H-benzo[b][1,4]thiazin-4(3H)-yl)propyl(methyl)carbamate (0.52 g, 1.541 mmol) in dry ethanol (20 mL) was treated with methyl thiophene-2-carbimidothioate hydroiodide (0.879 g, 3.08 mmol) at room temperature and stirred over night (18 hours). The reaction was basified with saturated $NaHCO_3$ solution (50 mL), and the product was extracted into $CH_2Cl_2$ (2×25 mL). The combined $CH_2Cl_2$ layers were washed with brine (20 mL) and dried ($Na_2SO_4$). The solvent was evaporated, and the crude material was purified by column chromatography (2:98 (2 M $NH_3$ in MeOH):$CH_2Cl_2$) on silica gel to obtain the title product (0.60 g, 87%) as a solid. ESI-MS (m/z, %): 447 (MH$^+$, 100).

N-(4-(3-(Methylamino)propyl)-3,4-dihydro-2H-benzo[b][1,4]thiazin-7-yl)thiophene-2-carboximidamide: A suspension of tert-butyl methyl(3-(7-(thiophene-2-carboximidamido)-2H-benzo[b][1,4]thiazin-4(3H)-yl)propyl)carbamate (0.55 g, 1.231 mmol) in 3M hydrochloric acid (25 mL) was refluxed for 1 hour. The reaction was brought to room temperature, filtered, and washed with water (2×10 mL). The combined aqueous layers were evaporated. The crude material was basified with 3 M NaOH solution (50 mL), and the product was extracted into $CH_2Cl_2$ (3×20 mL). The combined $CH_2Cl_2$ layers were washed with brine (15 mL) and dried ($Na_2SO_4$). The organic solvent was evaporated, and the crude material was purified by column chromatography (5:95 to 1:9 (2M $NH_3$ in MeOH):$CH_2Cl_2$) on silica gel to obtain compound 23 (0.4 g, 94%) as a solid. $^1$H NMR (DMSO-$d_6$) δ 7.68 (dd, 1H, J=1.2, 3.7 Hz), 7.56 (dd, 1H, J=0.9, 5.1 Hz), 7.06 (dd, 1H, J=3.6, 4.9 Hz), 6.70 (d, 1H, J=8.7 Hz), 6.51-6.44 (m, 2H), 6.31 (s, 2H), 3.50-3.47 (m, 2H), 3.32-3.25 (m, 4H), 3.04-3.01 (m, 2H), 2.27 (s, 3H), 1.70-1.61 (m, 2H); ESI-MS (m/z, %): 347 (MH$^+$, 80), 276 (100); HPLC purity: 96.05% by area.

N-(4-(3-(Methylamino)propyl)-3,4-dihydro-2H-benzo[b][1,4]thiazin-7-yl)thiophene-2-carboximidamide dihydrochloride: A solution of N-(4-(3-(methylamino)propyl)-3,4-dihydro-2H-benzo[b][1,4]thiazin-7-yl)thiophene-2-carboximidamide (0.37 g, 1.068 mmol) in dry methanol (10 mL) was treated with hydrogen chloride (1 M in ether) (3.20 mL, 3.20 mmol) and stirred for 15 minutes. The solvent was evaporated, and the crude material was dried under high vacuum to obtain the dihydrochloride (0.44 g, 98%) as a solid. $^1$H NMR (DMSO-$d_6$) δ 11.22 (s, 1H), 9.66 (s, 1H), 9.19 (brs, 2H), 8.69 (s, 1H), 8.15-8.12 (m, 2H), 7.35 (t, 1H, J=4.2 Hz), 7.04-6.89 (m, 3H), 3.64-3.61 (m, 2H), 3.44 (t, 2H, J=6.9 Hz), 3.10-3.07 (m, 2H), 2.96-2.86 (m, 2H), 2.53 (t, 3H, J=5.7 Hz), 1.98-1.86 (m, 2H); ESI-MS (m/z, %): 347 (MH$^+$, free base, 65), 276 (100); ESI-HRMS calculated for $C_{17}H_{23}N_4S_2$ (MH$^+$, free base), calculated: 347.1358, observed: 347.1345; HPLC purity: 96.11% by area.

Example 24

Synthesis of N-(4-(2-(ethylamino)ethyl)-3,4-dihydro-2H-benzo[b][1,4]thiazin-6-yl)thiophene-2-carboximidamide (24)

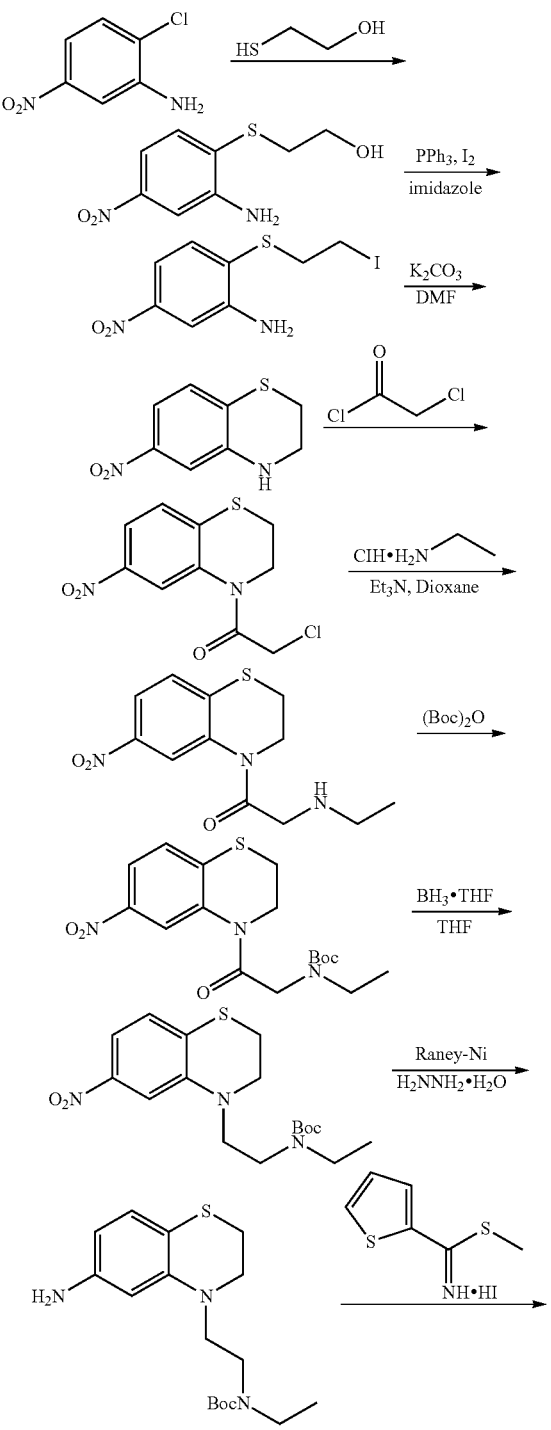

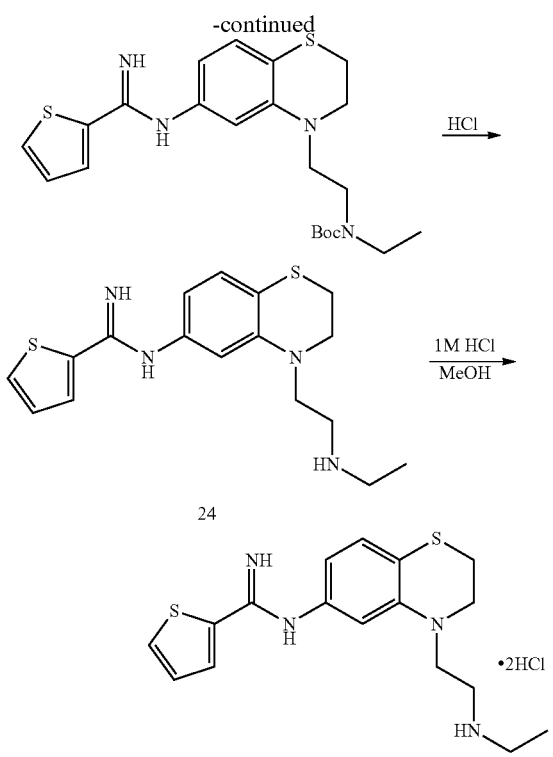

3.56-3.49 (m, 2H), 3.08-3.03 (m, 2H); EI-MS (m/z, %): 196 (M+, 100), 181 (45), 122 (73).

2-Chloro-1-(6-nitro-2H-benzo[b][1,4]thiazin-4(3H)-yl) ethanone: To a stirred solution of 6-nitro-3,4-dihydro-2H-benzo[b][1,4]thiazine (620 mg, 3.16 mmol) in THF (10 mL) was added 2-chloroacetyl chloride (0.277 mL, 3.48 mmol). The resulting mixture was then stirred at 60° C. for 10 minutes The mixture was then diluted with ethyl acetate and washed with water (3×), 1:1 water:saturated sodium carbonate, and brine. The organic phase was dried, filtered, and concentrated, giving the desired product (860 mg, 100%). $^1$H NMR (DMSO-$d_6$) δ 8.36 (d, J=2.1 Hz, 1H), 7.96 (dd, J=8.7, 2.1 Hz, 1H), 7.52 (d, J=8.7 Hz, 1H), 4.63 (s, 2H), 3.99-3.92 (m, 2H), 3.39-3.33 (m, 2H); ESI-MS (m/z, %): 295 (M+Na, 68), 273 (MH+, 100), 197 (43).

2-(Ethylamino)-1-(6-nitro-2H-benzo[b][1,4]thiazin-4 (3H)-yl)ethanone: To a stirred solution of 2-chloro-1-(6-nitro-2H-benzo[b][1,4]thiazin-4(3H)-yl)ethanone (855 mg, 3.14 mmol) in dioxane (15 mL) and triethylamine (0.881 mL, 6.27 mmol) was added ethanamine hydrochloride (1.278 g, 15.68 mmol) as a solution in water (7.50 mL). The resulting mixture was stirred vigorously at room temperature over the weekend. The mixture was then diluted with water and extracted with dichloromethane (2×). The combined organics were dried, filtered, concentrated, and then chromatographed in 1:9 (2M NH$_3$ in methanol):ethyl acetate, giving the desired product (775 mg, 88%). $^1$H NMR (DMSO-$d_6$) δ 8.37 (d, J=2.4 Hz, 1H), 7.93 (dd, J=8.7, 2.4 Hz, 1H), 7.50 (d, J=8.7 Hz, 1H), 3.97-3.90 (m, 2H), 3.52 (s, 2H), 3.37-3.33 (m, 2H), 2.58-2.50 (m, 2H), 2.07 (brs, 1H), 1.00 (t, J=7.0 Hz, 3H); ESI-MS (m/z, %): 282 (MH+, 100).

tert-Butyl ethyl(2-(6-nitro-2H-benzo[b][1,4]thiazin-4 (3H)-yl)-2-oxoethyl)carbamate: To a stirred solution of 2-(ethylamino)-1-(6-nitro-2H-benzo[b][1,4]thiazin-4(3H)-yl)ethanone (770 mg, 2.74 mmol) in dioxane (10 mL) and triethylamine (0.769 mL, 5.47 mmol) was added di-tert-butyl dicarbonate (627 mg, 2.87 mmol). The resulting mixture was stirred at room temperature for 30 minutes. The mixture was then diluted with ethyl acetate and washed sequentially with water and a 1:1 mixture of water and brine. The organic phase was dried, filtered, and concentrated, giving a pale yellow solid (1.02 g, 98%). $^1$H NMR (DMSO-$d_6$) δ 8.33 (s, 1H), 7.94 (d, J=8.4 Hz, 1H), 7.51 (d, J=8.7 Hz, 1H), 4.18 (s, 2H), 3.96-3.89 (m, 2H), 3.32-3.19 (m, 4H), 1.38, 1.30 (2s, 9H), 1.09-1.00 (m, 3H); ESI-MS (m/z, %): 404 (M+Na, 51), 382 (MH+, 36), 282 (100).

tert-Butyl ethyl(2-(6-nitro-2H-benzo[b][1,4]thiazin-4 (3H)-yl)ethyl)carbamate: To a stirred solution of tert-butyl ethyl(2-(6-nitro-2H-benzo[b][1,4]thiazin-4(3H)-yl)-2-oxoethyl)carbamate (1.01 g, 2.65 mmol) in tetrahydrofuran (5 mL) was added borane-tetrahydrofuran complex (1 M in tetrahydrofuran; 7.94 mL, 7.94 mmol). The resulting mixture was stirred at room temperature for 2 hours. The mixture was then quenched via the slow dropwise addition (to avoid excessive bubbling) of MeOH (5 mL). The quenched reaction was then diluted with ethyl acetate and washed with water (2×) and saturated sodium carbonate (2×). The organic phase was dried, filtered, and concentrated, giving a red-orange oil (925 mg, 95%). $^1$H NMR (DMSO-$d_6$) δ 7.59-7.41 (m, 1H), 7.39-7.32 (m, 1H), 7.24-7.13 (m, 1H), 3.69-3.62 (m, 2H), 3.58-3.48 (m, 2H), 3.45-3.35 (m, 2H), 3.28-3.16 (m, 2H), 3.15-3.08 (m, 2H), 1.32, 1.24 (2s, 9H), 1.04 (t, J=6.9 Hz, 3H); ESI-MS (m/z, %): 390 (M+Na, 70), 368 (MH+, 12), 312 (47), 268 (100).

2-(2-Amino-4-nitrophenylthio)ethanol: To a stirred solution of 2-chloro-5-nitroaniline (1.0 g, 5.79 mmol) in DMF (10 mL) was added potassium carbonate (1.60 g, 11.59 mmol) followed by 2-mercaptoethanol (0.813 mL, 11.59 mmol). The resulting mixture was then heated at 60° C. for 2 hours and then at room temperature overnight. The mixture was then diluted with ethyl acetate and washed with water (3×), 1N NaOH, and brine. The organic phase was dried, filtered, and concentrated, giving a red/orange solid (1.19 g, 96%). $^1$H NMR (DMSO-$d_6$) δ 7.52 (s, 1H), 7.42-7.33 (m, 2H), 5.79 (s, 2H), 4.99 (t, J=5.4 Hz, 1H), 3.55 (q, J=6.2 Hz, 2H), 3.02 (t, J=6.6 Hz, 2H); ESI-MS (m/z, %): 215 (MH+, 23), 169 (100), 111 (63).

2-(2-Iodoethylthio)-5-nitroaniline: To a stirred solution of triphenylphosphine (1.81 g, 6.93 mmol) and imidazole (1.887 mL, 13.86 mmol) in THF (15 mL) at 0° C. was added iodine (1.759 g, 6.93 mmol). After stirring for 5 minutes, 2-(2-amino-4-nitrophenylthio)ethanol (990 mg, 4.62 mmol) was added as a solution in THF (5 mL). The resulting mixture was stirred at 0° C. for 1 hour, then diluted with ethyl acetate and washed with water (3×) and brine. The organic phase was dried, filtered, and concentrated then chromatographed in 4:1 hexanes:ethyl acetate giving the desired compound (1.18 g, 79%) as an orange solid. $^1$H NMR (DMSO-$d_6$) δ 7.55 (d, J=2.4 Hz, 1H), 7.45 (d, J=8.4 Hz, 1H), 7.34 (dd, J=8.4, 2.4 Hz, 1H), 5.89 (brs, 2H), 3.38-3.26 (m, 4H); EI-MS (m/z, %): 324 (M+, 46), 196 (81), 154 (100), 126 (95).

6-Nitro-3,4-dihydro-2H-benzo[b][1,4]thiazine: To a stirred solution of 2-(2-iodoethylthio)-5-nitroaniline (1.18 g, 3.64 mmol) in DMF (10 mL) was added potassium carbonate (1.006 g, 7.28 mmol). The resulting mixture was then stirred at 90° C. for 1 hour. The mixture was then cooled to room temperature and diluted with water (40 mL). The resulting red precipitate was collected by vacuum filtration, giving the title compound (625 mg, 87%). $^1$H NMR (DMSO-$d_6$) δ 7.38 (s, 1H), 7.28 (d, J=8.4 Hz, 1H), 7.12 (d, J=8.7 Hz, 6.78 (brs, 1H), tert-Butyl 2-(6-amino-2H-benzo[b][1,4]thiazin-4(3H)-yl) ethyl(ethyl)carbamate: To a stirred solution of tert-butyl ethyl (2-(6-nitro-2H-benzo[b][1,4]thiazin-4(3H)-yl)ethyl)carbamate (925 mg, 2.52 mmol) in ethanol (10 mL) was added Raney-Nickel (~148 mg, 2.52 mmol) followed by hydrazine hydrate (1.225 mL, 25.2 mmol). The resulting mixture was stirred vigorously at 50° C. for 10 minutes. The mixture was then cooled to room temperature, diluted with ethyl acetate, and then washed sequentially with a 1:1 mixture of water and saturated sodium carbonate (3×) and saturated sodium carbonate. The organic phase was dried, filtered, and concentrated giving a red oil (810 mg, 95%); ESI-MS (m/z, %): 338 (MH+, 100), 282 (53), 238 (36).

tert-Butyl ethyl(2-(6-(thiophene-2-carboximidamido)-2H-benzo[b][1,4]thiazin-4(3H)-yl)ethyl)carbamate: To a stirred solution of tert-butyl 2-(6-amino-2H-benzo[b][1,4]thiazin-4(3H)-yl)ethyl(ethyl)carbamate (800 mg, 2.371 mmol) in ethanol (8 mL) was added methyl thiophene-2-carbimidothioate hydroiodide (1.014 g, 3.56 mmol). The resulting mixture was stirred at room temperature for 3 hours. The mixture was then diluted with ethyl acetate and washed with saturated sodium carbonate (3×). The organic phase was dried, filtered, concentrated, and then chromatographed in 1:1 hexanes:ethyl acetate giving the desired product (415 mg, 39.2%). $^1$H NMR (DMSO-d$_6$) δ 7.70 (d, J=3.0 Hz, 1H), 7.58 (d, J=2.4 Hz, 1H), 7.49-7.44 (m, 1H), 7.07 (t, J=4.4 Hz, 1H), 6.84 (d, J=7.8 Hz, 1H), 6.35-6.26 (m, 2H), 6.08 (d, J=7.5 Hz, 1H), 3.64-3.49 (m, 2H), 3.45-3.25 (m, 4H), 3.24-3.12 (m, 2H), 3.01-2.85 (m, 2H), 1.39-1.29 (m, 9H), 1.02 (t, J=6.9 Hz, 3H); ESI-MS (m/z, %): 447 (MH+, 100).

N-(4-(2-(Ethylamino)ethyl)-3,4-dihydro-2H-benzo[b][1,4]thiazin-6-yl)thiophene-2-carboximidamide: To a stirred suspension of tert-butyl ethyl(2-(6-(thiophene-2-carboximidamido)-2H-benzo[b][1,4]thiazin-4(3H)-yl)ethyl)carbamate (410 mg, 0.918 mmol) in methanol (6 mL) was added a 3N HCl solution (3.06 mL, 9.18 mmol). The resulting mixture was stirred at 90° C. for 30 minutes The mixture was then passed through a 0.45 μM syringe filter, and the filtrate was concentrated in vacuo to dry foam. The residue was then partitioned between 1:1 water:saturated sodium carbonate and dichloromethane. The organic layer was separated, and the aqueous phase was extracted again with dichloromethane. The organic phase was dried, filtered, concentrated, and then chromatographed in 1:4:5 (2M NH$_3$ in methanol):ethyl acetate:dichloromethane giving the desired product 24 (135 mg, 42.4%). $^1$H NMR (DMSO-d$_6$) δ 7.71 (d, J=3.6 Hz, 1H), 7.58 (d, 5.1 Hz, 1H), 7.08 (t, J=4.4 Hz, 1H), 6.82 (d, J=7.8 Hz, 1H), 6.33 (brs, 2H), 6.21 (s, 1H), 6.07 (dd, J=8.1, 1.5 Hz, 1H), 3.63-3.57 (m, 2H), 3.33-3.28 (m, 2H), 3.01-2.96 (m, 2H), 2.71-2.65 (m, 2H), 2.53 (q, J=7.0 Hz, 2H), 1.66 (brs, 1H), 1.17 (t, J=7.0 Hz, 3H); ESI-MS (m/z, %): 347 (MH+, 83), 276 (100); HRMS calculated for C$_{17}$H$_{23}$N$_4$S$_2$ (MH+), calculated: 347.1358, observed: 347.1346; HPLC purity: 97% by area.

N-(4-(2-(Ethylamino)ethyl)-3,4-dihydro-2H-benzo[b][1,4]thiazin-6-yl)thiophene-2-carboximidamide dihydrochloride: To a solution of N-(4-(2-(ethylamino)ethyl)-3,4-dihydro-2H-benzo[b][1,4]thiazin-6-yl)thiophene-2-carboximidamide (131 mg, 0.378 mmol) in methanol (2 mL) was added hydrogen chloride (1M in diethyl ether; 1.134 mL, 1.134 mmol). The resulting mixture was concentrated in vacuo, giving an orange solid, (159 mg, 100%). $^1$H NMR (DMSO-d$_6$) δ 11.43 (s, 1H), 9.72 (s, 1H), 9.22 (brs, 2H), 8.73 (s, 1H), 8.18-8.12 (m, 2H), 7.38-7.34 (m, 1H), 7.14-7.05 (m, 2H), 6.64-6.60 (m, 1H), 3.70-3.61 (m, 4H), 3.16-3.02 (m, 4H), 2.99-2.88 (m, 2H), 1.21 (t, J=7.2 Hz, 3H); HRMS (C$_{17}$H$_{23}$N$_4$S$_2$, MH+, free base): calculated: 347.1358, observed: 347.1346. HPLC purity: 97% by area.

Example 25

Synthesis of N-(4-(2-(pyrrolidin-1-yl)ethyl)-3,4-dihydro-2H-benzo[b][1,4]thiazin-6-yl)thiophene-2-carboximidamide (25)

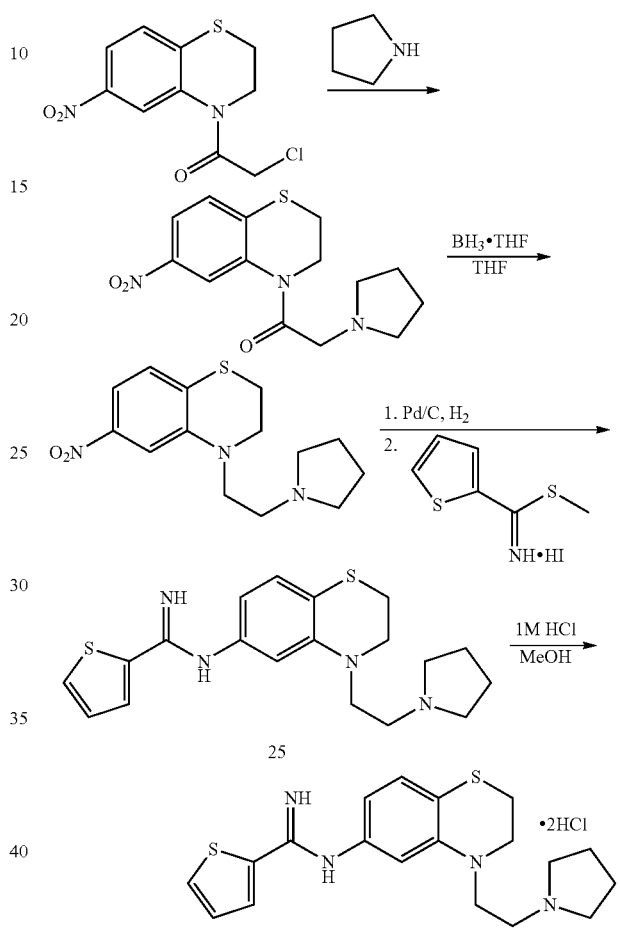

2-Chloro-1-(6-nitro-2H-benzo[b][1,4]thiazin-4(3H)-yl)ethanone: Prepared according to the procedure reported in Example 24.

1-(6-Nitro-2H-benzo[b][1,4]thiazin-4(3H)-yl)-2-(pyrrolidin-1-yl)ethanone: To a stirred solution of 2-chloro-1-(6-nitro-2H-benzo[b][1,4]thiazin-4(3H)-yl)ethanone (685 mg, 2.51 mmol) in dioxane (10 mL), cooled to 0° C. was added HCl, 1 M in diethyl ether (2.51 mL, 2.51 mmol) followed by pyrrolidine (0.21 mL, 2.51 mmol) dropwise. The resulting mixture was stirred at 0° C. for 5 minutes and then warmed to room temperature, stirring overnight. At this time, additional pyrrolidine (0.21 mL, 2.51 mmol) was added, followed by water (1 mL) to aid dissolution. After 1 hour of stirring at room temperature, the mixture was then diluted with ethyl acetate and washed with saturated sodium carbonate, water (3×), and brine. The organic phase was dried, filtered, and concentrated, giving a yellow/orange oil (756 mg, 98%). $^1$H NMR (DMSO-d$_6$) δ 8.52 (brs, 1H), 7.93 (dd, J=9.0, 1.6 Hz, 1H), 7.49 (d, J=9.0 Hz, 1H), 4.01-3.91 (m, 4H), 3.56 (s, 2H), 3.45-3.35 (m, 2H), 2.55-2.50 (m, 2H), 2.22-2.14 (m, 4H); ESI-MS (m/z, %): 308 (MH+, 100).

6-Nitro-4-(2-(pyrrolidin-1-yl)ethyl)-3,4-dihydro-2H-benzo[b][1,4]thiazine: To a stirred solution of 1-(6-nitro-2H-benzo[b][1,4]thiazin-4(3H)-yl)-2-(pyrrolidin-1-yl)ethanone (750 mg, 2.440 mmol) in tetrahydrofuran (5 mL) was added borane-tetrahydrofuran complex (1M in tetrahydrofuran; 7.32 mL, 7.32 mmol). The resulting mixture was then stirred at 55° C. overnight. The reaction mixture was then cooled to room temperature and quenched carefully via the slow, dropwise addition of methanol (5 mL). The quenched mixture was then stirred at 55° C. overnight. At this time, the reaction was vented to the atmosphere. The mixture was then concentrated and chromatographed on silica gel, eluting with 1:4:5 (2M NH$_3$ in methanol):ethyl acetate:dichloromethane, giving the desired product (654 mg, 91%) as a red oil. $^1$H NMR (DMSO-d$_6$) δ 7.46 (d, J=2.4 Hz, 1H), 7.36 (dd, J=8.4, 2.1 Hz, 1H), 7.19 (d, J=8.4 Hz, 1H), 3.69-3.65 (m, 2H), 3.50 (t, J=6.9 Hz, 2H), 3.14-3.10 (m, 2H), 2.63 (t, J=6.9 Hz, 2H), 2.56-2.51 (m, 2H), 1.71-1.66 (m, 4H); ESI-MS (m/z, %): 294 (MH$^+$, 100).

N-(4-(2-(Pyrrolidin-1-yl)ethyl)-3,4-dihydro-2H-benzo[b][1,4]thiazin-6-yl)thiophene-2-carboximidamide: To a stirred solution of 6-nitro-4-(2-(pyrrolidin-1-yl)ethyl)-3,4-dihydro-2H-benzo[b][1,4]thiazine (649 mg, 2.212 mmol) in ethanol (5 mL) was added palladium, 10 wt. % on activated carbon (235 mg, 0.221 mmol) as a suspension in ethanol (5 mL). The resulting suspension was stirred under an atmosphere of hydrogen (balloon pressure) for 3 hours (yellow color disappears). The balloon was removed, and methyl thiophene-2-carbimidothioate hydroiodide (1.262 g, 4.42 mmol) was added to the mixture. The resulting mixture was stirred under argon overnight at room temperature. The mixture was then diluted with dichloromethane and filtered through Celite. The filtrate was then diluted with saturated sodium carbonate and extracted with dichloromethane (2×). The combined organics were dried, filtered, concentrated, and then chromatographed in 1:19 (2M NH$_3$ in methanol):ethyl acetate, giving the desired product 25 (438 mg, 53.1%). $^1$H NMR (DMSO-d$_6$) δ 7.71 (d, J=3.3 Hz, 1H), 7.58 (d, J=5.1 Hz, 1H), 7.10-7.06 (m, 1H), 6.83 (d, J=8.1 Hz, 1H), 6.38 (brs, 2H), 6.19 (s, 1H), 6.08 (d, J=1H), 3.63-3.58 (m, 2H), 3.40-3.33 (m, 2H), 3.01-2.97 (m, 2H), 2.61 (t, J=6.8 Hz, 2H), 2.49-2.42 (m, 4H), 1.70-1.61 (m, 4H); ESI-MS (m/z, %): 373 (MH$^+$, 62), 276 (100); HRMS calculated for C$_{19}$H$_{25}$N$_4$S$_2$ (MH$^+$), calculated: 373.1515, observed: 373.1512; HPLC purity: 97% by area.

N-(4-(2-(Pyrrolidin-1-yl)ethyl)-3,4-dihydro-2H-benzo[b][1,4]thiazin-6-yl)thiophene-2-carboximidamide dihydrochloride: To a solution of N-(4-(2-(pyrrolidin-1-yl)ethyl)-3,4-dihydro-2H-benzo[b][1,4]thiazin-6-yl)thiophene-2-carboximidamide (424 mg, 1.138 mmol) in methanol (4 mL) was added hydrogen chloride (1 M in diethyl ether; 3.41 mL, 3.41 mmol). The resulting mixture was concentrated in vacuo, giving an orange solid (507 mg, 100%). $^1$H NMR (DMSO-d$_6$) δ 11.60-11.40 (m, 2H), 9.75 (s, 1H), 8.78 (s, 1H), 8.22-8.10 (m, 2H), 7.36 (t, J=8.4 Hz, 1H), 7.15-7.05 (m, 2H), 6.64 (d, J=8.1 Hz, 1H), 3.80-3.71 (m, 2H), 3.70-3.61 (m, 2H), 3.58-3.45 (m, 2H), 3.43-3.30 (m, 2H), 3.16-3.07 (m, 2H), 3.06-2.95 (m, 2H), 2.05-1.92 (m, 2H), 1.90-1.79 (m, 2H); HRMS (C$_{19}$H$_{25}$N$_4$S$_2$, MH$^+$, free base): calculated: 373.1515, observed: 373.1512. HPLC purity: 97% by area.

Example 26

Synthesis of N-(4-(2-(2-hydroxyethylamino)ethyl)-3,4-dihydro-2H-benzo[b][1,4]thiazin-6-yl)thiophene-2-carboximidamide (26)

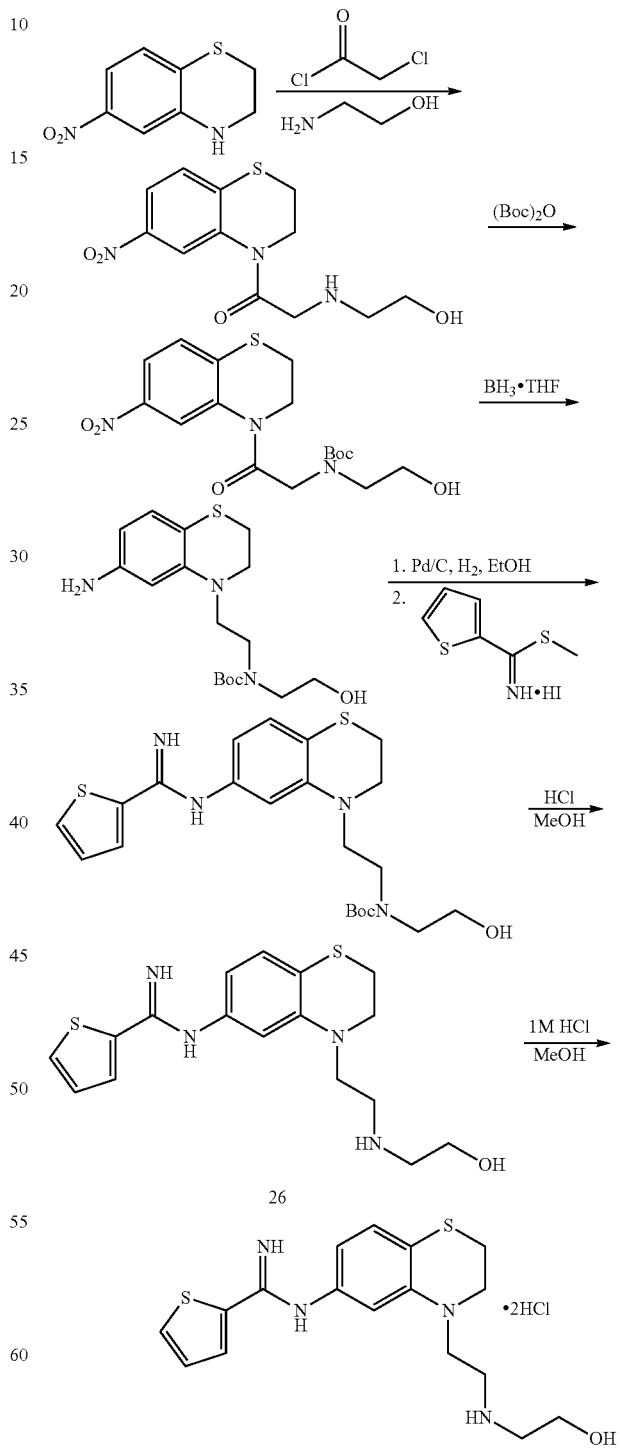

6-Nitro-3,4-dihydro-2H-benzo[b][1,4]thiazine: Prepared according to the reported procedure in Example 24.

2-(2-Hydroxyethylamino)-1-(6-nitro-2H-benzo[b][1,4]thiazin-4(3H)-yl)ethanone: To a stirred solution of 6-nitro-3,4-dihydro-2H-benzo[b][1,4]thiazine (500 mg, 2.55 mmol) in tetrahydrofuran (10 mL) was added 2-chloroacetyl chloride (302 mg, 2.68 mmol). The resulting mixture was stirred at 60° C. for 5 minutes. The reaction first turns cloudy then clarifies. At this time, the reaction was cooled to 0° C., and hydrogen chloride (4 M in dioxane; 5.10 mL, 20.38 mmol) and 2-aminoethanol (1.868 g, 30.6 mmol) were added to the reaction simultaneously in a dropwise fashion. The resulting mixture was warmed to room temperature, and water (5 mL) was added to aid dissolution. The mixture was then stirred at 60° C. for 3 hours. The mixture was then diluted with water and saturated sodium carbonate and then extracted with dichloromethane (5×). The combined organic layers were dried, filtered, concentrated, and then chromatographed in 1:4:5 (2M $NH_3$ in methanol):ethyl acetate:dichloromethane giving the desired product (473 mg, 62.4%) as a pale yellow solid. $^1$H NMR (DMSO-$d_6$) δ 8.36 (d, J=2.1 Hz, 1H), 7.93 (dd, J=8.7, 2.1 Hz, 1H), 7.50 (d, J=9.0 Hz, 1H), 4.50 (t, J=5.1 Hz, 1H), 3.96-3.90 (m, 2H), 3.56 (s, 2H), 3.48-3.40 (m, 2H), 3.32-3.26 (m, 2H), 2.58 (t, J=5.0 Hz, 2H), 2.18-2.08 (brs, 1H); ESI-MS (m/z, %): 298 (MH$^+$, 100).

tert-Butyl 2-hydroxyethyl(2-(6-nitro-2H-benzo[b][1,4]thiazin-4(3H)-yl)-2-oxoethyl)carbamate: To a stirred solution of 2-(2-hydroxyethylamino)-1-(6-nitro-2H-benzo[b][1,4]thiazin-4(3H)-yl)ethanone (470 mg, 1.581 mmol) in dioxane (10 mL) and triethylamine (0.444 mL, 3.16 mmol) was added di-tert-butyl dicarbonate (362 mg, 1.660 mmol). The resulting mixture was stirred for 30 minutes at room temperature. The mixture was then diluted with ethyl acetate and washed three times with a 1:1 mixture of water and saturated sodium carbonate. The organic phase was dried, filtered, and concentrated giving a pale yellow foam (625 mg, 99%). $^1$H NMR (DMSO-$d_6$) δ 8.35-8.30 (m, 1H), 7.99-7.91 (m, 1H), 7.56-7.48 (m, 1H), 4.67-4.59 (m, 1H), 4.26-4.21 (m, 2H), 3.96-3.88 (m, 2H), 3.51-3.43 (m, 2H), 3.31-3.21 (m, 4H), 1.38, 1.31 (2s, 9H); ESI-MS (m/z, %): 420 (M+Na, 47), 398 (MH$^+$, 34), 320 (35), 298 (100).

tert-Butyl 2-hydroxyethyl(2-(6-nitro-2H-benzo[b][1,4]thiazin-4(3H)-yl)ethyl)carbamate: To a stirred solution of tert-butyl 2-hydroxyethyl(2-(6-nitro-2H-benzo[b][1,4]thiazin-4(3H)-yl)-2-oxoethyl)carbamate (620 mg, 1.560 mmol) in tetrahydrofuran (5 mL) was added borane-tetrahydrofuran complex (1 M in tetrahydrofuran; 4.68 mL, 4.68 mmol), dropwise to avoid excessive bubbling. The mixture was then stirred at room temperature for 2 hours. The mixture was then quenched via the slow, dropwise addition of MeOH. The quenched reaction was then diluted with ethyl acetate and washed with saturated sodium carbonate (3×). The organic phase was dried, filtered, and concentrated giving a red oil (595 mg, 99%). $^1$H NMR (DMSO-$d_6$) δ 7.59-7.44 (m, 1H), 7.38-7.32 (m, 1H), 7.22-7.13 (m, 1H), 4.74 (t, J=5.1 Hz, 1H), 3.69-3.62 (m, 2H), 3.61-3.39 (m, 6H), 3.29-3.17 (m, 2H), 3.15-3.04 (m, 2H), 1.31, 1.24 (2s, 9H); ESI-MS (m/z, %): 406 (M+Na, 55), 328 (40), 284 (100).

tert-Butyl 2-hydroxyethyl(2-(6-(thiophene-2-carboximidamido)-2H-benzo[b][1,4]thiazin-4(3H)-yl)ethyl)carbamate: A stirred suspension of tert-butyl 2-hydroxyethyl(2-(6-nitro-2H-benzo[b][1,4]thiazin-4(3H)-yl)ethyl)carbamate (590 mg, 1.539 mmol) and palladium, 10 wt. % on activated carbon (164 mg, 0.154 mmol) in ethanol (10 mL) was stirred at room temperature under an atmosphere of hydrogen (1 atm) for 2 hours (yellow color disappears). To this mixture was then added methyl thiophene-2-carbimidothioate hydroiodide (878 mg, 3.08 mmol), and the resulting mixture was stirred overnight at room temperature. The mixture was then diluted with dichloromethane and then filtered through Celite. The filtrate was then diluted with water and extracted with dichloromethane (4×). The combined organics were dried, filtered, concentrated, and then chromatographed in ethyl acetate, giving the desired product (339 mg, 47.6%) as a yellow foam. $^1$H NMR (DMSO-$d_6$) δ 7.69 (s, 1H), 7.58 (d, J=4.8 Hz, 1H), 7.07 (t, J=4.2 Hz, 1H), 6.41-6.25 (m, 3H), 6.08 (d, J=8.1 Hz, 1H), 4.71-4.65 (m, 1H), 3.63-3.54 (m, 2H), 3.49-3.33 (m, 6H), 3.27-3.15 (m, 2H), 3.02-2.94 (m, 2H), 1.39-1.29 (m, 9H); ESI-MS (m/z, %): 463 (MH$^+$, 100).

N-(4-(2-(2-Hydroxyethylamino)ethyl)-3,4-dihydro-2H-benzo[b][1,4]thiazin-6-yl)thiophene-2-carboximidamide: To a stirred solution of tert-butyl 2-hydroxyethyl(2-(6-(thiophene-2-carboximidamido)-2H-benzo[b][1,4]thiazin-4(3H)-yl)ethyl)carbamate (334 mg, 0.722 mmol) in methanol (5 mL) was added HCl, 3M in water (2.407 mL, 7.22 mmol). The resulting solution was stirred at 90° C. for 1 hour. The mixture was then cooled to room temperature, diluted with saturated sodium carbonate and extracted with dichloromethane (6×). The combined organics were dried, filtered, concentrated, and then chromatographed in 1:9 (2M $NH_3$ in methanol):ethyl acetate, giving the desired product 26 (175 mg, 66.9%). $^1$H NMR (DMSO-$d_6$) δ 7.71 (d, J=3.3 Hz, 1H), 7.58 (d, J=5.1 Hz, 1H), 7.10-7.06 (m, 1H), 6.83 (d, J=8.1 Hz, 1H), 6.34 (brs, 2H), 6.22 (s, 1H), 6.07 (d, J=7.5 Hz, 1H), 4.49-4.43 (m, 1H), 3.63-3.55 (m, 2H), 3.46-3.38 (m, 2H), 3.37-3.28 (m, 2H), 3.01-2.95 (m, 2H), 2.71 (t, J=6.4 Hz, 2H), 2.59 (t, J=5.7 Hz, 2H), 1.91-1.75 (m, 1H); ESI-MS (m/z, %): 363 (MH$^+$, 100), 276 (99), 268 (62); HRMS calculated for $C_{17}H_{23}N_4OS_2$ (MH$^+$), calculated: 363.1307, observed: 363.1290; HPLC purity: 97% by area.

N-(4-(2-(2-Hydroxyethylamino)ethyl)-3,4-dihydro-2H-benzo[b][1,4]thiazin-6-yl)thiophene-2-carboximidamide dihydrochloride: To a solution of N-(4-(2-(2-hydroxyethylamino)ethyl)-3,4-dihydro-2H-benzo[b][1,4]thiazin-6-yl)thiophene-2-carboximidamide (165 mg, 0.455 mmol) in methanol (2 mL) was added HCl (1M in diethyl ether; 1.365 mL, 1.365 mmol). The resulting solution was concentrated, giving a yellow solid (197 mg, 99%). $^1$H NMR (DMSO-$d_6$) δ 11.46 (s, 1H), 9.75 (s, 1H), 9.21-9.09 (m, 2H), 8.74 (s, 1H), 8.21-8.11 (m, 2H), 7.40-7.32 (m, 1H), 7.12 (d, J=8.1 Hz, 1H), 7.03 (s, 1H), 6.62 (d, J=7.8 Hz, 1H), 3.73-3.60 (m, 6H), 3.18-3.07 (m, 4H), 3.06-2.98 (m, 2H); HRMS ($C_{17}H_{23}N_4OS_2$, MH$^+$, free base): calculated: 363.1307, observed: 363.1290. HPLC purity: 97% by area.

Example 27

Synthesis of N-(4-(2-(dimethylamino)ethyl)-3,4-dihydro-2H-benzo[b][1,4]thiazin-6-yl)thiophene-2-carboximidamide (27)

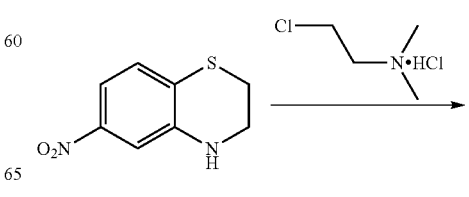

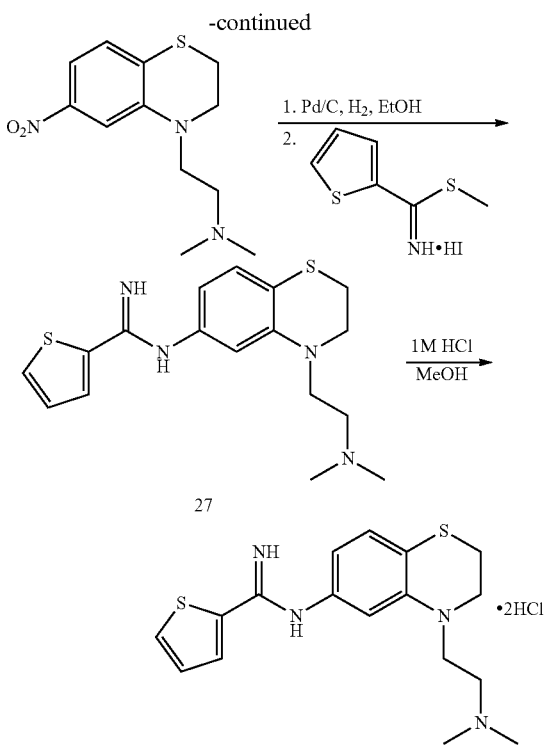

6-Nitro-3,4-dihydro-2H-benzo[b][1,4]thiazine: Prepared according to the reported procedure in Example 24.

N,N-Dimethyl-2-(6-nitro-2H-benzo[b][1,4]thiazin-4 (3H)-yl)ethanamine: To a stirred suspension of 6-nitro-3,4-dihydro-2H-benzo[b][1,4]thiazine (500 mg, 2.55 mmol), 2-chloro-N,N-dimethylethanamine hydrochloride (734 mg, 5.10 mmol), and tetrabutylammonium bromide (41.1 mg, 0.127 mmol) in dichloromethane (5 mL) was added 50% aqueous NaOH (5 mL). The reaction vessel was then sealed, and the mixture was stirred vigorously overnight at room temperature. The mixture was then diluted with water and extracted with dichloromethane (3×). The combined organics were dried, filtered, concentrated, and then chromatographed in 1:4:5 (2M NH$_3$ in methanol):ethyl acetate:dichloromethane, giving the desired product (80 mg, 11.74%) and significant amounts of starting material. $^1$H NMR (DMSO-d$_6$) δ 7.44 (d, J=2.4 Hz, 1H), 7.36 (dd, J=8.4, 2.4 Hz, 1H), 7.19 (d, J=8.4 Hz, 1H), 3.69-3.64 (m, 2H), 3.48 (t, J=6.9 Hz, 2H), 3.14-3.09 (m, 2H), 2.45 (t, J=6.9 Hz, 2H), 2.22 (s, 6H); ESI-MS (m/z, %): 268 (MH$^+$, 100).

N-(4-(2-(Dimethylamino)ethyl)-3,4-dihydro-2H-benzo[b][1,4]thiazin-6-yl)thiophene-2-carboximidamide: A suspension of N,N-dimethyl-2-(6-nitro-2H-benzo[b][1,4]thiazin-4(3H)-yl)ethanamine (75 mg, 0.281 mmol) and palladium, 10 wt. % on activated carbon (29.9 mg, 0.028 mmol) in ethanol (5 mL) was stirred at room temperature under an atmosphere of hydrogen (balloon pressure) for 90 minutes. During this time, the yellow color of the reaction dissipated. To this mixture was then added methyl thiophene-2-carbimidothioate hydroiodide (160 mg, 0.561 mmol), and the resulting suspension was stirred overnight at room temperature. The mixture was then diluted with dichloromethane and filtered to remove palladium. The organic filtrate was further diluted with water and saturated sodium carbonate (1:1). The organic layer was separated, and the aqueous layer was extracted again with dichloromethane. The combined organics were dried, filtered, concentrated, and then chromatographed in 1:19 (2M NH$_3$ in methanol):ethyl acetate, giving the desired product 27 (61 mg, 62.8%). $^1$H NMR (DMSO-d$_6$) δ 7.71 (d, J=3.3 Hz, 1H), 7.58 (d, J=5.1 Hz, 1H), 7.10-7.06 (m, 1H), 6.83 (d, J=8.1 Hz, 1H), 6.37 (brs, 2H), 6.17 (s, 1H), 6.08 (d, J=7.8 Hz, 1H), 3.63-3.58 (m, 2H), 3.39-3.32 (m, 2H), 3.01-2.96 (m, 2H), 2.42 (t, J=6.9 Hz, 2H), 2.10 (s, 6H); ESI-MS (m/z, %): 347 (MH$^+$, 100), 276 (74); ESI-HRMS calculated for C$_{17}$H$_{23}$N$_4$S$_2$ (MH$^+$), calculated: 347.1358, observed: 347.1349; HPLC purity: 95% by area.

N-(4-(2-(Dimethylamino)ethyl)-3,4-dihydro-2H-benzo[b][1,4]thiazin-6-yl)thiophene-2-carboximidamide dihydrochloride: To a solution of N-(4-(2-(dimethylamino)ethyl)-3,4-dihydro-2H-benzo[b][1,4]thiazin-6-yl)thiophene-2-carboximidamide (57 mg, 0.164 mmol) in methanol (2 mL) was added hydrogen chloride (1 M in diethyl ether; 0.493 mL, 0.493 mmol). The resulting mixture was then concentrated in vacuo to give a yellow-orange solid (68 mg, 99%). $^1$H NMR (DMSO-d$_6$) δ 11.49 (s, 1H), 11.09 (brs, 1H), 9.74 (s, 1H), 8.78 (s, 1H), 8.19-8.12 (m, 2H), 7.39-7.33 (m, 1H), 7.15-7.05 (m, 2H), 6.66-6.60 (m, 1H), 3.79-3.70 (m, 2H), 3.70-3.60 (m, 2H), 3.32-3.21 (m, 2H), 3.16-3.08 (m, 2H), 2.81-2.74 (m, 6H); HRMS (C$_{17}$H$_{23}$N$_4$S$_2$, MH$^+$, free base): calculated: 347.1358, observed: 347.1349. HPLC purity: 95% by area.

Example 28

Synthesis of N-(4-(2-(methylamino)ethyl)-3,4-dihydro-2H-benzo[b][1,4]thiazin-6-yl)thiophene-2-carboximidamide (28)

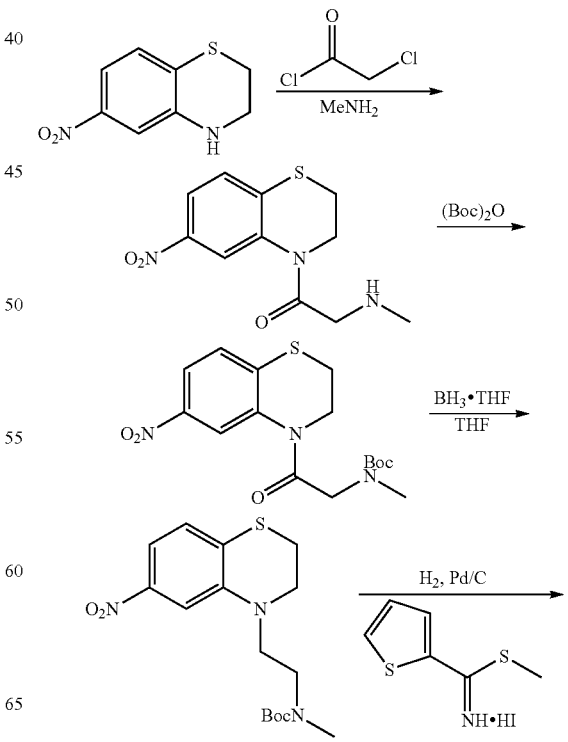

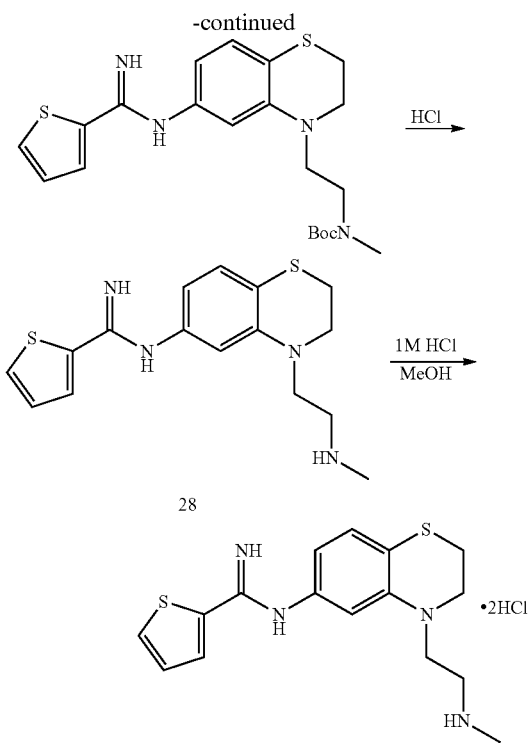

6-Nitro-3,4-dihydro-2H-benzo[b][1,4]thiazine: Prepared according to the reported procedure in Example 24.

2-(Methylamino)-1-(6-nitro-2H-benzo[b][1,4]thiazin-4(3H)-yl)ethanone: To a stirred solution of 6-nitro-3,4-dihydro-2H-benzo[b][1,4]thiazine (500 mg, 2.55 mmol) in tetrahydrofuran (4 mL) was added 2-chloroacetyl chloride (0.223 mL, 2.80 mmol). The resulting mixture was stirred at 60° C. for 10 minutes, at which time the reaction was cooled to 0° C. To the mixture was then added methylamine (2 M in tetrahydrofuran; 12.7 mL, 25.4 mmol). The resulting mixture was stirred at room temperature for 30 minutes. The mixture was then diluted with water and saturated sodium carbonate then extracted with dichloromethane (3×). The combined organics were dried, filtered, concentrated, and then chromatographed in 1:4:5 (2M $NH_3$ in methanol:ethyl acetate:dichloromethane, giving the desired product (511 mg, 75%) as a yellow solid. $^1$H NMR (DMSO-$d_6$) δ 8.36 (d, J=2.4 Hz, 1H), 7.93 (dd, J=8.7, 2.4 Hz, 1H), 7.50 (d, J=9.0 Hz, 1H), 3.93 (t, J=5.1 Hz, 2H), 3.48 (s, 2H), 3.34-3.28 (m, 2H), 2.28 (s, 3H), 2.00 (brs, 1H); ESI-MS (m/z, %): 268 (MH$^+$, 100).

tert-Butyl methyl(2-(6-nitro-2H-benzo[b][1,4]thiazin-4(3H)-yl)-2-oxoethyl)carbamate: To a stirred solution of 2-(methylamino)-1-(6-nitro-2H-benzo[b][1,4]thiazin-4(3H)-yl)ethanone (506.5 mg, 1.895 mmol) in dioxane (10 mL) and triethylamine (0.533 mL, 3.79 mmol) was added di-tert-butyl dicarbonate (434 mg, 1.990 mmol), and the resulting mixture was then stirred at room temperature for 30 minutes The mixture was then diluted with ethyl acetate and washed with water (3×) and brine. The organic phase was dried, filtered, and concentrated giving the desired product (695 mg, 100%) as a pale foam. $^1$H NMR (DMSO-$d_6$) δ 8.36-8.28 (m, 1H), 7.98-7.92 (m, 1H), 7.56-7.48 (m, 1H), 4.23-4.16 (m, 2H), 3.96-3.88 (m, 2H), 3.33-3.28 (m, 2H), 2.84 (m, 3H), 1.39. 1.30 (2s, 9H); ESI-MS (m/z, %): 390 (M+Na, 100), 368 (MH$^+$, 16), 312 (35), 268 (100).

tert-Butyl methyl(2-(6-nitro-2H-benzo[b][1,4]thiazin-4(3H)-yl)ethyl)carbamate: To a stirred solution of tert-butyl methyl(2-(6-nitro-2H-benzo[b][1,4]thiazin-4(3H)-yl)-2-oxoethyl)carbamate (691 mg, 1.881 mmol) in tetrahydrofuran (5 mL) was added borane-tetrahydrofuran complex (1 M in tetrahydrofuran; 5.64 mL, 5.64 mmol). The resulting mixture was then stirred at room temperature for 2 hours and quenched carefully via the slow, dropwise addition of methanol (5 mL). The quenched mixture was then diluted with ethyl acetate and washed sequentially with a 1:1 mixture of water:saturated sodium carbonate (2×) and then with brine. The organic phase was dried, filtered, and concentrated giving a red oil (659 mg, 99%). $^1$H NMR (DMSO-$d_6$) δ 7.56-7.39 (m, 1H), 7.39-7.31 (m, 1H), 7.24-7.14 (m, 1H), 3.68-3.61 (m, 2H), 3.60-3.49 (m, 2H), 3.48-3.36 (m, 2H), 3.13-3.05 (m, 2H), 2.83 (s, 3H), 1.30, 1.17 (2s, 9H); ESI-MS (m/z, %): 376 (M+Na, 85), 354 (MH$^+$, 24), 298 (100).

tert-Butyl methyl(2-(6-(thiophene-2-carboximidamido)-2H-benzo[b][1,4]thiazin-4(3H)-yl)ethyl)carbamate: A stirred suspension of tert-butyl methyl(2-(6-nitro-2H-benzo[b][1,4]thiazin-4(3H)-yl)ethyl)carbamate (650 mg, 1.839 mmol) and palladium, 10 wt. % on activated carbon (196 mg, 0.184 mmol) in ethanol (10 mL) was stirred under an atmosphere of hydrogen (balloon pressure) at room temperature for 2 hours. To the mixture was then added methyl thiophene-2-carbimidothioate hydroiodide (787 mg, 2.76 mmol), and the resulting suspension was stirred at room temperature overnight. The mixture was filtered to remove palladium, diluted with water and saturated sodium carbonate, and then extracted with dichloromethane (3×). The combined organics were dried, filtered, concentrated, and then chromatographed in 2:3 ethyl acetate:hexanes to afford the desired product (420 mg, 52.8%). $^1$H NMR (DMSO-$d_6$) δ 7.72-7.68 (m, 1H), 7.58 (d, J=5.1 Hz, 1H), 7.09-7.05 (m, 1H), 6.84 (d, J=7.8 Hz, 1H), 6.38-6.21 (m, 3H), 6.08 (d, J=8.4 Hz, 1H), 3.64-3.56 (m, 2H), 3.42-3.33 (m, 4H), 3.03-2.94 (m, 2H), 2.81 (s, 3H), 1.36-1.22 (m, 9H); ESI-MS (m/z, %): 433 (MH$^+$, 100).

N-(4-(2-(Methylamino)ethyl)-3,4-dihydro-2H-benzo[b][1,4]thiazin-6-yl)thiophene-2-carboximidamide: To a stirred solution of tert-butyl methyl(2-(6-(thiophene-2-carboximidamido)-2H-benzo[b][1,4]thiazin-4(3H)-yl)ethyl)carbamate (415 mg, 0.959 mmol) in methanol (4 mL) was added a 3N HCl solution (3.198 mL, 9.59 mmol). The resulting mixture was then stirred at 90° C. for 1 hour. The mixture was then cooled to room temperature, diluted with water, basified with 3N sodium hydroxide to pH 12, and extracted with dichloromethane (3×). The combined organics were dried, filtered, and concentrated then chromatographed in 1:9 (2M $NH_3$ in methanol):ethyl acetate, giving the desired product 28 (165 mg, 51.7%). $^1$H NMR (DMSO-$d_6$) δ 7.71 (d, J=3.0 Hz, 1H), 7.58 (d, J=5.1 Hz, 1H), 7.10-7.06 (m, 1H), 6.82 (d, J=8.1 Hz, 1H), 6.34 (brs, 2H), 6.22 (s, 1H), 6.07 (d, J=8.1 Hz, 1H), 3.62-3.57 (m, 2H), 3.32 (t, J=6.8 Hz, 2H), 3.01-2.97 (m, 2H), 2.64 (t, J=6.8 Hz, 1H), 2.29 (s, 3H). ESI-MS (m/z, %): 333 (MH$^+$, 100), 276 (71); ESI-HRMS calculated for $C_{16}H_{21}N_4S_2$ (MH$^+$), calculated: 333.1202, observed: 333.1207; HPLC purity: 97% by area.

N-(4-(2-(Methylamino)ethyl)-3,4-dihydro-2H-benzo[b][1,4]thiazin-6-yl)thiophene-2-carboximidamide dihydrochloride: To a solution of N-(4-(2-(methylamino)ethyl)-3,4-dihydro-2H-benzo[b][1,4]thiazin-6-yl)thiophene-2-carboximidamide (158 mg, 0.475 mmol) in methanol (3 mL) was added hydrogen chloride (1M in diethyl ether; 1.426 mL, 1.426 mmol). The resulting mixture was concentrated in vacuo, giving a yellow solid (192 mg, 100%). $^1$H NMR (DMSO-$d_6$) δ 11.47 (s, 1H), 9.76 (s, 1H), 9.31-9.19 (m, 2H), 8.74 (s, 1H), 8.20-8.11 (m, 2H), 7.39-7.33 (m, 1H), 7.11 (d, J=8.1 Hz, 1H), 7.04 (s, 1H), 6.62 (d, J=7.8 Hz, 1H), 3.71-3.61 (m, 4H), 3.18-3.04 (m, 4H), 2.58-2.52 (m, 3H); HRMS ($C_{16}H_{21}N_4S_2$, $MH^+$, free base): calculated: 333.1202, observed: 333.1207. HPLC purity: 97% by area.

Example 29

Synthesis of N-(4-(piperidin-4-yl)-3,4-dihydro-2H-benzo[b][1,4]thiazin-6-yl)thiophene-2-carboximidamide (29)

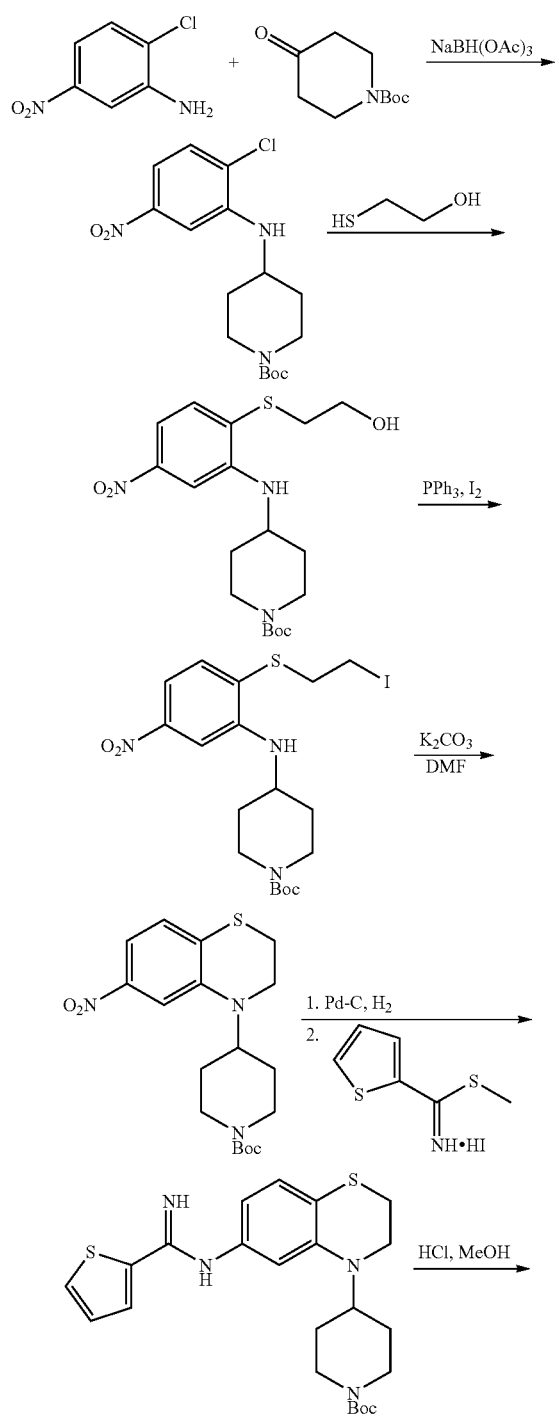

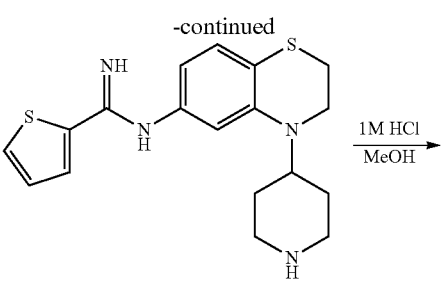

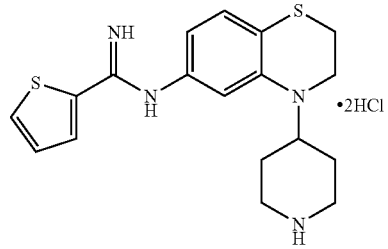

tert-Butyl 4-(2-chloro-5-nitrophenylamino)piperidine-1-carboxylate: A solution of 2-chloro-5-nitroaniline (1 g, 5.79 mmol) and tert-butyl 4-oxopiperidine-1-carboxylate (2.309 g, 11.59 mmol) in dichloroethane (15 mL) and acetic acid (0.995 mL, 17.38 mmol) was stirred at room temperature for 30 minutes. At this time, the reaction was treated with sodium triacetoxyborohydride (3.07 g, 14.49 mmol), and the resulting mixture was stirred over the weekend. Additional tert-butyl 4-oxopiperidine-1-carboxylate (2.309 g, 11.59 mmol), sodium triacetoxyborohydride (3.07 g, 14.49 mmol), and dichloroethane (15 mL) were added. Stirring was continued for 2 days. The mixture was then diluted with water and 1N sodium hydroxide (basified to pH 10) and then extracted with dichloromethane (3×). The combined organics were dried, filtered, concentrated, and then chromatographed in 1:19 ethyl acetate:hexanes, giving a yellow/orange foam (1.26 g, 61.1%). $^1$H NMR (DMSO-$d_6$) δ 7.54 (d, J=8.7 Hz, 1H), 7.51 (d, J=2.4 Hz, 1H), 7.39 (dd, J=8.7, 2.4 Hz, 1H), 5.76-5.63 (m, 1H), 3.99-3.90 (m, 2H), 3.74-3.62 (m, 1H), 3.05-2.80 (m, 2H), 1.89-1.80 (m, 2H), 1.49-1.32 (m, 11H); ESI-MS (m/z, %): 378 (M+Na, 100), 356 ($MH^+$, 40), 300 (62).

tert-Butyl 4-(2-(2-hydroxyethylthio)-5-nitrophenylamino)piperidine-1-carboxylate: To a stirred solution of tert-butyl 4-(2-chloro-5-nitrophenylamino)piperidine-1-carboxylate (1.25 g, 3.51 mmol) in DMF (10 mL) were added sequentially potassium carbonate (0.971 g, 7.03 mmol) and 2-mercaptoethanol (0.493 mL, 7.03 mmol). The resulting mixture was stirred at 60° C. for 1 hour, after which TLC analysis (2:3 ethyl acetate:hexanes) showed that the reaction was complete. The mixture was then diluted with ethyl acetate and washed sequentially with water and saturated sodium carbonate (3×). The organic phase was dried, filtered, concentrated, and then chromatographed in 2:3 ethyl acetate:hexanes, giving the desired product (1.202 g, 86%) as an orange foam. $^1$H NMR (DMSO-$d_6$) δ 7.51 (d, J=8.4 Hz, 1H), 7.43-7.37 (m, 2H), 5.40 (d, J=8.1 Hz, 1H), 5.06 (t, J=5.4 Hz, 1H), 3.95-3.86 (m, 2H), 3.75-3.60 (m, 1H), 3.59-3.50 (m, 2H), 3.01-2.85 (m, 4H), 1.94-1.83 (m, 2H), 1.49-1.29 (m, 11H); ESI-MS (m/z, %): 420 (M+Na, 22), 342 (100).

tert-Butyl 4-(2-(2-iodoethylthio)-5-nitrophenylamino)piperidine-1-carboxylate: To a stirred solution of triphenylphosphine (1.178 g, 4.49 mmol) and imidazole (0.611 g, 8.98 mmol) in tetrahydrofuran (10 mL) at 0° C. was added iodine (1.292 g, 5.09 mmol). The resulting dark mixture was stirred at 0° C. After 5 minutes, tert-butyl 4-(2-(2-hydroxyethylthio)-5-nitrophenylamino)piperidine-1-carboxylate (1.19 g, 2.99 mmol) was added as a solution in tetrahydrofuran (5 mL). The mixture was then warmed to room temperature and stirred for 1 hour. The mixture was then diluted with ethyl acetate and washed with saturated sodium carbonate, saturated sodium thiosulfate, water, and brine. The organic phase was dried, filtered, concentrated, and then chromatographed in 1:2 ethyl acetate:hexanes, giving the desired product (1.50 g, 99%) as an orange foam. $^1$H NMR (DMSO-$d_6$) δ 7.59-7.54 (m, 1H), 7.45-7.38 (m, 2H), 5.45-5.37 (m, 1H), 3.98-3.85 (m, 2H), 3.73-3.61 (m, 1H), 3.35-3.27 (m, 5H), 3.19-3.03 (m, 1H), 3.02-2.82 (m, 2H), 1.92-1.84 (m, 2H), 1.45-1.34 (m, 11H); ESI-MS (m/z, %): 530 (M+Na, 6), 452 (25), 279 (100).

tert-Butyl 4-(6-nitro-2H-benzo[b][1,4]thiazin-4(3H)-yl)piperidine-1-carboxylate: To a stirred solution of tert-butyl 4-(2-(2-iodoethylthio)-5-nitrophenylamino)piperidine-1-carboxylate (1.49 g, 2.94 mmol) in DMF (10 mL) was added potassium carbonate (0.812 g, 5.87 mmol). The resulting mixture was stirred at 90° C. for 3 hours. The reaction mixture was then diluted with ethyl acetate and washed sequentially with water and saturated sodium carbonate (2×). The organic phase was dried, filtered, concentrated, and then chromatographed in 1:4 ethyl acetate:hexanes, giving the desired product (473 mg, 42.4%) as an orange foam. $^1$H NMR (DMSO-$d_6$) δ 7.57 (d, J=2.4 Hz, 1H), 7.41 (dd, J=8.7, 2.4 Hz, 1H), 7.22 (d, J=8.7 Hz, 1H), 4.09-3.88 (m, 3H), 3.47-3.42 (m, 2H), 3.12-3.08 (m, 2H), 3.01-2.85 (m, 2H), 1.72-1.51 (m, 4H), 1.41 (s, 9H); ESI-MS (m/z, %): 402 (M+Na, 95), 380 (MH$^+$, 28), 324 (100), 280 (55).

tert-Butyl 4-(6-(thiophene-2-carboximidamido)-2H-benzo[b][1,4]thiazin-4(3H)-yl)piperidine-1-carboxylate: A suspension of tert-butyl 4-(6-nitro-2H-benzo[b][1,4]thiazin-4(3H)-yl)piperidine-1-carboxylate (468 mg, 1.233 mmol) and palladium, 10 wt. % on activated carbon (131 mg, 0.123 mmol) in ethanol (10 mL) and tetrahydrofuran (1 mL) was stirred under an atmosphere of hydrogen (balloon pressure) for 2 hours. During this time, the reaction mixture turned colorless. To the mixture was then added methyl thiophene-2-carbimidothioate hydroiodide (528 mg, 1.850 mmol), and the resulting suspension was stirred at room temperature overnight. The mixture was then diluted with ethyl acetate and filtered through a pad of Celite. The filtrate was washed with saturated sodium carbonate (3×). The organic phase was dried, filtered, concentrated, and then chromatographed in 1:5 ethyl acetate:dichloromethane to give the desired product (403 mg, 71.2%). $^1$H NMR (DMSO-$d_6$) δ 7.72 (d, J=3.0 Hz, 1H), 7.59 (d, J=5.1 Hz, 1H), 7.10-7.06 (m, 1H), 6.86 (d, J=8.1 Hz, 1H), 6.42-6.28 (m, 3H), 6.13 (d, J=8.1 Hz, 1H), 4.06-3.95 (m, 2H), 3.85-3.76 (m, 1H), 3.40-3.33 (m, 2H), 2.99-2.93 (m, 2H), 2.92-2.75 (m, 2H), 1.69-1.48 (m, 4H), 1.39 (s, 9H); ESI-MS (m/z, %): 459 (MH$^+$, 100).

N-(4-(Piperidin-4-yl)-3,4-dihydro-2H-benzo[b][1,4]thiazin-6-yl)thiophene-2-carboximidamide: To a stirred solution of tert-butyl 4-(6-(thiophene-2-carboximidamido)-2H-benzo[b][1,4]thiazin-4(3H)-yl)piperidine-1-carboxylate (398 mg, 0.868 mmol) in MeOH (6 mL) was added aqueous hydrogen chloride, 3M (2.893 mL, 8.68 mmol). The resulting solution was stirred at 90° C. for 45 minutes The mixture was then cooled to room temperature, basified (pH 12) with saturated sodium carbonate, and then extracted with dichloromethane (3×). The combined organics were dried, filtered, concentrated, and then chromatographed in 1:6 (2M NH$_3$ in MeOH):ethyl acetate to give the desired product 29 (216 mg, 69.4%) as a pale yellow foam. $^1$H NMR (DMSO-$d_6$) δ 7.71 (d, J=2.7 Hz, 1H), 7.59 (d, J=4.8 Hz, 1H), 7.08 (dd, J=5.1, 3.6 Hz, 1H), 6.86 (d, J=8.1 Hz, 1H), 6.37 (brs, 2H), 6.26 (s, 1H), 6.13-6.08 (m, 1H), 3.68-3.52 (m, 1H), 3.43-3.38 (m, 2H), 3.01-2.93 (m, 4H), 2.61-2.51 (m, 2H), 1.64-1.52 (m, 4H); ESI-MS (m/z, %): 359 (MH$^+$, 100); ESI-HRMS calculated for $C_{18}H_{23}N_4S_2$ (MH$^+$), calculated: 359.1358, observed: 359.1351; HPLC purity: 97% by area.

N-(4-(Piperidin-4-yl)-3,4-dihydro-2H-benzo[b][1,4]thiazin-6-yl)thiophene-2-carboximidamide dihydrochloride: To a solution of N-(4-(piperidin-4-yl)-3,4-dihydro-2H-benzo[b][1,4]thiazin-6-yl)thiophene-2-carboximidamide (210 mg, 0.586 mmol) in methanol (4 mL) was added hydrogen chloride (1 M in diethyl ether; 1.757 mL, 1.757 mmol). The resulting solution was concentrated in vacuo to give a pale yellow solid (252 mg, 100%). $^1$H NMR (DMSO-$d_6$) δ 11.45 (s, 1H), 9.76 (s, 1H), 9.22 (s, 2H), 8.75 (s, 1H), 7.40-7.34 (m, 1H), 7.13 (d, J=8.1 Hz, 1H), 7.02 (s, 1H), 6.64 (d, J=8.1 Hz, 1H), 4.02-3.92 (m, 1H), 3.46-3.39 (m, 2H), 3.37-3.26 (m, 2H), 3.12-2.91 (m, 4H), 2.15-1.98 (m, 2H), 1.86-1.78 (m, 2H); HRMS ($C_{18}H_{23}N_4S_2$, MH$^+$, free base): calculated: 359.1358, observed: 359.1351. HPLC purity: 97% by area.

Example 30

Synthesis of N-(4-(pyrrolidin-3-yl)-3,4-dihydro-2H-benzo[b][1,4]thiazin-7-yl)thiophene-2-carboximidamide (30)

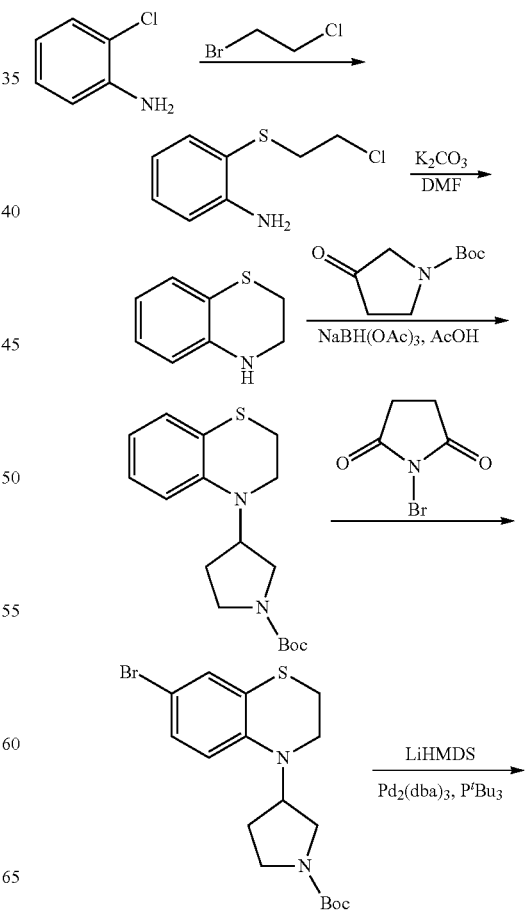

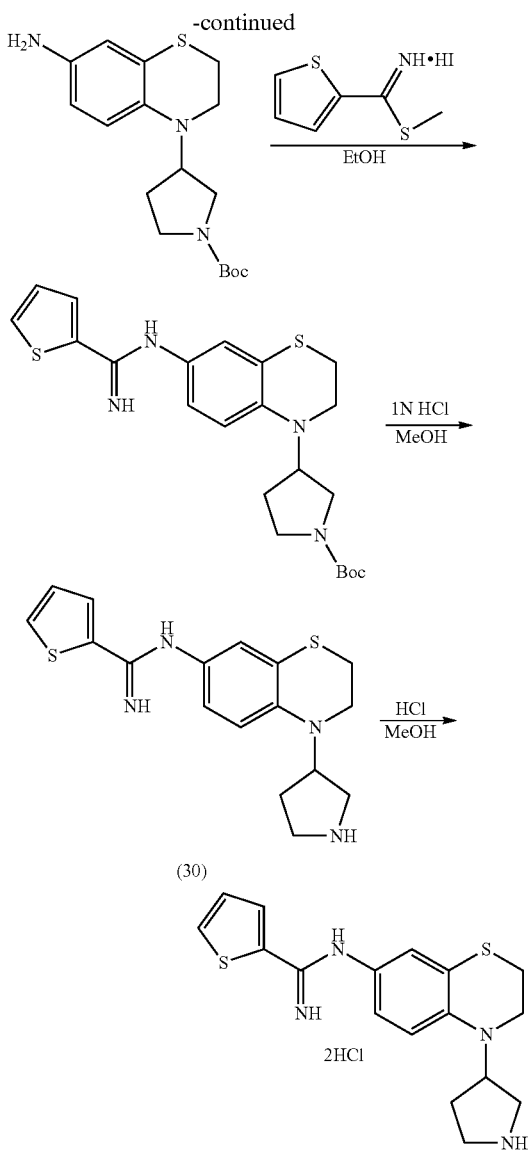

(30)

2-(2-Chloroethylthio)aniline: To a stirred solution of 2-aminobenzenethiol (0.513 mL, 4.79 mmol) in ethanol (5 mL) was added sodium hydroxide (192 mg, 4.79 mmol) as a solution in water (5.00 mL). To the resulting mixture was added 1-bromo-2-chloroethane (1.197 mL, 14.38 mmol), and the resulting mixture was stirred vigorously for 20 minutes The mixture was then diluted with ethyl acetate and washed with saturated sodium carbonate (3×). The organic phase was dried, filtered, and concentrated, giving a yellow liquid, 2-(2-chloroethylthio)aniline (875 mg, 97%). $^1$H NMR (DMSO-$d_6$) δ 7.27 (d, J=7.5 Hz, 1H), 7.10-7.04 (m, 1H), 6.73 (d, J=8.1 Hz, 1H), 6.56-6.49 (m, 1H), 5.41 (brs, 2H), 3.62 (t, J=7.4 Hz, 2H), 3.02 (t, J=7.4 Hz, 2H). ESI-MS (m/z, %): 188 (MH$^+$, 100).

3,4-Dihydro-2H-benzo[b][1,4]thiazine: To a stirred solution of 2-(2-chloroethylthio)aniline (850 mg, 4.53 mmol) in DMF (10 mL) was added potassium carbonate (1878 mg, 13.59 mmol) followed by sodium iodide (67.9 mg, 0.453 mmol). The resulting mixture was heated to 90° C. and stirred overnight. The reaction mixture was then cooled to room temperature, diluted with ethyl acetate, and washed with water (3×) and brine. The organic phase was dried, filtered, concentrated, and then chromatographed in 9:1 hexanes:ethyl acetate, giving an orange oil (675 mg, 99%). $^1$H NMR (DMSO-$d_6$) δ 6.85-6.75 (m, 2H), 6.51-6.39 (m, 2H), 6.00 (brs, 1H), 3.49-3.44 (m, 2H), 2.98-2.93 (m, 2H); ESI-MS (m/z, %): 152 (MH$^+$, 100), 124 (44).

tert-Butyl 3-(2H-benzo[b][1,4]thiazin-4(3H)-yl)pyrrolidine-1-carboxylate: A mixture of 3,4-dihydro-2H-benzo[b][1,4]thiazine (1.00 g, 6.61 mmol), N-boc-3-pyrrolidinone (1.34 g, 7.27 mmol), and acetic acid (0.94 mL, 16.52 mmol) in 1,2-dichloroethane (20 mL) was cooled to 0° C. and then treated with solid sodium triacetoxyborohydride (2.10 g, 9.92 mmol). The reaction was brought to room temperature and was stirred for 11 hours. Additional equivalents of each of sodium triacetoxyborohydride (1.40 g, 6.61 mmol) and N-boc-3-pyrrolidinone (1.22 g, 6.61 mmol) were added to the reaction mixture. The reaction was stirred for 2 more days and was then quenched with 3 N NaOH (50 mL). The mixture was transferred to a separatory funnel and extracted with EtOAc (2×50 mL). The organic phase was washed with brine (50 mL) and dried (Na$_2$SO$_4$). The crude material was subject to flash chromatography on silica gel (10% EtOAc/hexanes then 20% EtOAc/hexanes). The sample was subject to additional flash chromatography on silica gel (7.5-15% EtOAc/hexanes) to give viscous oil (0.41 g, 19%). $^1$H NMR (CDCl$_3$) δ 7.08 (dd, J=0.9, 7.5 Hz, 1H), 7.04-6.99 (m, 1H), 6.77 (d, J=8.1 Hz, 1H), 6.67-6.72 (m, 1H), 4.39-4.36 (m, 1H), 3.73-3.72 (m, 6H), 3.10-3.06 (m, 2H), 2.20-2.00 (m, 2H), 1.47 (s, 9H); ESI-MS (m/z, %): 345, 343 (M+Na, 4), 322, 320 (MH$^+$, 3), 267, 265 (100).

tert-Butyl 3-(7-bromo-2H-benzo[b][1,4]thiazin-4(3H)-yl)pyrrolidine-1-carboxylate: A solution of tert-butyl 3-(2H-benzo[b][1,4]thiazin-4(3H)-yl)pyrrolidine-1-carboxylate (0.41 g, 1.302 mmol) in DMF (5 mL), was cooled to 0° C. and treated dropwise with N-bromosuccinimide (0.17 g, 0.977 mmol) in DMF (5 mL) for 15 minutes. The reaction was kept at 0° C. and was stirred for 1 hour at this temperature. At this time, N-bromosuccinimide (0.023 g, 0.130 mmol) in DMF (1 mL) was added dropwise to the reaction, which was then stirred for 1 hour at 0° C. The solution was treated again with N-bromosuccinimide (0.023 g, 0.130 mmol) in DMF (1 mL) and was stirred for 1 hour at 0° C. The solution was diluted in water (100 mL) and extracted with EtOAc (2×100 mL). The aqueous phase was washed once with EtOAc (50 mL). The organic solutions were combined, washed with water (100 mL) and brine (50 mL), and dried (Na$_2$SO$_4$). The crude material was filtered through a silica pad (20% EtOAc/hexanes) and concentrated to give clear oil (0.47 g, 90%). $^1$H NMR (CDCl$_3$) δ 7.18 (d, J=2.4 Hz, 1H), 7.07 (d, J=8.7 Hz, 1H), 6.62 (d, J=8.7 Hz, 1H), 4.34-4.28 (m, 1H), 3.71-3.23 (m, 6H), 3.03-3.04 (m, 2H), 2.19-1.95 (m, 2H), 1.47 (s, 9H); ESI-MS (m/z, %): 423, 421 (M+Na, 8), 401, 399 (MH$^+$, 2), 343, 345 (100).

tert-Butyl 3-(7-amino-2H-benzo[b][1,4]thiazin-4(3H)-yl)pyrrolidine-1-carboxylate: Tris(dibenzylideneacetone)dipalladium(0) (0.056 g, 0.062 mmol) in THF (3 mL) was treated with tri-tert-butylphosphine 10% wt in hexanes (0.748 mL, 0.247 mmol) and was stirred vigorously under argon atmosphere for 10 minutes. tert-Butyl 3-(7-bromo-2H-benzo[b][1,4]thiazin-4(3H)-yl)pyrrolidine-1-carboxylate (0.49 g, 1.233 mmol) in THF (9 mL) and IM LiHMDS in THF (3.70 mL, 3.70 mmol) were added to the mixture. The reaction was sealed, placed in a preheated oil bath, and refluxed at 100° C. The solution was cooled to room temperature, treated with 1M TBAF in THF (8 mL), and was stirred for 40 minutes. The mixture was concentrated and treated with 1N NaOH (50 mL). The mixture was transferred to a separatory funnel, diluted with water (50 mL), and extracted with EtOAc (2×50 mL). The organic phase was washed with brine (50 mL) and dried (Na₂SO₄). The crude material was subject to flash chromatography on silica gel (25-70% EtOAc/hexanes). The collected fractions were concentrated to give a clear brown oil (0.34 g, 83%). $^1$H NMR (CDCl₃) δ 6.64 (d, J=8.7 Hz, 1H), 6.48 (s, 1H), 6.39 (brs, 1H), 4.08-4.02 (m, 1H), 3.70-3.07 (m, 6H), 3.09-3.07 (m, 2H), 2.08-1.92 (m, 2H), 1.46 (s, 9H); ESI-MS (m/z, %): 338, 336 (MH⁺, 40), 282, 280 (100).

tert-Butyl 3-(7-(thiophene-2-carboximidamido)-2H-benzo[b][1,4]thiazin-4(3H)-yl)pyrrolidine-1-carboxylate: Methyl thiophene-2-carbimidothioate hydroiodide (0.53 g, 1.874 mmol) was added to a mixture of tert-butyl 3-(7-amino-2H-benzo[b][1,4]thiazin-4(3H)-yl)pyrrolidine-1-carboxylate (0.31 g, 0.937 mmol) in EtOH (20 mL). The mixture was stirred under room temperature overnight. The mixture was quenched with saturated sodium bicarbonate solution (50 mL). The solution was then transferred to a separatory funnel, diluted with water (50 mL), and extracted with CH₂Cl₂ (2×50 mL). The crude material was subjected to flash chromatography on silica gel (50-90% EtOAc/hexanes). The concentrated fractions afforded a yellow oil (0.29 g, 69%). $^1$H NMR (CDCl₃) δ 7.41 (dd, J=0.9, 5.1 Hz, 1H), 7.38 (d, J=3.6 Hz, 1H), 7.06 (dd, J=3.9, 4.9 Hz, 1H), 6.79-6.76 (m, 2H), 6.68-6.66 (m, 1H), 4.84 (brs, 2H), 4.35-4.23 (m, 1H), 3.74-3.22 (m, 6H), 3.12-3.07 (m, 2H), 2.19-1.99 (m, 2H), 1.47 (s, 9H); ESI-MS (m/z, %): 447, 445 (MH⁺, 100).

N-(4-(Pyrrolidin-3-yl)-3,4-dihydro-2H-benzo[b][1,4]thiazin-7-yl)thiophene-2-carboximidamide: A solution of tert-butyl 3-(7-(thiophene-2-carboximidamido)-2H-benzo[b][1,4]thiazin-4(3H)-yl)pyrrolidine-1-carboxylate (0.24 g, 0.554 mmol) in MeOH (5 mL) was treated with 1N HCl solution (9.98 mL, 9.98 mmol) at room temperature. The resulting mixture was refluxed for 30 minutes and brought to room temperature. The mixture was filtered and quenched with 1N NaOH (10 mL). The mixture was diluted with water (50 mL) and extracted with CH₂Cl₂ (2×50 mL). The organic phase was washed with brine (50 mL) and dried (Na₂SO₄). The crude material was subject to flash chromatography on silica gel (5-20% 2M NH₃ MeOH/CH₂Cl₂). The collected fractions gave compound 30 as yellow foam (0.15 g, 79%). $^1$H NMR (DMSO-d₆) δ 7.69 (d, J=3.0 Hz, 1H), 7.56 (dd, J=0.9, 4.9 Hz, 1H), 7.07 (dd, J=3.9, 4.9 Hz, 1H), 6.79 (d, J=9.0 Hz, 1H), 6.52-6.49 (m, 2H), 6.31 (brs, 2H), 4.26-4.17 (m, 1H), 3.42-3.22 (m, 2H), 3.10-2.90 (m, 4H), 2.83-2.69 (m, 2H), 2.07-1.96 (m, 1H), 1.68-1.57 (m, 1H); ESI-MS (m/z, %): 347, 345 (MH⁺, 72), 278, 276 (100).

N-(4-(Pyrrolidin-3-yl)-3,4-dihydro-2H-benzo[b][1,4]thiazin-7-yl)thiophene-2-carboximidamide dihydrochloride: N-(4-(Pyrrolidin-3-yl)-3,4-dihydro-2H-benzo[b][1,4]thiazin-7-yl)thiophene-2-carboximidamide (0.1264 g, 0.367 mmol) in MeOH (3 mL) was treated with 1M HCl in ether (1.835 mL, 1.835 mmol). The mixture was stirred at room temperature for 5 minutes and was concentrated to give a light yellow solid (0.16 g, quantitative). $^1$H NMR (DMSO-d₆) δ 11.30 (s, 1H), 9.83 (brs, 1H), 9.70 (s, 1H), 9.57 (brs, 1H), 8.70 (s, 1H), 8.15-8.13 (m, 2H), 7.37-7.34 (m, 1H), 7.10-7.00 (m, 3H), 4.74-4.63 (m, 1H), 3.60-3.40 (m, 5H), 3.16-3.05 (m, 3H), 2.26-2.15 (m, 1H), 2.05-1.92 (m, 1H); ESI-MS (m/z, %): 347, 345 (MH⁺, freebase, 61), 278, 276 (100); HRMS (C₁₇H₂₁N₄S₂, MH⁺, freebase): calculated: 345.1202, observed: 345.1195. HPLC purity: 99% by area.

Example 31

Synthesis of N-(7-fluoro-4-(piperidin-4-yl)-3,4-dihydro-2H-benzo[b][1,4]thiazin-6-yl)thiophene-2-carboximidamide (31)

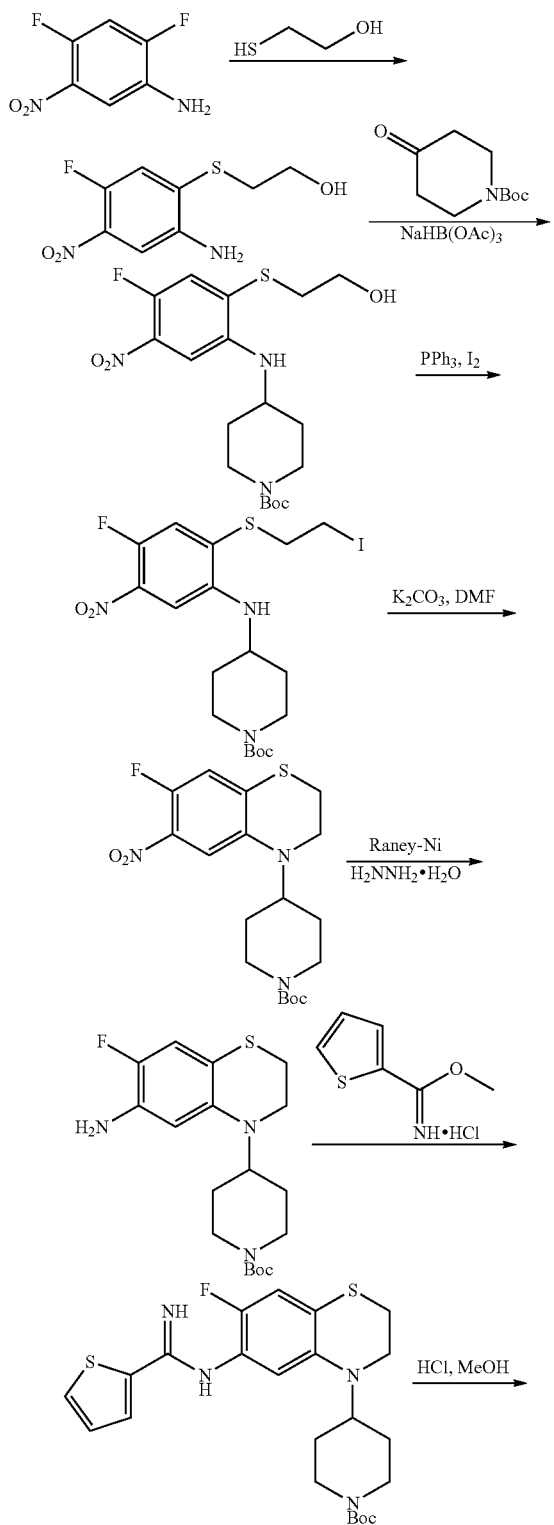

-continued

31

2-(2-Amino-5-fluoro-4-nitrophenylthio)ethanol: To a stirred suspension of 2,4-difluoro-5-nitroaniline (100 mg, 0.574 mmol) and potassium carbonate (159 mg, 1.149 mmol) in DMF (1 mL) was added 2-mercaptoethanol (0.081 mL, 1.149 mmol). The resulting mixture was stirred at room temperature for 2 hours. The mixture was then diluted with ethyl acetate and washed with saturated sodium carbonate (3×). The organic phase was dried, filtered, concentrated, and then chromatographed (1:1 EtOAc:hexanes) to give the major product. Ethyl acetate was then used as the eluent to give a minor product. The major product was determined to be the desired product (112 mg, 84%). $^1$H NMR (DMSO-d$_6$) δ 7.32 (d, J=3.5 Hz, 1H), 7.27 (d, J=10.7 Hz, 1H), 4.39 (s, 2H), 3.85-3.76 (m, 2H), 3.16-3.08 (m, 2H), 2.13-2.05 (m, 1H); ESI-MS (m/z, %): 233 (MH$^+$, 100), 215 (14), 187 (100), 129 (65).

tert-Butyl 4-(4-fluoro-2-(2-hydroxyethylthio)-5-nitrophenylamino)piperidine-1-carboxylate: To a stirred solution of 2-(2-amino-5-fluoro-4-nitrophenylthio)ethanol (434 mg, 1.869 mmol) and tert-butyl 4-oxopiperidine-1-carboxylate (372 mg, 1.869 mmol) in dichloroethane (10 mL) and acetic acid (0.321 mL, 5.61 mmol) was added sodium triacetoxyborohydride (594 mg, 2.80 mmol). The resulting mixture was stirred at room temperature. After 1 hour, additional tert-butyl 4-oxopiperidine-1-carboxylate (372 mg, 1.869 mmol) was added, followed by additional sodium triacetoxyborohydride (594 mg, 2.80 mmol). After a further 3 hours, more tert-butyl 4-oxopiperidine-1-carboxylate (372 mg, 1.869 mmol) was added followed by more sodium triacetoxyborohydride (594 mg, 2.80 mmol). The reaction mixture was stirred overnight. The mixture was then quenched with 1 N NaOH (10 mL), water (20 mL), and saturated sodium carbonate (20 mL). The organic products were then extracted with dichloromethane (3×20 mL). The combined organics were dried, filtered, concentrated, and then chromatographed using 1:3 ethyl acetate:hexanes on silica gel to give the desired product (710 mg, 91%). $^1$H NMR (DMSO-d$_6$) δ 7.45 (d, J=12.0 Hz, 1H), 7.23 (d, J=6.6 Hz, 1H), 5.08 (t, J=5.4 Hz, 1H), 5.02 (d, J=8.1 Hz, 1H), 3.96-3.84 (m, 2H), 3.69-3.55 (m, 5H), 2.99-2.83 (m, 2H), 1.92-1.83 (m, 2H), 1.45-1.18 (m, 11H); ESI-MS (m/z, %): 360 (100), 128 (30).

tert-Butyl 4-(4-fluoro-2-(2-iodoethylthio)-5-nitrophenylamino)piperidine-1-carboxylate: To a stirred solution of triphenylphosphine (668 mg, 2.55 mmol) and imidazole (0.693 mL, 5.09 mmol) in tetrahydrofuran (10 mL) cooled to 0° C. was added iodine (732 mg, 2.88 mmol). The resulting mixture was stirred at 0° C. for 5 minutes. To this mixture was then added tert-butyl 4-(4-fluoro-2-(2-hydroxyethylthio)-5-nitrophenylamino)piperidine-1-carboxylate (705 mg, 1.697 mmol) as a solution in tetrahydrofuran (5 mL), and the resulting mixture was stirred at room temperature for 20 minutes. The mixture was then diluted with ethyl acetate and washed with saturated sodium carbonate, water, saturated sodium thiosulfate, and brine. The organic phase was dried, filtered, concentrated, and then chromatographed in 1:9 ethyl acetate:hexanes to afford the desired product (398 mg, 44.6%). $^1$H NMR (DMSO-d$_6$) δ 7.53 (d, J=11.7 Hz, 1H), 7.27 (d, J=6.6 Hz, 1H), 5.10 (d, J=8.1 Hz, 1H), 3.96-3.85 (m, 2H), 3.64-3.52 (m, 1H), 3.50-3.41 (m, 2H), 3.39-3.32 (m, 2H), 2.99-2.81 (m, 2H), 1.91-1.81 (m, 2H), 1.48-1.32 (m, 11H); ESI-MS (m.z, %): 470 (100), 426 (81).

tert-Butyl 4-(7-fluoro-6-nitro-2H-benzo[b][1,4]thiazin-4(3H)-yl)piperidine-1-carboxylate: To a stirred solution of tert-butyl 4-(4-fluoro-2-(2-iodoethylthio)-5-nitrophenylamino)piperidine-1-carboxylate (394 mg, 0.750 mmol) in DMF (5 mL) was added potassium carbonate (207 mg, 1.500 mmol), and the resulting mixture was stirred at 60° C. for 2 hours and then at 90° C. overnight. The mixture was then cooled to room temperature, diluted with ethyl acetate, and washed with saturated sodium carbonate (3×), water, and brine. The organic phase was dried, filtered, concentrated, and then chromatographed using 1:9 ethyl acetate:hexanes giving the desired product (193 mg, 64.7%) as a red foam. $^1$H NMR (DMSO-d$_6$) δ 7.42 (d, J=6.6 Hz, 1H), 7.30 (d, J=11.7 Hz, 1H), 4.10-3.95 (m, 2H), 3.91-3.79 (m, 1H), 3.41-3.36 (m, 2H), 3.13-3.09 (m, 2H), 2.99-2.78 (m, 2H), 1.73-1.63 (m, 2H), 1.63-1.51 (m, 2H), 1.41 (s, 9H); ESI-MS (m/z, %): 420 (MNa$^+$, 52), 398 (MH$^+$, 35), 342 (100), 298 (64).

tert-Butyl 4-(6-amino-7-fluoro-2H-benzo[b][1,4]thiazin-4(3H)-yl)piperidine-1-carboxylate: To a stirred solution of tert-butyl 4-(7-fluoro-6-nitro-2H-benzo[b][1,4]thiazin-4(3H)-yl)piperidine-1-carboxylate (190 mg, 0.478 mmol) in tetrahydrofuran (3.00 mL) was added Raney-Nickel (28.1 mg, 0.478 mmol) as a suspension in methanol (3 mL). To this mixture was then added hydrazine hydrate (0.233 mL, 4.78 mmol), and the resulting mixture was stirred at 60° C. for 8 minutes. During this time, the reaction mixture turns light red. The mixture was then diluted with ethyl acetate and washed with saturated sodium carbonate (2×), water (2×), and brine. The organic phase was dried, filtered, and concentrated, giving a red oil (172 mg, 98%). $^1$H NMR (DMSO-d$_6$) δ 6.61 (d, J=11.1 Hz, 1H), 6.34 (d, J=8.4 Hz, 1H), 4.76 (s, 2H), 4.11-4.01 (m, 2H), 3.62-3.51 (m, 1H), 3.29-3.25 (m, 2H), 2.93-2.88 (m, 2H), 2.87-2.69 (m, 2H), 1.71-1.61 (m, 2H), 1.59-1.48 (m, 2H), 1.40 (m, 9H); ESI-MS (m/z, %): 368 (MH$^+$, 25), 312 (100).

tert-Butyl 4-(7-fluoro-6-(thiophene-2-carboximidamido)-2H-benzo[b][1,4]thiazin-4(3H)-yl)piperidine-1-carboxylate: To a stirred solution of tert-butyl 4-(6-amino-7-fluoro-2H-benzo[b][1,4]thiazin-4(3H)-yl)piperidine-1-carboxylate (168 mg, 0.457 mmol) in ethanol (5 mL) and triethylamine (0.643 mL, 4.57 mmol) was added methyl thiophene-2-carbimidate hydrochloride (325 mg, 1.829 mmol). The resulting mixture was stirred at 65° C. over the weekend. The mixture was then cooled to room temperature, diluted with ethyl acetate, and washed with saturated sodium carbonate (3×). The organic phase was dried, filtered, and concentrated, and chromatographed in 1:9 ethyl acetate:hexanes giving a yellow oil (18 mg, 8.26%); $^1$H NMR (MeOD-d$_4$) δ 7.65-7.61 (m, 1H), 7.59-7.54 (m, 1H), 7.14-7.08 (m, 1H), 6.79 (d, J=10.5 Hz, 1H), 6.49 (d, J=7.5 Hz, 1H), 4.22-4.12 (m, 2H), 3.80-3.67 (m, 1H), 3.43-3.38 (m, 2H), 3.05-3.01 (m, 2H), 2.96-2.79 (m, 2H), 1.83-1.73 (m, 2H), 1.72-1.57 (m, 2H), 1.46 (s, 9H); ESI-MS (m/z, %): 477 (MH$^+$, 100).

N-(7-Fluoro-4-(piperidin-4-yl)-3,4-dihydro-2H-benzo[b][1,4]thiazin-6-yl)thiophene-2-carboximidamide dihydrochloride: To a stirred solution of tert-butyl 4-(7-fluoro-6-(thiophene-2-carboximidamido)-2H-benzo[b][1,4]thiazin-4(3H)-yl)piperidine-1-carboxylate (16 mg, 0.034 mmol) in methanol (1 mL) was added 1 drop of concentrated hydrochloric acid. The resulting mixture was heated at 70° C. for 1 hour. The mixture was then cooled to room temperature and diluted with diethyl ether (4 mL). The resulting pale precipitate was collected via vacuum filtration, giving the desired dihydrochloride salt product 31 (8 mg, 53.0%). $^1$H NMR (DMSO-d$_6$) δ 11.35 (s, 1H), 9.92 (s, 1H), 8.96 (s, 1H), 8.57-8.51 (m, 2H), 8.25-8.10 (m, 2H), 7.40 (s, 1H), 7.24-7.15 (m, 1H), 7.05-6.99 (m, 1H), 3.96-3.83 (m, 1H), 3.45-3.20 (m, 2H), 3.18-3.09 (m, 2H), 3.09-2.91 (m, 2H), 2.02-1.87 (m, 2H), 1.87-1.75 (m, 2H); $^1$H NMR (DMSO-d$_6$+D$_2$O) δ 8.16-8.09 (m, 1H), 8.08-8.01 (m, 1H), 7.39-7.33 (m, 1H), 7.14 (d, J=10.5 Hz, 1H), 6.95-6.88 (m, 1H), 3.91-3.80 (m, 1H), 3.39-3.29 (m, 4H), 3.11-3.05 (m, 2H), 3.05-2.91 (m, 2H), 1.90-1.78 (m, 4H); ESI-MS (m/z, %): 377 (MH$^+$, free base, 50), 294 (100); ESI-HRMS (C$_{18}$H$_{22}$N$_4$FS$_2$, MH$^+$ free base), calculated: 377.1264, observed: 377.1263.

Example 32

Synthesis of N-(4-(2-(ethylamino)ethyl)-3,4-dihydro-2H-benzo[b][1,4]thiazin-7-yl)thiophene-2-carboximidamide (32)

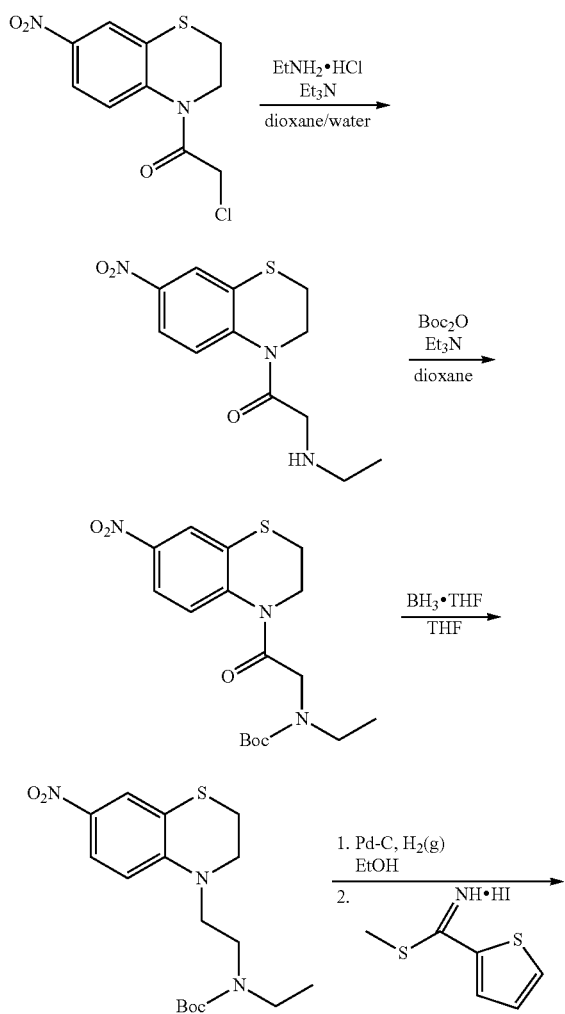

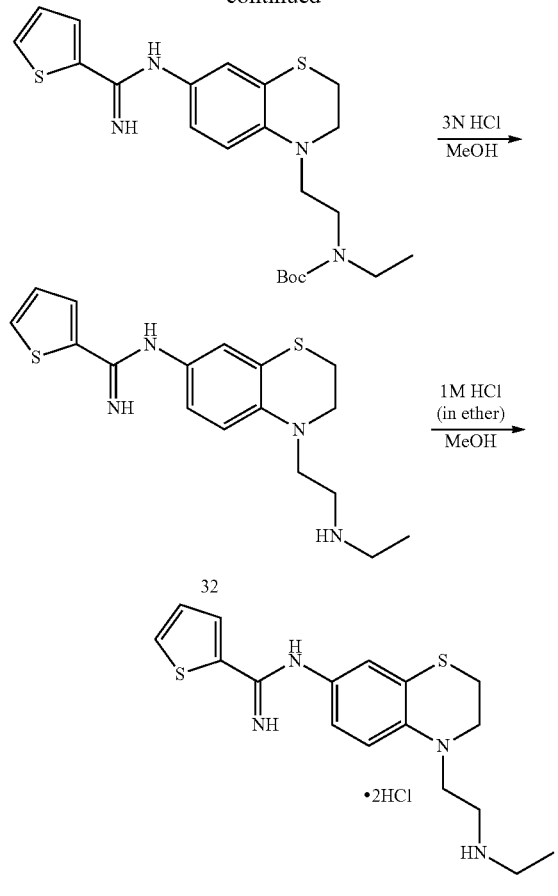

2-Chloro-1-(7-nitro-2H-benzo[b][1,4]thiazin-4(3H)-yl)ethanone: Prepared according to the reported procedure in Example 18.

2-(Ethylamino)-1-(7-nitro-2H-benzo[b][1,4]thiazin-4(3H)-yl)ethanone: A solution of 2-chloro-1-(7-nitro-2H-benzo[b][1,4]thiazin-4(3H)-yl)ethanone (1.5 g, 5.50 mmol) in dioxane (15 mL) and triethylamine (1.533 mL, 11.00 mmol) was treated with a solution of ethanamine hydrochloride (2.243 g, 27.5 mmol) in water (7.5 mL). The reaction was then stirred at room temperature overnight (16 hours). At this time, the reaction mixture was diluted with water (50 mL) and extracted into dichloromethane (3×30 mL). The combined organic layer was dried (Na$_2$SO$_4$), filtered, and concentrated. The residue was subjected to column chromatography on silica gel (1:1 ethyl acetate:hexanes then 5:95 (2M NH$_3$ in MeOH):CH$_2$Cl$_2$) to give a brown solid (0.56 g, 36.2%). $^1$H-NMR (DMSO-d$_6$) δ 8.10 (d, J=5.1 Hz, 1H), 7.92 (dd, J=2.4, 9.0 Hz, 1H), 7.70 (d, J=9.0 Hz, 1H), 3.94 (t, J=5.1 Hz, 2H), 3.52 (s, 2H), 3.33-3.28 (m, 2H), 2.55-2.52 (m, 2H), 0.98 (t, J=6.9 Hz, 3H); ESI-MS (m/z, %): 282 (MH$^+$, 100%).

tert-Butyl ethyl(2-(7-nitro-2H-benzo[b][1,4]thiazin-4(3H)-yl)-2-oxoethyl)carbamate: A solution of 2-(ethylamino)-1-(7-nitro-2H-benzo[b][1,4]thiazin-4(3H)-yl)ethanone (0.56 g, 1.991 mmol) in anhydrous dioxane (10 mL) and triethylamine (0.555 mL, 3.98 mmol) was treated with di-tert-butyl dicarbonate (0.478 g, 2.190 mmol) and stirred at room temperature for half an hour. The reaction was then diluted with ethyl acetate (50 mL) and washed with water (50 mL) and brine (3×15 mL). The organic layer was dried (Na$_2$SO$_4$), filtered, and concentrated to give a brown syrup (0.803 g, 100%). $^1$H-NMR (DMSO-d$_6$) δ 8.13-8.11 (m, 1H), 7.97-7.91

(m, 1H), 7.71 (d, J=9.0 Hz, 1H), 4.18-4.16 (m, 2H), 3.95-3.92 (m, 2H), 3.28-3.19 (m, 4H), 1.38, 1.29 (2×s, 9H), 1.05-1.02 (m, 3H); ESI-MS (m/z, %): 404 (M+Na, 42%), 382 (MH+, 17%), 282 (100%).

tert-Butyl ethyl(2-(7-nitro-2H-benzo[b][1,4]thiazin-4(3H)-yl)ethyl)carbamate: A solution of tert-butyl ethyl(2-(7-nitro-2H-benzo[b][1,4]thiazin-4(3H)-yl)-2-oxoethyl)carbamate (0.8 g, 2.097 mmol) in anhydrous tetrahydrofuran (5 mL) was treated with borane-THF complex (1M in THF; 6.29 mL, 6.29 mmol) and stirred at room temperature for 3 hours. The reaction was quenched dropwise with methanol (10 mL) and then concentrated. The crude residue was diluted with methanol (25 mL) and refluxed for 10 minutes. The mixture was then concentrated, and the residue was subjected to column chromatography on silica gel (1:9-3:7 EtOAc:CH$_2$Cl$_2$) to give a yellow syrup (0.493 g, 64%). $^1$H-NMR (DMSO-d$_6$) δ 7.85-7.78 (m, 2H), 6.94-6.85 (m, 1H), 3.76-3.79 (m, 2H), 3.62-3.57 (m, 2H), 3.37-3.33 (m, 2H), 3.22-3.19 (m, 2H), 3.08-3.04 (m, 2H), 1.35 and 1.30 (2×brs, 9H), 1.03 (t, J=6.9 Hz, 3H). ESI-MS (m/z, %): 390 (M+Na, 67%), 368 (MH+, 17%), 312 (83%), 268 (100%).

tert-Butyl ethyl(2-(7-(thiophene-2-carboximidamido)-2H-benzo[b][1,4]thiazin-4(3H)-yl)ethyl)carbamate: A suspension of palladium on carbon (10% wt; 0.142 g, 0.133 mmol), and tert-butyl ethyl(2-(7-nitro-2H-benzo[b][1,4]thiazin-4(3H)-yl)ethyl)carbamate (0.49 g, 1.333 mmol) in dry ethanol (15 mL) was stirred under hydrogen gas (balloon pressure) for 3 hours. The reaction was then placed under argon, methyl thiophene-2-carbimidothioate hydroiodide (0.761 g, 2.67 mmol) was added, and the mixture stirred at room temperature overnight (16 hours). The mixture was poured over Celite, and the Celite was rinsed with methanol. The filtrate was concentrated and subjected to column chromatography on silica gel (1:1 EtOAc:hexanes then 5:95 (2M NH$_3$ in MeOH):CH$_2$Cl$_2$) to give a solid (0.4 g, 67.2%). $^1$H-NMR (DMSO-d$_6$) δ 7.69 (brd, J=3.3 Hz, 1H), 7.57 (dd, J=1.2, 5.2 Hz, 1H), 7.07 (dd, J=3.6, 4.8 Hz, 1H), 6.81-6.74 (m, 1H), 6.49-6.46 (m, 2H), 6.31 (brs, 2H), 3.59-3.54 (m, 2H), 3.36-3.31 (overlap with solvent peak m, 4H), 3.23-3.20 (m, 2H), 3.03-3.00 (m, 2H), 1.41 (s, 9H), 1.04 (t, J=6.9 Hz, 3H); ESI-MS (m/z, %): 447 (MH+, 100%).

N-(4-(2-(Ethylamino)ethyl)-3,4-dihydro-2H-benzo[b][1,4]thiazin-7-yl)thiophene-2-carboximidamide: A solution of tert-butyl ethyl(2-(7-(thiophene-2-carboximidamido)-2H-benzo[b][1,4]thiazin-4(3H)-yl)ethyl)carbamate (0.4 g, 0.896 mmol) in methanol (10 mL) was treated with 3 N HCl (3.88 mL, 11.64 mmol) and stirred at reflux for 1.5 hours. The mixture was cooled to room temperature, diluted with water (20 mL), and basified with 1N NaOH. The product was extracted into dichloromethane (2×25 mL). The combined organic layer was dried (Na$_2$SO$_4$) and concentrated. The crude material was subjected to column chromatography on silica gel (5:95 (2M NH$_3$ in MeOH):CH$_2$Cl$_2$) to give a yellow solid (0.142 g, 45.8%). $^1$H-NMR (DMSO-d$_6$) δ 7.69 (dd, J=0.9, 3.6 Hz, 1H), 7.56 (d, J=5.1 Hz, 1H), 7.07 (dd, J=3.6, 4.8 Hz, 1H), 6.72 (d, J=8.7 Hz, 1H), 6.49 (dd, J=2.1, 8.4 Hz, 1H), 6.45 (d, J=2.1 Hz, 1H), 6.31 (brs, 2H), 3.55-3.51 (m, 2H), 3.30-3.24 (m, 2H), 3.04-3.00 (m, 2H), 2.62 (t, J=6.9 Hz, 2H), 2.56 (q, J=7.2 Hz, 2H), 1.01 (t, J=7.2 Hz, 3H); ESI-MS (m/z, %): 347 (MH+, 75%), 276 (100%); HPLC purity: 99.5% by area.

N-(4-(2-(Ethylamino)ethyl)-3,4-dihydro-2H-benzo[b][1,4]thiazin-7-yl)thiophene-2-carboximidamide dihydrochloride: A solution of N-(4-(2-(ethylamino)ethyl)-3,4-dihydro-2H-benzo[b][1,4]thiazin-7-yl)thiophene-2-carboximidamide (0.142 g, 0.410 mmol) in dry methanol (5 mL) was treated with hydrochloric acid (1M in ether; 2.049 mL, 2.049 mmol) and stirred at room temperature for 1 hour. The reaction was then concentrated to give a yellow solid. $^1$H-NMR (DMSO-d$_6$) δ 11.22 (brs, 1H) 9.68 (brs, 1H), 9.32 (brs, 2H), 8.69 (brs, 1H), 8.15-8.11 (m, 2H), 7.36 (pseudo t, J=7.2 Hz, 1H), 7.06-6.99 (m, 3H), 3.70-3.60 (overlap with solvent peak, m, 4H), 3.12-3.02 (m, 4H), 3.02-2.93 (m, 2H), 1.23 (t, J=7.2 Hz, 3H).

Example 33

Synthesis of N-(4-(2-(dimethylamino)ethyl)-3-oxo-3,4-dihydro-2H-benzo[b][1,4]thiazin-7-yl)thiophene-2-carboximidamide (33)

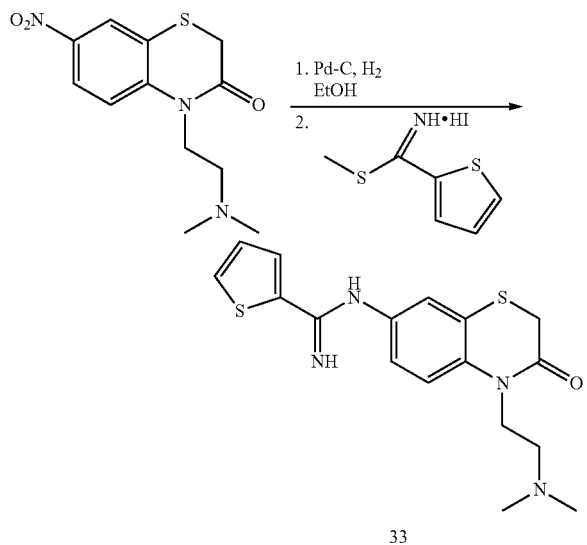

4-(2-(Dimethylamino)ethyl)-7-nitro-2H-benzo[b][1,4]thiazin-3(4H)-one: Prepared according to the reported procedure in Example 8.

N-(4-(2-(Dimethylamino)ethyl)-3-oxo-3,4-dihydro-2H-benzo[b][1,4]thiazin-7-yl)thiophene-2-carboximidamide: A suspension of 4-(2-(dimethylamino)ethyl)-7-nitro-2H-benzo[b][1,4]thiazin-3(4H)-one (0.3 g, 1.066 mmol) and palladium on carbon (10% wt, 0.113 g, 0.107 mmol) in dry ethanol (10 mL) was stirred under a hydrogen atmosphere (balloon pressure) for 2 hours. The mixture was passed over a pad of Celite, and the Celite was rinsed with ethanol. The filtrate was treated with methyl thiophene-2-carbimidothioate hydroiodide (0.608 g, 2.133 mmol), and this reaction mixture was stirred at room temperature for 3 days. The solvent was evaporated, and the residue was partitioned between dichloromethane (50 mL) and saturated sodium bicarbonate solution (25 mL), stirring for half an hour. The mixture was then transferred to a separatory funnel, and the aqueous layer was removed. The organic layer was dried (Na$_2$SO$_4$) and concentrated. The residue was subjected to column chromatography on silica gel (2.5:97.5 (2M NH$_3$ in MeOH):CH$_2$Cl$_2$ then 5:95 (2M NH$_3$ in MeOH):CH$_2$Cl$_2$ then 7.5:92.5 (2M NH$_3$ in MeOH):CH$_2$Cl$_2$) to give a yellow solid (0.117 g, 30.4%). $^1$H-NMR (DMSO-d$_6$) δ 7.75 (brd, J=3.0 Hz, 1H), 7.61 (dd, J=0.9, 5.1 Hz, 1H), 7.28 (d, J=8.7 Hz, 1H), 7.09 (dd, J=3.6, 4.8 Hz, 1H), 6.85 (brd, J=1.8 Hz, 1H), 6.79 (dd, J=1.5, 8.4 Hz, 1H), 6.58 (brs, 2H), 4.00 (t, 6.9 Hz, 2H), 3.44 (s, 2H), 2.41 (t, J=9.0 Hz, 2H), 2.19 (s, 6H).

Example 34 nNOS (Human), eNOS (Human) and iNOS (Human) Enzyme Assay

The human iNOS assay was carried by either one of the two protocols as described herein:

Protocol 1:

Recombinant human inducible NOS (iNOS) was produced in Baculovirus-infected Sf9 cells (ALEXIS). In a radiometric method, NO synthase activity was determined by measuring the conversion of [$^3$H]L-arginine to [$^3$H]L-citrulline. To measure iNOS, 10 µL of enzyme was added to 100 µL of 100 mM HEPES, pH=7.4, containing 1 mM $CaCl_2$, 1 mM EDTA, 1 mM dithiothreitol, 1 µM FMN, 1 µM FAD, 10 µM tetrahydrobiopterin, 120 µM NADPH, and 100 nM CaM.

To measure enzyme inhibition, a 15 µL solution of a test substance was added to the enzyme assay solution, followed by a pre-incubation time of 15 min at RT. The reaction was initiated by addition of 20 µL L-arginine containing 0.25 µCi of [$^3$H] arginine/mL and 24 µM L-arginine. The total volume of the reaction mixture was 150 µL in every well. The reactions were carried out at 37° C. for 45 minutes The reaction was stopped by adding 20 µL of ice-cold buffer containing 100 mM HEPES, 3 mM EGTA, 3 mM EDTA, pH=5.5. [$^3$H] L-citrulline was separated by DOWEX (ion-exchange resin DOWEX 50 W×8-400, SIGMA) and the DOWEX was removed by spinning at 12,000 g for 10 min in the centrifuge. An aliquot (70 µL) of the supernatant was added to 100 µL of scintillation fluid, and the samples were counted in a liquid scintillation counter (1450 Microbeta Jet, Wallac). Specific NOS activity was reported as the difference between the activity recovered from the test solution and that observed in a control sample containing 240 mM of the inhibitor L-NMMA. All assays were performed at least in duplicate. Standard deviations are 10% or less. These results show the selectivity of the compounds of the invention for nNOS inhibition. Results for exemplary compounds of the invention are also shown in Table 3.

Protocol 2:

| Reagents and Materials: | |
|---|---|
| Enzyme | Nitric oxide synthase (inducible, human recombinant) iNOS II, Cat. No. ALX-201-060, Axxora LLC, CA 92121, USA |
| L-NMMA | $N^G$-monomethyl-L-arginine dihydrochloride, Cat #M7033, Sigma Aldrich |
| Reaction Buffer | 50 mM Tris-HCl (pH 7.4), Cat. No. 93313, Sigma-Aldrich Co., St.Louis, MO 6 µM tetrahydrobiopterin dihydrochloride ($BH_4$), Cat. No. T4425, Sigma 2 µM flavin adenine dinucleotide (FAD), Cat. No. F6625, Sigma 2 µM flavin adenine mononucleotide (FMN), Cat. No. F8399, Sigma |
| Stop Buffer | 50 mM N-2-hydroxyethylpiperazine-N'-2-ethanesulfonic acid (HEPES) (pH 5.5), H7523, Sigma and 5 mM Ethylene diamine tetraacetic acid (EDTA), Cat. No. EDS, Sigma |
| NADPH | 12 mM prepared in 10 mM Tris-HCl (pH 7.4), Cat. No. N7505, Sigma |
| Calmodulin | 1 µM, Cat. No. P2277, Sigma |
| [$^3$H]-L-Arginine | 1 µCi/reaction, 40-70 Ci/mmol, Cat. No. TRK-698, Amersham Biosciences |
| L-Arginine | 2.5 µM (final assay concentration), Cat. No. A5131, Sigma |
| Equilibrated Resin | AG-50W X8 Resin in HEPES buffer (pH 5.5), Cat. No. 1421441, Bio-Rad Laboratories Ltd. |
| Spin Cups | Cat. No. C8163, Fisher Scientific |
| Microbeta | Wallac Microbeta Trilux, Perkin Elmer |
| Liquid Scintillation Fluid | Optiphase Supermix, Cat. No. 1200-439, Perkin Elmer |
| Incubator | Lab-Line Enviro Shaker |
| Microcentrifuge | Mikro 20 |

Procedure:

Primary stock solutions of each test compound were prepared in distilled water on the day of study to obtain a final concentration of 6 mM. For the determination of $IC_{50}$ values, 11 test compound concentrations were prepared as 3-fold serial dilutions. Test compounds were tested in the iNOS assay at a concentration of 1000 µM to 0.0169 µM. The vehicle of the test compound or inhibitor, distilled water, was used as blank control. For non-specific activity, 100 µM L-NMMA was run in parallel as a control.

All incubations were performed in duplicate

The reaction mixture was prepared on ice by the addition of the following components to the appropriate well of a 1.0 mL 96-well polypropylene plate:

10 µL of test compound, reference inhibitor, or control (vehicle or L-NMMA) solution;

25 µL of Reaction Buffer (50 mM Tris-HCl, 6 µM $BH_4$, 2 µM FMN, 2 µM FAD);

5 µL of 10 mM NADPH solution;

5 µL of distilled water;

5 µL of 1 µM Calmodulin; and

5 µL of 0.0024 µg/µL iNOS.

The reaction mixture was pre-incubated at room temperature for 15 minutes. Following this pre-incubation, the reaction was initiated by the addition of 5 µL of the substrate L-arginine (1 µCi of [$^3$H]-L-Arginine+30 µM of unlabeled L-Arginine) to the reaction mixture. The total reaction volume was 60 µL. The assay plate containing the reaction mixtures was sealed and incubated at 37° C. for 30 minutes. At the end of this incubation period, 400 µL of ice-cold Stop Buffer (the EDTA in the Stop Buffer chelates all of the available calcium) was added to each well to stop the reaction. 100 µL of equilibrated resin pH 5.5 was added to each of the assay wells. The reaction samples were vortexed and transferred to spin cups, after-which they were centrifuged at 13,000 rpm for 30 sec. The spin cups were removed from the holder and 20 µL eluate (containing the unbound L-citrulline) were added to the appropriate wells of a 96-well liquid scintillation plate. 175 µL of scintillation fluid were also added to each well. The plate was sealed, and radioactivity was quantitated using a Microbeta liquid scintillation counter.

Data were analyzed using a Sigmoidal dose-response (variable slope) curve to determine the $IC_{50}$ value of the test compound.

$$Y = \text{Bottom} + (\text{Top} - \text{Bottom})/(1 + 10^{\wedge}((\text{LogIC}_{50} - X)^* \text{Hill Slope}))$$

X is the logarithm of test compound or inhibitor concentration

Y is the amount of L-citrulline formation (pmol)

Bottom refers to the lowest Y value and Top refers to the highest Y value.

This is identical the "four parameter logistic equation"

The slope factor (also called Hill slope) describes the steepness of a curve. A standard competitive binding curve that follows the law of mass action has a slope of −1.0. If the slope is shallower, the slope factor will be a negative fraction (for example, −0.85 or −0.60).

Human nNOS and eNOS Protocol:

| Reagents and Materials | |
| --- | --- |
| Enzymes: | Nitric oxide synthase (neuronal, human recombinant) nNOS I, Cat. No. ALX-201-068, Axxora LLC, CA 92121, USA Nitric oxide synthase (endothelial, human recombinant) eNOS III, Cat. No. ALX-201-070, Axxora LLC |
| L-NMMA: | $N^G$-monomethyl-L-arginine Jan. 4, 2005, Cat # A17933, Novabiochem |
| L-NAME: | $N^G$-Nitro-L-arginine methyl ester Cat # N5751, Aldrich |
| 2X Reaction Buffer: | 50 mM Tris-HCl (pH 7.4), Cat. No. 93313, Sigma-Aldrich Co., St. Louis, MO 6 μM tetrahydrobiopterin ($BH_4$), Cat. No. T4425, Sigma 2 μM flavin adenine dinucleotide (FAD), Cat. No. F6625, Sigma 2 μM flavin adenine mononucleotide (FMN), Cat. No. F8399, Sigma |
| Stop Buffer: | 50 mM N-2-hydroxyethylpiperazine-N'-2-ethanesulfonic acid (HEPES) (pH 5.5), H7523, Sigma and 5 mM Ethylenediaminetetraacetic acid (EDTA), Cat. No. EDS, Sigma |
| NADPH: | 10 mM freshly prepared on day of assay, Cat. No. N7505, Sigma |
| Calcium Chloride: | 6 mM, Cat. No. 21107, Sigma |
| Calmodulin: | 1 mM, Cat. No. P2277, Sigma |
| [$^3$H]-L-Arginine: | 1 μCi/reaction, 40-70 Ci/mmol, Cat. No. TRK-698, Amersham Biosciences |
| L-Arginine: | 2.5 μM (final assay concentration), Cat. No. A5131, Sigma |
| Equilibrated Resin: | AG-50W X8 Resin in HEPES buffer (pH 5.5), Cat. No. 1421441, Bio-Rad Laboratories Ltd. |
| Spin Cups & Holder: | Cat. No. C8163, Fisher Scientific |
| Liquid Scintillation Counter: | Tri-Carb 2000CA/LL, Canberra Packard Canada |
| Liquid Scintillation Fluid: | Cat. No. 6012239, Ultima Gold, Perkin-Elmer Life and Analytical Sciences, MA |
| $CO_2$ Incubator: | Lab-Line Enviro Shaker |
| Microcentrifuge: | Mikro 20 |
| Vortex Mixer: | Mini Vortex mixer, IKA |

Procedure for Human nNOS and eNOS

Primary stock solutions of test compounds at a concentration of 6 mM were prepared from the 2 to 5 mg powder. The primary stock solutions of each test compound were prepared freshly in distilled water on the day of study to obtain a final concentration of 6 mM. For determination of $IC_{50}$ values, 12 test compound concentrations were prepared as 3-fold serial dilutions. Concentration range of test compound utilized for nNOS were 0.001 to 300 μM and for eNOS were 0.003 to 1000 μM. The vehicle of the test compound or inhibitor was used as blank control. For non-specific activity, 100 μM L-NMMA was used. Runs using the $IC_{50}$ concentration of L-NAME were done in parallel as controls.

All incubations are performed in duplicate:

The reaction mixture was prepared on ice by adding the following components with a micropipette to a polypropylene microcentrifuge tube:

10 μL of test compound, inhibitor or control (vehicle or L-NMMA) solution;

25 μL of Reaction Buffer {25 mM Tris-HCl, 0.6 μM $BH_4$, 0.2 μM FMN, 0.2 μM FAD};

5 μL of 10 mM NADPH solution {1 mM} (freshly prepared in 10 mM Tris-HCl (pH 7.4);

5 μL of 6 mM $CaCl_2$ {600 μM};

5 μL of 1 mM Calmodulin {100 μM}; and

5 μL of 0.02 μg/μL nNOS or 0.12 μg/μL eNOS.

The above reaction mixture was pre-incubated at room temperature for 15 mins.

The reaction was started by the addition of the substrate (in 5 μL containing 1 μCi of [$^3$H]-L-Arginine+2.5 μM of unlabeled L-Arginine) to the reaction mixture. Total reaction volume is 60 μL.

The reaction was mixed using a vortex mixer and incubate the above reaction mixture at 37° C. in an incubator for 30 minutes.

To stop the reaction, 400 μL of ice-cold Stop Buffer was added at the end of the incubation period.

The reaction was then mixed using a vortex mixer, and the reaction samples were transferred to spin cups, which were centrifuged using a microcentrifuge, at 13,000 rpm for 30 sec. at room temperature.

The spin cups were removed from the holder, 450 μL of eluate (containing the unbound L-citrulline) were transferred to scintillation vials. 3 mL of scintillation fluid were added and the radioactivity was quantified in a liquid scintillation counter.

Data was analyzed using a Sigmoidal dose-response (variable slope) curve to determine the $IC_{50}$ value of the test compound.

$$Y = \text{Bottom} + (\text{Top} - \text{Bottom})/(1 + 10^{\wedge}((\text{LogIC}_{50} - X)^* \text{Hill Slope}))$$

X is the logarithm of test compound or inhibitor concentration

Y is the amount of L-citrulline formation (pmol)

Bottom refers to the lowest Y value and Top refers to the highest Y value.

This is identical to the "four parameter logistic equation."

The slope factor (also called Hill slope) describes the steepness of a curve. A standard competitive binding curve that follows the law of mass action has a slope of −1.0. If the slope is shallower, the slope factor will be a negative fraction (for example, −0.85 or −0.60). Results for exemplary compounds of the invention are also shown in Table 3.

TABLE 3

Selective inhibition of human NOS by Compounds (1)-(33)

| Compound | Human nNOS IC50, μM | Human eNOS IC50, μM | Human iNOS IC50, μM | Selectivity eNOS/nNOS |
|---|---|---|---|---|
| 1 | 2.08 | 87.2 | >100 | 41.9 |
| 2 | 0.43 | 10.9 | 10.6 | 25.3 |
| 3 | 0.85 | 13.8 | 1.5 | 16.2 |
| 4 | 0.41 | 25.1 | 2.7 | 61.2 |
| 5 | 1.84 | 47 | >100 | 25.5 |
| 6 | 0.2 | 41.7 | 10.9 | 208.5 |
| 7 | 1.06 | 10.4 | >100 | 9.8 |
| 8 | 0.06 | 33.5 | 70.6 | 531 |
| 9 | 0.20 | 36.5 | 7.25 | 182.5 |
| 10 | 0.08 | 3.82 | 3.74 | 47.7 |
| 11 | 0.24 | 24.4 | 117 | 101.6 |
| 12 | 0.12 | 19.1 | 62.9 | 159.1 |
| 13 | 0.19 | 9.92 | 33.1 | 52.2 |
| 14 | 0.14 | 11.5 | 172 | 82.1 |
| 15 | 0.15 | 20.1 | 40.7 | 134 |
| 16 | 0.034 | 7.0 | 58.7 | 205 |
| 17 | 1.16 | 10.9 | 241 | 9.3 |
| 18 | 0.66 | 12.6 | 341 | 19 |
| 19 | 0.14 | 94.7 | 136 | 676 |
| 20 | 0.16 | 46.4 | 268 | 290 |
| 21 | 0.14 | 10.0 | 49.6 | 71.4 |
| 22 | 0.014 | 12.1 | 115 | 864 |
| 23 | 0.028 | 18.6 | 172 | 664 |
| 24 | 0.05 | 4.45 | 82.3 | 89 |
| 25 | 0.20 | 18.1 | 43.6 | 90.5 |
| 26 | 0.15 | 8.48 | 60.1 | 56.5 |
| 27 | 0.13 | 34.9 | 66.5 | 268.4 |
| 28 | 0.08 | 8.58 | 348 | 107.2 |
| 29 | 0.11 | 43.6 | 76.8 | 396 |
| 30 | NA | NA | NA | NA |
| 31 | NA | NA | NA | NA |
| 32 | NA | NA | NA | NA |
| 33 | NA | NA | NA | NA |

NA = Data not available

Example 35

Efficacy in Models Predictive of Neuropathic Pain States

Several animal models of neuropathic pain have been described that involve nerve injury including chronic constriction injury, including: CCI or Bennett model (see, for example, Bennett and Xie, *Pain,* 33: 87-107, 1988; Vissers et al. *Pharmacol. Biochem. Behav.* 84: 479-486, 2006), Spared Nerve Ligation (SNL or Chung model; see, for example, Kim et al. *Neurosci. Lett.* 199: 158-60, 1995), and the Seltzer model (Seltzer et al. *Pain* 43: 205-18, 1990). These models show good correlation between drugs with proven activity in humans and pharmacological activity in these models (Kontinen and Meert, In: Dostrovsky J., Carr D. B., Kotzenburg M., editors. 10th *World Congress on Pain,* 2003, 24. San Diego, Calif.: IASP Press, 489-98). In general, these animal models show changes in behavorial responses such as decreased mechanical thresholds, mechanical hyperalgesia, chemical hyperactivity, thermal hyperalgesia and cold allodynia (Dowdell et al. *Pharmacol. Biochem. Behavior* 80: 93-108, 2005).

The efficacy of the compounds of the invention for the treatment of neuropathic pain was assessed using standard animal models predictive of anti-hyperalgesic and anti-allodynic activity.

(a) Chung Model of Injury-Induced Neuropathic-Like Pain

Figure 2:
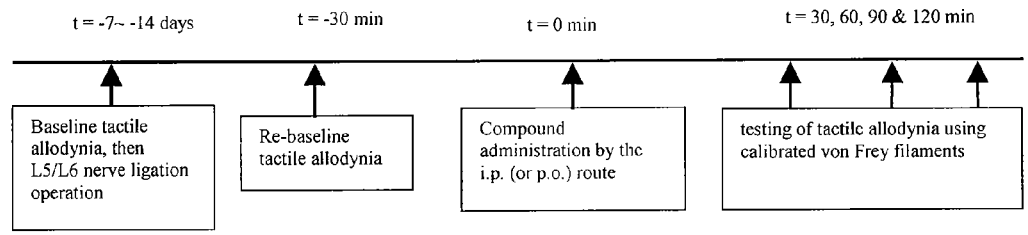
FIG. 2 shows the protocol for testing mechanical allodynia in the Chung neuropathic pain model. The L5/L6 spinal nerve was surgically ligated and animals allowed to recover for a period of 7-10 days. During this period animals develop neuropathic pain. The reduction of tactile thresholds (post-SNL) was measured following the induction period for comparison with pre-surgery baseline levels (BL). Following drug administration, tactile allodynia was measured at various time points with calibrated von-Frey filaments.

The experimental designs for the Chung Spinal Nerve Ligation SNL Model assay for neuropathic pain are depicted in FIGS. 1 and 2. Nerve ligation injury was performed according to the method described by Kim and Chung (Kim and Chung, *Pain* 50:355-363, 1992). This technique produces signs of neuropathic dysesthesias, including tactile allodynia, thermal hyperalgesia, and guarding of the affected paw. Rats were anesthetized with halothane, and the vertebrae over the L4 to S2 region were exposed. The L5 and L6 spinal nerves were exposed, carefully isolated, and tightly ligated with 4-0 silk suture distal to the DRG. After ensuring homeostatic stability, the wounds were sutured, and the animals allowed to recover in individual cages. Sham-operated rats were prepared in an identical fashion except that the L5/L6 spinal nerves were not ligated. Any rats exhibiting signs of motor deficiency were euthanized. After a period of recovery following the surgical intervention, rats show enhanced sensitivity to painful and normally non-painful stimuli.

Figure 3:
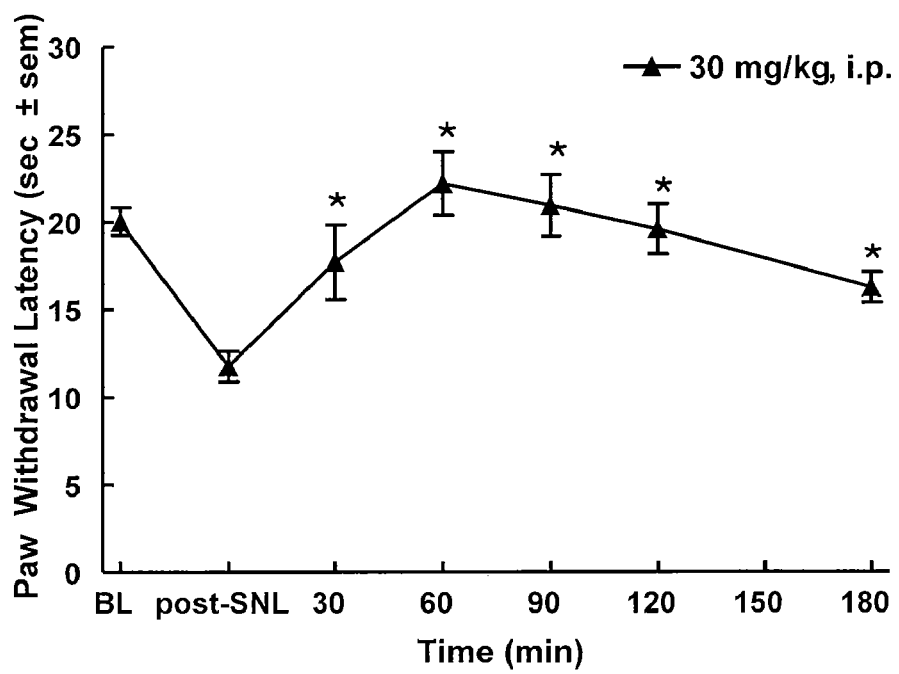
FIG. 3 shows the reversal of thermal hyperalgesia in rats after i.p. administration of Compound (8) (30 mg/kg) in the L5/L6 spinal nerve ligation model of neuropathic pain (Chung model).
Figure 4:
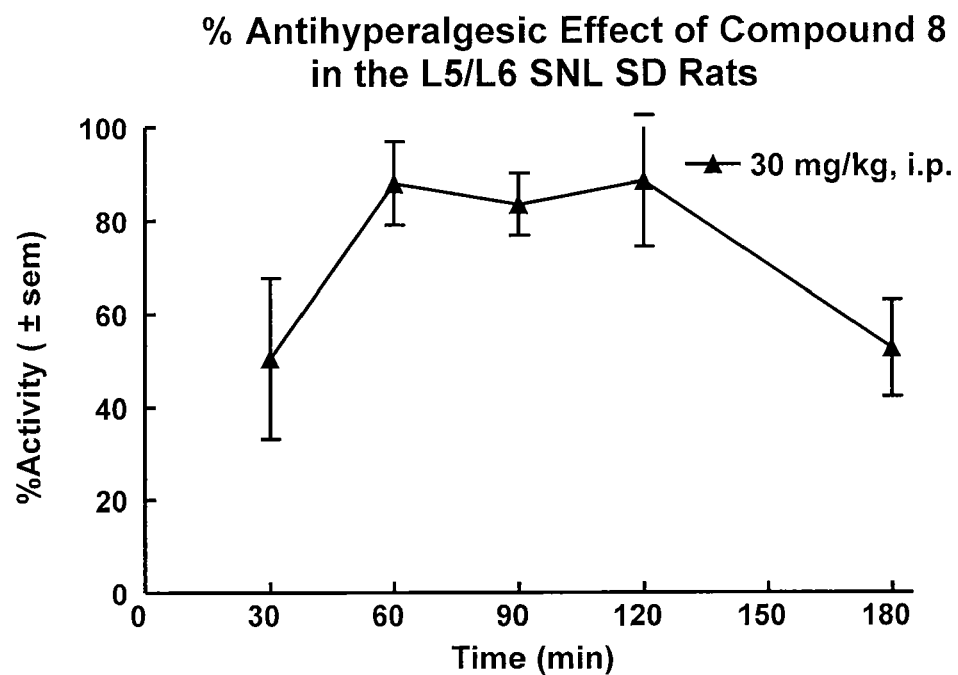
FIG. 4 shows the effects of Compound (8) after i.p. administration (30 mg/kg dose) on the reversal of tactile allodynia in rats after L5/L6 spinal nerve ligation (Chung model).

After a standard dosing (e.g., 3 mg/kg) injected i.p. according to the published procedure, there is a clear effect of Compound (8) on reversal of thermal hyperalgesia (FIGS. 3 and 4).

(b) Dural Inflammation as a Rat Model of Migraine

Figure 5:
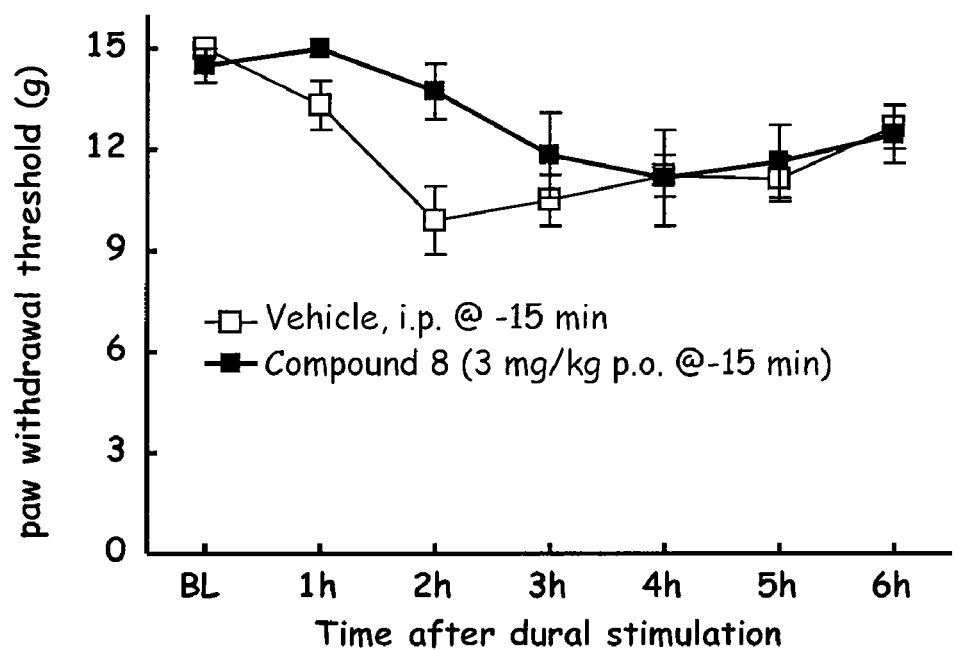
FIG. 5 shows the antiallodynic effect of Compound (8) after administration (3 mg/kg p.o.) in the dural inflammation model of migraine.

It has been demonstrated that application of an inflammatory soup (IS) or chemical stimulus to the top of the dura in rats elicits the development of central sensitization and the appearance of mechanical allodynia in the facial areas as well as the hindpaws of the animals. These features mimic the characteristic often seen in migraineurs during a headache, especially when treatment is delayed, and the development of central sensitization has occurred (Burstein et al., *Ann. Neurol.* 47:614-624, 2000; Burstein et al., *Brain,* 123:1703-1709, 2000). Compound (8) was tested in a dural inflammation model of migraine according to previously described procedures (WO 2007/120830 or as described in US-2008-0031822-A1). Baseline paw withdrawal thresholds were recorded approximately 30 min before the IS administration by application of calibrated von Frey filaments to the hindpaws to measure tactile allodynia. Approximately 15 minutes pre-IS administration, the test compound in water was administered by oral gavage (1 mL/kg) at a dose of 3 mg/kg per os (p.o.). Measurements of tactile allodynia were recorded at 1 hour intervals up to 6 hours post IS administration. The antiallodynic effect of compound 8 (3 mg/kg p.o.) is shown in FIG. 5.

(c) Carrageenan-Induced Inflammation as a Model of Primary and Secondary Pain

Figure 6:
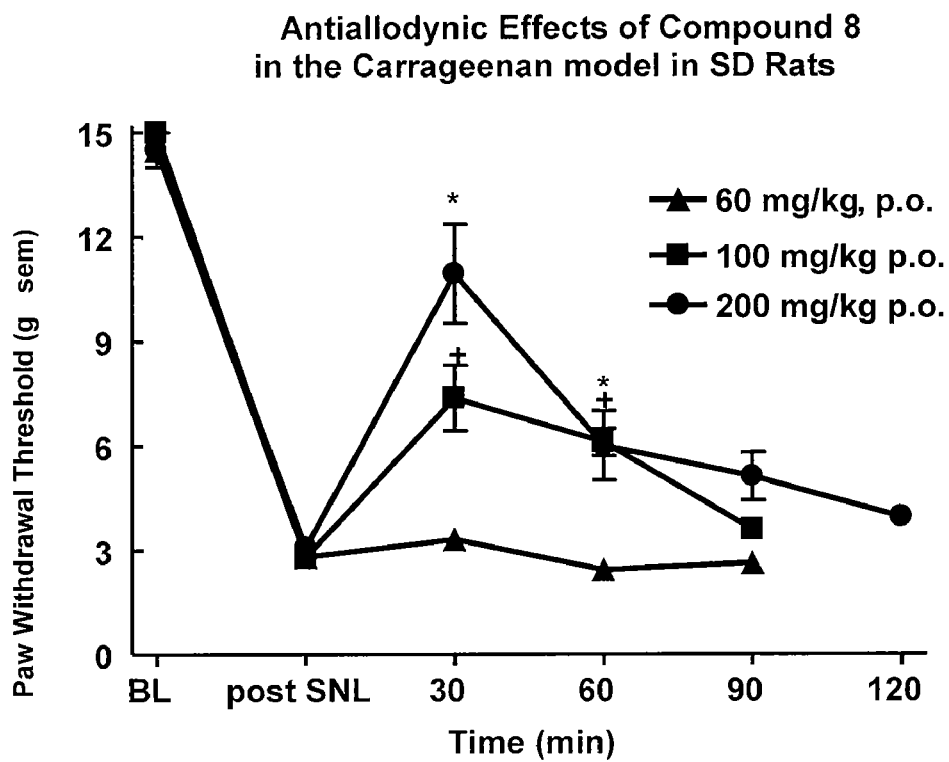
FIG. 6 shows the reversal of mechanical allodynia following administration (60, 100, or 200 mg/kg, p.o.) of Compound (8) in the Carrageenan model of inflammatory pain.
Figure 7:
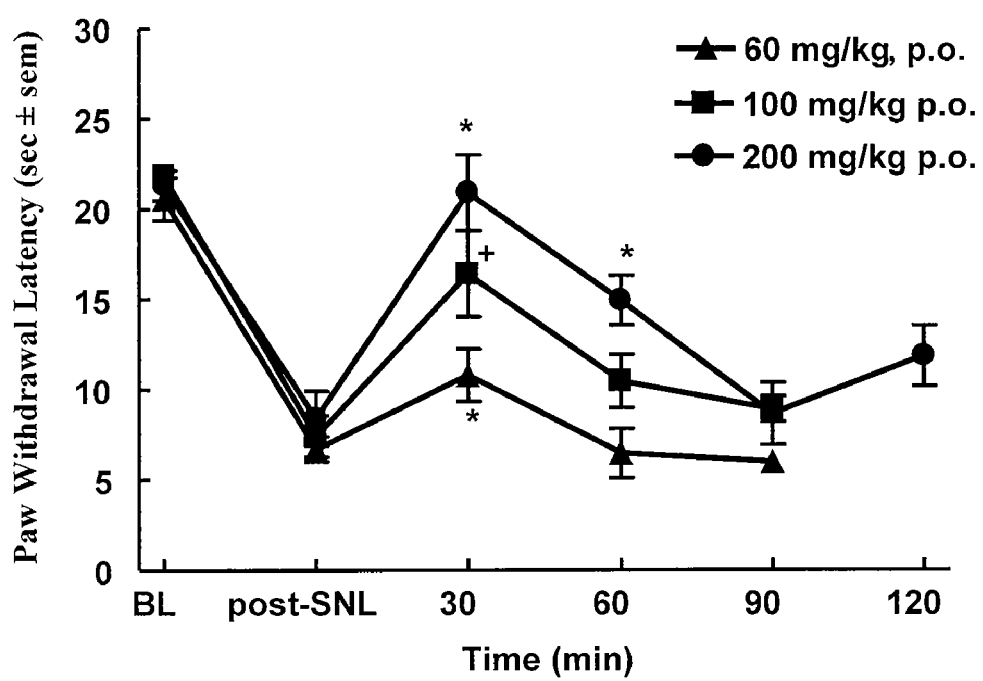
FIG. 7 shows the reversal of thermal hyperalgesia following administration (60, 100, or 200 mg/kg, p.o.) of Compound (8) in the Carrageenan model of inflammatory pain.

Inflammation was induced by injecting 0.1 mL of a 3% carrageenan suspension s.c. into the supplanter aspect of a hindpaw of lightly anesthetized rats. Typically, pronounced inflammation and edema were obvious within three hours of the injection. The carrageenan model is a model of inflammatory pain with two components: the first occurring immediately after injection provides information on the acute nociceptive response to a painful stimulus (in this case, the chemical carrageenan). There is also a second, neurogenic component that develops several hours later and reflects the type of neuronal activity due to the hyperalgesic and allodynic components as found in neuropathic pain. Considerable evidence has shown that NO and its enzymes are involved in the central mechanisms of inflammatory hyperalgesia at the spinal cord level and that peripheral inflammation can upregulate nNOS expression and induce iNOS expression in the spinal cord (Guhring et al., *J. Neurosci.* 20:6714-6720, 2000; Wu et al., *Exp. Brain Res.* 118:457-465, 1998; and Wu et al., *Pain* 94:47-58, 2001). Furthermore, iNOS knockout studies in animals reveals that nNOS is essential in the development and maintenance of the secondary components of carrageenan inflammatory pain while iNOS is sufficient, but not essential, in the late phase of thermal hyperalgesia (Tao et al., *Neuroscience* 120:847-854, 2003). FIG. 6 shows the reversal of mechanical allodynia in the ipsilateral paw of rats after carrageenan injection and administration of Compound (8). FIG. 7 shows the reversal of thermal hyperalgesia (late phase) in the ipsilateral paw of rats by Compound (8) after i.p. dosing as measured by the paw withdrawal latency to a thermal stimulus.

Thus, a compound of Formula (I) with activity at nNOS and iNOS is useful for treating both migraine, inflammatory, and neuropathic type pains and other pain states wherein a component of central neuronal sensitization exists.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:
1. A compound having the formula:

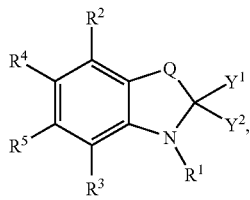

(I)

wherein,
Q is S—(CHR$^6$)$_1$;
R$^1$ and each R$^6$ is, independently, H, optionally substituted C$_{1-6}$ alkyl, optionally substituted C$_{1-4}$ alkaryl, optionally substituted C$_{1-4}$ alkheterocyclyl, optionally substituted C$_{2-9}$ heterocyclyl, optionally substituted C$_{3-8}$ cycloalkyl, optionally substituted C$_{1-4}$ alkcycloalkyl, or —(CR$^{1A}$R$^{1B}$)$_n$NR$^{1C}$R$^{1D}$;
R$^{1A}$ and R$^{1B}$ are, independently, H, hydroxy, halo, optionally substituted C$_{1-6}$ alkyl, optionally substituted C$_{1-6}$ alkoxy, optionally substituted C$_{1-4}$ alkcycloalkyl, optionally substituted C$_{1-4}$ alkaryl, optionally substituted C$_{1-4}$ alkheterocyclyl, optionally substituted C$_{1-4}$ alkheteroaryl, optionally substituted C$_{3-8}$ cycloalkyl, or optionally substituted C$_{2-9}$ heterocyclyl, or R$^{1A}$ and R$^{1B}$ combine to form =O;
R$^{1C}$ and R$^{1D}$ are, independently, H, optionally substituted C$_{1-6}$ alkyl, optionally substituted C$_{1-6}$ alkoxy, optionally substituted C$_{1-4}$ alkcycloalkyl, optionally substituted C$_{1-4}$ alkaryl, optionally substituted C$_{1-4}$ alkheterocyclyl, optionally substituted C$_{1-4}$ alkheteroaryl, optionally substituted C$_{3-8}$ cycloalkyl, optionally substituted C$_{2-9}$ heterocyclyl, or an N-protecting group selected from the group consisting of formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, alaninyl, leucinyl, phenylalaninyl, benzenesulfonyl, p-toluenesulfonyl, benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, benzyl, triphenylmethyl, benzyloxymethyl, and trimethylsilyl, or R$^{1C}$ and R$^{1D}$ combine to form an optionally substituted C$_{2-9}$ heterocyclyl;

n is an integer between 1-6;
each of R$^2$ and R$^3$ is, independently, H, hal, optionally substituted C$_{1-6}$ alkyl, optionally substituted C$_{6-10}$ aryl, optionally substituted C$_{1-6}$ alkaryl, optionally substituted C$_{2-9}$ heterocyclyl, hydroxy, optionally substituted C$_{1-6}$ alkoxy, optionally substituted C$_{1-6}$ thioalkoxy, or NHC(NH)R$^{2A}$, or optionally substituted C$_{1-4}$ alkheterocyclyl,
wherein R$^{2A}$ is

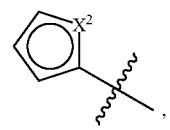

, wherein X$^2$ is O or S;
each of R$^4$ and R$^5$ is independently H, hal, or NHC(NH)R$^{2A}$;
wherein Y$^1$ and Y$^2$ are each H, or Y$^1$ and Y$^2$ together are =O, or Y$^1$ and Y$^2$ are independently H, optionally substituted C$_{1-6}$ alkyl, optionally substituted C$_{6-10}$ aryl, optionally substituted C$_{1-6}$ alkaryl, optionally substituted C$_{2-9}$ heterocyclyl, hydroxy, optionally substituted C$_{1-6}$ alkoxy, optionally substituted C$_{1-6}$ thioalkoxy, or optionally substituted C$_{1-4}$ alkheterocyclyl;
wherein one and only one of R$^2$, R$^3$, R$^4$, and R$^5$ is NHC(NH)R$^{2A}$;
or a pharmaceutically acceptable salt thereof.

2. The compound of claim 1, wherein
R$^1$ and each R$^6$ is, independently, H, optionally substituted C$_{1-6}$ alkyl, optionally substituted C$_{1-4}$ alkaryl, optionally substituted C$_{1-4}$ alkheterocyclyl, or optionally substituted C$_{2-9}$ heterocyclyl.

3. The compound of claim 1, wherein said compound has a structure selected from

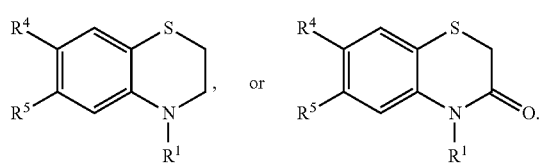

4. The compound of claim 1, wherein $Y^1$ and $Y^2$ are each H.

5. The compound of claim 1, wherein $Y^1$ and $Y^2$ together are =O.

6. The compound of claim 1, wherein $R^1$ is optionally substituted $C_{1-6}$ alkyl, optionally substituted $C_{2-9}$ heterocyclyl, or optionally substituted $C_{1-4}$ alkheterocyclyl.

7. The compound of claim 6, wherein $R^1$ is optionally substituted amino$C_{1-6}$alkyl.

8. The compound of claim 6, wherein $R^1$ is optionally substituted $C_{1-4}$ alkheterocyclyl, wherein said heterocyclyl is a 5- or 6-membered cyclic amine.

9. The compound of claim 8, wherein said cyclic amine is substituted with a carboxyl, $C_{1-6}$ alkoxycarbonyl, or carbamoyl group.

10. The compound of claim 6, wherein $R^1$ is an optionally substituted $C_{2-9}$ heterocyclyl.

11. The compound of claim 10, wherein said heterocyclyl is optionally substituted pyrrolidinyl or optionally substituted piperidinyl.

12. The compound of claim 11, wherein $R^1$ is

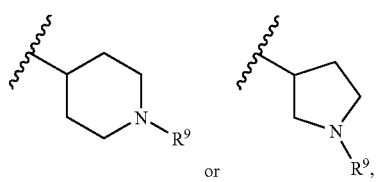

wherein $R^9$ is H, optionally substituted $C_{1-6}$ alkyl, or optionally substituted $C_{1-4}$ alkaryl.

13. The compound of claim 12, wherein $R^9$ is H.

14. The compound of claim 1, wherein $R^1$ is an optionally substituted $C_3$-$C_8$ cycloalkyl.

15. The compound of claim 1, wherein $R^1$ is —$(CR^{1A}R^{1B})_n$NR$^{1C}$R$^{1D}$.

16. The compound of claim 15, wherein $R^{1A}$ and $R^{1B}$ are each H, and n is 2 or 3.

17. The compound of claim 15, wherein $R^{1C}$ is H, and $R^{1D}$ is —$CH_3$, —$CH_2CH_3$, —$(CH_2)_2OH$, or —$CH_2CO_2H$; or $R^{1C}$ and $R^{1D}$ combine to form optionally substituted pyrrolidinyl or optionally substituted piperidinyl.

18. The compound of claim 15, wherein $R^1$ is —$CH_2CH_2N(CH_3)_2$ or —$CH_2CH_2NHCH_3$.

19. The compound of claim 14, wherein said $C_3$-$C_8$ cycloalkyl is substituted by an amino.

20. The compound of claim 1, wherein one of $R^4$ or $R^5$ is H or F.

21. A compound selected from the group consisting of:

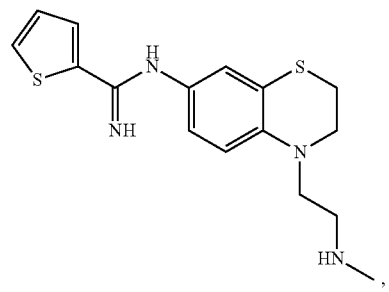

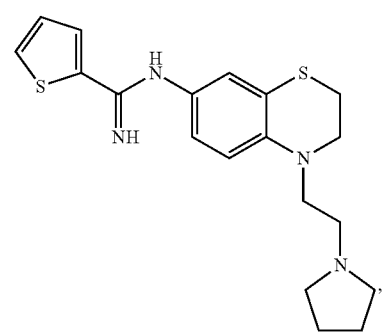

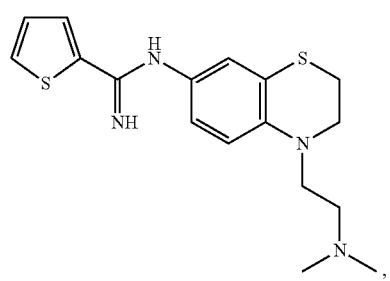

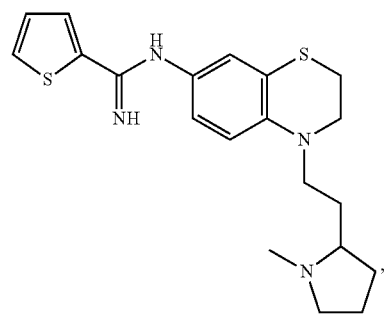

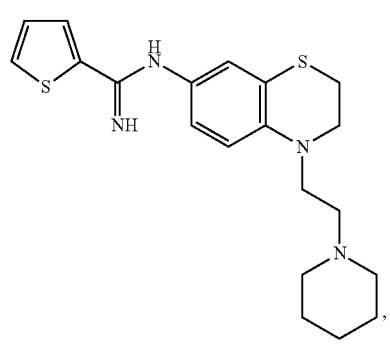

151
-continued
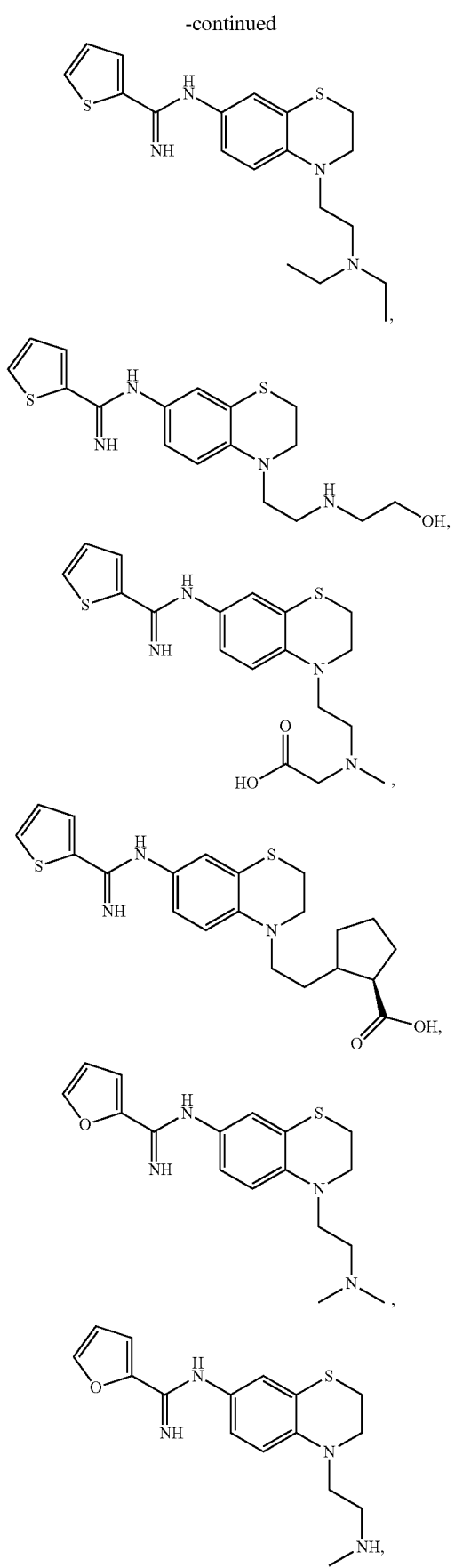
152
-continued
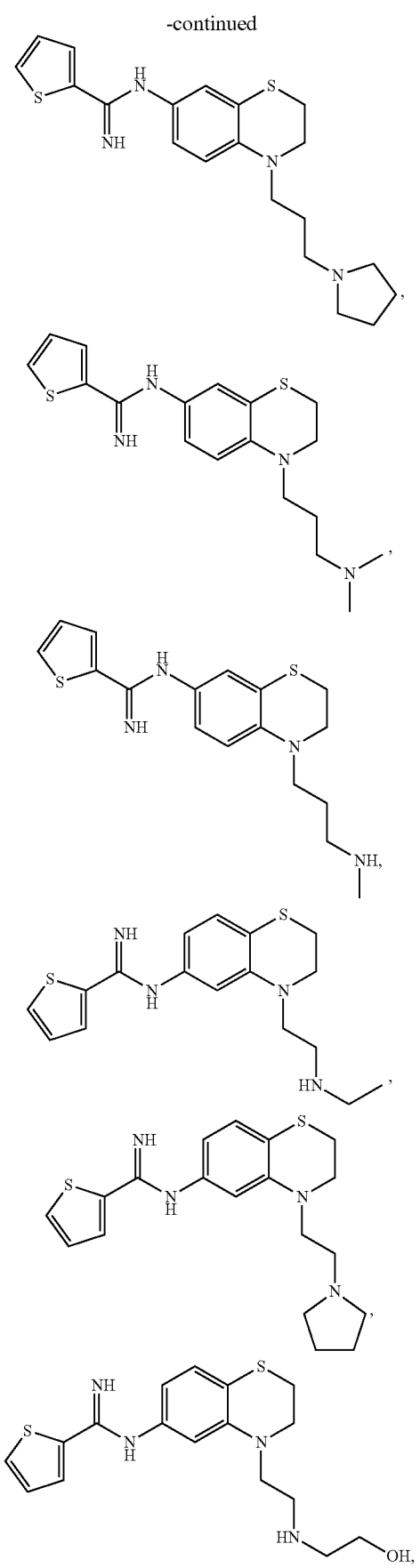

-continued

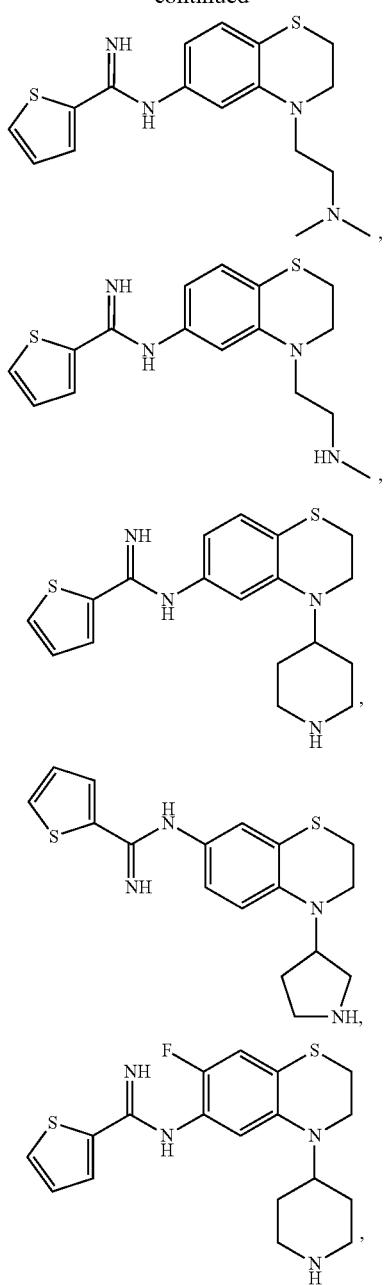

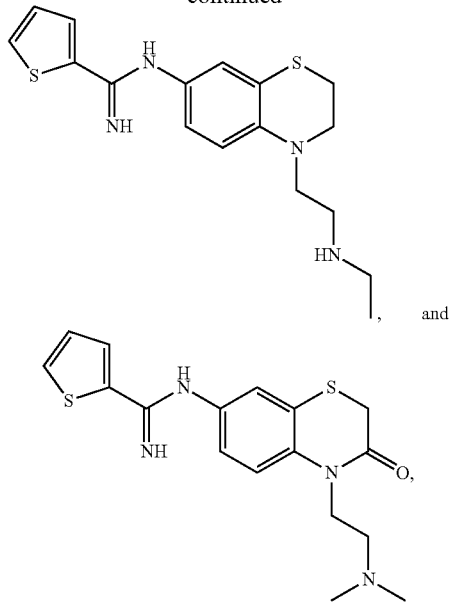

and

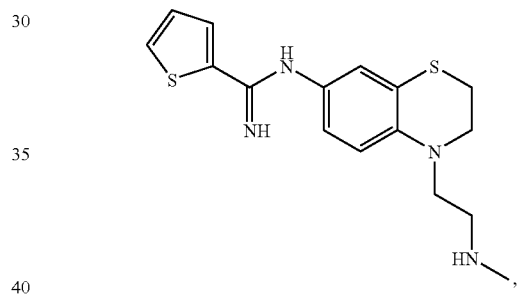

or a pharmaceutically acceptable salt thereof.

22. A compound having the formula:

or a pharmaceutically acceptable salt thereof.

23. A pharmaceutical composition comprising the compound of claim 1, or a pharmaceutically acceptable salt thereof, and a pharmaceutically acceptable excipient.

24. A pharmaceutical composition comprising the compound of claim 22, or a pharmaceutically acceptable salt thereof, and a pharmaceutically acceptable excipient.

25. The compound of claim 22, wherein said compound is the dihydrochloride salt.

* * * * *

UNITED STATES PATENT AND TRADEMARK OFFICE
CERTIFICATE OF CORRECTION

PATENT NO. : 8,106,043 B2
APPLICATION NO. : 12/498185
DATED : January 31, 2012
INVENTOR(S) : Ramnauth et al.

Page 1 of 1

It is certified that error appears in the above-identified patent and that said Letters Patent is hereby corrected as shown below:

Column 151, Claim 21, Lines 35-45, replace

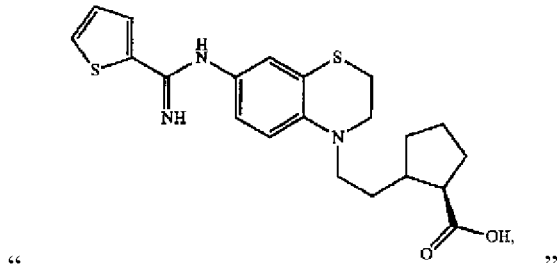

" "

with --

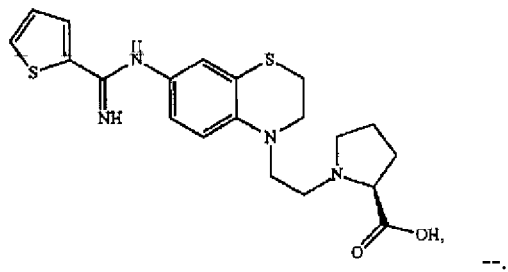

--.

Signed and Sealed this
Tenth Day of July, 2012

David J. Kappos
*Director of the United States Patent and Trademark Office*